US010335460B2

(12) United States Patent
Felber et al.

(10) Patent No.: US 10,335,460 B2
(45) Date of Patent: Jul. 2, 2019

(54) IL-15 AND IL-15Rα HETERODIMER DOSE ESCALATION REGIMENS FOR TREATING CONDITIONS

(71) Applicants: Novartis AG, Basel (CH); The United States of America, as Represented by the Secretary, Department of Health and Human Services, Washington, DC (US)

(72) Inventors: Barbara K. Felber, Rockville, MD (US); Sergio Finkielsztein, Newton, MA (US); George N. Pavlakis, Bethesda, MD (US); John N. Vournakis, Charleston, SC (US)

(73) Assignees: NOVARTIS AG, Basel (CH); The United States of America Department of Health and Human Services, Washington, DC (US)

(*) Notice: Subject to any disclaimer, the term of this patent is extended or adjusted under 35 U.S.C. 154(b) by 0 days.

(21) Appl. No.: 15/328,882

(22) PCT Filed: Jul. 28, 2015

(86) PCT No.: PCT/US2015/042489
§ 371 (c)(1),
(2) Date: Jan. 24, 2017

(87) PCT Pub. No.: WO2016/018920
PCT Pub. Date: Feb. 4, 2016

(65) Prior Publication Data
US 2017/0202924 A1 Jul. 20, 2017

Related U.S. Application Data

(60) Provisional application No. 62/030,394, filed on Jul. 29, 2014.

(51) Int. Cl.

| | |
|---|---|
| ***A61K 38/20*** | (2006.01) |
| ***A61K 38/16*** | (2006.01) |
| ***A61K 38/17*** | (2006.01) |
| ***A61K 39/395*** | (2006.01) |
| *C07K 14/715* | (2006.01) |
| *C07K 14/54* | (2006.01) |

(52) U.S. Cl.
CPC ...... *A61K 38/2086* (2013.01); *A61K 38/1793* (2013.01); *A61K 38/2046* (2013.01); *A61K 39/39558* (2013.01); *C12N 2740/16011* (2013.01)

(58) Field of Classification Search
CPC ............ A61K 2300/00; A61K 38/2086; A61K 45/06; A61K 48/005; C07K 14/5443; C07K 14/7155; C07K 2319/02; C07K 2319/30; C07K 2319/31; C07K 14/535; C07K 14/54; C07K 19/00; C07K 2319/00; Y02A 50/409; C12N 15/62; C12N 2740/16011; C12N 5/163; C12N 5/10
See application file for complete search history.

(56) References Cited

U.S. PATENT DOCUMENTS

| | | | |
|---|---|---|---|
| 5,965,726 A | 10/1999 | Pavlakis | |
| 6,174,666 B1 | 1/2001 | Pavlakis | |
| 6,291,664 B1 | 9/2001 | Pavlakis | |
| 6,414,132 B1 | 7/2002 | Pavlakis | |
| 6,794,498 B2 | 9/2004 | Pavlakis | |
| 8,124,084 B2 | 2/2012 | Lefrancois | |
| 8,163,879 B2 | 4/2012 | Wong | |
| 8,507,222 B2 | 8/2013 | Wong | |
| 8,940,288 B2 * | 1/2015 | Lefrancois ......... | C07K 14/5443 424/198.1 |
| 2009/0238791 A1 | 9/2009 | Jacques | |
| 2012/0141413 A1 | 6/2012 | Pavlakis | |

FOREIGN PATENT DOCUMENTS

| | | |
|---|---|---|
| WO | WO 1995/30695 | 11/1995 |
| WO | WO 2005/085282 | 9/2005 |
| WO | WO 2007/084342 | 7/2007 |
| WO | WO 2011/020047 | 2/2011 |
| WO | WO 2014/066527 | 5/2014 |

OTHER PUBLICATIONS

Dubois et al, The Journal of Immunology, 2008; pp. 2099-2106.*
Paxton, Current Protocols in Immunology; 1996.*
Genorise Scientific Inc. (2009); human IL-15 Elisa kit.*
Tai et al, Journal of Control Release, 2010, vol. 146, No. 3, pp. 264-275.*
Topalian et al, The New England Journal of Medicine, vol. 366, No. 26, pp. 2443-2454.*
Ohad Hammer, Landes Bioscience, 2012, vol. 4, No. 5, pp. 571-577.*
Yang et al, Oct. 2007, vol. 132, No. 4_Meeting Abstracts.*
Prins et al, The Journal of Immunology, 2006; vol. 176, pp. 157-164.*

(Continued)

*Primary Examiner* — Bridget E Bunner
*Assistant Examiner* — Fozia Hamud
(74) *Attorney, Agent, or Firm* — Tommy J. Noh

(57) ABSTRACT

Described herein are dose escalation regimens for the administration of complexes comprising interleukin-15 ("IL-15") covalently or noncovalently bound to IL-15 receptor alpha ("IL-15Rα") to patients in order to enhance IL-15-mediated immune function. In a specific aspect, the dose escalation regimens are useful in the prevention, treatment, and/or management of disorders in which enhancing IL-15-mediated function is beneficial, such as cancer, infectious diseases, immunodeficiencies and lymphopenia. In another specific aspect, the dose escalation regimens are useful for eradicating or reducing HIV in HIV-infected patients.

19 Claims, 12 Drawing Sheets

Figure 4:
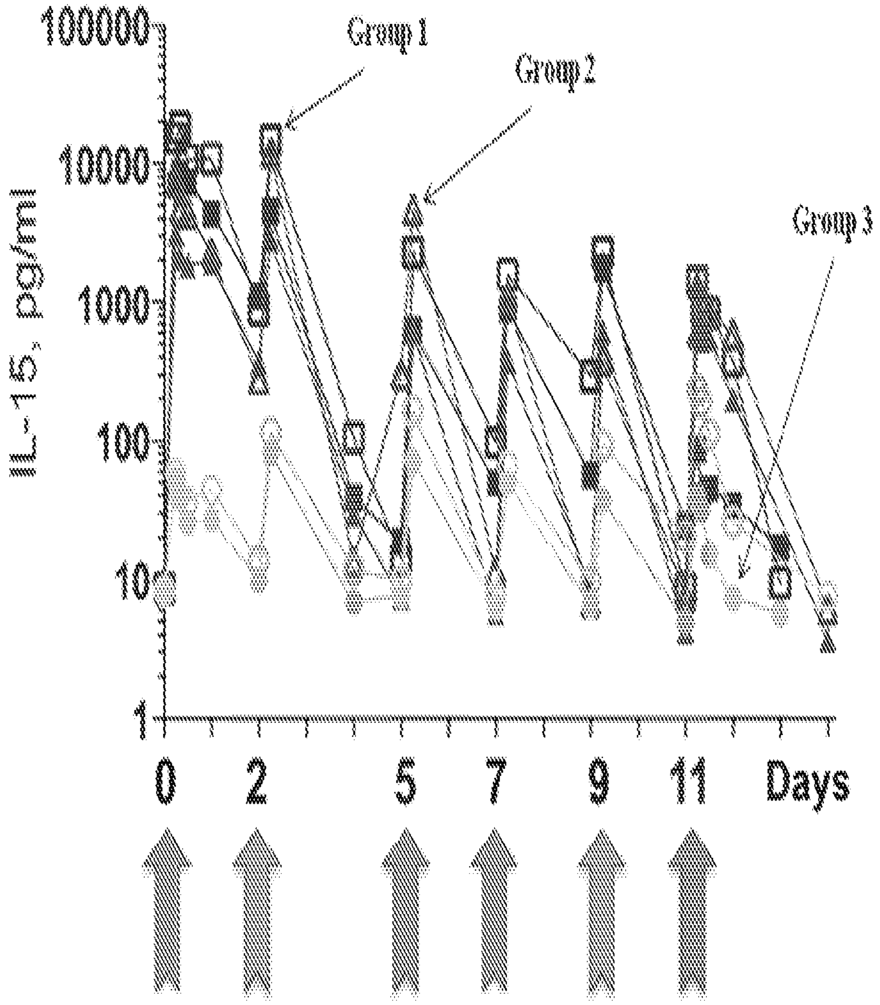

Specification includes a Sequence Listing.

(56) References Cited

OTHER PUBLICATIONS

Bergamaschi et al., "Circulating IL-15 exists as heterodimeric complex with soluble IL-15Rα in human and mouse serum" Blood 120:e1-e8, 2012.
Chertova et al., "Characterization and Favorable in Vivo Properties of Heterodimeric Soluble IL-15-IL-15Rα Cytokine Compared to IL-15 Monomer" Journal of Biological Chemistry 288(25):18093-18103, 2013.
Emini et al., "Priming for and induction of anti-poliovirus neutralizing antibodies by synthetic peptides" Nature 304:699, 1983.
Fehniger and Caligiuri, "Interleukin 15: Biology and Relevance to Human Disease" Blood 97(1):14-32, 2001.
Han et al., "IL-15:IL-15 Receptor Alpha Superagonist Complex: High-Level Co-Expression in Recombinant Mammalian Cells, Purification and Characterization" Cytokine 56(3):804-810, 2011.
Levy et al., "Enhanced T Cell Recovery in HIV-1-Infected Adults Through IL-7 Treatment" The Journal of Clinical Investigation 119(4):997-1007, 2009.
Kulkarni et al., "HIV-1 Conserved Elements p24CE DNA Vaccine Induces Humoral Immune Responses with Broad Epitope Recognition in Macaques" PLOS One 9(10):e111085, 2014.
Kulkarni et al., "Altered Response Hierarchy and Increased T-Cell Breadth upon HIV-1 Conserved Element DNA Vaccination in Macaques" PLOS One 9(1): e86254, 2014.
Mortier et al., "Soluble Interleukin-15 Receptor A (IL-15rα)-Sushi as a Selective and Potent Agonist of IL-15 Action Through IL-15rβ/Γ Hyperagonist IL-15-IL-15rα Fusion Proteins" J. Biol. Chem. 281(3):1612-1619, 2006.
Mothe et al., "A Human Immune Data-Informed Vaccine Concept Elicits Strong and Broad T-cell Specificities Associated with HIV-1 Control in Mice and Macaques" Journal of Translational Medicine 13:60, 2015.
Rasmussen et al., "Panobinostat, a histone deacetylase inhibitor, for latent-virus reactivation in HIV-infected patients on suppressive antiretroviral therapy: a phase 1/2, single group, clinical trial" Lancet HIV 1:e13-e21, 2014.
Rossi et al, "Histone deacetylase inhibitors impair NK cell viability and effector functions through inhibition of activation and receptor expression" Journal of Leukocyte Biology 91(2):321-331, 2012.
Wang et al., "IL-7 is a Potent and Proviral Strain-Specific Inducer of Latent HIV-1 Cellular Reservoirs of Infected Individuals" The Journal of Clinical Investigation 115(1):128-137, 2005.
Zhu et al., "Novel Human Interleukin-15 Agonists" Journal of Immunology 183:3598-3607, 2009.
Bergamaschi, "Intramuscular delivery of heterodimeric IL-15 DNA in macaques produces systemic levels of bioactive cytokine inducing proliferation of NK and T cells" Gene Therapy vol. 22(1):76-86, 2015.

* cited by examiner native human IL-15

ATGAGAAT TTCGAAACCA CATTTGAGAA GTATTTCCAT CCAGTGCTAC TTGTGTTTAC TTCTAAACAG TCATTTTCTA
ACTGAAGCTG GCATTCATGT CTTCATTTTG GGCTGTTTCA GTGCAGGGCT TCCTAAAACA GAAGCCAACT GGGTGAATGT
AATAAGTGAT TTGAAAAAAA TTGAAGATCT TATTCAATCT ATGCATATTG ATGCTACTTT ATATACGGAA AGTGATGTTC
ACCCCAGTTG CAAAGTAACA GCAATGAAGT GCTTTCTCTT GGAGTTACAA GTTATTTCAC TTGAGTCCGG AGATGCAAGT
ATTCATGATA CAGTAGAAAA TCTGATCATC CTAGCAAACA ACAGTTTGTC TTCTAATGGG AATGTAACAG AATCTGGATG
CAAAGAATGT GAGGAACTGG AGGAAAAAAA TATTAAAGAA TTTTTGCAGA GTTTTGTACA TATTGTCCAA ATGTTCATCA
ACACTTCTTG A

Fig. 1A

MRISKPHLRSISIQCYLCLLLNSHFLTEAGIHVFILGCFSAGLPKTEANWVNV
ISDLKKIEDLIQSMHIDATLYTESDVHPSCKVTAMKCFLLELQVISLESGDASIHDT
VENLIILANNSLSSNGNVTESGCKECEELEEKNIKEFLQSFVHIVQMFINTS

Fig. 1B native human IL-15Ra

ATGGCCCC GCGGCGGGCG CGCGGCTGCC GGACCCTCGG TCTCCCGGCG CTGCTACTGC TGCTGCTGCT CCGGCCGCCG
GCGACGCGGG GCATCACGTG CCCTCCCCCC ATGTCCGTGG AACACGCAGA CATCTGGGTC AAGAGCTACA GCTTGTACTC
CAGGGAGCGG TACATTTGTA ACTCTGGTTT CAAGCGTAAA GCCGGCACGT CCAGCCTGAC GGAGTGCGTG TTGAACAAGG
CCACGAATGT CGCCCACTGG ACAACCCCCA GTCTCAAATG CATTAGAGAC CCTGCCCTGG TTCACCAAAG GCCAGCGCCA
CCCTCCACAG TAACGACGGC AGGGGTGACC CCACAGCCAG AGAGCCTCTC CCCTTCTGGA AAAGAGCCCG CAGCTTCATC
TCCCAGCTCA AACAACACAG CGGCCACAAC AGCAGCTATT GTCCCGGGCT CCCAGCTGAT GCCTTCAAAA TCACCTTCCA
CAGGAACCAC AGAGATAAGC AGTCATGAGT CCTCCCACGG CACCCCCTCT CAGACAACAG CCAAGAACTG GGAACTCACA
GCATCCGCCT CCCACCAGCC GCCAGGTGTG TATCCACAGG GCCACAGCGA CACCACTGTG GCTATCTCCA CGTCCACTGT
CCTGCTGTGT GGGCTGAGCG CTGTGTCTCT CCTGGCATGC TACCTCAAGT CAAGGCAAAC TCCCCCGCTG GCCAGCGTTG
AAATGGAAGC CATGGAGGCT CTGCCGGTGA CTTGGGGGAC CAGCAGCAGA GATGAAGACT TGGAAAACTG CTCTCACCAC
CTATGA

Fig. 2A

MAPRRARGCRTLGLPALLLLLLLRPPATRGITCPPPMSVEHADIWVKSYSLYSRERYICNSGFKRKAGTSSLTECVLNKATNVAHWTTPSL
KCIRDPALVHQRPAPPSTVTTAGVTPQPESLSPSGKEPAASSPSSNNTAATTAAIVPGSQLMPSKSPSTGTTEISSHESSHGTPSQTTAKNWEL
TASASHQPPGVYPQGHSDTTVAISTSTVLLCGLSAVSLLACYLKSRQTPPLASVEMEAMEALPVTWGTSSRDEDLENCSHHL

Fig. 2B truncated soluble human IL-15Ra in cell clone 2.66 (Fig. 3A-B)

ATGGCCCC GCGGCGGGCG CGCGGCTGCC GGACCCTCGG TCTCCCGGCG CTGCTACTGC TGCTGCTGCT CCGGCCGCCG
GCGACGCGGG GCATCACGTG CCCTCCCCCC ATGTCCGTGG AACACGCAGA CATCTGGGTC AAGAGCTACA GCTTGTACTC
CAGGGAGCGG TACATTTGTA ACTCTGGTTT CAAGCGTAAA GCCGGCACGT CCAGCCTGAC GGAGTGCGTG TTGAACAAGG
CCACGAATGT CGCCCACTGG ACAACCCCCA GTCTCAAATG CATTAGAGAC CCTGCCCTGG TTCACCAAAG GCCAGCGCCA
CCCTCCACAG TAACGACGGC AGGGGTGACC CCACAGCCAG AGAGCCTCTC CCCTTCTGGA AAAGAGCCCG CAGCTTCATC
TCCCAGCTCA AACAACACAG CGGCCACAAC AGCAGCTATT GTCCCGGGCT CCCAGCTGAT GCCTTCAAAA TCACCTTCCA
CAGGAACCAC AGAGATAAGC AGTCATGAGT CCTCCCACGG CACCCCCTCT CAGACAACAG CCAAGAACTG GGAACTCACA
GCATCCGCCT CCCACCAGCC GCCAGGTGTG TATCCACAGG GCCACAGCGA CACCACT

Fig. 3A

MAPRRARGCRTLGLPALLLLLLLRPPATRG*ITCPPPMSVEHADIWVKSYSLYSRERYICNSGFKRKAGTSSLTECVLNKATNVAHWTTPSL*
*KCIRDPALVHQRPAPPSTVTTAGVTPQPESLSPSGKEPAASSPSSNNTAATTAAIVPGSQLMPSKSPSTGTTEISSHESSHGTPSQTTAKNWEL*
*TASASHQPPGVYPQGHSDTT*

Fig. 3B native soluble human IL-15Ra (Fig. 3C-D)

ATGGCCCC GCGGCGGGCG CGCGGCTGCC GGACCCTCGG TCTCCCGGCG CTGCTACTGC TGCTGCTGCT CCGGCCGCCG
GCGACGCGGG *GCATCACGTG CCCTCCCCCC ATGTCCGTGG AACACGCAGA CATCTGGGTC AAGAGCTACA GCTTGTACTC*
*CAGGGAGCGG TACATTTGTA ACTCTGGTTT CAAGCGTAAA GCCGGCACGT CCAGCCTGAC GGAGTGCGTG TTGAACAAGG*
*CCACGAATGT CGCCCACTGG ACAACCCCCA GTCTCAAATG CATTAGAGAC CCTGCCCTGG TTCACCAAAG GCCAGCGCCA*
*CCCTCCACAG TAACGACGGC AGGGGTGACC CCACAGCCAG AGAGCCTCTC CCCTTCTGGA AAAGAGCCCG CAGCTTCATC*
*TCCCAGCTCA AACAACACAG CGGCCACAAC AGCAGCTATT GTCCCGGGCT CCCAGCTGAT GCCTTCAAAA TCACCTTCCA*
*CAGGAACCAC AGAGATAAGC AGTCATGAGT CCTCCCACGG CACCCCCTCT CAGACAACAG CCAAGAACTG GGAACTCACA*
*GCATCCGCCT CCCACCAGCC GCCAGGTGTG TATCCACAGG GC*

Fig. 3C

MAPRRARGCRTLGLPALLLLLLLRPPATRG*ITCPPPMSVEHADIWVKSYSLYSRERYICNSGFKRKAGTSSLTECVLNKATNVAHWTTPSL*
*KCIRDPALVHQRPAPPSTVTTAGVTPQPESLSPSGKEPAASSPSSNNTAATTAAIVPGSQLMPSKSPSTGTTEISSHESSHGTPSQTTAKNWEL*
*TASASHQPPGVYPQG*

Fig. 3D

Group 1: 50 ug/kg IL-15/sIL-15Ra N = 2
Group 2: 20 ug/kg IL-15/sIL-15Ra N = 2
Group 3: 1 ug/kg IL-15/sIL-15Ra N = 2

SEQUENCE LISTING

<160> NUMBER OF SEQ ID NOS: 46

<210> SEQ ID NO 1
<211> LENGTH: 162
<212> TYPE: PRT
<213> ORGANISM: Homo sapiens
<220> FEATURE:
<221> NAME/KEY: SIGNAL
<222> LOCATION: (1)...(48)
<220> FEATURE:
<223> OTHER INFORMATION: immature/precursor form of native human IL-15

<400> SEQUENCE: 1

Met Arg Ile Ser Lys Pro His Leu Arg Ser Ile Ser Ile Gln Cys Tyr
1 5 10 15

Leu Cys Leu Leu Leu Asn Ser His Phe Leu Thr Glu Ala Gly Ile His
20 25 30

Val Phe Ile Leu Gly Cys Phe Ser Ala Gly Leu Pro Lys Thr Glu Ala
35 40 45

Asn Trp Val Asn Val Ile Ser Asp Leu Lys Lys Ile Glu Asp Leu Ile
50 55 60

Gln Ser Met His Ile Asp Ala Thr Leu Tyr Thr Glu Ser Asp Val His
65 70 75 80

Pro Ser Cys Lys Val Thr Ala Met Lys Cys Phe Leu Leu Glu Leu Gln
85 90 95

Val Ile Ser Leu Glu Ser Gly Asp Ala Ser Ile His Asp Thr Val Glu
100 105 110

Asn Leu Ile Ile Leu Ala Asn Asn Ser Leu Ser Ser Asn Gly Asn Val
115 120 125

Thr Glu Ser Gly Cys Lys Glu Cys Glu Glu Leu Glu Glu Lys Asn Ile
130 135 140

Lys Glu Phe Leu Gln Ser Phe Val His Ile Val Gln Met Phe Ile Asn
145 150 155 160

Thr Ser

<210> SEQ ID NO 2
<211> LENGTH: 489
<212> TYPE: DNA
<213> ORGANISM: Homo sapiens
<220> FEATURE:
<221> NAME/KEY: sig_peptide
<222> LOCATION: (1)...(145)
<220> FEATURE:
<223> OTHER INFORMATION: coding sequence of immature/precursor form of native human IL-15

<400> SEQUENCE: 2

```
atgagaattt cgaaaccaca tttgagaagt atttccatcc agtgctactt gtgtttactt      60

ctaaacagtc attttctaac tgaagctggc attcatgtct tcattttggg ctgtttcagt     120

gcagggcttc ctaaaacaga agccaactgg gtgaatgtaa taagtgattt gaaaaaaatt     180

gaagatctta ttcaatctat gcatattgat gctactttat atacggaaag tgatgttcac     240

cccagttgca aagtaacagc aatgaagtgc tttctcttgg agttacaagt tatttcactt     300

gagtccggag atgcaagtat tcatgataca gtagaaaatc tgatcatcct agcaaacaac     360

agtttgtctt ctaatgggaa tgtaacagaa tctggatgca aagaatgtga ggaactggag     420

gaaaaaaata ttaaagaatt tttgcagagt tttgtacata ttgtccaaat gttcatcaac     480

acttcttga                                                             489
```

<210> SEQ ID NO 3
<211> LENGTH: 267
<212> TYPE: PRT
<213> ORGANISM: Homo sapiens
<220> FEATURE:
<221> NAME/KEY: SIGNAL
<222> LOCATION: (1)...(30)
<220> FEATURE:
<223> OTHER INFORMATION: immature form of the native full length human IL-15 receptor alpha

<400> SEQUENCE: 3

```
Met Ala Pro Arg Arg Ala Arg Gly Cys Arg Thr Leu Gly Leu Pro Ala
 1               5                  10                  15

Leu Leu Leu Leu Leu Leu Leu Arg Pro Pro Ala Thr Arg Gly Ile Thr
            20                  25                  30

Cys Pro Pro Pro Met Ser Val Glu His Ala Asp Ile Trp Val Lys Ser
        35                  40                  45

Tyr Ser Leu Tyr Ser Arg Glu Arg Tyr Ile Cys Asn Ser Gly Phe Lys
    50                  55                  60

Arg Lys Ala Gly Thr Ser Ser Leu Thr Glu Cys Val Leu Asn Lys Ala
65                  70                  75                  80

Thr Asn Val Ala His Trp Thr Thr Pro Ser Leu Lys Cys Ile Arg Asp
                85                  90                  95

Pro Ala Leu Val His Gln Arg Pro Ala Pro Pro Ser Thr Val Thr Thr
            100                 105                 110

Ala Gly Val Thr Pro Gln Pro Glu Ser Leu Ser Pro Ser Gly Lys Glu
        115                 120                 125

Pro Ala Ala Ser Ser Pro Ser Ser Asn Asn Thr Ala Ala Thr Thr Ala
    130                 135                 140

Ala Ile Val Pro Gly Ser Gln Leu Met Pro Ser Lys Ser Pro Ser Thr
145                 150                 155                 160

Gly Thr Thr Glu Ile Ser Ser His Glu Ser Ser His Gly Thr Pro Ser
                165                 170                 175

Gln Thr Thr Ala Lys Asn Trp Glu Leu Thr Ala Ser Ala Ser His Gln
            180                 185                 190

Pro Pro Gly Val Tyr Pro Gln Gly His Ser Asp Thr Thr Val Ala Ile
        195                 200                 205
```

```
Ser Thr Ser Thr Val Leu Leu Cys Gly Leu Ser Ala Val Ser Leu Leu
    210                 215                 220

Ala Cys Tyr Leu Lys Ser Arg Gln Thr Pro Pro Leu Ala Ser Val Glu
225                 230                 235                 240

Met Glu Ala Met Glu Ala Leu Pro Val Thr Trp Gly Thr Ser Ser Arg
                245                 250                 255

Asp Glu Asp Leu Glu Asn Cys Ser His His Leu
            260                 265


<210> SEQ ID NO 4
<211> LENGTH: 205
<212> TYPE: PRT
<213> ORGANISM: Homo sapines
<220> FEATURE:
<221> NAME/KEY: SIGNAL
<222> LOCATION: (1)...(30)
<220> FEATURE:
<223> OTHER INFORMATION: immature form of the native soluble human IL-15
      receptor alpha

<400> SEQUENCE: 4

Met Ala Pro Arg Arg Ala Arg Gly Cys Arg Thr Leu Gly Leu Pro Ala
 1               5                  10                  15

Leu Leu Leu Leu Leu Leu Leu Arg Pro Pro Ala Thr Arg Gly Ile Thr
            20                  25                  30

Cys Pro Pro Pro Met Ser Val Glu His Ala Asp Ile Trp Val Lys Ser
        35                  40                  45

Tyr Ser Leu Tyr Ser Arg Glu Arg Tyr Ile Cys Asn Ser Gly Phe Lys
    50                  55                  60

Arg Lys Ala Gly Thr Ser Ser Leu Thr Glu Cys Val Leu Asn Lys Ala
65                  70                  75                  80

Thr Asn Val Ala His Trp Thr Thr Pro Ser Leu Lys Cys Ile Arg Asp
                85                  90                  95

Pro Ala Leu Val His Gln Arg Pro Ala Pro Pro Ser Thr Val Thr Thr
            100                 105                 110

Ala Gly Val Thr Pro Gln Pro Glu Ser Leu Ser Pro Ser Gly Lys Glu
        115                 120                 125

Pro Ala Ala Ser Ser Pro Ser Ser Asn Asn Thr Ala Ala Thr Thr Ala
    130                 135                 140

Ala Ile Val Pro Gly Ser Gln Leu Met Pro Ser Lys Ser Pro Ser Thr
145                 150                 155                 160

Gly Thr Thr Glu Ile Ser Ser His Glu Ser Ser His Gly Thr Pro Ser
                165                 170                 175

Gln Thr Thr Ala Lys Asn Trp Glu Leu Thr Ala Ser Ala Ser His Gln
            180                 185                 190

Pro Pro Gly Val Tyr Pro Gln Gly His Ser Asp Thr Thr
        195                 200                 205


<210> SEQ ID NO 5
<211> LENGTH: 804
<212> TYPE: DNA
<213> ORGANISM: Homo sapiens
<220> FEATURE:
<221> NAME/KEY: sig_peptide
<222> LOCATION: (1)...(90)
<220> FEATURE:
<223> OTHER INFORMATION: coding sequence of immature form of the native
      full length human IL-15 receptor alpha

<400> SEQUENCE: 5
```

```
atggccccgc ggcgggcgcg cggctgccgg accctcggtc tcccggcgct gctactgctg    60

ctgctgctcc ggccgccggc gacgcggggc atcacgtgcc ctccccccat gtccgtggaa   120

cacgcagaca tctgggtcaa gagctacagc ttgtactcca gggagcggta catttgtaac   180

tctggtttca agcgtaaagc cggcacgtcc agcctgacgg agtgcgtgtt gaacaaggcc   240

acgaatgtcg cccactggac aacccccagt ctcaaatgca ttagagaccc tgccctggtt   300

caccaaaggc cagcgccacc ctccacagta acgacggcag gggtgacccc acagccagag   360

agcctctccc cttctggaaa agagcccgca gcttcatctc ccagctcaaa caacacagcg   420

gccacaacag cagctattgt cccgggctcc cagctgatgc cttcaaaatc accttccaca   480

ggaaccacag agataagcag tcatgagtcc tcccacggca ccccctctca gacaacagcc   540

aagaactggg aactcacagc atccgcctcc caccagccgc aggtgtgta tccacagggc   600

cacagcgaca ccactgtggc tatctccacg tccactgtcc tgctgtgtgg gctgagcgct   660

gtgtctctcc tggcatgcta cctcaagtca aggcaaactc cccgctggc cagcgttgaa    720

atggaagcca tggaggctct gccggtgact tggggacca gcagcagaga tgaagacttg   780

gaaaactgct ctcaccacct atga                                           804
```

<210> SEQ ID NO 6
<211> LENGTH: 615
<212> TYPE: DNA
<213> ORGANISM: Homo sapiens
<220> FEATURE:
<221> NAME/KEY: sig_peptide
<222> LOCATION: (1)...(90)
<220> FEATURE:
<223> OTHER INFORMATION: coding sequence of immature form of the native soluble human IL-15 receptor alpha

<400> SEQUENCE: 6

```
atggccccgc ggcgggcgcg cggctgccgg accctcggtc tcccggcgct gctactgctg    60

ctgctgctcc ggccgccggc gacgcggggc atcacgtgcc ctccccccat gtccgtggaa   120

cacgcagaca tctgggtcaa gagctacagc ttgtactcca gggagcggta catttgtaac   180

tctggtttca agcgtaaagc cggcacgtcc agcctgacgg agtgcgtgtt gaacaaggcc   240

acgaatgtcg cccactggac aacccccagt ctcaaatgca ttagagaccc tgccctggtt   300

caccaaaggc cagcgccacc ctccacagta acgacggcag gggtgacccc acagccagag   360

agcctctccc cttctggaaa agagcccgca gcttcatctc ccagctcaaa caacacagcg   420

gccacaacag cagctattgt cccgggctcc cagctgatgc cttcaaaatc accttccaca   480

ggaaccacag agataagcag tcatgagtcc tcccacggca ccccctctca gacaacagcc   540

aagaactggg aactcacagc atccgcctcc caccagccgc aggtgtgta tccacagggc   600

cacagcgaca ccact                                                     615
```

<210> SEQ ID NO 7
<211> LENGTH: 4
<212> TYPE: PRT
<213> ORGANISM: Artificial Sequence
<220> FEATURE:
<223> OTHER INFORMATION: heterologous protease cleavage sites recognized by furin protease
<220> FEATURE:
<221> NAME/KEY: VARIANT
<222> LOCATION: 2,3
<223> OTHER INFORMATION: Xaa = any amino acid

<400> SEQUENCE: 7

```
Arg Xaa Xaa Arg
1


<210> SEQ ID NO 8
<211> LENGTH: 6
<212> TYPE: PRT
<213> ORGANISM: Artificial Sequence
<220> FEATURE:
<223> OTHER INFORMATION: heterologous protease cleavage sites recognized
      by thrombin protease
<220> FEATURE:
<221> NAME/KEY: VARIANT
<222> LOCATION: 1,2
<223> OTHER INFORMATION: Xaa = hydrophobic amino acids
<220> FEATURE:
<221> NAME/KEY: VARIANT
<222> LOCATION: 5,6
<223> OTHER INFORMATION: Xaa = nonacidic amino acids

<400> SEQUENCE: 8

Xaa Xaa Pro Arg Xaa Xaa
 1               5


<210> SEQ ID NO 9
<211> LENGTH: 1847
<212> TYPE: DNA
<213> ORGANISM: Artificial Sequence
<220> FEATURE:
<223> OTHER INFORMATION: huIL15opt - nucleic acid construct encoding
      optimized human IL-15

<400> SEQUENCE: 9

cctggccatt gcatacgttg tatccatatc ataatatgta catttatatt ggctcatgtc     60

caacattacc gccatgttga cattgattat tgactagtta ttaatagtaa tcaattacgg    120

ggtcattagt tcatagccca tatatggagt tccgcgttac ataacttacg gtaaatggcc    180

cgcctggctg accgcccaac gacccccgcc cattgacgtc aataatgacg tatgttccca    240

tagtaacgcc aatagggact ttccattgac gtcaatgggt ggagtattta cggtaaactg    300

cccacttggc agtacatcaa gtgtatcata tgccaagtac gccccctatt gacgtcaatg    360

atggtaaatg gcccgcctgg cattatgccc agtacatgac cttatgggac tttcctactt    420

ggcagtacat ctacgtatta gtcatcgcta ttaccatggt gatgcggttt tggcagtaca    480

tcaatgggcg tggatagcgg tttgactcac ggggatttcc aagtctccac cccattgacg    540

tcaatgggag tttgttttgg caccaaaatc aacgggactt tccaaaatgt cgtaacaact    600

ccgccccatt gacgcaaatg ggcggtaggc gtgtacggtg ggaggtctat ataagcagag    660

ctcgtttagt gaaccgtcag atcgcctgga gacgccatcc acgctgtttt gacctccata    720

gaagacaccg ggaccgatcc agcctccgcg ggcgcgcgtc gacaagaaat gcggatctcg    780

aagccgcacc tgcggtcgat atcgatccag tgctacctgt gcctgctcct gaactcgcac    840

ttcctcacgg aggccggtat acacgtcttc atcctgggct gcttctcggc ggggctgccg    900

aagacggagg cgaactgggt gaacgtgatc tcggacctga agaagatcga ggacctcatc    960

cagtcgatgc acatcgacgc gacgctgtac acggagtcgg acgtccaccc gtcgtgcaag   1020

gtcacggcga tgaagtgctt cctcctggag ctccaagtca tctcgctcga gtcgggggac   1080

gcgtcgatcc acgacacggt ggagaacctg atcatcctgg cgaacaactc gctgtcgtcg   1140

aacgggaacg tcacggagtc gggctgcaag gagtgcgagg agctggagga gaagaacatc   1200

aaggagttcc tgcagtcgtt cgtgcacatc gtccagatgt tcatcaacac gtcgtgaggg   1260
```

```
cccggcgcgc cgaattcgcg gatatcggtt aacggatcca gatctgctgt gccttctagt   1320

tgccagccat ctgttgtttg cccctccccc gtgccttcct tgaccctgga aggtgccact   1380

cccactgtcc tttcctaata aaatgaggaa attgcatcgc attgtctgag taggtgtcat   1440

tctattctgg ggggtggggt ggggcaggac agcaaggggg aggattggga agacaatagc   1500

aggcatgctg gggatgcggt gggctctatg ggtacccagg tgctgaagaa ttgacccggt   1560

tcctcctggg ccagaaagaa gcaggcacat ccccttctct gtgacacacc ctgtccacgc   1620

ccctggttct tagttccagc cccactcata ggacactcat agctcaggag ggctccgcct   1680

tcaatcccac ccgctaaagt acttggagcg gtctctccct ccctcatcag cccaccaaac   1740

caaacctagc ctccaagagt gggaagaaat taaagcaaga taggctatta agtgcagagg   1800

gagagaaaat gcctccaaca tgtgaggaag taatgagaga aatcata                 1847


<210> SEQ ID NO 10
<211> LENGTH: 162
<212> TYPE: PRT
<213> ORGANISM: Artificial Sequence
<220> FEATURE:
<223> OTHER INFORMATION: huIL15opt - amino acid sequence of optimized
      human IL-15

<400> SEQUENCE: 10

Met Arg Ile Ser Lys Pro His Leu Arg Ser Ile Ser Ile Gln Cys Tyr
 1               5                  10                  15

Leu Cys Leu Leu Leu Asn Ser His Phe Leu Thr Glu Ala Gly Ile His
            20                  25                  30

Val Phe Ile Leu Gly Cys Phe Ser Ala Gly Leu Pro Lys Thr Glu Ala
        35                  40                  45

Asn Trp Val Asn Val Ile Ser Asp Leu Lys Lys Ile Glu Asp Leu Ile
    50                  55                  60

Gln Ser Met His Ile Asp Ala Thr Leu Tyr Thr Glu Ser Asp Val His
65                  70                  75                  80

Pro Ser Cys Lys Val Thr Ala Met Lys Cys Phe Leu Leu Glu Leu Gln
                85                  90                  95

Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
        115                 120                 125

Thr Glu Ser Gly Cys Lys Glu Cys Glu Glu Leu Glu Glu Lys Asn Ile
    130                 135                 140

Lys Glu Phe Leu Gln Ser Phe Val His Ile Val Gln Met Phe Ile Asn
145                 150                 155                 160

Thr Ser


<210> SEQ ID NO 11
<211> LENGTH: 1808
<212> TYPE: DNA
<213> ORGANISM: Artificial Sequence
<220> FEATURE:
<223> OTHER INFORMATION: CMV huIL15tPA6 - nucleic acid construct
      encoding optimized human IL-15

<400> SEQUENCE: 11

cctggccatt gcatacgttg tatccatatc ataatatgta catttatatt ggctcatgtc     60

caacattacc gccatgttga cattgattat tgactagtta ttaatagtaa tcaattacgg    120

ggtcattagt tcatagccca tatatggagt tccgcgttac ataacttacg gtaaatggcc    180
```

```
cgcctggctg accgcccaac gacccccgcc cattgacgtc aataatgacg tatgttccca    240
tagtaacgcc aatagggact ttccattgac gtcaatgggt ggagtattta cggtaaactg    300
cccacttggc agtacatcaa gtgtatcata tgccaagtac gccccctatt gacgtcaatg    360
atggtaaatg gcccgcctgg cattatgccc agtacatgac cttatgggac tttcctactt    420
ggcagtacat ctacgtatta gtcatcgcta ttaccatggt gatgcggttt tggcagtaca    480
tcaatgggcg tggatagcgg tttgactcac ggggatttcc aagtctccac cccattgacg    540
tcaatgggag tttgttttgg caccaaaatc aacgggactt tccaaaatgt cgtaacaact    600
ccgccccatt gacgcaaatg ggcggtaggc gtgtacggtg ggaggtctat ataagcagag    660
ctcgtttagt gaaccgtcag atcgcctgga gacgccatcc acgctgtttt gacctccata    720
gaagacaccg ggaccgatcc agcctccgcg ggcgcgcgtc gacaagaaat ggatgcaatg    780
aagagagggc tctgctgtgt gctgctgctg tgtggagcag tcttcgtttc gcccagccag    840
gaaatccatg cccgattcag aagaggagcc agaaactggg tgaacgtgat ctcggacctg    900
aagaagatcg aggacctcat ccagtcgatg cacatcgacg cgacgctgta cacggagtcg    960
gacgtccacc cgtcgtgcaa ggtcacggcg atgaagtgct tcctcctgga gctccaagtc   1020
atctcgctcg agtcggggga cgcgtcgatc cacgacacgg tggagaacct gatcatcctg   1080
gcgaacaact cgctgtcgtc gaacgggaac gtcacggagt cgggctgcaa ggagtgcgag   1140
gagctggagg agaagaacat caaggagttc ctgcagtcgt tcgtgcacat cgtccagatg   1200
ttcatcaaca cgtcgtgagg gcccggcgcg ccgaattcgc ggatatcggt taacggatcc   1260
agatctgctg tgccttctag ttgccagcca tctgttgttt gcccctcccc cgtgccttcc   1320
ttgaccctgg aaggtgccac tcccactgtc ctttcctaat aaaatgagga aattgcatcg   1380
cattgtctga gtaggtgtca ttctattctg gggggtgggg tggggcagga cagcaagggg   1440
gaggattggg aagacaatag caggcatgct ggggatgcgg tgggctctat gggtacccag   1500
gtgctgaaga attgacccgg ttcctcctgg gccagaaaga agcaggcaca tccccttctc   1560
tgtgacacac cctgtccacg cccctggttc ttagttccag ccccactcat aggacactca   1620
tagctcagga gggctccgcc ttcaatccca cccgctaaag tacttggagc ggtctctccc   1680
tccctcatca gcccaccaaa ccaaacctag cctccaagag tgggaagaaa ttaaagcaag   1740
ataggctatt aagtgcagag ggagagaaaa tgcctccaac atgtgaggaa gtaatgagag   1800
aaatcata                                                            1808
```

```
<210> SEQ ID NO 12
<211> LENGTH: 149
<212> TYPE: PRT
<213> ORGANISM: Artificial Sequence
<220> FEATURE:
<223> OTHER INFORMATION: CMV huIL15tPA6 - amino acid sequence of
      optimized human IL-15

<400> SEQUENCE: 12

Met Asp Ala Met Lys Arg Gly Leu Cys Cys Val Leu Leu Leu Cys Gly
 1               5                  10                  15

Ala Val Phe Val Ser Pro Ser Gln Glu Ile His Ala Arg Phe Arg Arg
            20                  25                  30

Gly Ala Arg Asn Trp Val Asn Val Ile Ser Asp Leu Lys Lys Ile Glu
        35                  40                  45

Asp Leu Ile Gln Ser Met His Ile Asp Ala Thr Leu Tyr Thr Glu Ser
    50                  55                  60
```

```
Asp Val His Pro Ser Cys Lys Val Thr Ala Met Lys Cys Phe Leu Leu
65                  70                  75                  80

Glu Leu Gln Val Ile Ser Leu Glu Ser Gly Asp Ala Ser Ile His Asp
                85                  90                  95

Thr Val Glu Asn Leu Ile Ile Leu Ala Asn Asn Ser Leu Ser Ser Asn
            100                 105                 110

Gly Asn Val Thr Glu Ser Gly Cys Lys Glu Cys Glu Glu Leu Glu Glu
        115                 120                 125

Lys Asn Ile Lys Glu Phe Leu Gln Ser Phe Val His Ile Val Gln Met
    130                 135                 140

Phe Ile Asn Thr Ser
145
```

<210> SEQ ID NO 13
<211> LENGTH: 2140
<212> TYPE: DNA
<213> ORGANISM: Artificial Sequence
<220> FEATURE:
<223> OTHER INFORMATION: huIL15Ra - nucleic acid construct encoding
      optimized human IL-15Ra

<400> SEQUENCE: 13

```
cctggccatt gcatacgttg tatccatatc ataatatgta catttatatt ggctcatgtc     60

caacattacc gccatgttga cattgattat tgactagtta ttaatagtaa tcaattacgg    120

ggtcattagt tcatagccca tatatggagt tccgcgttac ataacttacg gtaaatggcc    180

cgcctggctg accgcccaac gacccccgcc cattgacgtc aataatgacg tatgttccca    240

tagtaacgcc aatagggact ttccattgac gtcaatgggt ggagtattta cggtaaactg    300

cccacttggc agtacatcaa gtgtatcata tgccaagtac gccccctatt gacgtcaatg    360

atggtaaatg gcccgcctgg cattatgccc agtacatgac cttatgggac tttcctactt    420

ggcagtacat ctacgtatta gtcatcgcta ttaccatggt gatgcggttt tggcagtaca    480

tcaatgggcg tggatagcgg tttgactcac ggggatttcc aagtctccac cccattgacg    540

tcaatgggag tttgttttgg caccaaaatc aacgggactt tccaaaatgt cgtaacaact    600

ccgccccatt gacgcaaatg ggcggtaggc gtgtacggtg ggaggtctat ataagcagag    660

ctcgtttagt gaaccgtcag atcgcctgga gacgccatcc acgctgtttt gacctccata    720

gaagacaccg ggaccgatcc agcctccgcg ggcgcgcgtc gacgctagca agaaatggcc    780

ccgaggcggg cgcgaggctg ccggaccctc ggtctcccgg cgctgctact gctcctgctg    840

ctccggccgc cggcgacgcg gggcatcacg tgcccgcccc ccatgtccgt ggagcacgca    900

gacatctggg tcaagagcta cagcttgtac tcccgggagc ggtacatctg caactcgggt    960

ttcaagcgga aggccggcac gtccagcctg acggagtgcg tgttgaacaa ggccacgaat   1020

gtcgcccact ggacgacccc ctcgctcaag tgcatccgcg acccggccct ggttcaccag   1080

cggcccgcgc caccctccac cgtaacgacg gcgggggtga ccccgcagcc ggagagcctc   1140

tccccgtcgg gaaaggagcc cgccgcgtcg tcgcccagct cgaacaacac ggcggccaca   1200

actgcagcga tcgtcccggg ctcccagctg atgccgtcga agtcgccgtc cacgggaacc   1260

acggagatca gcagtcatga gtcctcccac ggcaccccct cgcaaacgac ggccaagaac   1320

tgggaactca cggcgtccgc ctcccaccag ccgccggggg tgtatccgca aggccacagc   1380

gacaccacgg tggcgatctc cacgtccacg gtcctgctgt gtgggctgag cgcggtgtcg   1440

ctcctggcgt gctacctcaa gtcgaggcag actcccccgc tggccagcgt tgagatggag   1500
```

```
gccatggagg ctctgccggt gacgtggggg accagcagca gggatgagga cttggagaac   1560

tgctcgcacc acctataatg agaattcgat ccagatctgc tgtgccttct agttgccagc   1620

catctgttgt ttgcccctcc cccgtgcctt ccttgaccct ggaaggtgcc actcccactg   1680

tcctttccta ataaaatgag gaaattgcat cgcattgtct gagtaggtgt cattctattc   1740

tggggggtgg ggtggggcag gacagcaagg gggaggattg ggaagacaat agcaggcatg   1800

ctggggatgc ggtgggctct atgggtaccc aggtgctgaa gaattgaccc ggttcctcct   1860

gggccagaaa gaagcaggca catccccttc tctgtgacac accctgtcca cgcccctggt   1920

tcttagttcc agccccactc ataggacact catagctcag gagggctccg ccttcaatcc   1980

cacccgctaa agtacttgga gcggtctctc cctccctcat cagcccacca aaccaaacct   2040

agcctccaag agtgggaaga aattaaagca agataggcta ttaagtgcag agggagagaa   2100

aatgcctcca acatgtgagg aagtaatgag agaaatcata                         2140
```

```
<210> SEQ ID NO 14
<211> LENGTH: 267
<212> TYPE: PRT
<213> ORGANISM: Artificial Sequence
<220> FEATURE:
<223> OTHER INFORMATION: huIL15Ra - amino acid sequence of optimized
      human IL-15Ra

<400> SEQUENCE: 14

Met Ala Pro Arg Arg Ala Arg Gly Cys Arg Thr Leu Gly Leu Pro Ala
1               5                   10                  15

Leu Leu Leu Leu Leu Leu Leu Arg Pro Pro Ala Thr Arg Gly Ile Thr
            20                  25                  30

Cys Pro Pro Pro Met Ser Val Glu His Ala Asp Ile Trp Val Lys Ser
        35                  40                  45

Tyr Ser Leu Tyr Ser Arg Glu Arg Tyr Ile Cys Asn Ser Gly Phe Lys
    50                  55                  60

Arg Lys Ala Gly Thr Ser Ser Leu Thr Glu Cys Val Leu Asn Lys Ala
65                  70                  75                  80

Thr Asn Val Ala His Trp Thr Thr Pro Ser Leu Lys Cys Ile Arg Asp
                85                  90                  95

Pro Ala Leu Val His Gln Arg Pro Ala Pro Pro Ser Thr Val Thr Thr
            100                 105                 110

Ala Gly Val Thr Pro Gln Pro Glu Ser Leu Ser Pro Ser Gly Lys Glu
        115                 120                 125

Pro Ala Ala Ser Ser Pro Ser Ser Asn Asn Thr Ala Ala Thr Thr Ala
    130                 135                 140

Ala Ile Val Pro Gly Ser Gln Leu Met Pro Ser Lys Ser Pro Ser Thr
145                 150                 155                 160

Gly Thr Thr Glu Ile Ser Ser His Glu Ser Ser His Gly Thr Pro Ser
                165                 170                 175

Gln Thr Thr Ala Lys Asn Trp Glu Leu Thr Ala Ser Ala Ser His Gln
            180                 185                 190

Pro Pro Gly Val Tyr Pro Gln Gly His Ser Asp Thr Thr Val Ala Ile
        195                 200                 205

Ser Thr Ser Thr Val Leu Leu Cys Gly Leu Ser Ala Val Ser Leu Leu
    210                 215                 220

Ala Cys Tyr Leu Lys Ser Arg Gln Thr Pro Pro Leu Ala Ser Val Glu
225                 230                 235                 240
```

-continued

Met Glu Ala Met Glu Ala Leu Pro Val Thr Trp Gly Thr Ser Ser Arg
245 250 255

Asp Glu Asp Leu Glu Asn Cys Ser His His Leu
260 265

<210> SEQ ID NO 15
<211> LENGTH: 1971
<212> TYPE: DNA
<213> ORGANISM: Artificial Sequence
<220> FEATURE:
<223> OTHER INFORMATION: CMV hu sIL15Ra - nucleic acid construct encoding optimized human IL-15Ra

<400> SEQUENCE: 15
cctggccatt gcatacgttg tatccatatc ataatatgta catttatatt ggctcatgtc 60
caacattacc gccatgttga cattgattat tgactagtta ttaatagtaa tcaattacgg 120
ggtcattagt tcatagccca tatatggagt tccgcgttac ataacttacg gtaaatggcc 180
cgcctggctg accgcccaac gacccccgcc cattgacgtc aataatgacg tatgttccca 240
tagtaacgcc aatagggact ttccattgac gtcaatgggt ggagtattta cggtaaactg 300
cccacttggc agtacatcaa gtgtatcata tgccaagtac gccccctatt gacgtcaatg 360
atggtaaatg gcccgcctgg cattatgccc agtacatgac cttatgggac tttcctactt 420
ggcagtacat ctacgtatta gtcatcgcta ttaccatggt gatgcggttt tggcagtaca 480
tcaatgggcg tggatagcgg tttgactcac ggggatttcc aagtctccac cccattgacg 540
tcaatgggag tttgttttgg caccaaaatc aacgggactt tccaaaatgt cgtaacaact 600
ccgccccatt gacgcaaatg ggcggtaggc gtgtacggtg ggaggtctat ataagcagag 660
ctcgtttagt gaaccgtcag atcgcctgga gacgccatcc acgctgtttt gacctccata 720
gaagacaccg ggaccgatcc agcctccgcg ggcgcgcgtc gacgctagca agaaatggcc 780
ccgaggcggg cgcgaggctg ccggaccctc ggtctcccgg cgctgctact gctcctgctg 840
ctccggccgc cggcgacgcg gggcatcacg tgcccgcccc ccatgtccgt ggagcacgca 900
gacatctggg tcaagagcta cagcttgtac tcccgggagc ggtacatctg caactcgggt 960
ttcaagcgga aggccggcac gtccagcctg acggagtgcg tgttgaacaa ggccacgaat 1020
gtcgcccact ggacgacccc ctcgctcaag tgcatccgcg acccggccct ggttcaccag 1080
cggcccgcgc caccctccac cgtaacgacg gcgggggtga ccccgcagcc ggagagcctc 1140
tccccgtcgg gaaaggagcc cgccgcgtcg tcgcccagct cgaacaacac ggcggccaca 1200
actgcagcga tcgtcccggg ctcccagctg atgccgtcga agtcgccgtc cacgggaacc 1260
acggagatca gcagtcatga gtcctcccac ggcaccccct cgcaaacgac ggccaagaac 1320
tgggaactca cggcgtccgc ctcccaccag ccgccggggg tgtatccgca aggccacagc 1380
gacaccacgt aatgagaatt cgcggatatc ggttaacgga tccagatctg ctgtgccttc 1440
tagttgccag ccatctgttg tttgcccctc ccccgtgcct tccttgaccc tggaaggtgc 1500
cactcccact gtcctttcct aataaaatga ggaaattgca tcgcattgtc tgagtaggtg 1560
tcattctatt ctggggggtg gggtggggca ggacagcaag ggggaggatt gggaagacaa 1620
tagcaggcat gctggggatg cggtgggctc tatgggtacc caggtgctga agaattgacc 1680
cggttcctcc tgggccagaa agaagcaggc acatcccctt ctctgtgaca caccctgtcc 1740
acgcccctgg ttcttagttc cagccccact cataggacac tcatagctca ggagggctcc 1800
gccttcaatc ccacccgcta aagtacttgg agcggtctct ccctccctca tcagcccacc 1860
aaaccaaacc tagcctccaa gagtgggaag aaattaaagc aagataggct attaagtgca 1920
gagggagaga aaatgcctcc aacatgtgag gaagtaatga gagaaatcat a 1971

<210> SEQ ID NO 16
<211> LENGTH: 205
<212> TYPE: PRT
<213> ORGANISM: Artificial Sequence
<220> FEATURE:
<223> OTHER INFORMATION: CMV hu sIL15Ra - amino acid sequence of optimized human IL-15Ra

<400> SEQUENCE: 16

Met Ala Pro Arg Arg Ala Arg Gly Cys Arg Thr Leu Gly Leu Pro Ala
1               5                   10                  15

Leu Leu Leu Leu Leu Leu Leu Arg Pro Pro Ala Thr Arg Gly Ile Thr
            20                  25                  30

Cys Pro Pro Pro Met Ser Val Glu His Ala Asp Ile Trp Val Lys Ser
        35                  40                  45

Tyr Ser Leu Tyr Ser Arg Glu Arg Tyr Ile Cys Asn Ser Gly Phe Lys
    50                  55                  60

Arg Lys Ala Gly Thr Ser Ser Leu Thr Glu Cys Val Leu Asn Lys Ala
65                  70                  75                  80

Thr Asn Val Ala His Trp Thr Thr Pro Ser Leu Lys Cys Ile Arg Asp
                85                  90                  95

Pro Ala Leu Val His Gln Arg Pro Ala Pro Pro Ser Thr Val Thr Thr
            100                 105                 110

Ala Gly Val Thr Pro Gln Pro Glu Ser Leu Ser Pro Ser Gly Lys Glu
        115                 120                 125

Pro Ala Ala Ser Ser Pro Ser Ser Asn Asn Thr Ala Ala Thr Thr Ala
    130                 135                 140

Ala Ile Val Pro Gly Ser Gln Leu Met Pro Ser Lys Ser Pro Ser Thr
145                 150                 155                 160

Gly Thr Thr Glu Ile Ser Ser His Glu Ser Ser His Gly Thr Pro Ser
                165                 170                 175

Gln Thr Thr Ala Lys Asn Trp Glu Leu Thr Ala Ser Ala Ser His Gln
            180                 185                 190

Pro Pro Gly Val Tyr Pro Gln Gly His Ser Asp Thr Thr
        195                 200                 205

<210> SEQ ID NO 17
<211> LENGTH: 1754
<212> TYPE: DNA
<213> ORGANISM: Artificial Sequence
<220> FEATURE:
<223> OTHER INFORMATION: huIL-15 huGM-CSF - nucleic acid construct encoding optimized human IL-15 with a signal peptide of human GM-CSF

<400> SEQUENCE: 17
cctggccatt gcatacgttg tatccatatc ataatatgta catttatatt ggctcatgtc 60
caacattacc gccatgttga cattgattat tgactagtta ttaatagtaa tcaattacgg 120
ggtcattagt tcatagccca tatatggagt tccgcgttac ataacttacg gtaaatggcc 180
cgcctggctg accgcccaac gacccccgcc cattgacgtc aataatgacg tatgttccca 240
tagtaacgcc aatagggact ttccattgac gtcaatgggt ggagtattta cggtaaactg 300
cccacttggc agtacatcaa gtgtatcata tgccaagtac gccccctatt gacgtcaatg 360
atggtaaatg gcccgcctgg cattatgccc agtacatgac cttatgggac tttcctactt 420

-continued

```
ggcagtacat ctacgtatta gtcatcgcta ttaccatggt gatgcggttt tggcagtaca    480

tcaatgggcg tggatagcgg tttgactcac ggggatttcc aagtctccac cccattgacg    540

tcaatgggag tttgttttgg caccaaaatc aacgggactt tccaaaatgt cgtaacaact    600

ccgccccatt gacgcaaatg ggcggtaggc gtgtacggtg ggaggtctat ataagcagag    660

ctcgtttagt gaaccgtcag atcgcctgga gacgccatcc acgctgtttt gacctccata    720

gaagacaccg ggaccgatcc agcctccgcg ggcgcgcgtc gacaagaaat gtggctccag    780

agcctgctac tcctggggac ggtggcctgc agcatctcga actgggtgaa cgtgatctcg    840

gacctgaaga agatcgagga cctcatccag tcgatgcaca tcgacgcgac gctgtacacg    900

gagtcggacg tccacccgtc gtgcaaggtc acggcgatga agtgcttcct cctggagctc    960

caagtcatct cgctcgagtc gggggacgcg tcgatccacg acacggtgga gaacctgatc   1020

atcctggcga acaactcgct gtcgtcgaac gggaacgtca cggagtcggg ctgcaaggag   1080

tgcgaggagc tggaggagaa gaacatcaag gagttcctgc agtcgttcgt gcacatcgtc   1140

cagatgttca tcaacacgtc gtgagggccc ggcgcgccga attcgcggat atcggttaac   1200

ggatccagat ctgctgtgcc ttctagttgc cagccatctg ttgtttgccc ctcccccgtg   1260

ccttccttga ccctggaagg tgccactccc actgtccttt cctaataaaa tgaggaaatt   1320

gcatcgcatt gtctgagtag gtgtcattct attctggggg gtggggtggg gcaggacagc   1380

aagggggagg attgggaaga caatagcagg catgctgggg atgcggtggg ctctatgggt   1440

acccaggtgc tgaagaattg acccggttcc tcctgggcca gaaagaagca ggcacatccc   1500

cttctctgtg acacaccctg tccacgcccc tggttcttag ttccagcccc actcatagga   1560

cactcatagc tcaggagggc tccgccttca atcccacccg ctaaagtact tggagcggtc   1620

tctccctccc tcatcagccc accaaaccaa acctagcctc caagagtggg aagaaattaa   1680

agcaagatag gctattaagt gcagagggag agaaaatgcc tccaacatgt gaggaagtaa   1740

tgagagaaat cata                                                      1754
```

```
<210> SEQ ID NO 18
<211> LENGTH: 131
<212> TYPE: PRT
<213> ORGANISM: Artificial Sequence
<220> FEATURE:
<223> OTHER INFORMATION: huIL-15 huGM-CSF - amino acid sequence of
      optimized human IL-15 with a signal peptide of human GM-CSF

<400> SEQUENCE: 18

Met Trp Leu Gln Ser Leu Leu Leu Leu Gly Thr Val Ala Cys Ser Ile
 1               5                  10                  15

Ser Asn Trp Val Asn Val Ile Ser Asp Leu Lys Lys Ile Glu Asp Leu
            20                  25                  30

Ile Gln Ser Met His Ile Asp Ala Thr Leu Tyr Thr Glu Ser Asp Val
        35                  40                  45

His Pro Ser Cys Lys Val Thr Ala Met Lys Cys Phe Leu Leu Glu Leu
    50                  55                  60

Gln Val Ile Ser Leu Glu Ser Gly Asp Ala Ser Ile His Asp Thr Val
65                  70                  75                  80

Glu Asn Leu Ile Ile Leu Ala Asn Asn Ser Leu Ser Ser Asn Gly Asn
                85                  90                  95

Val Thr Glu Ser Gly Cys Lys Glu Cys Glu Glu Leu Glu Glu Lys Asn
            100                 105                 110
```

```
Ile Lys Glu Phe Leu Gln Ser Phe Val His Ile Val Gln Met Phe Ile
        115                 120                 125

Asn Thr Ser
    130


<210> SEQ ID NO 19
<211> LENGTH: 267
<212> TYPE: PRT
<213> ORGANISM: Artificial Sequence
<220> FEATURE:
<223> OTHER INFORMATION: synthetic human interleukin-15 (IL-15)
      receptor alpha (IL15Ra), isoform 1 (OPT)

<400> SEQUENCE: 19

Met Ala Pro Arg Arg Ala Arg Gly Cys Arg Thr Leu Gly Leu Pro Ala
 1               5                  10                  15

Leu Leu Leu Leu Leu Leu Leu Arg Pro Pro Ala Thr Arg Gly Ile Thr
            20                  25                  30

Cys Pro Pro Pro Met Ser Val Glu His Ala Asp Ile Trp Val Lys Ser
        35                  40                  45

Tyr Ser Leu Tyr Ser Arg Glu Arg Tyr Ile Cys Asn Ser Gly Phe Lys
    50                  55                  60

Arg Lys Ala Gly Thr Ser Ser Leu Thr Glu Cys Val Leu Asn Lys Ala
65                  70                  75                  80

Thr Asn Val Ala His Trp Thr Thr Pro Ser Leu Lys Cys Ile Arg Asp
                85                  90                  95

Pro Ala Leu Val His Gln Arg Pro Ala Pro Pro Ser Thr Val Thr Thr
            100                 105                 110

Ala Gly Val Thr Pro Gln Pro Glu Ser Leu Ser Pro Ser Gly Lys Glu
        115                 120                 125

Pro Ala Ala Ser Ser Pro Ser Ser Asn Asn Thr Ala Ala Thr Thr Ala
    130                 135                 140

Ala Ile Val Pro Gly Ser Gln Leu Met Pro Ser Lys Ser Pro Ser Thr
145                 150                 155                 160

Gly Thr Thr Glu Ile Ser Ser His Glu Ser Ser His Gly Thr Pro Ser
                165                 170                 175

Gln Thr Thr Ala Lys Asn Trp Glu Leu Thr Ala Ser Ala Ser His Gln
            180                 185                 190

Pro Pro Gly Val Tyr Pro Gln Gly His Ser Asp Thr Thr Val Ala Ile
        195                 200                 205

Ser Thr Ser Thr Val Leu Leu Cys Gly Leu Ser Ala Val Ser Leu Leu
    210                 215                 220

Ala Cys Tyr Leu Lys Ser Arg Gln Thr Pro Pro Leu Ala Ser Val Glu
225                 230                 235                 240

Met Glu Ala Met Glu Ala Leu Pro Val Thr Trp Gly Thr Ser Ser Arg
                245                 250                 255

Asp Glu Asp Leu Glu Asn Cys Ser His His Leu
            260                 265


<210> SEQ ID NO 20
<211> LENGTH: 205
<212> TYPE: PRT
<213> ORGANISM: Artificial Sequence
<220> FEATURE:
<223> OTHER INFORMATION: synthetic human soluble interleukin-15
      (IL-15) receptor alpha (IL-15sRa) (OPT)

<400> SEQUENCE: 20
```

-continued

```
Met Ala Pro Arg Arg Ala Arg Gly Cys Arg Thr Leu Gly Leu Pro Ala
 1              5                   10                  15

Leu Leu Leu Leu Leu Leu Leu Arg Pro Pro Ala Thr Arg Gly Ile Thr
            20                  25                  30

Cys Pro Pro Pro Met Ser Val Glu His Ala Asp Ile Trp Val Lys Ser
        35                  40                  45

Tyr Ser Leu Tyr Ser Arg Glu Arg Tyr Ile Cys Asn Ser Gly Phe Lys
    50                  55                  60

Arg Lys Ala Gly Thr Ser Ser Leu Thr Glu Cys Val Leu Asn Lys Ala
65                  70                  75                  80

Thr Asn Val Ala His Trp Thr Thr Pro Ser Leu Lys Cys Ile Arg Asp
                85                  90                  95

Pro Ala Leu Val His Gln Arg Pro Ala Pro Pro Ser Thr Val Thr Thr
            100                 105                 110

Ala Gly Val Thr Pro Gln Pro Glu Ser Leu Ser Pro Ser Gly Lys Glu
        115                 120                 125

Pro Ala Ala Ser Ser Pro Ser Ser Asn Asn Thr Ala Ala Thr Thr Ala
    130                 135                 140

Ala Ile Val Pro Gly Ser Gln Leu Met Pro Ser Lys Ser Pro Ser Thr
145                 150                 155                 160

Gly Thr Thr Glu Ile Ser Ser His Glu Ser Ser His Gly Thr Pro Ser
                165                 170                 175

Gln Thr Thr Ala Lys Asn Trp Glu Leu Thr Ala Ser Ala Ser His Gln
            180                 185                 190

Pro Pro Gly Val Tyr Pro Gln Gly His Ser Asp Thr Thr
        195                 200                 205


<210> SEQ ID NO 21
<211> LENGTH: 436
<212> TYPE: PRT
<213> ORGANISM: Artificial Sequence
<220> FEATURE:
<223> OTHER INFORMATION: synthetic sIL-15Ralpha-Fc fusion protein
      huIL15sRa205-Fc

<400> SEQUENCE: 21

Met Ala Pro Arg Arg Ala Arg Gly Cys Arg Thr Leu Gly Leu Pro Ala
 1              5                   10                  15

Leu Leu Leu Leu Leu Leu Leu Arg Pro Pro Ala Thr Arg Gly Ile Thr
            20                  25                  30

Cys Pro Pro Pro Met Ser Val Glu His Ala Asp Ile Trp Val Lys Ser
        35                  40                  45

Tyr Ser Leu Tyr Ser Arg Glu Arg Tyr Ile Cys Asn Ser Gly Phe Lys
    50                  55                  60

Arg Lys Ala Gly Thr Ser Ser Leu Thr Glu Cys Val Leu Asn Lys Ala
65                  70                  75                  80

Thr Asn Val Ala His Trp Thr Thr Pro Ser Leu Lys Cys Ile Arg Asp
                85                  90                  95

Pro Ala Leu Val His Gln Arg Pro Ala Pro Pro Ser Thr Val Thr Thr
            100                 105                 110

Ala Gly Val Thr Pro Gln Pro Glu Ser Leu Ser Pro Ser Gly Lys Glu
        115                 120                 125

Pro Ala Ala Ser Ser Pro Ser Ser Asn Asn Thr Ala Ala Thr Thr Ala
    130                 135                 140

Ala Ile Val Pro Gly Ser Gln Leu Met Pro Ser Lys Ser Pro Ser Thr
145                 150                 155                 160
```

Gly Thr Thr Glu Ile Ser Ser His Glu Ser Ser His Gly Thr Pro Ser
165 170 175

Gln Thr Thr Ala Lys Asn Trp Glu Leu Thr Ala Ser Ala Ser His Gln
180 185 190

Pro Pro Gly Val Tyr Pro Gln Gly His Ser Asp Thr Thr Pro Lys Ser
195 200 205

Cys Asp Lys Thr His Thr Cys Pro Pro Cys Pro Ala Pro Glu Leu Leu
210 215 220

Gly Gly Pro Ser Val Phe Leu Phe Pro Pro Lys Pro Lys Asp Thr Leu
225 230 235 240

Met Ile Ser Arg Thr Pro Glu Val Thr Cys Val Val Val Asp Val Ser
245 250 255

His Glu Asp Pro Glu Val Lys Phe Asn Trp Tyr Val Asp Gly Val Glu
260 265 270

Val His Asn Ala Lys Thr Lys Pro Arg Glu Glu Gln Tyr Asn Ser Thr
275 280 285

Tyr Arg Val Val Ser Val Leu Thr Val Leu His Gln Asp Trp Leu Asn
290 295 300

Gly Lys Glu Tyr Lys Cys Lys Val Ser Asn Lys Ala Leu Pro Ala Pro
305 310 315 320

Ile Glu Lys Thr Ile Ser Lys Ala Lys Gly Gln Pro Arg Glu Pro Gln
325 330 335

Val Tyr Thr Leu Pro Pro Ser Arg Asp Glu Leu Thr Lys Asn Gln Val
340 345 350

Ser Leu Thr Cys Leu Val Lys Gly Phe Tyr Pro Ser Asp Ile Ala Val
355 360 365

Glu Trp Glu Ser Asn Gly Gln Pro Glu Asn Asn Tyr Lys Thr Thr Pro
370 375 380

Pro Val Leu Asp Ser Asp Gly Ser Phe Phe Leu Tyr Ser Lys Leu Thr
385 390 395 400

Val Asp Lys Ser Arg Trp Gln Gln Gly Asn Val Phe Ser Cys Ser Val
405 410 415

Met His Glu Ala Leu His Asn His Tyr Thr Gln Lys Ser Leu Ser Leu
420 425 430

Ser Pro Gly Lys
435

<210> SEQ ID NO 22
<211> LENGTH: 431
<212> TYPE: PRT
<213> ORGANISM: Artificial Sequence
<220> FEATURE:
<223> OTHER INFORMATION: synthetic sIL-15Ralpha-Fc fusion protein
huIL15sRa200-Fc

<400> SEQUENCE: 22

Met Ala Pro Arg Arg Ala Arg Gly Cys Arg Thr Leu Gly Leu Pro Ala
1 5 10 15

Leu Leu Leu Leu Leu Leu Leu Arg Pro Pro Ala Thr Arg Gly Ile Thr
20 25 30

Cys Pro Pro Pro Met Ser Val Glu His Ala Asp Ile Trp Val Lys Ser
35 40 45

Tyr Ser Leu Tyr Ser Arg Glu Arg Tyr Ile Cys Asn Ser Gly Phe Lys
50 55 60

Arg Lys Ala Gly Thr Ser Ser Leu Thr Glu Cys Val Leu Asn Lys Ala

-continued

```
65                  70                  75                  80

Thr Asn Val Ala His Trp Thr Thr Pro Ser Leu Lys Cys Ile Arg Asp
                85                  90                  95

Pro Ala Leu Val His Gln Arg Pro Ala Pro Pro Ser Thr Val Thr Thr
            100                 105                 110

Ala Gly Val Thr Pro Gln Pro Glu Ser Leu Ser Pro Ser Gly Lys Glu
        115                 120                 125

Pro Ala Ala Ser Ser Pro Ser Ser Asn Asn Thr Ala Ala Thr Thr Ala
    130                 135                 140

Ala Ile Val Pro Gly Ser Gln Leu Met Pro Ser Lys Ser Pro Ser Thr
145                 150                 155                 160

Gly Thr Thr Glu Ile Ser Ser His Glu Ser Ser His Gly Thr Pro Ser
                165                 170                 175

Gln Thr Thr Ala Lys Asn Trp Glu Leu Thr Ala Ser Ala Ser His Gln
            180                 185                 190

Pro Pro Gly Val Tyr Pro Gln Gly Pro Lys Ser Cys Asp Lys Thr His
        195                 200                 205

Thr Cys Pro Pro Cys Pro Ala Pro Glu Leu Leu Gly Gly Pro Ser Val
    210                 215                 220

Phe Leu Phe Pro Pro Lys Pro Lys Asp Thr Leu Met Ile Ser Arg Thr
225                 230                 235                 240

Pro Glu Val Thr Cys Val Val Val Asp Val Ser His Glu Asp Pro Glu
                245                 250                 255

Val Lys Phe Asn Trp Tyr Val Asp Gly Val Glu Val His Asn Ala Lys
            260                 265                 270

Thr Lys Pro Arg Glu Glu Gln Tyr Asn Ser Thr Tyr Arg Val Val Ser
        275                 280                 285

Val Leu Thr Val Leu His Gln Asp Trp Leu Asn Gly Lys Glu Tyr Lys
    290                 295                 300

Cys Lys Val Ser Asn Lys Ala Leu Pro Ala Pro Ile Glu Lys Thr Ile
305                 310                 315                 320

Ser Lys Ala Lys Gly Gln Pro Arg Glu Pro Gln Val Tyr Thr Leu Pro
                325                 330                 335

Pro Ser Arg Asp Glu Leu Thr Lys Asn Gln Val Ser Leu Thr Cys Leu
            340                 345                 350

Val Lys Gly Phe Tyr Pro Ser Asp Ile Ala Val Glu Trp Glu Ser Asn
        355                 360                 365

Gly Gln Pro Glu Asn Asn Tyr Lys Thr Thr Pro Pro Val Leu Asp Ser
    370                 375                 380

Asp Gly Ser Phe Phe Leu Tyr Ser Lys Leu Thr Val Asp Lys Ser Arg
385                 390                 395                 400

Trp Gln Gln Gly Asn Val Phe Ser Cys Ser Val Met His Glu Ala Leu
                405                 410                 415

His Asn His Tyr Thr Gln Lys Ser Leu Ser Leu Ser Pro Gly Lys
            420                 425                 430
```

<210> SEQ ID NO 23
<211> LENGTH: 396
<212> TYPE: DNA
<213> ORGANISM: Homo sapiens
<220> FEATURE:
<223> OTHER INFORMATION: human IL-15 with GMCSF signal peptide

<400> SEQUENCE: 23
atgtggctcc agagcctgct actcctgggg acggtggcct gcagcatctc gaactgggtg 60

```
aacgtgatct cggacctgaa gaagatcgag gacctcatcc agtcgatgca catcgacgcg    120

acgctgtaca cggagtcgga cgtccacccg tcgtgcaagg tcacggcgat gaagtgcttc    180

ctcctggagc tccaagtcat ctcgctcgag tcgggggacg cgtcgatcca cgacacggtg    240

gagaacctga tcatcctggc gaacaactcg ctgtcgtcga acgggaacgt cacggagtcg    300

ggctgcaagg agtgcgagga gctggaggag aagaacatca aggagttcct gcagtcgttc    360

gtgcacatcg tccagatgtt catcaacacg tcgtga                              396
```

<210> SEQ ID NO 24
<211> LENGTH: 131
<212> TYPE: PRT
<213> ORGANISM: Homo sapiens
<220> FEATURE:
<223> OTHER INFORMATION: human IL-15 with GMCSF signal peptide

<400> SEQUENCE: 24

```
Met Trp Leu Gln Ser Leu Leu Leu Leu Gly Thr Val Ala Cys Ser Ile
 1               5                  10                  15

Ser Asn Trp Val Asn Val Ile Ser Asp Leu Lys Lys Ile Glu Asp Leu
            20                  25                  30

Ile Gln Ser Met His Ile Asp Ala Thr Leu Tyr Thr Glu Ser Asp Val
        35                  40                  45

His Pro Ser Cys Lys Val Thr Ala Met Lys Cys Phe Leu Leu Glu Leu
    50                  55                  60

Gln Val Ile Ser Leu Glu Ser Gly Asp Ala Ser Ile His Asp Thr Val
65                  70                  75                  80

Glu Asn Leu Ile Ile Leu Ala Asn Asn Ser Leu Ser Ser Asn Gly Asn
                85                  90                  95

Val Thr Glu Ser Gly Cys Lys Glu Cys Glu Glu Leu Glu Glu Lys Asn
            100                 105                 110

Ile Lys Glu Phe Leu Gln Ser Phe Val His Ile Val Gln Met Phe Ile
        115                 120                 125

Asn Thr Ser
    130
```

<210> SEQ ID NO 25
<211> LENGTH: 807
<212> TYPE: DNA
<213> ORGANISM: Homo sapiens
<220> FEATURE:
<223> OTHER INFORMATION: Human interleukin 15 receptor alpha (IL15Ra)

<400> SEQUENCE: 25

```
atggccccga ggcgggcgcg aggctgccgg accctcggtc tcccggcgct gctactgctc     60

ctgctgctcc ggccgccggc gacgcggggc atcacgtgcc cgccccccat gtccgtggag    120

cacgcagaca tctgggtcaa gagctacagc ttgtactccc gggagcggta catctgcaac    180

tcgggtttca agcggaaggc cggcacgtcc agcctgacgg agtgcgtgtt gaacaaggcc    240

acgaatgtcg cccactggac gaccccctcg ctcaagtgca tccgcgaccc ggccctggtt    300

caccagcggc ccgcgccacc ctccaccgta acgacggcgg gggtgacccc gcagccggag    360

agcctctccc cgtcgggaaa ggagcccgcc gcgtcgtcgc ccagctcgaa caacacggcg    420

gccacaactg cagcgatcgt cccgggctcc cagctgatgc cgtcgaagtc gccgtccacg    480

ggaaccacgg agatcagcag tcatgagtcc tcccacggca ccccctcgca aacgacggcc    540

aagaactggg aactcacggc gtccgcctcc caccagccgc cgggggtgta tccgcaaggc    600
```

-continued

```
cacagcgaca ccacggtggc gatctccacg tccacggtcc tgctgtgtgg gctgagcgcg    660

gtgtcgctcc tggcgtgcta cctcaagtcg aggcagactc ccccgctggc cagcgttgag    720

atggaggcca tggaggctct gccggtgacg tgggggacca gcagcaggga tgaggacttg    780

gagaactgct cgcaccacct ataatga                                        807
```

<210> SEQ ID NO 26
<211> LENGTH: 8
<212> TYPE: PRT
<213> ORGANISM: homo sapiens
<220> FEATURE:
<223> OTHER INFORMATION: C-terminal end of the soluble form of human
      IL-15Ra

<400> SEQUENCE: 26

Pro Gln Gly His Ser Asp Thr Thr
1               5

<210> SEQ ID NO 27
<211> LENGTH: 7
<212> TYPE: PRT
<213> ORGANISM: Artificial Sequence
<220> FEATURE:
<223> OTHER INFORMATION: C-terminal end of the soluble form of human
      IL-15Ra

<400> SEQUENCE: 27

Pro Gln Gly His Ser Asp Thr
1               5

<210> SEQ ID NO 28
<211> LENGTH: 6
<212> TYPE: PRT
<213> ORGANISM: Artificial Sequence
<220> FEATURE:
<223> OTHER INFORMATION: C-terminal end of the soluble form of human
      IL-15Ra

<400> SEQUENCE: 28

Pro Gln Gly His Ser Asp
1               5

<210> SEQ ID NO 29
<211> LENGTH: 5
<212> TYPE: PRT
<213> ORGANISM: Artificial Sequence
<220> FEATURE:
<223> OTHER INFORMATION: C-terminal end of the soluble form of human
      IL-15Ra

<400> SEQUENCE: 29

Pro Gln Gly His Ser
1               5

<210> SEQ ID NO 30
<211> LENGTH: 4
<212> TYPE: PRT
<213> ORGANISM: Artificial Sequence
<220> FEATURE:
<223> OTHER INFORMATION: C-terminal end of the soluble form of human
      IL-15Ra

<400> SEQUENCE: 30

Pro Gln Gly His
1

```
<210> SEQ ID NO 31
<211> LENGTH: 3
<212> TYPE: PRT
<213> ORGANISM: Artificial Sequence
<220> FEATURE:
<223> OTHER INFORMATION: C-terminal end of the soluble form of human
      IL-15Ra

<400> SEQUENCE: 31

Pro Gln Gly
 1


<210> SEQ ID NO 32
<211> LENGTH: 200
<212> TYPE: PRT
<213> ORGANISM: Homo sapiens
<220> FEATURE:
<223> OTHER INFORMATION: immature form of the native soluble human
      IL-15Ra

<400> SEQUENCE: 32

Met Ala Pro Arg Arg Ala Arg Gly Cys Arg Thr Leu Gly Leu Pro Ala
 1               5                  10                  15

Leu Leu Leu Leu Leu Leu Leu Arg Pro Pro Ala Thr Arg Gly Ile Thr
            20                  25                  30

Cys Pro Pro Pro Met Ser Val Glu His Ala Asp Ile Trp Val Lys Ser
        35                  40                  45

Tyr Ser Leu Tyr Ser Arg Glu Arg Tyr Ile Cys Asn Ser Gly Phe Lys
    50                  55                  60

Arg Lys Ala Gly Thr Ser Ser Leu Thr Glu Cys Val Leu Asn Lys Ala
65                  70                  75                  80

Thr Asn Val Ala His Trp Thr Thr Pro Ser Leu Lys Cys Ile Arg Asp
                85                  90                  95

Pro Ala Leu Val His Gln Arg Pro Ala Pro Pro Ser Thr Val Thr Thr
            100                 105                 110

Ala Gly Val Thr Pro Gln Pro Glu Ser Leu Ser Pro Ser Gly Lys Glu
        115                 120                 125

Pro Ala Ala Ser Ser Pro Ser Ser Asn Asn Thr Ala Ala Thr Thr Ala
    130                 135                 140

Ala Ile Val Pro Gly Ser Gln Leu Met Pro Ser Lys Ser Pro Ser Thr
145                 150                 155                 160

Gly Thr Thr Glu Ile Ser Ser His Glu Ser Ser His Gly Thr Pro Ser
                165                 170                 175

Gln Thr Thr Ala Lys Asn Trp Glu Leu Thr Ala Ser Ala Ser His Gln
            180                 185                 190

Pro Pro Gly Val Tyr Pro Gln Gly
        195                 200


<210> SEQ ID NO 33
<211> LENGTH: 170
<212> TYPE: PRT
<213> ORGANISM: Artificial Sequence
<220> FEATURE:
<223> OTHER INFORMATION: a soluble form of human IL-15Ra

<400> SEQUENCE: 33

Ile Thr Cys Pro Pro Pro Met Ser Val Glu His Ala Asp Ile Trp Val
 1               5                  10                  15

Lys Ser Tyr Ser Leu Tyr Ser Arg Glu Arg Tyr Ile Cys Asn Ser Gly
            20                  25                  30
```

Phe Lys Arg Lys Ala Gly Thr Ser Ser Leu Thr Glu Cys Val Leu Asn
35 40 45

Lys Ala Thr Asn Val Ala His Trp Thr Thr Pro Ser Leu Lys Cys Ile
50 55 60

Arg Asp Pro Ala Leu Val His Gln Arg Pro Ala Pro Pro Ser Thr Val
65 70 75 80

Thr Thr Ala Gly Val Thr Pro Gln Pro Glu Ser Leu Ser Pro Ser Gly
85 90 95

Lys Glu Pro Ala Ala Ser Ser Pro Ser Ser Asn Asn Thr Ala Ala Thr
100 105 110

Thr Ala Ala Ile Val Pro Gly Ser Gln Leu Met Pro Ser Lys Ser Pro
115 120 125

Ser Thr Gly Thr Thr Glu Ile Ser Ser His Glu Ser Ser His Gly Thr
130 135 140

Pro Ser Gln Thr Thr Ala Lys Asn Trp Glu Leu Thr Ala Ser Ala Ser
145 150 155 160

His Gln Pro Pro Gly Val Tyr Pro Gln Gly
165 170

<210> SEQ ID NO 34
<211> LENGTH: 201
<212> TYPE: PRT
<213> ORGANISM: Artificial Sequence
<220> FEATURE:
<223> OTHER INFORMATION: a soluble form of human IL-15Ra

<400> SEQUENCE: 34

Met Ala Pro Arg Arg Ala Arg Gly Cys Arg Thr Leu Gly Leu Pro Ala
1 5 10 15

Leu Leu Leu Leu Leu Leu Leu Arg Pro Pro Ala Thr Arg Gly Ile Thr
20 25 30

Cys Pro Pro Pro Met Ser Val Glu His Ala Asp Ile Trp Val Lys Ser
35 40 45

Tyr Ser Leu Tyr Ser Arg Glu Arg Tyr Ile Cys Asn Ser Gly Phe Lys
50 55 60

Arg Lys Ala Gly Thr Ser Ser Leu Thr Glu Cys Val Leu Asn Lys Ala
65 70 75 80

Thr Asn Val Ala His Trp Thr Thr Pro Ser Leu Lys Cys Ile Arg Asp
85 90 95

Pro Ala Leu Val His Gln Arg Pro Ala Pro Pro Ser Thr Val Thr Thr
100 105 110

Ala Gly Val Thr Pro Gln Pro Glu Ser Leu Ser Pro Ser Gly Lys Glu
115 120 125

Pro Ala Ala Ser Ser Pro Ser Ser Asn Asn Thr Ala Ala Thr Thr Ala
130 135 140

Ala Ile Val Pro Gly Ser Gln Leu Met Pro Ser Lys Ser Pro Ser Thr
145 150 155 160

Gly Thr Thr Glu Ile Ser Ser His Glu Ser Ser His Gly Thr Pro Ser
165 170 175

Gln Thr Thr Ala Lys Asn Trp Glu Leu Thr Ala Ser Ala Ser His Gln
180 185 190

Pro Pro Gly Val Tyr Pro Gln Gly His
195 200

<210> SEQ ID NO 35

<211> LENGTH: 171
<212> TYPE: PRT
<213> ORGANISM: Artificial Sequence
<220> FEATURE:
<223> OTHER INFORMATION: a soluble form of human IL-15Ra

<400> SEQUENCE: 35

```
Ile Thr Cys Pro Pro Pro Met Ser Val Glu His Ala Asp Ile Trp Val
 1               5                  10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Asp Pro Ala Leu Val His Gln Arg Pro Ala Pro Pro Ser Thr Val
65                  70                  75                  80

Thr Thr Ala Gly Val Thr Pro Gln Pro Glu Ser Leu Ser Pro Ser Gly
                85                  90                  95

Lys Glu Pro Ala Ala Ser Ser Pro Ser Ser Asn Asn Thr Ala Ala Thr
            100                 105                 110

Thr Ala Ala Ile Val Pro Gly Ser Gln Leu Met Pro Ser Lys Ser Pro
        115                 120                 125

Ser Thr Gly Thr Thr Glu Ile Ser Ser His Glu Ser Ser His Gly Thr
    130                 135                 140

Pro Ser Gln Thr Thr Ala Lys Asn Trp Glu Leu Thr Ala Ser Ala Ser
145                 150                 155                 160

His Gln Pro Pro Gly Val Tyr Pro Gln Gly His
                165                 170
```

<210> SEQ ID NO 36
<211> LENGTH: 202
<212> TYPE: PRT
<213> ORGANISM: Artificial Sequence
<220> FEATURE:
<223> OTHER INFORMATION: a soluble form of human IL-15Ra

<400> SEQUENCE: 36

```
Met Ala Pro Arg Arg Ala Arg Gly Cys Arg Thr Leu Gly Leu Pro Ala
 1               5                  10                  15

Leu Leu Leu Leu Leu Leu Leu Arg Pro Pro Ala Thr Arg Gly Ile Thr
            20                  25                  30

Cys Pro Pro Pro Met Ser Val Glu His Ala Asp Ile Trp Val Lys Ser
        35                  40                  45

Tyr Ser Leu Tyr Ser Arg Glu Arg Tyr Ile Cys Asn Ser Gly Phe Lys
    50                  55                  60

Arg Lys Ala Gly Thr Ser Ser Leu Thr Glu Cys Val Leu Asn Lys Ala
65                  70                  75                  80

Thr Asn Val Ala His Trp Thr Thr Pro Ser Leu Lys Cys Ile Arg Asp
                85                  90                  95

Pro Ala Leu Val His Gln Arg Pro Ala Pro Pro Ser Thr Val Thr Thr
            100                 105                 110

Ala Gly Val Thr Pro Gln Pro Glu Ser Leu Ser Pro Ser Gly Lys Glu
        115                 120                 125

Pro Ala Ala Ser Ser Pro Ser Ser Asn Asn Thr Ala Ala Thr Thr Ala
    130                 135                 140

Ala Ile Val Pro Gly Ser Gln Leu Met Pro Ser Lys Ser Pro Ser Thr
```

145 150 155 160

Gly Thr Thr Glu Ile Ser Ser His Glu Ser Ser His Gly Thr Pro Ser
165 170 175

Gln Thr Thr Ala Lys Asn Trp Glu Leu Thr Ala Ser Ala Ser His Gln
180 185 190

Pro Pro Gly Val Tyr Pro Gln Gly His Ser
195 200

<210> SEQ ID NO 37
<211> LENGTH: 172
<212> TYPE: PRT
<213> ORGANISM: Artificial Sequence
<220> FEATURE:
<223> OTHER INFORMATION: a soluble form of human IL-15Ra

<400> SEQUENCE: 37

Ile Thr Cys Pro Pro Pro Met Ser Val Glu His Ala Asp Ile Trp Val
1 5 10 15

Lys Ser Tyr Ser Leu Tyr Ser Arg Glu Arg Tyr Ile Cys Asn Ser Gly
20 25 30

Phe Lys Arg Lys Ala Gly Thr Ser Ser Leu Thr Glu Cys Val Leu Asn
35 40 45

Lys Ala Thr Asn Val Ala His Trp Thr Thr Pro Ser Leu Lys Cys Ile
50 55 60

Arg Asp Pro Ala Leu Val His Gln Arg Pro Ala Pro Pro Ser Thr Val
65 70 75 80

Thr Thr Ala Gly Val Thr Pro Gln Pro Glu Ser Leu Ser Pro Ser Gly
85 90 95

Lys Glu Pro Ala Ala Ser Ser Pro Ser Ser Asn Asn Thr Ala Ala Thr
100 105 110

Thr Ala Ala Ile Val Pro Gly Ser Gln Leu Met Pro Ser Lys Ser Pro
115 120 125

Ser Thr Gly Thr Thr Glu Ile Ser Ser His Glu Ser Ser His Gly Thr
130 135 140

Pro Ser Gln Thr Thr Ala Lys Asn Trp Glu Leu Thr Ala Ser Ala Ser
145 150 155 160

His Gln Pro Pro Gly Val Tyr Pro Gln Gly His Ser
165 170

<210> SEQ ID NO 38
<211> LENGTH: 203
<212> TYPE: PRT
<213> ORGANISM: Artificial Sequence
<220> FEATURE:
<223> OTHER INFORMATION: a soluble form of human IL-15Ra

<400> SEQUENCE: 38

Met Ala Pro Arg Arg Ala Arg Gly Cys Arg Thr Leu Gly Leu Pro Ala
1 5 10 15

Leu Leu Leu Leu Leu Leu Leu Arg Pro Pro Ala Thr Arg Gly Ile Thr
20 25 30

Cys Pro Pro Pro Met Ser Val Glu His Ala Asp Ile Trp Val Lys Ser
35 40 45

Tyr Ser Leu Tyr Ser Arg Glu Arg Tyr Ile Cys Asn Ser Gly Phe Lys
50 55 60

Arg Lys Ala Gly Thr Ser Ser Leu Thr Glu Cys Val Leu Asn Lys Ala
65 70 75 80

-continued

```
Thr Asn Val Ala His Trp Thr Thr Pro Ser Leu Lys Cys Ile Arg Asp
                85                  90                  95

Pro Ala Leu Val His Gln Arg Pro Ala Pro Pro Ser Thr Val Thr Thr
            100                 105                 110

Ala Gly Val Thr Pro Gln Pro Glu Ser Leu Ser Pro Ser Gly Lys Glu
        115                 120                 125

Pro Ala Ala Ser Ser Pro Ser Ser Asn Asn Thr Ala Ala Thr Thr Ala
    130                 135                 140

Ala Ile Val Pro Gly Ser Gln Leu Met Pro Ser Lys Ser Pro Ser Thr
145                 150                 155                 160

Gly Thr Thr Glu Ile Ser Ser His Glu Ser Ser His Gly Thr Pro Ser
                165                 170                 175

Gln Thr Thr Ala Lys Asn Trp Glu Leu Thr Ala Ser Ala Ser His Gln
            180                 185                 190

Pro Pro Gly Val Tyr Pro Gln Gly His Ser Asp
        195                 200


<210> SEQ ID NO 39
<211> LENGTH: 173
<212> TYPE: PRT
<213> ORGANISM: Artificial Sequence
<220> FEATURE:
<223> OTHER INFORMATION: a soluble form of human IL-15Ra

<400> SEQUENCE: 39

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Asp Pro Ala Leu Val His Gln Arg Pro Ala Pro Pro Ser Thr Val
65                  70                  75                  80

Thr Thr Ala Gly Val Thr Pro Gln Pro Glu Ser Leu Ser Pro Ser Gly
                85                  90                  95

Lys Glu Pro Ala Ala Ser Ser Pro Ser Ser Asn Asn Thr Ala Ala Thr
            100                 105                 110

Thr Ala Ala Ile Val Pro Gly Ser Gln Leu Met Pro Ser Lys Ser Pro
        115                 120                 125

Ser Thr Gly Thr Thr Glu Ile Ser Ser His Glu Ser Ser His Gly Thr
    130                 135                 140

Pro Ser Gln Thr Thr Ala Lys Asn Trp Glu Leu Thr Ala Ser Ala Ser
145                 150                 155                 160

His Gln Pro Pro Gly Val Tyr Pro Gln Gly His Ser Asp
                165                 170


<210> SEQ ID NO 40
<211> LENGTH: 204
<212> TYPE: PRT
<213> ORGANISM: Artificial Sequence
<220> FEATURE:
<223> OTHER INFORMATION: a soluble form of human IL-15Ra

<400> SEQUENCE: 40

Met Ala Pro Arg Arg Ala Arg Gly Cys Arg Thr Leu Gly Leu Pro Ala
1               5                   10                  15
```

```
Leu Leu Leu Leu Leu Leu Leu Arg Pro Pro Ala Thr Arg Gly Ile Thr
            20                  25                  30

Cys Pro Pro Pro Met Ser Val Glu His Ala Asp Ile Trp Val Lys Ser
        35                  40                  45

Tyr Ser Leu Tyr Ser Arg Glu Arg Tyr Ile Cys Asn Ser Gly Phe Lys
    50                  55                  60

Arg Lys Ala Gly Thr Ser Ser Leu Thr Glu Cys Val Leu Asn Lys Ala
65                  70                  75                  80

Thr Asn Val Ala His Trp Thr Thr Pro Ser Leu Lys Cys Ile Arg Asp
                85                  90                  95

Pro Ala Leu Val His Gln Arg Pro Ala Pro Pro Ser Thr Val Thr Thr
            100                 105                 110

Ala Gly Val Thr Pro Gln Pro Glu Ser Leu Ser Pro Ser Gly Lys Glu
        115                 120                 125

Pro Ala Ala Ser Ser Pro Ser Ser Asn Asn Thr Ala Ala Thr Thr Ala
    130                 135                 140

Ala Ile Val Pro Gly Ser Gln Leu Met Pro Ser Lys Ser Pro Ser Thr
145                 150                 155                 160

Gly Thr Thr Glu Ile Ser Ser His Glu Ser Ser His Gly Thr Pro Ser
                165                 170                 175

Gln Thr Thr Ala Lys Asn Trp Glu Leu Thr Ala Ser Ala Ser His Gln
            180                 185                 190

Pro Pro Gly Val Tyr Pro Gln Gly His Ser Asp Thr
        195                 200


<210> SEQ ID NO 41
<211> LENGTH: 174
<212> TYPE: PRT
<213> ORGANISM: Artificial Sequence
<220> FEATURE:
<223> OTHER INFORMATION: a soluble form of human IL-15Ra

<400> SEQUENCE: 41

Ile Thr Cys Pro Pro Pro Met Ser Val Glu His Ala Asp Ile Trp Val
 1               5                  10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Asp Pro Ala Leu Val His Gln Arg Pro Ala Pro Pro Ser Thr Val
65                  70                  75                  80

Thr Thr Ala Gly Val Thr Pro Gln Pro Glu Ser Leu Ser Pro Ser Gly
                85                  90                  95

Lys Glu Pro Ala Ala Ser Ser Pro Ser Ser Asn Asn Thr Ala Ala Thr
            100                 105                 110

Thr Ala Ala Ile Val Pro Gly Ser Gln Leu Met Pro Ser Lys Ser Pro
        115                 120                 125

Ser Thr Gly Thr Thr Glu Ile Ser Ser His Glu Ser Ser His Gly Thr
    130                 135                 140

Pro Ser Gln Thr Thr Ala Lys Asn Trp Glu Leu Thr Ala Ser Ala Ser
145                 150                 155                 160

His Gln Pro Pro Gly Val Tyr Pro Gln Gly His Ser Asp Thr
                165                 170
```

<210> SEQ ID NO 42
<211> LENGTH: 19
<212> TYPE: PRT
<213> ORGANISM: Artificial Sequence
<220> FEATURE:
<223> OTHER INFORMATION: purified glycosylated soluble form of human IL-15Ra

<400> SEQUENCE: 42

```
Asn Trp Glu Leu Thr Ala Ser Ala Ser His Gln Pro Pro Gly Val Tyr
 1               5                  10                  15

Pro Gln Gly
```

<210> SEQ ID NO 43
<211> LENGTH: 17
<212> TYPE: PRT
<213> ORGANISM: Artificial Sequence
<220> FEATURE:
<223> OTHER INFORMATION: purified glycosylated soluble form of human IL-15Ra

<400> SEQUENCE: 43

```
Ile Thr Cys Pro Pro Pro Met Ser Val Glu His Ala Asp Ile Trp Val
 1               5                  10                  15

Lys
```

<210> SEQ ID NO 44
<211> LENGTH: 31
<212> TYPE: PRT
<213> ORGANISM: Artificial Sequence
<220> FEATURE:
<223> OTHER INFORMATION: purified glycosylated soluble form of human IL-15Ra

<400> SEQUENCE: 44

```
Ile Thr Cys Pro Pro Pro Met Ser Val Glu His Ala Asp Ile Trp Val
 1               5                  10                  15

Lys Ser Tyr Ser Leu Tyr Ser Arg Glu Arg Tyr Ile Cys Asn Ser
            20                  25                  30
```

<210> SEQ ID NO 45
<211> LENGTH: 175
<212> TYPE: PRT
<213> ORGANISM: Artificial Sequence
<220> FEATURE:
<223> OTHER INFORMATION: a soluble form of human IL-15Ra

<400> SEQUENCE: 45

```
Ile Thr Cys Pro Pro Pro Met Ser Val Glu His Ala Asp Ile Trp Val
 1               5                  10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Asp Pro Ala Leu Val His Gln Arg Pro Ala Pro Pro Ser Thr Val
65                  70                  75                  80

Thr Thr Ala Gly Val Thr Pro Gln Pro Glu Ser Leu Ser Pro Ser Gly
                85                  90                  95

Lys Glu Pro Ala Ala Ser Ser Pro Ser Ser Asn Asn Thr Ala Ala Thr
```

```
                    100                 105                 110
Thr Ala Ala Ile Val Pro Gly Ser Gln Leu Met Pro Ser Lys Ser Pro
            115                 120                 125

Ser Thr Gly Thr Thr Glu Ile Ser Ser His Glu Ser Ser His Gly Thr
        130                 135                 140

Pro Ser Gln Thr Thr Ala Lys Asn Trp Glu Leu Thr Ala Ser Ala Ser
145                 150                 155                 160

His Gln Pro Pro Gly Val Tyr Pro Gln Gly His Ser Asp Thr Thr
                165                 170                 175

<210> SEQ ID NO 46
<211> LENGTH: 600
<212> TYPE: DNA
<213> ORGANISM: Homo sapiens
<220> FEATURE:
<223> OTHER INFORMATION: nucleotide sequence encoding the mature human
      soluble native IL-15Ra

<400> SEQUENCE: 46

atggccccgc ggcgggcgcg cggctgccgg accctcggtc tcccggcgct gctactgctg      60

ctgctgctcc ggccgccggc gacgcggggc atcacgtgcc ctccccccat gtccgtggaa     120

cacgcagaca tctgggtcaa gagctacagc ttgtactcca gggagcggta catttgtaac     180

tctggtttca gcgtaaagc cggcacgtcc agcctgacgg agtgcgtgtt gaacaaggcc     240

acgaatgtcg cccactggac aacccccagt ctcaaatgca ttagagaccc tgccctggtt     300

caccaaaggc cagcgccacc ctccacagta acgacggcag gggtgacccc acagccagag     360

agcctctccc cttctggaaa agagcccgca gcttcatctc ccagctcaaa caacacagcg     420

gccacaacag cagctattgt cccgggctcc cagctgatgc cttcaaaatc accttccaca     480

ggaaccacag agataagcag tcatgagtcc tcccacggca ccccctctca gacaacagcc     540

aagaactggg aactcacagc atccgcctcc caccagccgc caggtgtgta tccacagggc     600
```

IL-15 AND IL-15Rα HETERODIMER DOSE ESCALATION REGIMENS FOR TREATING CONDITIONS

CROSS-REFERENCE TO RELATED APPLICATIONS

This application is a U.S. National Phase filing of International Application Serial No. PCT/US2015/042489 filed Jul. 28, 2015 and claims the benefit of priority to U.S. Provisional Application No. 62/030,394, filed on Jul. 29, 2014, which is hereby incorporated by reference in its entirety.

GOVERNMENTAL INTERESTS

This invention was created in the performance of a Cooperative Research and Development Agreement with the National Institutes of Health, an Agency of the Department of Health and Human Services. The Government of the United States has certain rights in this invention.

SEQUENCE LISTING

The instant application contains a Sequence Listing, which is being concurrently submitted as an ASCII text file named "13346_018_228_SEQLIST.TXT", created Jul. 27, 2015, and being 65,536 bytes in size. The Sequence Listing is hereby incorporated by reference in its entirety.

1. FIELD

Described herein are dose escalation regimens for the administration of complexes comprising interleukin-15 ("IL-15") covalently or noncovalently bound to IL-15 receptor alpha ("IL-15Ra" or "IL-15Rα") to patients in order to enhance IL-15-mediated immune function. In a specific aspect, the dose escalation regimens are useful in the prevention, treatment, and/or management of disorders in which enhancing IL-15-mediated function is beneficial, such as cancer, infectious diseases, immunodeficiencies and lymphopenia. In another specific aspect, the dose escalation regimens are useful for eradicating or reducing HIV in HIV-infected patients.

2. BACKGROUND

The cytokine, interleukin-15 (IL-15), a member of the four alpha-helix bundle family of lymphokines, plays a pivotal role in modulating the activity of both the innate and adaptive immune system, e.g., expansion and maintenance of the memory T-cell response to invading pathogens, and induction of Natural Killer (NK) cell proliferation and cytotoxic activity.

The IL-15 receptor consists of two polypeptides, the IL-2/IL-15 receptor beta ("β") (or CD122), and the gamma chain ("γ") (or CD132) that is shared by multiple cytokine receptors. IL-15 signaling has been shown to occur through the heterodimeric complex of IL-15Rβ and IL-15Rγ. Despite existing theories suggesting that IL-15Rα is a receptor for IL-15, an alternative interpretation of the existing data is that IL-15Rα is not a receptor for the IL-15 polypeptide chain. IL-15Rα has evolved very high affinity for IL-15 and is always co-expressed with IL-15 in the same cell. The two molecules form heterodimeric complexes in the Endoplasmic Reticulum and are transported to the plasma membrane. See, e.g., Bergamaschi et al., 2012, Blood 120: e1-e8. This heterodimeric complex can bind to the IL-2/IL-15βγ receptor and activate the cells via the Jak/Stat pathway. Therefore, based upon this interpretation of the data, the IL-15Rα and the soluble form sIL-15Rα are part of the cytokine and not part of the receptor. Id.

IL-15 specifically binds to the IL-15Rα with high affinity via the "sushi domain" in exon 2 of the extracellular domain of the receptor. Endogenous heterodimeric IL-15 is found in two forms, as a membrane-bound form that is expressed by antigen presenting and stroma cells in various tissues; and as a soluble extracellular complex of IL-15 to the soluble IL-15Rα, which is produced by cleavage of the membrane-anchored IL-15Rα by cellular proteases. Although IL-15 mRNA has been reported in cells of both hematopoietic and non-hematopoietic lineage, T cells do not produce IL-15. Instead, IL-15 heterodimers released from the cell surface after cleavage of the membrane bound heterodimers binds to the IL-15βγ Receptor on lymphocytes.

Based on its multifaceted role in the immune system, various therapies designed to modulate IL-15-mediated function have been explored. For example, the administration of exogenous IL-15 can enhance the immune function of patients infected with human immunodeficiency virus (HIV). In keeping with its immune enhancing activity, increased expression of endogenous IL-15 is observed in patients with autoimmune diseases, e.g., rheumatoid arthritis, multiple sclerosis, ulcerative colitis, and psoriasis. Because some studies reported that the soluble form of the IL-15Rα (sIL-15Rα) is an antagonist of IL-15-mediated signaling, the sIL-15Rα has been explored for treating autoimmune inflammatory diseases. Nevertheless, recent reports suggest that IL-15, when complexed with the sIL-15Rα, or the sushi domain, maintains its immune enhancing function.

Despite the amount of progress made in understanding the function of IL-15, it is unclear how various forms of the IL-15Rα, alone or when complexed to IL-15, can be used to modulate IL-15 function as part of a therapeutic regimen.

3. SUMMARY

In one aspect, provided herein are methods for enhancing IL-15-mediated immune function, comprising administering to subjects agents that induce IL-15 signal transduction and enhance IL-15-mediated immune function in a dose escalation regimen. More specifically, provided herein are methods for enhancing IL-15-mediated immune function, comprising administering to subjects in a dose escalation regimen complexes that bind to the βγ subunits of the IL-15 receptor, induce IL-15 signal transduction and enhance IL-15-mediated immune function, wherein the complexes comprise IL-15 covalently or noncovalently bound to Interleukin-15 receptor alpha ("IL-15Rα") and referred to as "IL-15/IL-15Rα complexes" or "Therapeutic Agents". Since enhancing IL-15-mediated immune function is beneficial for the prevention, treatment and/or management of certain disorders, such as lymphopenia, cancer, and infectious diseases, provided herein are methods for the prevention, treatment and/or management of such disorders comprising administering to a subject in need thereof IL-15/IL-15Rα complexes in a dose escalation regimen. Further, provided herein are methods for eradicating or reducing HIV in HIV-infected cells in a subject comprising administering to a subject in need thereof IL-15/IL-15Rα complexes in a dose escalation regimen.

The methods described herein are based, in part, on the discovery that the amount of IL-15/IL-15Rα complex administered to a subject needs to be escalated over time in order to achieve an effective ratio of IL-15 to lymphocyte cell number so that lymphocytes remain activated or do not undergo cell death. In other words, the administration of IL-15/IL-15Rα complex to a subject causes lymphocytes to increase and in order for further proliferation and survival of lymphocytes, the amount of IL-15/IL-15Rα complex administered to the subject needs to be increased. The methods provided herein achieve an effective ratio of IL-15 to lymphocyte cell number while avoiding the toxicity associated with the administration of the high doses of IL-15. In a specific embodiment, the methods provided herein involve a dose escalation regimen that achieves a systemic effect (not just a local effect) with minimal side effects. In specific embodiments, the dose escalation regimens decrease the side effects associated with the administration of a high dose of an IL-15/IL-15Rα complex to a subject, such as a decrease in blood pressure or an increase in body temperature. In certain embodiments, the dose escalation regimens do not alter blood pressure or body temperature.

The methods described herein are also based, in part, on the discovery that a high dose of an IL-15/IL-15Rα complex activates lymphocytes including lymphocytes infected with HIV or the simian counterpart, Simian Immunodeficiency Virus (SIV), and such lymphocytes can become targets for elimination if they are activated, without a systemic increase in viral load. In chronically SIV infected macaques, the administration of an IL-15/IL-15Rα complex did not lead to a systemic increase in the virus. See, e.g., Example 3, infra.

In one embodiment, provided herein is a method for preventing, treating and/or managing disorders in a subject, wherein enhancement of IL-15-mediated immune function is beneficial for the prevention, treatment and/or management of such disorders, the method comprising (a) administering at least one initial low dose of an IL-15/IL-15Rα complex to a subject; and (b) administering successively higher doses of the IL-15/IL-15Rα complex to the subject to achieve an effective ratio of IL-15 to lymphocyte cell number. In a specific embodiment, provided herein is a method for preventing, treating and/or managing lymphocytopenia, cancer or an infectious disease in a subject, method comprising (a) administering at least one initial low dose of an IL-15/IL-15Rα complex to the subject; and (b) administering successively higher doses of the IL-15/IL-15Rα complex to the subject to achieve an effective ratio of IL-15 to lymphocyte cell number. In another specific embodiment, provided herein is a method for eradicating or reducing HIV in HIV-infected cells in a subject, the method comprising (a) administering at least one initial low dose of an IL-15/IL-15Rα complex to the subject; and (b) administering successively higher doses of the IL-15/IL-15Rα complex to the subject achieve an effective ratio of IL-15 to lymphocyte cell number. In a particular embodiment, the subject is a human subject. In a specific embodiment, the initial low dose is between 0.1 μg/kg and 1 μg/kg as determined based on the mass of single chain IL-15. In another embodiment, the initial low dose is between 0.1 μg/kg and 0.5 μg/kg as determined based on the mass of single chain IL-15. In another embodiment, the initial low dose is 0.5 μg/kg as determined based on the mass of single chain IL-15. In certain embodiments, the initial low dose is administered 1, 2, 3, 4, 5, 6 or more times, or 1 to 3, 1 to 4, 2 to 4, 2 to 5, 2 to 6, 3 to 6, 4 to 6 or 6 to 8 times. In some embodiments, the initial low dose is administered 1, 2, 3, 4, 5, 6 or more times, or 1 to 3, 1 to 4, 2 to 4, 2 to 5, 2 to 6, 3 to 6, 4 to 6 or 6 to 8 times over a 5 to 7 day, 5 to 10 day, 7 to 12 day, 7 to 14 day, 7 to 21 day or 14 to 21 day period of time. In certain embodiments, each successively higher dose is 1.2, 1.25, 1.3, 1.35, 1.4, 1.45, 1.5, 2, 2.5, 3, 3.5, 4, 4.5, 5, 5.5, or 6 times higher than the previous dose, or 1.2 to 2, 2 to 3, 2 to 4, 2 to 6, 3 to 4, 3 to 6, or 4 to 6 times higher than the previous dose. In some embodiments, each successively higher dose is 25%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 155%, 160%, 165%, 170%, 175%, 180%, 185%, 190%, 195%, or 200% higher than the previous dose. In specific embodiments, each dose is administered at least 1, 2, 3, 4, 5, 6, 7, 8, 9, 10 or more times over a 5 to 7 day, 5 to 10 day, 7 to 12 day, 7 to 14 day, 7 to 21 day or 14 to 21 day period of time. In certain embodiments, the subject is monitored for signs of an enlarged lymph node(s) and/or an enlarged spleen. In specific embodiments, the dose is not increased if the trough concentration of free IL-15 in a sample (e.g., plasma sample) from the subject is above 50 pg/ml, 55 pg/ml, 60 pg/ml, 65 pg/ml, 70 pg/ml, 75 pg/ml, 80 pg/ml, 85 pg/ml, 90 pg/ml, 95 pg/ml, or 100 pg/ml. In specific embodiments, the dose is not increased if the trough concentration of free IL-15 in a sample (e.g., plasma sample) from the subject is 50 pg/ml to 75 pg/ml, 60 pg/ml to 75 pg/ml, 75 pg/ml to 85 pg/ml, 75 pg/ml to 100 pg/ml, 85 pg/ml to 100 pg/ml or 50 pg/ml to 100 pg/ml. In some embodiments, the method further comprises (c) administering a maintenance dose of the IL-15/IL-15Rα complex to the subject, wherein the maintenance dose reaches trough levels of free IL-15 of approximately 1 to 50 pg/ml in a sample (e.g., a plasma sample) from the subject.

In another embodiment, provided herein is a method for preventing, treating and/or managing disorders in a subject, wherein enhancement of IL-15-mediated immune function is beneficial for the prevention, treatment and/or management of such disorders, the method comprising (a) administering at least one initial low dose of an IL-15/IL-15Rα complex to the subject; and (b) administering successively higher doses of the IL-15/IL-15Rα complex to the subject, if the concentration of free IL-15 in a sample (e.g., a plasma sample) obtained from the subject a certain period of time after the administration of a dose of the IL-15/IL-15Rα complex and before administration of another dose of the IL-15/IL-15Rα complex (e.g., approximately 24 hours to approximately 48 hours after the administration of a dose of the IL-15/IL-15Rα complex and before the administration of another dose of the IL-15/IL-15Rα complex) is within normal levels or less than normal levels. In another embodiment, provided herein is a method for preventing, treating and/or managing lymphocytopenia, cancer or an infectious disease in a subject, method comprising (a) administering at least one initial low dose of an IL-15/IL-15Rα complex to the subject; and (b) administering successively higher doses of the IL-15/IL-15Rα complex to the subject, if the concentration of free IL-15 in a sample (e.g., a plasma sample) obtained from the subject a certain period of time after the administration of a dose of the IL-15/IL-15Rα complex and before administration of another dose of the IL-15/IL-15Rα complex (e.g., approximately 24 hours to approximately 48 hours after the administration of a dose of the IL-15/IL-15Rα complex and before the administration of another dose of the IL-15/IL-15Rα complex) is within normal levels or less than normal levels. In another embodiment, provided herein is a method for eradicating or reducing HIV in HIV-infected cells in a subject, comprising (a) administering at least one initial low dose of an IL-15/IL-15Rα complex to the subject; and (b) administering successively higher doses of the IL-15/IL-15Rα complex to the subject, if the concentration of free IL-15 in a sample (e.g., a plasma sample) obtained from the subject a certain period of time after the administration of a dose of the IL-15/IL-15Rα complex and before administration of another dose of the IL-15/IL-15Rα complex (e.g., approximately 24 hours to approximately 48 hours after the administration of a dose of the IL-15/IL-15Rα complex and before the administration of another dose of the IL-15/IL-15Rα complex) is within normal levels or less than normal levels. In a particular embodiment, the subject is a human subject. In a specific embodiment, the initial low dose is between 0.1 μg/kg and 1 μg/kg as determined based on the mass of single chain IL-15. In another embodiment, the initial low dose is between 0.1 μg/kg and 0.5 μg/kg as determined based on the mass of single chain IL-15. In another embodiment, the initial low dose is 0.5 μg/kg as determined based on the mass of single chain IL-15. In certain embodiments, the initial low dose is administered 1, 2, 3, 4, 5, 6 or more times, or 1 to 3, 1 to 4, 2 to 4, 2 to 5, 2 to 6, 3 to 6, 4 to 6 or 6 to 8 times. In some embodiments, the initial low dose is administered 1, 2, 3, 4, 5, 6 or more times, or 1 to 3, 1 to 4, 2 to 4, 2 to 5, 2 to 6, 3 to 6, 4 to 6 or 6 to 8 times over a 5 to 7 day, 5 to 10 day, 7 to 12 day, 7 to 14 day, 7 to 21 day or 14 to 21 day period of time. In certain embodiments, each successively higher dose is 1.2, 1.25, 1.3, 1.35, 1.4, 1.45, 1.5, 2, 2.5, 3, 3.5, 4, 4.5, 5, 5.5, or 6 times higher than the previous dose, or 1.2 to 2, 2 to 3, 2 to 4, 2 to 6, 3 to 4, 3 to 6, or 4 to 6 times higher than the previous dose. In some embodiments, each successively higher dose is 25%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 155%, 160%, 165%, 170%, 175%, 180%, 185%, 190%, 195%, or 200% higher than the previous dose. In specific embodiments, each dose is administered at least 1, 2, 3, 4, 5, 6 or more times over a 5 to 7 day, 5 to 10 day, 7 to 12 day, 7 to 14 day, 7 to 21 day or 14 to 21 day period of time. In certain embodiments, the subject is monitored for signs of an enlarged lymph node(s) and/or an enlarged spleen. In specific embodiments, the dose is not increased if the trough concentration of free IL-15 in a sample (e.g., plasma sample) from the subject is above 50 pg/ml, 55 pg/ml, 60 pg/ml, 65 pg/ml, 70 pg/ml, 75 pg/ml, 80 pg/ml, 85 pg/ml, 90 pg/ml, 95 pg/ml, or 100 pg/ml. In specific embodiments, the dose is not increased if the trough concentration of free IL-15 in a sample (e.g., plasma sample) from the subject is 50 pg/ml to 75 pg/ml, 60 pg/ml to 75 pg/ml, 75 pg/ml to 85 pg/ml, 75 pg/ml to 100 pg/ml, 85 pg/ml to 100 pg/ml or 50 pg/ml to 100 pg/ml. In some embodiments, the method further comprises (c) administering a maintenance dose of the IL-15/IL-15Rα complex to the subject, wherein the maintenance dose reaches trough levels of free IL-15 of approximately 1 to 50 pg/ml in a sample (e.g., a plasma sample) from the subject.

In another embodiment, provided herein is a method for preventing, treating and/or managing disorders in a subject, wherein enhancement of IL-15-mediated immune function is beneficial for the prevention, treatment and/or management of such disorders, the method comprising (a) administering at least one initial low dose of an IL-15/IL-15Rα complex to the subject; and (b) administering successively higher doses of the IL-15/IL-15Rα complex to the subject, if the concentration of free IL-15 in a sample (e.g., a plasma sample) obtained from the subject a certain period of time after the administration of a dose of the IL-15/IL-15Rα complex and before administration of another dose of the IL-15/IL-15Rα complex (e.g., approximately 24 hours to approximately 48 hours after the administration of a dose of the IL-15/IL-15Rα complex and before the administration of another dose of the IL-15/IL-15Rα complex) is approximately 1 pg/ml to 50 pg/ml. In another embodiment, provided herein is a method for preventing, treating and/or managing lymphocytopenia, cancer or an infectious disease in a subject, method comprising (a) administering at least one initial low dose of an IL-15/IL-15Rα complex to the subject; and (b) administering successively higher doses of the IL-15/IL-15Rα complex to the subject, if the concentration of free IL-15 in a sample (e.g., a plasma sample) obtained from the subject a certain period of time after the administration of a dose of the IL-15/IL-15Rα complex and before administration of another dose of the IL-15/IL-15Rα complex (e.g., approximately 24 hours to approximately 48 hours after the administration of a dose of the IL-15/IL-15Rα complex and before the administration of another dose of the IL-15/IL-15Rα complex) is approximately 1 pg/ml to 50 pg/ml. In another embodiment, provided herein is a method for eradicating or reducing HIV in HIV-infected cells in a subject, comprising (a) administering at least one initial low dose of an IL-15/IL-15Rα complex to the subject; and (b) administering successively higher doses of the IL-15/IL-15Rα complex to the subject, if the concentration of free IL-15 in a sample (e.g., a plasma sample) obtained from the subject a certain period of time after the administration of a dose of the IL-15/IL-15Rα complex and before administration of another dose of the IL-15/IL-15Rα complex (e.g., approximately 24 hours to approximately 48 hours after the administration of a dose of the IL-15/IL-15Rα complex and before the administration of another dose of the IL-15/IL-15Rα complex) is approximately 1 pg/ml to 50 pg/ml. In a particular embodiment, the subject is a human subject. In a specific embodiment, the initial low dose is between 0.1 μg/kg and 1 μg/kg as determined based on the mass of single chain IL-15. In another embodiment, the initial low dose is between 0.1 μg/kg and 0.5 μg/kg as determined based on the mass of single chain IL-15. In another embodiment, the initial low dose is 0.5 μg/kg as determined based on the mass of single chain IL-15. In certain embodiments, the initial low dose is administered 1, 2, 3, 4, 5, 6 or more times, or 1 to 3, 1 to 4, 2 to 4, 2 to 5, 2 to 6, 3 to 6, 4 to 6 or 6 to 8 times. In some embodiments, the initial low dose is administered 1, 2, 3, 4, 5, 6 or more times, or 1 to 3, 1 to 4, 2 to 4, 2 to 5, 2 to 6, 3 to 6, 4 to 6 or 6 to 8 times over a 5 to 7 day, 5 to 10 day, 7 to 12 day, 7 to 14 day, 7 to 21 day or 14 to 21 day period of time. In certain embodiments, each successively higher dose is 1.2, 1.25, 1.3, 1.35, 1.4, 1.45, 1.5, 2, 2.5, 3, 3.5, 4, 4.5, 5, 5.5, or 6 times higher than the previous dose, or 1.2 to 2, 2 to 3, 2 to 4, 2 to 6, 3 to 4, 3 to 6, or 4 to 6 times higher than the previous dose. In some embodiments, each successively higher dose is 25%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 155%, 160%, 165%, 170%, 175%, 180%, 185%, 190%, 195%, or 200% higher than the previous dose. In specific embodiments, each dose is administered at least 1, 2, 3, 4, 5, 6 or more times over a 5 to 7 day, 5 to 10 day, 7 to 12 day, 7 to 14 day, 7 to 21 day or 14 to 21 day period of time. In certain embodiments, the subject is monitored for signs of an enlarged lymph node(s) and/or an enlarged spleen. In specific embodiments, the dose is not increased if the trough concentration of free IL-15 in a sample (e.g., plasma sample) from the subject is above 50 pg/ml, 55 pg/ml, 60 pg/ml, 65 pg/ml, 70 pg/ml, 75 pg/ml, 80 pg/ml, 85 pg/ml, 90 pg/ml, 95 pg/ml, or 100 pg/ml. In specific embodiments, the dose is not increased if the trough concentration of free IL-15 in a sample (e.g., plasma sample) from the subject is 50 pg/ml to 75 pg/ml, 60 pg/ml to 75 pg/ml, 75 pg/ml to 85 pg/ml, 75 pg/ml to 100 pg/ml, 85 pg/ml to 100 pg/ml or 50 pg/ml to 100 pg/ml. In some embodiments, the method further comprises (c) administering a maintenance dose of the IL-15/IL-15Rα complex to the subject, wherein the maintenance dose reaches trough levels of free IL-15 of approximately 1 to 50 pg/ml in a sample (e.g., a plasma sample) from the subject.

In another embodiment, provided herein is a method for preventing, treating and/or managing disorders in a subject, wherein enhancement of IL-15-mediated immune function is beneficial for the prevention, treatment and/or management of such disorders, the method comprising (a) administering at least one initial low dose of IL-15/IL-15Rα complex to the subject, wherein the initial low dose is between 0.1 μg/kg and 1 μg/kg as determined based on the mass of single chain IL-15; and (b) administering successively higher doses of the IL-15/IL-15Rα complex to the subject, if the concentration of free IL-15 in a sample (e.g., a plasma sample) obtained from the subject a certain period of time after the administration of a dose of the IL-15/IL-15Rα complex and before administration of another dose of the IL-15/IL-15Rα complex (e.g., approximately 24 hours to approximately 48 hours after the administration of a dose of the IL-15/IL-15Rα complex and before the administration of another dose of the IL-15/IL-15Rα complex) is within normal levels or less than normal levels as determined based on the mass of single chain IL-15, wherein each successively higher dose is from two to three times higher than the previous dose. In another embodiment, provided herein is a method for preventing, treating and/or managing lymphocytopenia, cancer or an infectious disease in a subject, method comprising (a) administering at least one initial low dose of IL-15/IL-15Rα complex to the subject, wherein the initial low dose is between 0.1 μg/kg and 1 μg/kg as determined based on the mass of single chain IL-15; and (b) administering successively higher doses of the IL-15/IL-15Rα complex to the subject, if the concentration of free IL-15 in a sample (e.g., a plasma sample) obtained from the subject a certain period of time after the administration of a dose of the IL-15/IL-15Rα complex and before administration of another dose of the IL-15/IL-15Rα complex (e.g., approximately 24 hours to approximately 48 hours after the administration of a dose of the IL-15/IL-15Rα complex and before the administration of another dose of the IL-15/IL-15Rα complex) is within normal levels or less than normal levels as determined based on the mass of single chain IL-15, wherein each successively higher dose is from two to three times higher than the previous dose. In another embodiment, provided herein is a method for eradicating or reducing HIV in HIV-infected cells in a subject, comprising (a) administering at least one initial low dose of IL-15/IL-15Rα complex to the subject, wherein the initial low dose is between 0.1 μg/kg and 1 μg/kg as determined based on the mass of single chain IL-15; and (b) administering successively higher doses of the IL-15/IL-15Rα complex to the subject, if the concentration of free IL-15 in a sample (e.g., a plasma sample) obtained from the subject a certain period of time after the administration of a dose of the IL-15/IL-15Rα complex and before administration of another dose of the IL-15/IL-15Rα complex (e.g., approximately 24 hours to approximately 48 hours after the administration of a dose of the IL-15/IL-15Rα complex and before the administration of another dose of the IL-15/IL-15Rα complex) is within normal levels or less than normal levels as determined based on the mass of single chain IL-15, wherein each successively higher dose is from two to three times higher than the previous dose. In a particular embodiment, the subject is a human. In a specific embodiment, the initial low dose is 0.5 μg/kg as determined based on the mass of single chain IL-15. In certain embodiments, the initial low dose is administered 1, 2, 3, 4, 5, 6 or more times, or 1 to 3, 1 to 4, 2 to 4, 2 to 5, 2 to 6, 3 to 6, 4 to 6 or 6 to 8 times. In some embodiments, the initial low dose is administered 1, 2, 3, 4, 5, 6 or more times, or 1 to 3, 1 to 4, 2 to 4, 2 to 5, 2 to 6, 3 to 6, 4 to 6 or 6 to 8 times over a 5 to 7 day, 5 to 10 day, 7 to 12 day, 7 to 14 day, 7 to 21 day or 14 to 21 day period of time. In specific embodiments, each dose is administered at least 1, 2, 3, 4, 5, 6 or more times over a 5 to 7 day, 5 to 10 day, 7 to 12 day, 7 to 14 day, 7 to 21 day or 14 to 21 day period of time. In certain embodiments, the subject is monitored for signs of an enlarged lymph node(s) and/or an enlarged spleen. In specific embodiments, the dose is not increased if the trough concentration of free IL-15 in a sample (e.g., plasma sample) from the subject is above 50 pg/ml, 55 pg/ml, 60 pg/ml, 65 pg/ml, 70 pg/ml, 75 pg/ml, 80 pg/ml, 85 pg/ml, 90 pg/ml, 95 pg/ml, or 100 pg/ml. In specific embodiments, the dose is not increased if the trough concentration of free IL-15 in a sample (e.g., plasma sample) from the subject is 50 pg/ml to 75 pg/ml, 60 pg/ml to 75 pg/ml, 75 pg/ml to 85 pg/ml, 75 pg/ml to 100 pg/ml, 85 pg/ml to 100 pg/ml or 50 pg/ml to 100 pg/ml. In some embodiments, the method further comprises (c) administering a maintenance dose of the IL-15/IL-15Rα complex to the subject, wherein the maintenance dose reaches trough levels of free IL-15 of approximately 1 pg/ml to 50 pg/ml in a sample (e.g., a plasma sample) from the subject.

In another embodiment, provided herein is a method for preventing, treating and/or managing disorders in a subject, wherein enhancement of IL-15-mediated immune function is beneficial for the prevention, treatment and/or management of such disorders, the method comprising (a) administering at least one initial low dose of IL-15/IL-15Rα complex to the human subject, wherein the initial low dose is between 0.1 μg/kg and 1 μg/kg as determined based on the mass of single chain IL-15; and (b) administering successively higher doses of the IL-15/IL-15Rα complex to the human subject, if the concentration of free IL-15 in a sample obtained from the subject a certain period of time after the administration of a dose of the IL-15/IL-15Rα complex and before administration of another dose of the IL-15/IL-15Rα complex is approximately 1 pg/ml to 50 pg/ml, wherein each successively higher dose is from two to three times higher than the previous dose. In another embodiment, provided herein is a method for preventing, treating and/or managing lymphocytopenia, cancer or an infectious disease in a subject, method comprising (a) administering at least one initial low dose of IL-15/IL-15Rα complex to the human subject, wherein the initial low dose is between 0.1 μg/kg and 1 μg/kg as determined based on the mass of single chain IL-15; and (b) administering successively higher doses of the IL-15/IL-15Rα complex to the human subject, if the concentration of free IL-15 in a sample obtained from the subject a certain period of time after the administration of a dose of the IL-15/IL-15Rα complex and before administration of another dose of the IL-15/IL-15Rα complex is approximately 1 pg/ml to 50 pg/ml, wherein each successively higher dose is from two to three times higher than the previous dose. In another embodiment, provided herein is a method for treating lymphocytopenia, cancer or an infectious disease in a human subject, or a method for eradicating or reducing HIV in HIV-infected cells in a human subject, comprising: (a) administering at least one initial low dose of IL-15/IL-15Rα complex to the human subject, wherein the initial low dose is between 0.1 μg/kg and 1 μg/kg as determined based on the mass of single chain IL-15; and (b) administering successively higher doses of the IL-15/IL-15Rα complex to the human subject, if the concentration of free IL-15 in a sample obtained from the subject a certain period of time after the administration of a dose of the IL-15/IL-15Rα complex and before administration of another dose of the IL-15/IL-15Rα complex is approximately 1 pg/ml to 50 pg/ml, wherein each successively higher dose is from two to three times higher than the previous dose. In a particular embodiment, the subject is a human. In a specific embodiment, the initial low dose is 0.5 μg/kg as determined based on the mass of single chain IL-15. In certain embodiments, the initial low dose is administered 1, 2, 3, 4, 5, 6 or more times, or 1 to 3, 1 to 4, 2 to 4, 2 to 5, 2 to 6, 3 to 6, 4 to 6 or 6 to 8 times. In some embodiments, the initial low dose is administered 1, 2, 3, 4, 5, 6 or more times, or 1 to 3, 1 to 4, 2 to 4, 2 to 5, 2 to 6, 3 to 6, 4 to 6 or 6 to 8 times over a 5 to 7 day, 5 to 10 day, 7 to 12 day, 7 to 14 day, 7 to 21 day or 14 to 21 day period of time. In specific embodiments, each dose is administered at least 1, 2, 3, 4, 5, 6 or more times over a 5 to 7 day, 5 to 10 day, 7 to 12 day, 7 to 14 day, 7 to 21 day or 14 to 21 day period of time. In certain embodiments, the subject is monitored for signs of an enlarged lymph node(s) and/or an enlarged spleen. In specific embodiments, the dose is not increased if the trough concentration of free IL-15 in a sample (e.g., plasma sample) from the subject is above 50 pg/ml, 55 pg/ml, 60 pg/ml, 65 pg/ml, 70 pg/ml, 75 pg/ml, 80 pg/ml, 85 pg/ml, 90 pg/ml, 95 pg/ml, or 100 pg/ml. In specific embodiments, the dose is not increased if the trough concentration of free IL-15 in a sample (e.g., plasma sample) from the subject is 50 pg/ml to 75 pg/ml, 60 pg/ml to 75 pg/ml, 75 pg/ml to 85 pg/ml, 75 pg/ml to 100 pg/ml, 85 pg/ml to 100 pg/ml or 50 pg/ml to 100 pg/ml. In some embodiments, the method further comprises (c) administering a maintenance dose of the IL-15/IL-15Rα complex to the subject, wherein the maintenance dose reaches trough levels of free IL-15 of approximately 1 pg/ml to 50 pg/ml in a sample (e.g., a plasma sample) from the subject.

In another embodiment, provided herein is a method for preventing, treating and/or managing disorders in a subject, wherein enhancement of IL-15-mediated immune function is beneficial for the prevention, treatment and/or management of such disorders, the method comprising administering an IL-15/IL-15Rα complex to the human subject in an escalating dose regimen beginning with an initial low dose of between 0.1 μg/kg and 1 μg/kg as determined based on the mass of single chain IL-15, and sequentially escalating the dose two to three times over the previous dose, wherein each dose is administered at least once, twice, or thrice before elevating the dose to the next level, and wherein the concentration of free IL-15 in a sample (e.g., a plasma sample) obtained from the subject a certain period of time after the administration of a dose of the IL-15/IL-15Rα complex (e.g., approximately 24 hours to approximately 48 hours after the administration of a dose of the IL-15/IL-15Rα complex and before the administration of another dose of the IL-15/IL-15Rα complex) is monitored before elevating the dose to the next level. In another embodiment, provided herein is a method for preventing, treating and/or managing lymphocytopenia, cancer or an infectious disease in a subject, method comprising administering an IL-15/IL-15Rα complex to the human subject in an escalating dose regimen beginning with an initial low dose of between 0.1 μg/kg and 1 μg/kg as determined based on the mass of single chain IL-15, and sequentially escalating the dose two to three times over the previous dose, wherein each dose is administered at least once, twice, or thrice before elevating the dose to the next level, and wherein the concentration of free IL-15 in a sample (e.g., a plasma sample) obtained from the subject a certain period of time after the administration of a dose of the IL-15/IL-15Rα complex (e.g., approximately 24 hours to approximately 48 hours after the administration of a dose of the IL-15/IL-15Rα complex and before the administration of another dose of the IL-15/IL-15Rα complex) is monitored before elevating the dose to the next level. In another embodiment, provided herein is a method for eradicating or reducing HIV in HIV-infected cells in a subject, the method comprising administering an IL-15/IL-15Rα complex to the subject in an escalating dose regimen beginning with an initial low dose of between 0.1 μg/kg and 1 μg/kg as determined based on the mass of single chain IL-15, and sequentially escalating the dose two to three times over the previous dose, wherein each dose is administered at least once, twice, or thrice before elevating the dose to the next level, and wherein the concentration of free IL-15 in a sample (e.g., a plasma sample) obtained from the subject a certain period of time after the administration of a dose of the IL-15/IL-15Rα complex (e.g., approximately 24 hours to approximately 48 hours after the administration of a dose of the IL-15/IL-15Rα complex and before the administration of another dose of the IL-15/IL-15Rα complex) is monitored before elevating the dose to the next level. In a particular embodiment, the subject is a human subject. In a specific embodiment, the initial low dose is 0.5 μg/kg as determined based on the mass of single chain IL-15. In some embodiments, the initial low dose is administered 1, 2, 3, 4, 5, or 6 times, or 1 to 3, 1 to 4, 2 to 4, 2 to 5, 2 to 6, 3 to 6, or 4 to 6 times over a 5 to 7 day, 5 to 10 day, 7 to 12 day, 7 to 14 day, 7 to 21 day or 14 to 21 day period of time. In specific embodiments, each dose is administered at least 1, 2, 3, 4, 5, or 6 or more times over a 5 to 7 day, 5 to 10 day, 7 to 12 day, 7 to 14 day, 7 to 21 day or 14 to 21 day period of time. In certain embodiments, the subject is monitored for signs of an enlarged lymph node(s) and/or an enlarged spleen. In specific embodiments, the dose is not increased if the trough concentration of free IL-15 in a sample (e.g., plasma sample) from the subject is above 50 pg/ml, 55 pg/ml, 60 pg/ml, 65 pg/ml, 70 pg/ml, 75 pg/ml, 80 pg/ml, 85 pg/ml, 90 pg/ml, 95 pg/ml, or 100 pg/ml. In specific embodiments, the dose is not increased if the trough concentration of free IL-15 in a sample (e.g., plasma sample) from the subject is 50 pg/ml to 75 pg/ml, 60 pg/ml to 75 pg/ml, 75 pg/ml to 85 pg/ml, 75 pg/ml to 100 pg/ml, 85 pg/ml to 100 pg/ml or 50 pg/ml to 100 pg/ml. In some embodiments, the method further comprises administering a maintenance dose of the IL-15/IL-15Rα complex to the subject, wherein the maintenance dose reaches trough levels of free IL-15 concentration of approximately 5 to 50 pg/ml in a sample (e.g., a plasma sample) from the subject. In some embodiments, the method further comprises administering a maintenance dose of the IL-15/IL-15Rα complex to the subject, wherein the maintenance dose reaches trough levels of free IL-15 of approximately 1 to 50 pg/ml in a sample (e.g., a plasma sample) from the subject.

In another embodiment, provided herein is a method for preventing, treating and/or managing disorders in a subject, wherein enhancement of IL-15-mediated immune function is beneficial for the prevention, treatment and/or management of such disorders, the method comprising administering an IL-15/IL-15Rα complex to the human subject in an escalating dose regimen beginning with an initial low dose of between 0.1 μg/kg and 1 μg/kg as determined based on the mass of single chain IL-15, and sequentially escalating the dose 1.2, 1.3, 1.4, 1.5, 1.6, 1.7, 1.8, or 1.9 fold over the previous dose, wherein each dose is administered at least once, twice, or thrice before elevating the dose to the next level, and wherein the concentration of free IL-15 in a sample (e.g., a plasma sample) obtained from the subject a certain period of time after the administration of a dose of the IL-15/IL-15Rα complex (e.g., approximately 24 hours to approximately 48 hours after the administration of a dose of the IL-15/IL-15Rα complex and before the administration of another dose of the IL-15/IL-15Rα complex) is monitored before elevating the dose to the next level. In another embodiment, provided herein is a method for preventing, treating and/or managing lymphocytopenia, cancer or an infectious disease in a subject, method comprising administering an IL-15/IL-15Rα complex to the human subject in an escalating dose regimen beginning with an initial low dose of between 0.1 μg/kg and 1 μg/kg as determined based on the mass of single chain IL-15, and sequentially escalating the dose 1.2, 1.3, 1.4, 1.5, 1.6, 1.7, 1.8, or 1.9 fold over the previous dose, wherein each dose is administered at least once, twice, or thrice before elevating the dose to the next level, and wherein the concentration of free IL-15 in a sample (e.g., a plasma sample) obtained from the subject a certain period of time after the administration of a dose of the IL-15/IL-15Rα complex (e.g., approximately 24 hours to approximately 48 hours after the administration of a dose of the IL-15/IL-15Rα complex and before the administration of another dose of the IL-15/IL-15Rα complex) is monitored before elevating the dose to the next level. In another embodiment, provided herein is a method for eradicating or reducing HIV in HIV-infected cells in a subject, the method comprising administering an IL-15/IL-15Rα complex to the subject in an escalating dose regimen beginning with an initial low dose of between 0.1 μg/kg and 1 μg/kg as determined based on the mass of single chain IL-15, and sequentially escalating the dose 1.2, 1.3, 1.4, 1.5, 1.6, 1.7, 1.8, or 1.9 fold over the previous dose, wherein each dose is administered at least once, twice, or thrice before elevating the dose to the next level, and wherein the concentration of free IL-15 in a sample (e.g., a plasma sample) obtained from the subject a certain period of time after the administration of a dose of the IL-15/IL-15Rα complex (e.g., approximately 24 hours to approximately 48 hours after the administration of a dose of the IL-15/IL-15Rα complex and before the administration of another dose of the IL-15/IL-15Rα complex) is monitored before elevating the dose to the next level. In a particular embodiment, the subject is a human subject. In a specific embodiment, the initial low dose is 0.5 μg/kg as determined based on the mass of single chain IL-15. In some embodiments, the initial low dose is administered 1, 2, 3, 4, 5, or 6 times, or 1 to 3, 1 to 4, 2 to 4, 2 to 5, 2 to 6, 3 to 6, or 4 to 6 times over a 5 to 7 day, 5 to 10 day, 7 to 12 day, 7 to 14 day, 7 to 21 day or 14 to 21 day period of time. In specific embodiments, each dose is administered at least 1, 2, 3, 4, 5, or 6 or more times over a 5 to 7 day, 5 to 10 day, 7 to 12 day, 7 to 14 day, 7 to 21 day or 14 to 21 day period of time. In certain embodiments, the subject is monitored for signs of an enlarged lymph node(s) and/or an enlarged spleen. In specific embodiments, the dose is not increased if the trough concentration of free IL-15 in a sample (e.g., plasma sample) from the subject is above 50 pg/ml, 55 pg/ml, 60 pg/ml, 65 pg/ml, 70 pg/ml, 75 pg/ml, 80 pg/ml, 85 pg/ml, 90 pg/ml, 95 pg/ml, or 100 pg/ml. In specific embodiments, the dose is not increased if the trough concentration of free IL-15 in a sample (e.g., plasma sample) from the subject is 50 pg/ml to 75 pg/ml, 60 pg/ml to 75 pg/ml, 75 pg/ml to 85 pg/ml, 75 pg/ml to 100 pg/ml, 85 pg/ml to 100 pg/ml or 50 pg/ml to 100 pg/ml. In some embodiments, the method further comprises administering a maintenance dose of the IL-15/IL-15Rα complex to the subject, wherein the maintenance dose reaches trough levels of free IL-15 concentration of approximately 5 to 50 pg/ml in a sample (e.g., a plasma sample) from the subject. In some embodiments, the method further comprises administering a maintenance dose of the IL-15/IL-15Rα complex to the subject, wherein the maintenance dose reaches trough levels of free IL-15 of approximately 1 to 50 pg/ml in a sample (e.g., a plasma sample) from the subject.

In another embodiment, provided herein is a method for preventing, treating and/or managing disorders in a subject, wherein enhancement of IL-15-mediated immune function is beneficial for the prevention, treatment and/or management of such disorders, the method comprising administering an IL-15/IL-15Rα complex to the subject in an escalating dose regimen at the following sequential doses: (i) 0.5 μg/kg; (ii) 1 μg/kg; (iv) 2 μg/kg; (v) 4 μg/kg; (v) 8 μg/kg; and (vi) 16 μg/kg, wherein the doses are determined based on the mass of single chain IL-15, wherein each dose is administered at least once, twice or thrice before elevating the dose to the next level, and wherein the concentration of free IL-15 in a sample (e.g., a plasma sample) obtained from the subject a certain period of time after the administration of a dose of the IL-15/IL-15Rα complex (e.g., approximately 24 hours to approximately 48 hours after the administration of a dose of the IL-15/IL-15Rα complex and before the administration of another dose of the IL-15/IL-15Rα complex) is monitored before elevating the dose to the next level. In another embodiment, provided herein is a method for preventing, treating and/or managing lymphocytopenia, cancer or an infectious disease in a subject, method comprising administering an IL-15/IL-15Rα complex to the subject in an escalating dose regimen at the following sequential doses: (i) 0.5 μg/kg; (ii) 1 μg/kg; (iv) 2 μg/kg; (v) 4 μg/kg; (v) 8 μg/kg; and (vi) 16 μg/kg, wherein the doses are determined based on the mass of single chain IL-15, wherein each dose is administered at least once, twice or thrice before elevating the dose to the next level, and wherein the concentration of free IL-15 in a sample (e.g., a plasma sample) obtained from the subject a certain period of time after the administration of a dose of the IL-15/IL-15Rα complex (e.g., approximately 24 hours to approximately 48 hours after the administration of a dose of the IL-15/IL-15Rα complex and before the administration of another dose of the IL-15/IL-15Rα complex) is monitored before elevating the dose to the next level. In another embodiment, provided herein is a method for eradicating or reducing HIV in HIV-infected cells in a subject, comprising administering an IL-15/IL-15Rα complex to the subject in an escalating dose regimen at the following sequential doses: (i) 0.5 μg/kg; (ii) 1 μg/kg; (iv) 2 μg/kg; (v) 4 μg/kg; (v) 8 μg/kg; and (vi) 16 μg/kg, wherein the doses are determined based on the mass of single chain IL-15, wherein each dose is administered at least once, twice or thrice before elevating the dose to the next level, and wherein the concentration of free IL-15 in a sample (e.g., a sample sample) obtained from the subject a certain period of time after the administration of a dose of the IL-15/IL-15Rα complex (e.g., approximately 24 hours to approximately 48 hours after the administration of a dose of the IL-15/IL-15Rα complex and before the administration of another dose of the IL-15/IL-15Rα complex) is monitored before elevating the dose to the next level. In a particular embodiment, the subject is a human subject. In some embodiments, the initial low dose is administered 1, 2, 3, 4, 5, or 6 times, or 1 to 3, 1 to 4, 2 to 4, 2 to 5, 2 to 6, 3 to 6, or 4 to 6 times over a 5 to 7 day, 5 to 10 day, 7 to 12 day, 7 to 14 day, 7 to 21 day or 14 to 21 day period of time. In specific embodiments, each dose is administered at least 1, 2, 3, 4, 5, or 6 or more times over a 5 to 7 day, 5 to 10 day, 7 to 12 day, 7 to 14 day, 7 to 21 day or 14 to 21 day period of time. In certain embodiments, the subject is monitored for signs of an enlarged lymph node(s) and/or an enlarged spleen. In specific embodiments, the dose is not increased if the trough concentration of free IL-15 in a sample (e.g., plasma sample) from the subject is above 50 pg/ml, 55 pg/ml, 60 pg/ml, 65 pg/ml, 70 pg/ml, 75 pg/ml, 80 pg/ml, 85 pg/ml, 90 pg/ml, 95 pg/ml, or 100 pg/ml. In specific embodiments, the dose is not increased if the trough concentration of free IL-15 in a sample (e.g., plasma sample) from the subject is 50 pg/ml to 75 pg/ml, 60 pg/ml to 75 pg/ml, 75 pg/ml to 85 pg/ml, 75 pg/ml to 100 pg/ml, 85 pg/ml to 100 pg/ml or 50 pg/ml to 100 pg/ml. In some embodiments, the method further comprises administering a maintenance dose of the IL-15/IL-15Rα complex to the subject, wherein the maintenance dose reaches trough levels of free IL-15 concentration of approximately 1 to 50 pg/ml in a sample (e.g., a plasma sample) from the subject. In some embodiments, the method further comprises further comprising administering a maintenance dose of 0.1 μg/kg to 10 μg/kg, 0.1 μg/kg to 20 μg/kg, 0.1 to 25 μg/kg, or 0.1 μg/kg to 30 μg/kg of IL-15/IL-15Rα complex to the subject, wherein the dose is determined based on the mass of single chain IL-15.

In specific embodiments, the methods described herein are not cylical in nature. In other words, in specific embodiments, the methods described herein do not include a cyclical administration regimen, wherein the cycle comprises administering a dose of the IL-15/IL-15Rα complex for a certain period of time (e.g., 1 to 4 weeks) followed by another period of time when the subject is not administered a dose of the IL-15/IL-15Rα complex (e.g., 1 week to 2 months) and this cycle is repeated any number of times (e.g, the cycle is repeated 2, 3, 4, 5, 6, 7, 8, 9, 10 or more times).

In another embodiment, provided herein is a method for treating lymphocytopenia, cancer or an infectious disease in a human subject, or a method for eradicating or reducing HIV in HIV-infected cells in a human subject, comprising administering an IL-15/IL-15Rα complex to the human subject in an escalating dose regimen beginning with an initial low dose of an IL-15/IL-15Rα complex to the human subject one to five times, and sequentially escalating the dose by at least 25%, 50%, 75%, 100%, 150%, or 200% over the previous dose, wherein each dose is administered at least once, twice, or thrice before elevating the dose to the next level, and wherein the concentration of free IL-15 in a sample obtained from the subject a certain period of time after the administration of a dose of the IL-15/IL-15Rα complex is monitored before elevating the dose to the next level.

In another embodiment, provided herein is a method for treating lymphocytopenia, cancer or an infectious disease in a human subject, or a method for eradicating or reducing HIV in HIV-infected cells in a human subject, comprising administering an IL-15/IL-15Rα complex to the human subject in an escalating dose regimen beginning with an initial low dose in the range of 0.1 μg/kg and 10 μg/kg as determined based on the mass of single chain IL-15, and sequentially escalating the dose by at least 25%, 50%, 75%, 100%, 150%, or 200% over the previous dose, wherein each dose is administered at least once, twice, or thrice before elevating the dose to the next level, and wherein the concentration of free IL-15 in a sample obtained from the subject a certain period of time after the administration of a dose of the IL-15/IL-15Rα complex is monitored before elevating the dose to the next level. In specific embodiments of the methods provided herein, an initial low dose is in the range of 0.5 μg/kg and 10 μg/kg as determined based on the mass of single chain IL-15. In specific embodiments of the methods provided herein, an initial low dose is in the range of 0.2 μg/kg and 10 μg/kg as determined based on the mass of single chain IL-15.

In another embodiment, provided herein is a method for treating lymphocytopenia, cancer or an infectious disease in a human subject, or a method for eradicating or reducing HIV in HIV-infected cells in a human subject, comprising administering an IL-15/IL-15Rα complex to the human subject in an escalating dose regimen at the following sequential doses: (i) 2 μg/kg; (ii) 4 μg/kg; (iv) 8 μg/kg; (v) 16 μg/kg; (v) 32 μg/kg; and (vi) 64 μg/kg, wherein the doses are determined based on the mass of single chain IL-15, wherein each dose is administered at least once, twice or thrice before elevating the dose to the next level, and wherein the concentration of free IL-15 in a sample obtained from the subject a certain period of time after the administration of a dose of the IL-15/IL-15Rα complex is monitored before elevating the dose to the next level.

In another embodiment, provided herein is a method for treating lymphocytopenia, cancer or an infectious disease in a human subject, or a method for eradicating or reducing HIV in HIV-infected cells in a human subject, comprising administering an IL-15/IL-15Rα complex to the human subject in an escalating dose regimen at the following sequential doses: (i) 5 μg/kg; (ii) 10 μg/kg; (iv) 20 μg/kg; (v) 40 μg/kg; (v) 80 μg/kg; and (vi) 120 μg/kg, wherein the doses are determined based on the mass of single chain IL-15, wherein each dose is administered at least once, twice or thrice before elevating the dose to the next level, and wherein the concentration of free IL-15 in a sample obtained from the subject a certain period of time after the administration of a dose of the IL-15/IL-15Rα complex is monitored before elevating the dose to the next level.

In another embodiment, provided herein is a method for treating lymphocytopenia, cancer or an infectious disease in a human subject, or a method for eradicating or reducing HIV in HIV-infected cells in a human subject, comprising administering an IL-15/IL-15Rα complex to the human subject in an escalating dose regimen at the following sequential doses: (i) 0.5 μg/kg; (ii) 1 μg/kg; (iv) 2 μg/kg; (v) 4 μg/kg; (v) 8 μg/kg; and (vi) 16 μg/kg, wherein the doses are determined based on the mass of single chain IL-15, wherein each dose is administered at least once, twice or thrice before elevating the dose to the next level. In particular embodiments, the concentration of free IL-15 in a sample obtained from the subject a certain period of time after the administration of a dose of the IL-15/IL-15Rα complex is monitored before elevating the dose to the next level.

In another embodiment, provided herein is a method for treating lymphocytopenia, cancer or an infectious disease in a human subject, or a method for eradicating or reducing HIV in HIV-infected cells in a human subject, comprising administering an IL-15/IL-15Rα complex to the human subject in an escalating dose regimen beginning with an initial low dose (in, e.g., the range of 0.1 μg/kg and 1 μg/kg as determined based on the mass of single chain IL-15), and sequentially escalating (e.g., by about 10%, 20%, 30%, 40%, 50%, 60%, 70%, 80%, 90%, 100%, 125%, 150%, 175%, 200%, 225%, 250%, 275% or 300%) the dose over the previous dose every two days initially for a period of time (e.g., 1, 2, 3 or 4 weeks) and then escalating the dose gradually everyday over the previous dose for a period of time (e.g., 1, 2, 3 or 4 weeks). In certain embodiments, the initial low dose is 0.1 μg/kg, 0.2 μg/kg, 0.3 μg/kg, 0.4 μg/kg, 0.5 μg/kg, 0.6 μg/kg, 0.7 μg/kg, 0.8 μg/kg, 0.9 μg/kg, or 1 μg/kg as determined based on the mass of single chain IL-15. In some embodiments, each dose is administered at least once, twice or thrice before the dose is escalated.

In specific embodiments, provided herein is a method for treating lymphocytopenia, cancer or an infectious disease in a human subject, or a method for eradicating or reducing HIV in HIV-infected cells in a human subject, comprising administering an IL-15/IL-15Rα complex to the human subject in an escalating dose regimen beginning with an initial low dose as determined based on the mass of single chain IL-15, and sequentially escalating (e.g., by about 10%, 20%, 30%, 40%, 50%, 60%, 70%, 80%, 90%, 100%, 125%, 150%, 175%, 200%, 250%, or 300%) the dose over the previous dose for a period of time (e.g., 1, 2, 3, 4, 5, 6 or more weeks) and then administering an IL-15/IL-15Rα complex to the human subject in a maintenance dose for a period of time. In certain embodiments, the initial low dose is 0.1 μg/kg, 0.2 μg/kg, 0.3 μg/kg, 0.4 μg/kg, 0.5 μg/kg, 0.6 μg/kg, 0.7 μg/kg, 0.8 μg/kg, 0.9 μg/kg, or 1 μg/kg as determined based on the mass of single chain IL-15. In some embodiments, each dose is administered at least once, twice or thrice before the dose is escalated. In certain embodiments, the dose is escalated every day, every 2 days, or every 3 days. In specific embodiments, in accordance with the methods described herein, the maintenance dose is at least ½ or ¼ lower than the highest escalating dose administered. In specific embodiments, in accordance with the methods described herein, the maintenance dose is at least 1%, 2%, 3%, 4%, 5%, 6%, 7%, 8%, 9%, 10%, 15%, 20%, 25%, 30%, 35%, 40%, 45%, or 50% lower than the highest escalating dose administered.

In specific embodiments, in accordance with the methods described herein, each dose is administered once, three times a week for two weeks. In specific embodiments, in accordance with the methods described herein, each dose is administered once, three times a week for two, three, or four weeks, or more than once, six times per week for two, three, or four weeks. In specific embodiments, in accordance with the methods described herein, each dose is administered once, every other day, for two, three, or four weeks. In specific embodiments, in accordance with the methods described herein, each dose is administered once a day for one, two, three, or four weeks.

In specific embodiments, the methods described herein further comprise administering to the human subject one or more other therapies. In particular embodiments, the one or more other therapies is an antibody (e.g., monoclonal antibody) that immunospecifically binds to Her2, PD-1 or a ligand of PD-1. In particular embodiments, the one or more other therapies is an histone deacetylase (HDAC) inhibitor (e.g., panobinstat or vorinostat), TLR7 agonist, an antibody (e.g., monoclonal antibody), or a cytokine (e.g., IL-7).

The IL-15/IL-15Rα complex administered to a subject in accordance with the methods described herein may comprise native IL-15 or an IL-15 derivative covalently or noncovalently bound to native IL-15Rα or an IL-15Rα derivative. In one embodiment, the IL-15/IL-15Rα complex comprises native IL-15 and native IL-15Rα. In another embodiment, the IL-15/IL-15Rα complex comprises an IL-15 derivative and native IL-15Rα. In another embodiment, the IL-15/IL-15Rα complex is in the native heterodimeric form. In another embodiment, the IL-15 is human IL-15 and IL-15Rα is human IL-15Rα. In a specific embodiment, the human IL-15 comprises the amino acid sequence of SEQ ID NO: 1 or amino acid residues 49 to 162 of SEQ ID NO:1 and the human IL-15Rα comprises the amino acid sequence of SEQ ID NO: 3 or a fragment thereof. In another embodiment, the IL-15 comprises the amino acid sequence of SEQ ID NO:1 or amino acid residues 49 to 162 of SEQ ID NO:1 and the IL-15Rα comprises the amino acid sequence of SEQ ID NO:4, 32, 33, 34, 35, 36, 37, 38, 39, 40, 41 or 45. In specific embodiments, the human IL-15 comprises amino acid residues 49 to 162 of the amino acid sequence of SEQ ID NO: 1 and human IL-15Rα comprises the amino acid sequence of SEQ ID NO: 33. In certain embodiments, the IL-15Rα is glycosylated such that glycosylation accounts for at least or more than 20%, 30%, 40% or 50% of the mass of the IL-15Rα. In another embodiment, the IL-15/IL-15Rα complex comprises native IL-15 and an IL-15Rα derivative. In another embodiment, the IL-15/IL-15Rα complex comprises an IL-15 derivative and an IL-15Rα derivative. In one embodiment, the IL-15Rα derivative is a soluble form of the native IL-15Rα. In another embodiment, the IL-15Rα derivative comprises mutation that inhibits cleavage by an endogenous protease. In a specific embodiment, the extracellular domain cleavage site of IL-15Rα is replaced with a cleavage site that is specifically recognized by a heterologous protease. In one embodiment, the extracellular domain cleavage site of IL-15Rα is replaced with a heterologous extracellular domain cleavage site (e.g., heterologous transmembrane domain that is recognized and cleaved by another enzyme unrelated to the endogenous processing enzyme that cleaves the IL-15Rα).

In some embodiments, the human IL-15Rα is modified either simultaneously or alternatively as follows: 0-glycosylated on Thr5 of amino acid sequence NWELTASASHQPPGVYPQG (SEQ ID NO: 42) in the IL-15Rα; 0-glycosylated on Ser7 of amino acid sequence NWELTASASHQPPGVYPQG (SEQ ID NO: 42) in the IL-15Rα; N-glycosylated on Ser 8 of amino acid sequence ITCPPPMSVEHADIWVK (SEQ ID NO: 43) in the IL-15Rα; N-glycosylated on Ser 8 of amino acid sequence ITCPPPMSVEHADIWVKSYSLYSRERYICNS (SEQ ID NO: 44) in the IL-15Rα; N-glycosylated on Ser 18 of amino acid sequence ITCPPPMSVEHADIWVKSYSLYSRERYICNS (SEQ ID NO: 44) in the IL-15Rα; N-glycosylated on Ser 20 of amino acid sequence ITCPPPMSVEHADIWVKSYSLYSRERYICNS (SEQ ID NO: 44) in the IL-15Rα; N-glycosylated on Ser 23 of amino acid sequence ITCPPPMSVEHADIWVKSYSLYSRERYICNS (SEQ ID NO: 44) in the IL-15Rα; and/or N-glycosylated on Ser 31 of amino acid sequence ITCPPPMSVEHADIWVKSYSLYSRERYICNS (SEQ ID NO: 44) in the IL-15Rα.

In some embodiments, the IL-15Rα is a soluble form of IL-15Rα. In a specific embodiment, the soluble form of IL-15Rα is a soluble form of human IL-15Rα. In a particular embodiment, the human IL-15Rα comprises SEQ ID NO: 3. In one embodiment, the last amino acids at the C-terminal end of the soluble form of human IL-15Rα consist of amino acid residues PQGHSDTT (SEQ ID NO: 26), wherein T is at the C-terminal end of the amino acid sequence. In one embodiment, the last amino acids at the C-terminal end of the soluble form of human IL-15Rα consist of amino acid residues PQGHSDT (SEQ ID NO: 27), wherein T is at the C-terminal end of the amino acid sequence. In one embodiment, the last amino acids at the C-terminal end of the soluble form of human IL-15Rα consist of amino acid residues PQGHSD (SEQ ID NO: 28), wherein D is at the C-terminal end of the amino acid sequence. In one embodiment, the last amino acids at the C-terminal end of the soluble form of IL-15Rα consist of amino acid residues PQGHS (SEQ ID NO: 29), wherein S is at the C-terminal end of the amino acid sequence. In one embodiment, the last amino acids at the C-terminal end of the soluble form of human IL-15Rα consist of amino acid residues PQGH (SEQ ID NO: 30), wherein H is at the C-terminal end of the amino acid sequence. In one embodiment, the last amino acids at the C-terminal end of the soluble form of human IL-15Rα consist of amino acid residues PQG (SEQ ID NO: 31), wherein G is at the C-terminal end of the amino acid sequence. In some embodiments, the IL-15 is human IL-15. In specific embodiments of the methods provided herein, the human IL-15 comprises SEQ ID NO:1 or amino acid residues 49 to 162 of SEQ ID NO:1.

In certain embodiments, an IL-15/IL-15Rα complex is associated with a cell. In a specific embodiment, the extracellular domain cleavage site of IL-15Rα that is cleaved by an endogenous processing enzyme is replaced with a heterologous domain (e.g., heterologous transmembrane domain) or a synthetic amino acid sequence that does not allow cleavage and generation of soluble IL-15Rα. In certain embodiments, the extracellular domain cleavage site of IL-15Rα that is cleaved by an endogenous processing enzyme is mutated to inhibit cleavage and generation of soluble IL-15Rα.

In addition to IL-15 and IL-15Rα, the IL-15/IL-15Rα complexes may comprise a heterologous molecule. The heterologous molecule may be conjugated to IL-15 and/or IL-15Rα. The heterologous molecule is conjugated to IL-15 or IL-15Rα in a manner that does not interfere or prevent IL-15 and IL-15Rα from binding to one another and does not interfere or prevent the interaction between the IL-15/IL-15Rα complex and the βγ subunits of the IL-15 receptor. In some embodiments, the heterologous molecule is an antigen associated with a disease that one intends to prevent, treat and/or manage. Non-limiting examples of such antigens include viral antigens, bacterial antigens, parasitic antigens, and tumor antigens. In other embodiments, the heterologous molecule is an antibody that specifically binds to an antigen associated with a disease that one intends to prevent, treat and/or manage. In some embodiments, the antibody specifically binds to a cellular antigen (e.g., a receptor) expressed by a cell that one desires to target. In some embodiments, the heterologous molecule increases protein stability. In certain embodiments, the heterologous molecule is an Fc domain of an immunoglobulin or a fragment thereof. In a specific embodiment, IL-15Rα is conjugated/fused to the Fc domain of an immunoglobulin (e.g., an IgG1). In other embodiments, the heterologous molecule is not an Fc domain of an immunoglobulin molecule or a fragment thereof.

In certain embodiments, the IL-15/IL-15Rα complex is administered subcutaneously to a subject in accordance with the methods described herein. In some embodiments, the IL-15/IL-15Rα complex is administered intravenously or intramuscularly to a subject in accordance with the methods described herein. In certain embodiments, the IL-15/IL-15Rα complex is administered intratumorally to a subject in accordance with the methods described herein. In some embodiments, the IL-15/IL-15Rα complex is administered locally to a site (e.g., a tumor site, a site of infection) in a subject in accordance with the methods described herein.

In certain embodiments, in accordance with the methods described herein, the cancer is melanoma, colon cancer, lung cancer, prostate cancer or renal cell carcinoma. In specific embodiments, in accordance with the methods described herein, the cancer is metastastic. In certain embodiments, in accordance with the methods described herein, the infectious disease is chronic. In a specific embodiment, in accordance with the methods described herein, the infectious disease is AIDS, pneumonia or tuberculosis.

3.1 Terminology

As used herein, the terms "about" and "approximately," when used to modify a numeric value or numeric range, indicate that the numeric value or range as well as reasonable deviations from the value or range, typically 10% or 20% above and 10% or 20% below the value or range, are within the intended meaning of the recited value or range.

As used herein, the terms "disease" and "disorder" are used interchangeably to refer to a condition, in particular, a pathological condition. In certain embodiments, the terms "disease" and "disorder" are used interchangeably to refer to a disease affected by IL-15 signal transduction.

As used herein, the term "peak level" and "peak concentration" refer to the highest levels of free IL-15 in a sample (e.g., a plasma sample) from a subject over a period of time. In certain embodiments, the period of time is the entire period of time between the administration of one dose of IL-15/IL-15Rα complex and another dose of the complex. In some embodiments, the period of time is approximately 24 hours, approximately 48 hours or approximately 72 hours after the administration of one dose of IL-15/IL-15Rα complex and before the administration of another dose of the complex.

As used herein, the terms "trough level" and "trough concentration" refer to the lowest levels of free IL-15 in a sample (e.g., a plasma sample) from a subject over a period of time. In certain embodiments, the period of time is the entire period of time between the administration of one dose of IL-15/IL-15Rα complex and another dose of the complex. In some embodiments, the period of time is approximately 24 hours, approximately 48 hours or approximately 72 hours after the administration of one dose of IL-15/IL-15Rα complex and before the administration of another dose of the complex.

As used herein, the term "normal levels" in the context of the concentration of free IL-15 refers to the concentration of free IL-15 found in a sample obtained or derived from a healthy subject. Basal plasma levels of free IL-15 in healthy subjects are approximately 1 pg/ml in humans, approximately 8-15 pg/ml in monkeys (such as macaques), and approximately 12 pg/ml in rodents (such as mice). Normal levels depend on the exact method used for measurement and may vary because of this.

As used herein, the phase "an effective ratio of IL-15 to lymphocyte cell number" means that the amount of IL-15 available for lymphocytes keeps pace with the number of lymphocytes so that lymphocytes continue proliferating or survive. In a specific embodiment, a trough concentration of approximately 1 pg/ml to 5 pg/ml, approximately 1 pg/ml to 10 pg/ml, approximately 1 pg/ml to 15 pg/ml, approximately 1 pg/ml to 20 pg/ml, approximately 1 to 25 pg/ml, approximately 1 pg/ml to 30 pg/ml, approximately 1 pg/ml to 40 pg/ml, or approximately 1 pg/ml to 50 pg/ml of free IL-15 in a plasma sample from a subject is indicative of "an effective ratio of IL-15 to lymphocyte cell number." In a specific embodiment, a trough concentration of below 50 pg/ml, below 45 pg/ml, below 40 pg/ml, below 35 pg/ml, below 30 pg/ml, below 25 pg/ml, below 20 pg/ml, below 15 pg/ml, below 10 pg/ml, below 5 pg/ml, or below 1 pg/ml of free IL-15 in a plasma sample from a subject is indicative of "an effective ratio of IL-15 to lymphocyte cell number." In another specific embodiment, a trough concentration above 50 pg/ml, 55 pg/ml, 60 pg/ml, 65 pg/ml, 70 pg/ml, 75 pg/ml, 80 pg/ml, 85 pg/ml, 90 pg/ml, 95 pg/ml, or 100 pg/ml of free IL-15 in a plasma sample from a subject is indicative that the ratio of IL-15 to lymphocyte cell number is excessive. In another specific embodiment, a trough concentration 50 pg/ml to 75 pg/ml, 60 pg/ml to 75 pg/ml, 75 pg/ml to 85 pg/ml, 75 pg/ml to 100 pg/ml, 85 pg/ml to 100 pg/ml or 50 pg/ml to 100 pg/ml of free IL-15 in a plasma sample from a subject is indicative that the ratio of IL-15 to lymphocyte cell number is excessive. Any method known to one skilled in the art for measuring free IL-15 concentration in a sample from a subject may be used, such as, e.g., an immunoassay. In a specific embodiment, an ELISA is used to measure the free IL-15 concentration in a sample from a subject.

As used herein, the terms "specifically binds," "specifically recognizes" and analogous terms in the context of a receptor (e.g., native IL-15Rα or IL-15 receptor βγ) and a ligand (e.g., native IL-15) interaction refer to the specific binding or association between the ligand and receptor. Preferably, the ligand has higher affinity for the receptor than for other molecules. In a specific embodiment, the ligand is native IL-15 and the native receptor is IL-15Rα. In another specific embodiment, the ligand is the native IL-15/IL-15Rα complex and the native receptor is the βγ receptor complex. In a further embodiment, the IL-15/IL-15Rα complex binds to the βγ receptor complex and activates IL-15 mediated signal transduction. Ligands that specifically bind a receptor can be identified, for example, by immunoassays, BIAcore, or other techniques known to those of skill in the art.

As used herein, the terms "native IL-15" and "native interleukin-15" in the context of proteins or polypeptides refer to any naturally occurring mammalian interleukin-15 amino acid sequences, including immature or precursor and mature forms. Non-limiting examples of GeneBank Accession Nos. for the amino acid sequence of various species of native mammalian interleukin-15 include NP_000576 (human, immature form), CAA62616 (human, immature form), NP_001009207 (*Felis catus*, immature form), AAB94536 (*rattus*, immature form), AAB41697 (*rattus*, immature form), NP_032383 (*Mus musculus*, immature form), AAR19080 (canine), AAB60398 (*macaca mulatta*, immature form), AAI00964 (human, immature form), AAH23698 (*mus musculus*, immature form), and AAH18149 (human). In one embodiment, the amino acid sequence of the immature/precursor form of native human IL-15, which comprises the long signal peptide (underlined) and the mature human native IL-15 (italicized), is provided:

(SEQ ID NO: 1; FIG. 1B)

MRISKPHLRSISIQCYLCLLLNSHFLTEAGIHVFILGCFSAGLPKTEA

*NWVNVISDLKKIEDLIQSMHIDATLYTESDVHPSCKVTAMKCFLLELQV*

*ISLESGDASIHDTVENLIILANNSLSSNGNVTESGCKECEELEEKNIKE*

*FLQSFVHIVQMFINTS.*

In some embodiments, native IL-15 is the immature or precursor form of a naturally occurring mammalian IL-15. In other embodiments, native IL-15 is the mature form of a naturally occurring mammalian IL-15. In a specific embodiment, native IL-15 is the precursor form of naturally occurring human IL-15. In another embodiment, native IL-15 is the mature form of naturally occurring human IL-15. In one embodiment, the native IL-15 protein/polypeptide is isolated or purified.

As used herein, the terms "native IL-15" and "native "interleukin-15" in the context of nucleic acids refer to any naturally occurring nucleic acid sequences encoding mammalian interleukin-15, including the immature or precursor and mature forms. Non-limiting examples of GeneBank Accession Nos. for the nucleotide sequence of various species of native mammalian IL-15 include NM 000585 (human), NM 008357 (*Mus musculus*), and RNU69272 (*rattus norvegicus*). In one embodiment, the nucleotide sequence encoding the immature/precursor form of native human IL-15, which comprises the nucleotide sequence encoding the long signal peptide (underlined) and the nucleotide sequence encoding the mature human native IL-15 (italicized), is provided:

(SEQ ID NO: 2; FIG. IA)

atgagaat ttcgaaacca catttgagaa gtatttccat ccagtgctac ttgtgtttac ttctaaacag tcattttcta actgaagctg gcattcatgt cttcattttg ggctgtttca gtgcagggct tcctaaaaca gaagcc*aact gggtgaatgt*

*aataagtgat ttgaaaaaaattgaagatct tattcaatct*

*atgcatattg atgctacttt atatacggaa agtgatgttc*

*accccagttg caaagtaaca gcaatgaagt gctttctctt*

*ggagttacaa gttatttcac ttgagtccgg agatgcaagt*

*attcatgata cagtagaaaa tctgatcatc ctagcaaaca*

*acagtttgtc ttctaatggg aatgtaacag aatctggatg*

*caaagaatgt gaggaactgg aggaaaaaaa tattaaagaa*

*tttttgcaga gttttgtaca tattgtccaa atgttcatca*

*acacttcttg a.*

In a specific embodiment, the nucleic acid is an isolated or purified nucleic acid. In some embodiments, nucleic acids encode the immature or precursor form of a naturally occurring mammalian IL-15. In other embodiments, nucleic acids encode the mature form of a naturally occurring mammalian IL-15. In a specific embodiment, nucleic acids encoding native IL-15 encode the precursor form of naturally occurring human IL-15. In another embodiment, nucleic acids encoding native IL-15 encode the mature form of naturally occurring human IL-15.

As used herein, the terms "IL-15 derivative" and "interleukin-15 derivative" in the context of proteins or polypeptides refer to: (a) a polypeptide that is at least 40%, 45%, 50%, 55%, 60%, 65%, 70%, 75%, 80%, 85%, 90%, 95%, 98% or 99% identical to a native mammalian IL-15 polypeptide; (b) a polypeptide encoded by a nucleic acid sequence that is at least 40%, 45%, 50%, 55%, 60%, 65%, 70%, 75%, 80%, 85%, 90%, 95%, 98% or 99% identical a nucleic acid sequence encoding a native mammalian IL-15 polypeptide; (c) a polypeptide that contains 1, 2, 3, 4, 5, 6, 7, 8, 9, 10, 11, 12, 13, 14, 15, 16, 17, 18, 19, 20 or more amino acid mutations (i.e., additions, deletions and/or substitutions) relative to a native mammalian IL-15 polypeptide; (d) a polypeptide encoded by nucleic acids that can hybridize under high, moderate or typical stringency hybridization conditions to nucleic acids encoding a native mammalian IL-15 polypeptide; (e) a polypeptide encoded by a nucleic acid sequence that can hybridize under high, moderate or typical stringency hybridization conditions to a nucleic acid sequence encoding a fragment of a native mammalian IL-15 polypeptide of at least 20 contiguous amino acids, at least 30 contiguous amino acids, at least 40 contiguous amino acids, at least 50 contiguous amino acids, at least 100 contiguous amino acids, or at least 150 contiguous amino acids; and/or (f) a fragment of a native mammalian IL-15 polypeptide. IL-15 derivatives also include a polypeptide that comprises the amino acid sequence of a naturally occurring mature form of a mammalian IL-15 polypeptide and a heterologous signal peptide amino acid sequence. In a specific embodiment, an IL-15 derivative is a derivative of a native human IL-15 polypeptide. In another embodiment, an IL-15 derivative is a derivative of an immature or precursor form of naturally occurring human IL-15 polypeptide. In another embodiment, an IL-15 derivative is a derivative of a mature form of naturally occurring human IL-15 polypeptide. In another embodiment, an IL-15 derivative is the IL-15N72D described in, e.g., Zhu et al., 2009, J. Immunol. 183: 3598 or U.S. Pat. No. 8,163,879. In another embodiment, an IL-15 derivative is one of the IL-15 variants described in U.S. Pat. No. 8,163,879. In one embodiment, an IL-15 derivative is isolated or purified.

In a preferred embodiment, IL-15 derivatives retain at least 50%, 55%, 60%, 65%, 70%, 75%, 80%, 85%, 90%, 95%, 98% or 99% of the function of native mammalian IL-15 polypeptide to bind IL-15Rα polypeptide, as measured by assays well known in the art, e.g., ELISA, Biacore, co-immunoprecipitation. In another preferred embodiment, IL-15 derivatives retain at least 50%, 55%, 60%, 65%, 70%, 75%, 80%, 85%, 90%, 95%, 98% or 99% of the function of native mammalian IL-15 polypeptide to induce IL-15-mediated signal transduction, as measured by assays well-known in the art, e.g., electromobility shift assays, western blots, phosphoprotein analysis, ELISAs and other immunoassays. In a specific embodiment, IL-15 derivatives bind to IL-15Rα and/or IL-15Rβγ as assessed by, e.g., ligand/receptor binding assays well-known in the art.

Percent identity can be determined using any method known to one of skill in the art. In a specific embodiment, the percent identity is determined using the "Best Fit" or "Gap" program of the Sequence Analysis Software Package (Version 10; Genetics Computer Group, Inc., University of Wisconsin Biotechnology Center, Madison, Wis.). Information regarding hybridization conditions (e.g., high, moderate, and typical stringency conditions) has been described, see, e.g., U.S. Patent Application Publication No. US 2005/0048549 (e.g., paragraphs 72-73).

As used herein, the terms "IL-15 derivative" and "interleukin-15 derivative" in the context of nucleic acids refer to: (a) a nucleic acid sequence that is at least 40%, 45%, 50%, 55%, 60%, 65%, 70%, 75%, 80%, 85%, 90%, 95%, 98% or 99% identical to the naturally occurring nucleic acid sequence encoding a mammalian IL-15 polypeptide; (b) a nucleic acid sequence encoding a polypeptide that is at least 40%, 45%, 50%, 55%, 60%, 65%, 70%, 75%, 80%, 85%, 90%, 95%, 98% or 99% identical the amino acid sequence of a native mammalian IL-15 polypeptide; (c) a nucleic acid sequence that contains 1, 2, 3, 4, 5, 6, 7, 8, 9, 10, 11, 12, 13, 14, 15, 16, 17, 18, 19, 20 or more nucleic acid base mutations (i.e., additions, deletions and/or substitutions) relative to the naturally occurring nucleic acid sequence encoding a mammalian IL-15 polypeptide; (d) a nucleic acid sequence that hybridizes under high, moderate or typical stringency hybridization conditions to a naturally occurring nucleic acid sequence encoding a mammalian IL-15 polypeptide; (e) a nucleic acid sequence that hybridizes under high, moderate or typical stringency hybridization conditions to a fragment of a naturally occurring nucleic acid sequence encoding a mammalian IL-15 polypeptide; and/or (f) a nucleic acid sequence encoding a fragment of a naturally occurring nucleic acid sequence encoding a mammalian IL-15 polypeptide. In a specific embodiment, an IL-15 derivative in the context of nucleic acids is a derivative of a naturally occurring nucleic acid sequence encoding a human IL-15 polypeptide. In another embodiment, an IL-15 derivative in the context of nucleic acids is a derivative of a naturally occurring nucleic acid sequence encoding an immature or precursor form of a human IL-15 polypeptide. In another embodiment, an IL-15 derivative in the context of nucleic acids is a derivative of a naturally occurring nucleic acid sequence encoding a mature form of a human IL-15 polypeptide. In another embodiment, an IL-15 derivative in the context of nucleic acids is the nucleic acid sequence encoding the IL-15N72D described in, e.g., Zhu et al., 2009, J. Immunol. 183: 3598 or U.S. Pat. No. 8,163,879. In another embodiment, an IL-15 derivative in the context of nucleic acids is the nucleic acid sequence encoding one of the IL-15 variants described in U.S. Pat. No. 8,163,879.

IL-15 derivative nucleic acid sequences include codon-optimized/RNA-optimized nucleic acid sequences that encode native mammalian IL-15 polypeptide, including mature and immature forms of IL-15 polypeptide. In other embodiments, IL-15 derivative nucleic acids include nucleic acids that encode mammalian IL-15 RNA transcripts containing mutations that eliminate potential splice sites and instability elements (e.g., A/T or A/U rich elements) without affecting the amino acid sequence to increase the stability of the mammalian IL-15 RNA transcripts. In certain embodiments, the IL-15 derivative nucleic acid sequence is the codon-optimized sequence in SEQ ID NO: 9 (the amino acid sequence encoded by such a nucleic acid sequence is provided in SEQ ID NO: 10).

In a preferred embodiment, IL-15 derivative nucleic acid sequences encode proteins or polypeptides that retain at least 50%, 55%, 60%, 65%, 70%, 75%, 80%, 85%, 90%, 95%, 98% or 99% of the function of a native mammalian IL-15 polypeptide to bind IL-15Rα, as measured by assays well known in the art, e.g., ELISA, Biacore, co-immunoprecipitation or gel electrophoresis. In another preferred embodiment, IL-15 derivative nucleic acid sequences encode proteins or polypeptides that retain at least 50%, 55%, 60%, 65%, 70%, 75%, 80%, 85%, 90%, 95%, 98% or 99% of the function of a native mammalian IL-15 polypeptide to induce IL-15-mediated signal transduction, as measured by assays well-known in the art, e.g., electromobility shift assays, ELISAs and other immunoassays. In a specific embodiment, IL-15 derivative nucleic acid sequences encode proteins or polypeptides that bind to IL-15Rα and/or IL-15Rβγ as assessed by, e.g., ligand/receptor assays well-known in the art.

As used herein, the terms "IL-15" and "interleukin-15" refer to a native IL-15, an IL-15 derivative, or a native IL-15 and an IL-15 derivative.

As used herein, the terms "native IL-15Rα" and "native interleukin-15 receptor alpha" in the context of proteins or polypeptides refer to any naturally occurring mammalian interleukin-15 receptor alpha ("IL-15Rα") amino acid sequence, including immature or precursor and mature forms and naturally occurring isoforms. Non-limiting examples of GeneBank Accession Nos. for the amino acid sequence of various native mammalian IL-15Rα include NP_002180 (human), ABK41438 (*Macaca mulatta*), NP_032384 (*Mus musculus*), Q60819 (*Mus musculus*), CAI41082 (human). In one embodiment, the amino acid sequence of the immature form of the native full length human IL-15Rα, which comprises the signal peptide (underlined) and the mature human native IL-15Rα (italicized), is provided

```
                                  (SEQ ID NO: 3; FIG. 2B)
MAPRRARGCR TLGLPALLLL LLLRPPATRG ITCPPPMSVE
HADIWVKSYS LYSRERYICN SGFKRKAGTS SLTECVLNKA
TNVAHWTTPS LKCIRDPALV HQRPAPPSTV TTAGVTPQPE
SLSPSGKEPA ASSPSSNNTA ATTAAIVPGS QLMPSKSPST
GTTEISSHES SHGTPSQTTA KNWELTASAS HQPPGVYPQG
HSDTTVAIST STVLLCGLSA VSLLACYLKS RQTPPLASVE
MEAMEALPVT WGTSSRDEDL ENCSHHL.
```

The amino acid sequence of the immature form of the native soluble human IL-15Rα, which comprises the signal peptide (underlined) and the mature human native soluble IL-15Rα (italicized), is provided:

```
                                 (SEQ ID NO: 32, FIG. 3D)
MAPRRARGCR TLGLPALLLL LLLRPPATRG ITCPPPMSVE
HADIWVKSYS LYSRERYICN SGFKRKAGTS SLTECVLNKA
TNVAHWTTPS LKCIRDPALV HQRPAPPSTV TTAGVTPQPE
SLSPSGKEPA ASSPSSNNTA ATTAAIVPGS QLMPSKSPST
GTTEISSHES SHGTPSQTTA KNWELTASAS HQPPGVYPQG.
```

See Section 5.1, infra, for further discussion regarding the immature and mature forms of human native soluble IL-15Rα. In some embodiments, native IL-15Rα is the immature form of a naturally occurring mammalian IL-15Rα polypeptide. In other embodiments, native IL-15Rα is the mature form of a naturally occurring mammalian IL-15Rα polypeptide. In certain embodiments, native IL-15Rα is the naturally occurring soluble form of mammalian IL-15Rα polypeptide. In other embodiments, native IL-15Rα is the full-length form of a naturally occurring mammalian IL-15Rα polypeptide. In a specific embodiment, native IL-15Rα is the immature form of a naturally occurring human IL-15Rα polypeptide. In another embodiment, native IL-15Rα is the mature form of a naturally occurring human IL-15Rα polypeptide. In certain embodiments, native IL-15Rα is the naturally occurring soluble form of human IL-15Rα polypeptide. In other embodiments, native IL-15Rα is the full-length form of a naturally occurring human IL-15Rα polypeptide. In one embodiment, a native IL-15Rα protein or polypeptide is isolated or purified.

As used herein, the terms "native IL-15Rα" and "native interleukin-15 receptor alpha" in the context of nucleic acids refer to any naturally occurring nucleic acid sequences encoding mammalian interleukin-15 receptor alpha, including the immature or precursor and mature forms. Non-limiting examples of GeneBank Accession Nos. for the nucleotide sequence of various species of native mammalian IL-15Rα include NM 002189 (human), EF033114 (*Macaca mulatta*), and NM_008358 (*Mus musculus*). In one embodiment, the nucleotide sequence encoding the immature form of native human IL-15Rα, which comprises the nucleotide sequence encoding the signal peptide (underlined) and the nucleotide sequence encoding the mature human native IL-15Rα (italicized), is provided:

```
                                  (SEQ ID NO: 5; FIG. 2A)
atggcccc gcggcgggcg cgcggctgcc ggaccctcgg
tctcccggcg ctgctactgc tgctgctgct ccggccgccg
gcgacgcggg gcatcacgtg ccctcccccc atgtccgtgg
aacacgcaga catctgggtc aagagctaca gcttgtactc
cagggagcgg tacatttgta actctggttt caagcgtaaa
gccggcacgt ccagcctgac ggagtgcgtg ttgaacaagg
ccacgaatgt cgcccactgg acaaccccca gtctcaaatg
cattagagac cctgccctgg ttcaccaaag gccagcgcca
ccctccacag taacgacggc aggggtgacc ccacagccag
agagcctctc cccttctgga aaagagcccg cagcttcatc
tcccagctca aacaacacag cggccacaac agcagctatt
gtcccgggct cccagctgat gccttcaaaa tcaccttcca
caggaaccac agagataagc agtcatgagt cctcccacgg
caccccctct cagacaacag ccaagaactg ggaactcaca
gcatccgcct cccaccagcc gccaggtgtg tatccacagg
gccacagcga caccactgtg gctatctcca cgtccactgt
cctgctgtgt gggctgagcg ctgtgtctct cctggcatgc
tacctcaagt caaggcaaac tcccccgctg gccagcgttg
aaatggaagc catggaggct ctgccggtga cttgggggac
cagcagcaga gatgaagact tggaaaactg ctctcaccac
ctatga.
```

immature form of native soluble human IL-15Rα protein or polypeptide, which comprises the nucleotide sequence encoding the signal peptide (underlined) and the nucleotide sequence encoding the mature human soluble native IL-15Rα (italicized), is provided:

```
                                 (SEQ ID NO: 46, FIG. 3C)
atggcccc gcggcgggcg cgcggctgcc ggaccctcgg
tctcccggcg ctgctactgc tgctgctgct ccggccgccg
gcgacgcggg gcatcacgtg ccctcccccc atgtccgtgg
aacacgcaga catctgggtc aagagctaca gcttgtactc
cagggagcgg tacatttgta actctggttt caagcgtaaa
gccggcacgt ccagcctgac ggagtgcgtg ttgaacaagg
ccacgaatgt cgcccactgg acaaccccca gtctcaaatg
cattagagac cctgccctgg ttcaccaaag gccagcgcca
ccctccacag taacgacggc aggggtgacc ccacagccag
agagcctctc cccttctgga aaagagcccg cagcttcatc
```

-continued

*tcccagctca aacaacacag cggccacaac agcagctatt*

*gtcccgggct cccagctgat gccttcaaaa tcaccttcca*

*caggaaccac agagataagc agtcatgagt cctcccacgg*

*caccccctct cagacaacag ccaagaactg ggaactcaca*

*gcatccgcct cccaccagcc gccaggtgtg tatccacagg gc.* embodiment, the nucleic acid is an isolated or purified nucleic acid. In some embodiments, naturally occurring nucleic acids encode the immature form of a naturally occurring mammalian IL-15Rα polypeptide. In other embodiments, naturally occurring nucleic acids encode the mature form of a naturally occurring mammalian IL-15Rα polypeptide. In certain embodiments, naturally occurring nucleic acids encode the soluble form of a naturally occurring mammalian IL-15Rα polypeptide. In other embodiments, naturally occurring nucleic acids encode the full-length form of a naturally occurring mammalian IL-15Rα polypeptide. In a specific embodiment, naturally occurring nucleic acids encode the precursor form of naturally occurring human IL-15 polypeptide. In another embodiment, naturally occurring nucleic acids encode the mature of naturally occurring human IL-15 polypeptide. In certain embodiments, naturally occurring nucleic acids encode the soluble form of a naturally occurring human IL-15Rα polypeptide. In other embodiments, naturally occurring nucleic acids encode the full-length form of a naturally occurring human IL-15Rα polypeptide.

As used herein, the terms "IL-15Rα derivative" and "interleukin-15 receptor alpha derivative" in the context of a protein or polypeptide refer to: (a) a polypeptide that is at least 40%, 45%, 50%, 55%, 60%, 65%, 70%, 75%, 80%, 85%, 90%, 95%, 98% or 99% identical to a native mammalian IL-15 polypeptide; (b) a polypeptide encoded by a nucleic acid sequence that is at least 40%, 45%, 50%, 55%, 60%, 65%, 70%, 75%, 80%, 85%, 90%, 95%, 98% or 99% identical a nucleic acid sequence encoding a native mammalian IL-15Rα polypeptide; (c) a polypeptide that contains 1, 2, 3, 4, 5, 6, 7, 8, 9, 10, 11, 12, 13, 14, 15, 16, 17, 18, 19, 20 or more amino acid mutations (i.e., additions, deletions and/or substitutions) relative to a native mammalian IL-15Rα polypeptide; (d) a polypeptide encoded by a nucleic acid sequence that can hybridize under high, moderate or typical stringency hybridization conditions to a nucleic acid sequence encoding a native mammalian IL-15Rα polypeptide; (e) a polypeptide encoded by a nucleic acid sequence that can hybridize under high, moderate or typical stringency hybridization conditions to nucleic acid sequences encoding a fragment of a native mammalian IL-15 polypeptide of at least 20 contiguous amino acids, at least 30 contiguous amino acids, at least 40 contiguous amino acids, at least 50 contiguous amino acids, at least 100 contiguous amino acids, or at least 150 contiguous amino acids; (f) a fragment of a native mammalian IL-15Rα polypeptide; and/or (g) a specific IL-15Rα derivative described herein. IL-15Rα derivatives also include a polypeptide that comprises the amino acid sequence of a naturally occurring mature form of mammalian IL-15Rα polypeptide and a heterologous signal peptide amino acid sequence. In a specific embodiment, an IL-15Rα derivative is a derivative of a native human IL-15Rα polypeptide. In another embodiment, an IL-15Rα derivative is a derivative of an immature form of naturally occurring human IL-15 polypeptide. In another embodiment, an IL-15Rα derivative is a derivative of a mature form of naturally occurring human IL-15 polypeptide. In one embodiment, an IL-15Rα derivative is a soluble form of a native mammalian IL-15Rα polypeptide. In other words, in certain embodiments, an IL-15Rα derivative includes soluble forms of native mammalian IL-15Rα, wherein those soluble forms are not naturally occurring. An example of an amino acid sequence of a truncated, soluble form of an immature form of the native human IL-15Rα comprises the following signal peptide (underlined) and the following truncated form of human native IL-15Rα (italicized):

(SEQ ID NO: 4; FIG. 3B)

MAPRRARGCR TLGLPALLLL LLLRPPATRG *ITCPPPMSVE*

*HADIWVKSYS LYSRERYICN SGFKRKAGTS SLTECVLNKA*

*TNVAHWTTPS LKCIRDPALV HQRPAPPSTV TTAGVTPQPE*

*SLSPSGKEPA ASSPSSNNTA ATTAAIVPGS QLMPSKSPST*

*GTTEISSHES SHGTPSQTTA KNWELTASAS HQPPGVYPQG HSDTT.*

Other examples of IL-15Rα derivatives include the truncated, soluble forms of native human IL-15Rα described in Section 5.1, infra or the sushi domain, which is the binding site to IL-15. In a specific embodiment, an IL-15Rα derivative is purified or isolated.

In a preferred embodiment, IL-15Rα derivatives retain at least 50%, 55%, 60%, 65%, 70%, 75%, 80%, 85%, 90%, 95%, 98% or 99% of the function of a native mammalian IL-15Rα polypeptide to bind an IL-15 polypeptide, as measured by assays well known in the art, e.g., ELISA, Biacore, co-immunoprecipitation. In another preferred embodiment, IL-15Rα derivatives retain at least 50%, 55%, 60%, 65%, 70%, 75%, 80%, 85%, 90%, 95%, 98% or 99% of the function of a native mammalian IL-15Rα polypeptide to induce IL-15-mediated signal transduction, as measured by assays well-known in the art, e.g., electromobility shift assays, ELISAs and other immunoassays. In a specific embodiment, IL-15Rα derivatives bind to IL-15 as assessed by methods well-known in the art, such as, e.g., ELISAs.

As used herein, the terms "IL-15Rα derivative" and "interleukin-15 receptor alpha derivative" in the context of nucleic acids refer to: (a) a nucleic acid sequence that is at least 40%, 45%, 50%, 55%, 60%, 65%, 70%, 75%, 80%, 85%, 90%, 95%, 98% or 99% identical to the naturally occurring nucleic acid sequence encoding a mammalian IL-15Rα polypeptide; (b) a nucleic acid sequence encoding a polypeptide that is at least 40%, 45%, 50%, 55%, 60%, 65%, 70%, 75%, 80%, 85%, 90%, 95%, 98% or 99% identical the amino acid sequence of a native mammalian IL-15Rα polypeptide; (c) a nucleic acid sequence that contains 1, 2, 3, 4, 5, 6, 7, 8, 9, 10, 11, 12, 13, 14, 15, 16, 17, 18, 19, 20 or more nucleic acid mutations (i.e., additions, deletions and/or substitutions) relative to the naturally occurring nucleic acid sequence encoding a mammalian IL-15Rα polypeptide; (d) a nucleic acid sequence that hybridizes under high, moderate or typical stringency hybridization conditions to a naturally occurring nucleic acid sequence encoding a mammalian IL-15Rα polypeptide; (e) a nucleic acid sequence that hybridizes under high, moderate or typical stringency hybridization conditions to a fragment of a naturally occurring nucleic acid sequence encoding a mammalian IL-15Rα polypeptide; (f) a nucleic acid sequence encoding a fragment of a naturally occurring nucleic acid sequence encoding a mammalian IL-15Rα polypeptide; and/or (g) a nucleic acid sequence encoding a specific IL-15Rα derivative described herein. In a specific embodiment, an IL-15Rα derivative in the context of nucleic acids is a derivative of a naturally occurring nucleic acid sequence encoding a human IL-15Rα polypeptide. In another embodiment, an IL-15Rα derivative in the context of nucleic acids is a derivative of a naturally occurring nucleic acid sequence encoding an immature form of a human IL-15Rα polypeptide. In another embodiment, an IL-15Rα derivative in the context of nucleic acids is a derivative of a naturally occurring nucleic acid sequence encoding a mature form of a human IL-15Rα polypeptide. In one embodiment, an IL-15Rα derivative in the context of nucleic acids refers to a nucleic acid sequence encoding a derivative of mammalian IL-15Rα polypeptide that is soluble. In certain embodiments, an IL-15Rα derivative in context of nucleic acids refers to a nucleic acid sequence encoding a soluble form of native mammalian IL-15Rα, wherein the soluble form is not naturally occurring. In some embodiments, an IL-15Rα derivative in the context of nucleic acids refers to a nucleic acid sequence encoding a derivative of human IL-15Rα, wherein the derivative of the human IL-15Rα is a soluble form of IL-15Rα that is not naturally occurring. An example of an IL-15Rα derivative nucleic acid sequence is the nucleotide sequence encoding the truncated, soluble, immature form of a native human IL-15Rα protein or polypeptide that comprises the following nucleotide sequence encoding the signal peptide (underlined) and the following nucleotide sequence encoding a truncated form of the mature human native IL-15Rα (italicized):

(SEQ ID NO: 6; FIG. 3A)

atggcccc gcggcgggcg cgcggctgcc ggaccctcgg tctcccggcg ctgctactgc tgctgctgct ccggccgccg gcgacgcggg gc*atcacgtg ccctcccccc atgtccgtgg*

*aacacgcaga catctgggtc aagagctaca gcttgtactc*

*cagggagcgg tacatttgta actctggttt caagcgtaaa*

*gccggcacgt ccagcctgac ggagtgcgtg ttgaacaagg*

*ccacgaatgt cgcccactgg acaaccccca gtctcaaatg*

*cattagagac cctgccctgg ttcaccaaag gccagcgcca*

*ccctccacag taacgacggc aggggtgacc ccacagccag*

*agagcctctc cccttctgga aaagagcccg cagcttcatc*

*tcccagctca aacaacacag cggccacaac agcagctatt*

*gtcccgggct cccagctgat gccttcaaaa tcaccttcca*

*caggaaccac agagataagc agtcatgagt cctcccacgg* cacccccctct *cagacaacag ccaagaactg ggaactcaca*

*gcatccgcct cccaccagcc gccaggtgtg tatccacagg*

*gccacagcga caccact.*

In specific embodiments, an IL-15Rα derivative nucleic acid sequence is isolated or purified.

IL-15Rα derivative nucleic acid sequences include RNA or codon-optimized nucleic acid sequences that encode native IL-15Rα polypeptide, including mature and immature forms of IL-15Rα polypeptide. In other embodiments, IL-15Rα derivative nucleic acids include nucleic acids that encode IL-15Rα RNA transcripts containing mutations that eliminate potential splice sites and instability elements (e.g., A/T or A/U rich elements) without affecting the amino acid sequence to increase the stability of the IL-15Rα RNA transcripts. In certain embodiments, the IL-15Rα derivative nucleic acid sequence is the RNA or codon-optimized sequence in SEQ ID NO: 11, 13, 15 or 17 (the amino acid sequences encoded by such a nucleic acid sequences are provided in SEQ ID NO: 12, 14, 16 and 18, respectively).

In a preferred embodiment, IL-15Rα derivative nucleic acid sequences encode proteins or polypeptides that retain at least 50%, 55%, 60%, 65%, 70%, 75%, 80%, 85%, 90%, 95%, 98% or 99% of the function of a native mammalian IL-15Rα polypeptide to bind IL-15, as measured by assays well known in the art, e.g., ELISA, Biacore, co-immunoprecipitation. In another preferred embodiment, IL-15Rα derivative nucleic acid sequences encode proteins or polypeptides that retain at least 50%, 55%, 60%, 65%, 70%, 75%, 80%, 85%, 90%, 95%, 98% or 99% of the function of a native mammalian IL-15Rα to induce IL-15-mediated signal transduction, as measured by assays well-known in the art, e.g., electromobility shift assays, ELISAs and other immunoassays. In a specific embodiment, IL-15Rα derivative nucleic acid sequences encode proteins or polypeptides that bind to IL-15 as assessed by methods well-known in the art, such as, e.g., ELISAs.

As used herein, the terms "IL-15Rα" and "interleukin-15 receptor alpha" refer to a native IL-15Rα, an IL-15Rα derivative, or a native IL-15Rα and an IL-15Rα derivative.

As used herein, the term "IL-15/IL-15Rα complex" refers to a complex comprising IL-15 and IL-15Rα covalently or noncovalently bound to each other. In a preferred embodiment, the IL-15Rα has a relatively high affinity for IL-15, e.g., $K_d$ of 10 to 50 pM as measured by a technique known in the art, e.g., KinEx A assay, plasma surface resonance (e.g., BIAcore assay). In another preferred embodiment, the IL-15/IL-15Rα complex induces IL-15-mediated signal transduction, as measured by assays well-known in the art, e.g., electromobility shift assays, ELISAs and other immunoassays. In some embodiments, the IL-15/IL-15Rα complex retains the ability to specifically bind to the βγ chain. In a specific embodiment, the IL-15/IL-15Rα complex is isolated from a cell.

As used herein, the terms "subject" and "patient" are used interchangeably and refer to a mammal such as a non-primate (e.g., cows, pigs, horses, cats, dogs, rats etc.) and a primate (e.g., monkey and human), most preferably a human.

As used herein, the terms "purified" and "isolated" in the context of a compound or agent (including, e.g., proteinaceous agents) that is chemically synthesized refers to a compound or agent that is substantially free of chemical precursors or other chemicals when chemically synthesized. In a specific embodiment, the compound or agent is 60%, 65%, 75%, 80%, 85%, 90%, 95%, or 99% free (by dry weight) of other, different compounds or agents.

As used herein, the terms "purified" and "isolated" when used in the context of a compound or agent (including proteinaceous agents such as polypeptides) that can be obtained from a natural source, e.g., cells, refers to a compound or agent which is substantially free of contaminating materials from the natural source, e.g., soil particles, minerals, chemicals from the environment, and/or cellular materials from the natural source, such as but not limited to cell debris, cell wall materials, membranes, organelles, the bulk of the nucleic acids, carbohydrates, proteins, and/or lipids present in cells. The phrase "substantially free of natural source materials" refers to preparations of a compound or agent that has been separated from the material (e.g., cellular components of the cells) from which it is isolated. Thus, a compound or agent that is isolated includes preparations of a compound or agent having less than about 30%, 20%, 10%, 5%, 2%, or 1% (by dry weight) of cellular materials and/or contaminating materials.

An "isolated" nucleic acid sequence or nucleotide sequence is one which is separated from other nucleic acid molecules which are present in a natural source of the nucleic acid sequence or nucleotide sequence. Moreover, an "isolated", nucleic acid sequence or nucleotide sequence, such as a cDNA molecule, can be substantially free of other cellular material or culture medium when produced by recombinant techniques, or substantially free of chemical precursors when chemically synthesized. In certain embodiments, an "isolated" nucleic acid sequence or nucleotide sequence is a nucleic acid sequence or nucleotide sequence that is recombinantly expressed in a heterologous cell.

In some embodiments, the terms "nucleic acid", "nucleotide" and "polynucleotide" refer to deoxyribonucleotides, deoxyribonucleic acids, ribonucleotides, and ribonucleic acids, and polymeric forms thereof, and include either single- or double-stranded forms. In certain embodiments, such terms include known analogues of natural nucleotides, for example, peptide nucleic acids ("PNA" s), that have similar binding properties as the reference nucleic acid. In some embodiments, such terms refer to deoxyribonucleic acids (e.g., cDNA or DNA). In other embodiments, such terms refer to ribonucleic acid (e.g., mRNA or RNA).

As used herein, the terms "therapies" and "therapy" can refer to any protocol(s), method(s), compositions, formulations, and/or agent(s) that can be used in the prevention, treatment, management, or amelioration of a disease, e.g., cancer, infectious disease, lymphopenia, and immunodeficiencies, or a symptom associated therewith. In certain embodiments, the terms "therapies" and "therapy" refer to biological therapy, supportive therapy, and/or other therapies useful in treatment, management, prevention, or amelioration of a disease or a symptom associated therewith known to one of skill in the art. In one embodiment, a therapy includes a Therapeutic Agent. In another embodiment, a therapy is not a Therapeutic Agent.

As used herein, the terms "protein(s)" and "polypeptide(s)" interchangeably to refer to a chain of amino acids linked together by peptide bonds. In some embodiments, the terms "protein(s)" and "polypeptide(s)" refer to a macromolecule which comprises amino acids that are linked together by peptide bonds.

As used herein, the term "fragment" in the context of a nucleotide sequence refers to a nucleotide sequence comprising an nucleic acid sequence of at least 5 contiguous nucleic acid bases, at least 10 contiguous nucleic acid bases, at least 15 contiguous nucleic acid bases, at least 20 contiguous nucleic acid bases, at least 25 contiguous nucleic acid bases, at least 40 contiguous nucleic acid bases, at least 50 contiguous nucleic acid bases, at least 60 contiguous nucleic acid bases, at least 70 contiguous nucleic acid bases, at least 80 contiguous nucleic acid bases, at least 90 contiguous nucleic acid bases, at least 100 contiguous nucleic acid bases, at least 125 contiguous nucleic acid bases, at least 150 contiguous nucleic acid bases, at least 175 contiguous nucleic acid bases, at least 200 contiguous nucleic acid bases, or at least 250 contiguous nucleic acid bases of the nucleotide sequence of the gene of interest, e.g., IL-15, IL-15Rα. The nucleic acid may be RNA, DNA, or a chemically modified variant thereof. In a specific embodiment, the fragment is a fragment of IL-15 or IL-15Rα.

As used herein, the term "fragment" is the context of a fragment of a proteinaceous agent (e.g., a protein or polypeptide) refers to a fragment that is composed of 8 or more contiguous amino acids, 10 or more contiguous amino acids, 15 or more contiguous amino acids, 20 or more contiguous amino acids, 25 or more contiguous amino acids, 50 or more contiguous amino acids, 75 or more contiguous amino acids, 100 or more contiguous amino acids, 150 or more contiguous amino acids, 200 or more contiguous amino acids, 10 to 150 contiguous amino acids, 10 to 200 contiguous amino acids, 10 to 250 contiguous amino acids, 10 to 300 contiguous amino acids, 50 to 100 contiguous amino acids, 50 to 150 contiguous amino acids, 50 to 200 contiguous amino acids, 50 to 250 contiguous amino acids or 50 to 300 contiguous amino acids of a proteinaceous agent, e.g., IL-15 and IL-15Rα polypeptides.

As used herein, the term "in combination" refers to the use of more than one therapies (e.g., one or more prophylactic and/or therapeutic agents). The use of the term "in combination" does not restrict the order in which therapies are administered to a subject with a disease or disorder. A first therapy (e.g., a prophylactic or therapeutic agent) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to a subject with a disease or disorder or a symptom thereof.

As used herein, the term "host cell" refers to any type of cell, e.g., a primary cell or a cell from a cell line. In specific embodiments, the term "host cell" refers a cell transfected with a nucleic acid molecule and the progeny or potential progeny of such a cell. Progeny of such a cell may not be identical to the parent cell transfected with the nucleic acid molecule due to mutations or environmental influences that may occur in succeeding generations or integration of the nucleic acid molecule into the host cell genome.

As used herein, the term "premature human infant" refers to a human infant born at less than 37 weeks of gestational age.

As used herein, the term "human infant" refers to a newborn to 1 year old human.

As used herein, the term "human child" refers to a human that is 1 year to 18 years old.

As used herein, the term "human adult" refers to a human that is 18 years or older.

As used herein, the term "elderly human" refers to a human 65 years or older.

As used herein, the terms "treat", "treating" and "treatment" in the context of the administration of a therapy to a subject refer to the beneficial effects that a subject derives from a therapy. Non-limiting examples of such benefits include the reduction or inhibition of the progression, spread and/or duration of a disease or disorder, the reduction or amelioration of the severity of a disease or disorder, amelioration of one or more symptoms of a disease or disorder, and/or the reduction in the duration of one or more symptom of a disease or disorder resulting from the administration of one or more therapies.

As used herein, the terms "prevent," "preventing" and "prevention" in the context of the administration of a therapy to a subject refer to the inhibition of the onset or recurrence of a disease or disorder in a subject.

As used herein, the terms "manage," "managing," and "management," in the context of the administration of a therapy to a subject, refer to the beneficial effects that a subject derives from a therapy, which does not result in a cure of a disease or disorder. In certain embodiments, a subject is administered one or more therapies to "manage" a disease or disorder so as to prevent the progression or worsening of symptoms associated with a disease or disorder.

As used herein, the term "immunospecifically binds" and "specifically binds" in the context of antibodies refer to molecules that specifically bind to an antigen (e.g., an epitope or an immune complex) and do not specifically bind to another molecule. A molecule that specifically binds to an antigen may bind to other antigens with a lower affinity as determined by, e.g., immunoassays, BIAcore or other assays known in the art. In a specific embodiment, molecules that bind to an antigen do not cross-react with other antigens.

When a dose of an IL-15/IL-15Rα complex is referenced herein, the dose is according to the mass of the single-chain IL-15. The single-chain IL-15 equivalent is calculated from (i) the mass of an IL-15/IL-15Rα complex by amino acid analysis and (ii) the ratio of IL-15 to IL-15Rα (e.g., soluble IL-15Rα) in the specific preparation as determined experimentally by RP-HPLC or by amino acid analysis.

4. BRIEF DESCRIPTION OF THE DRAWINGS

FIGS. 1A-B: Nucleic acid and amino acid sequences of native human IL-15. The nucleic acid sequence (FIG. 1A) (SEQ ID NO: 2) and amino acid sequence (FIG. 1B) (SEQ ID NO: 1) are shown. The amino acid sequence and nucleic acid sequence of the long signal peptide (underlined) and mature form (italicized) are indicated.

FIGS. 2A-B: Nucleic acid and amino acid sequences of full length native human IL-15Rα. The nucleic acid sequence (FIG. 2A) (SEQ ID NO: 5) and amino acid sequence (FIG. 2B) (SEQ ID NO: 3) are shown. The amino acid sequence and nucleic acid sequence of the signal peptide (underlined) and mature form (italicized) are indicated.

FIGS. 3A-D: Nucleic acid and amino acid sequences of soluble forms of human IL-15Rα. The nucleic acid sequence (FIG. 3A) (SEQ ID NO: 6) and amino acid sequence (FIG. 3B) (SEQ ID NO: 4) for a truncated soluble human IL-15Rα in cell clone 2.66 are shown in FIG. 3A-B. The nucleic acid sequence (FIG. 3C) (SEQ ID NO: 46) and amino acid sequence (FIG. 3D) (SEQ ID NO: 32) for a native soluble human IL-15Rα are shown in FIGS. 3C-D. The amino acid sequences and nucleic acid sequences of the signal peptide (underlined) and mature form (italicized) are indicated.

FIG. 4. Plasma IL-15 levels in 6 macaques injected with IL-15 heterodimer at escalated doses of 1 μg/kg, 20 μg/kg, and 50 μg/kg. The 6 macaques received 6 s.c. injections of IL-15/IL-15Rα at the dose of 1 μg/Kg, 20 μg/Kg, or 50 μg/Kg (on day 0, 2, 4, 7, 9 and 11. Group 1: 50 μg/kg IL-15/sIL-15Rα; Group 2: 20 μg/kg IL-15/sIL-15Rα; Group 3: 1 μg/kg IL-15/sIL-15Rα. Squares: 50 μg/kg; triangles: 20 μg/kg; circles: 1 μg/kg.

Figure 5:
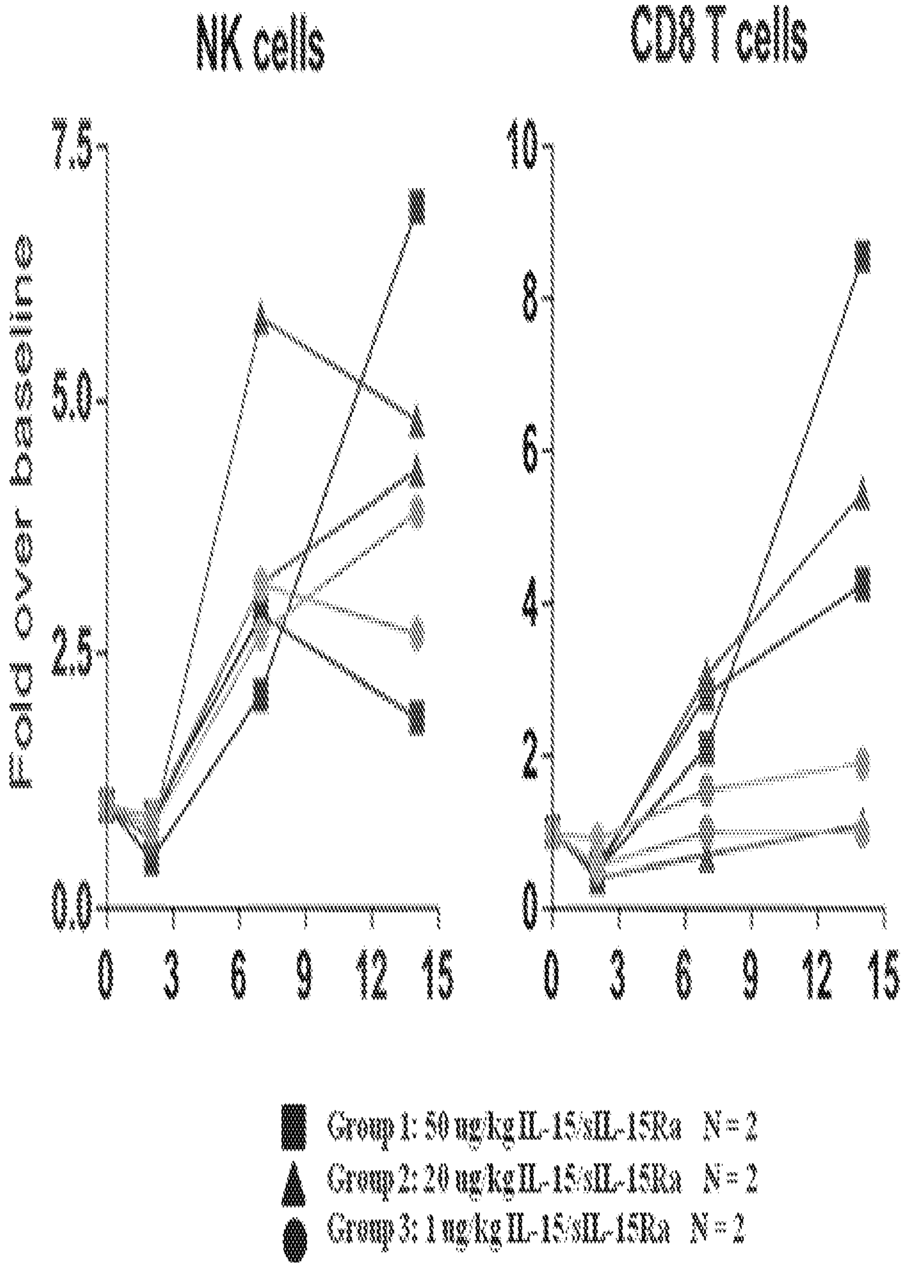

FIG. 5. The fold over baseline increase of NK cells and CD8 T cells in peripheral blood in 6 macaques injected with IL-15 heterodimer at escalated doses of 1 μg/kg, 20 μg/kg, and 50 μg/kg. Group 1: 50 μg/kg IL-15/sIL-15Rα; Group 2: 20 μg/kg IL-15/sIL-15Rα; Group 3: 1 μg/kg IL-15/sIL-15Rα. Squares: 50 μg/kg; triangles: 20 μg/kg; circles: 1 μg/kg.

Figure 6:
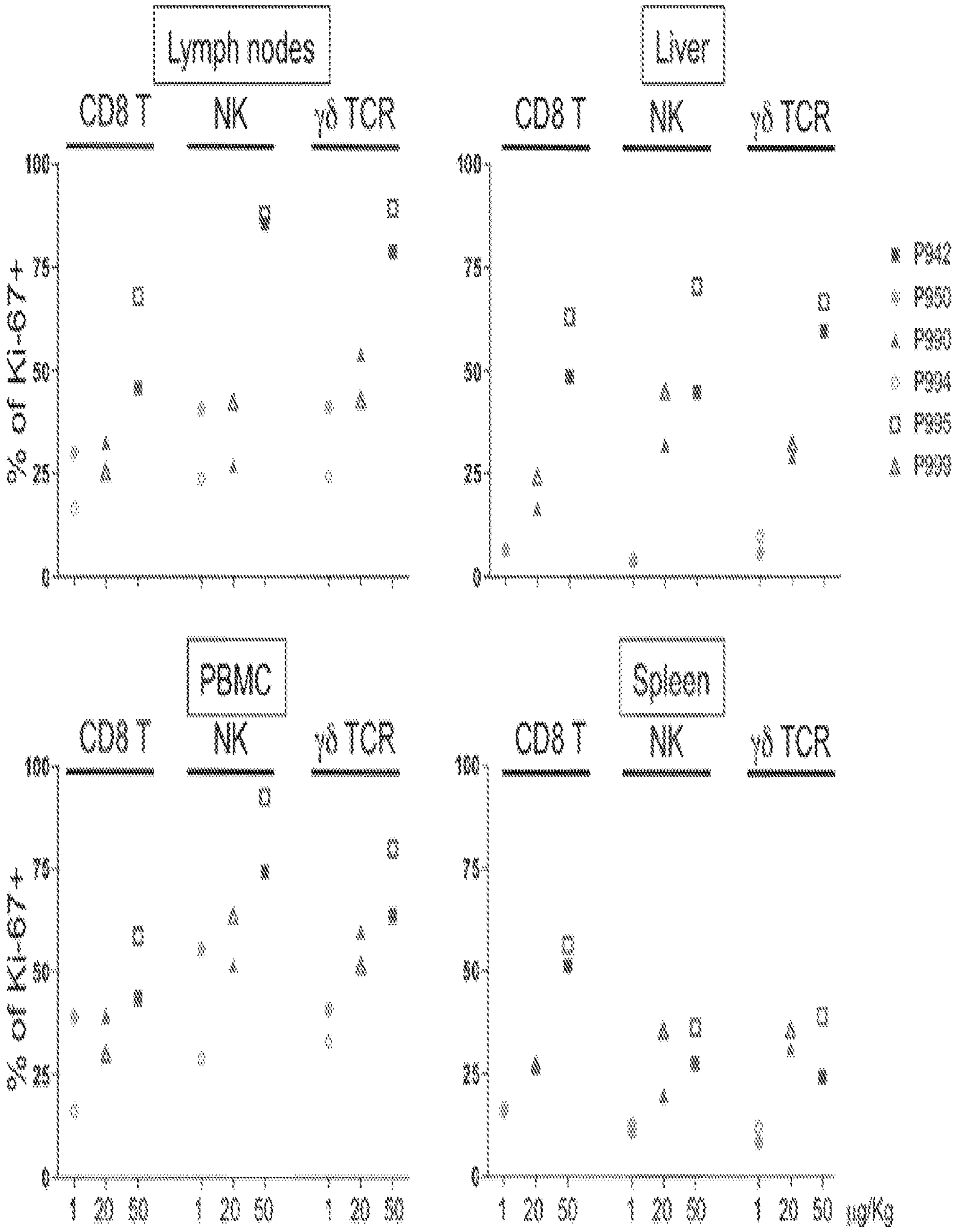

FIG. 6. Dose-dependent proliferation of lymphocytes in different tissues, including lymph nodes, liver, PBMC, spleen, upon IL-15 heterodimer s.c. administration. Squares: 50 μg/kg; triangles: 20 μg/kg; circles: 1 μg/kg.

Figure 7:
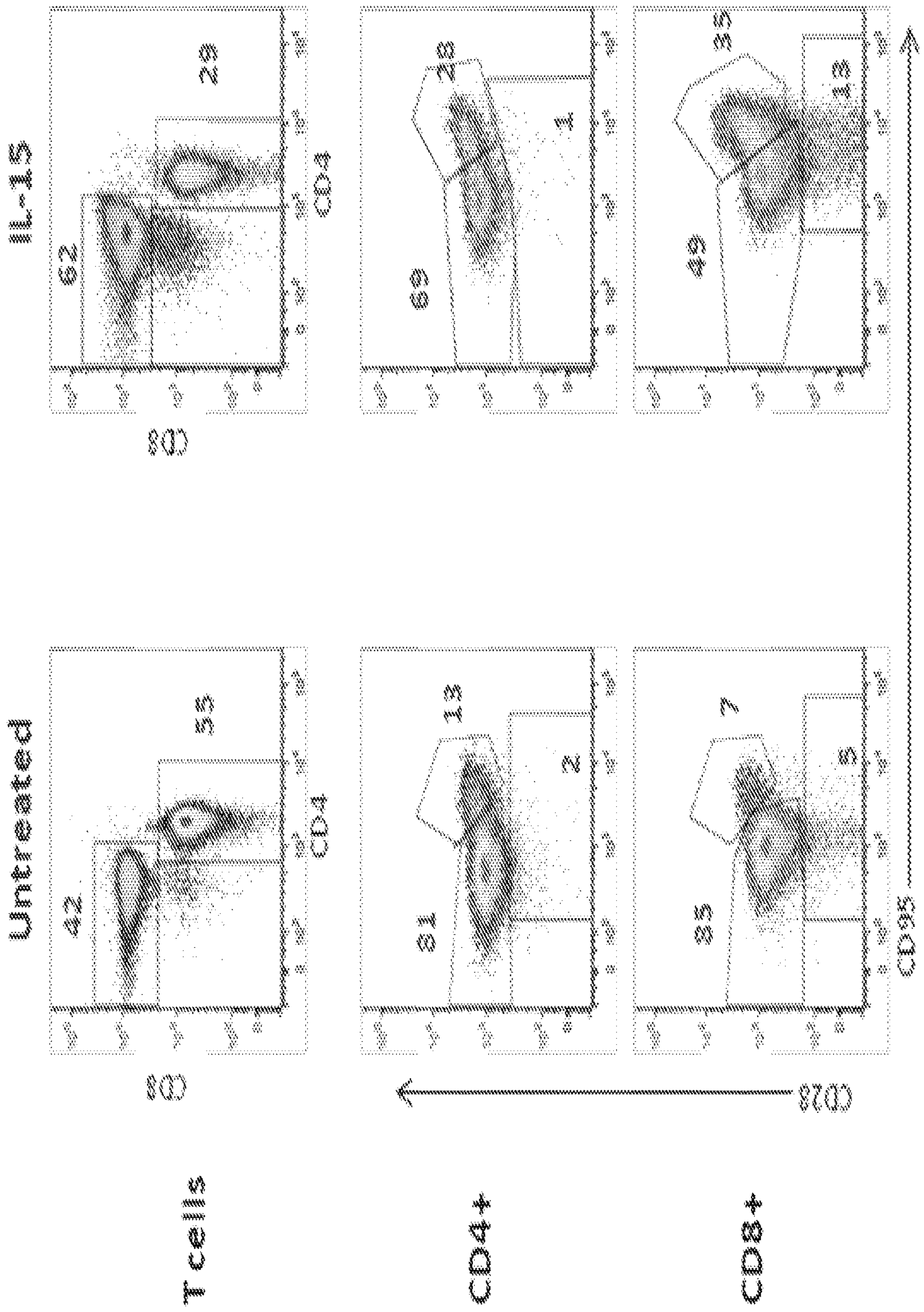

FIG. 7. Lymphocytes profiles (T cells, CD4+, CD8+) by flow cytometry in the lymph node upon IL-15 heterodimer (hetIL-15) s.c. administration. hetIL-15 treatment increases the frequency of CD8 T cells in lymph nodes. hetIL-15 preferentially increases lymphocytes with memory phenotype, including effector CD8+ T cells ($CD28^{-}CD95^{+}$).

Figure 8:
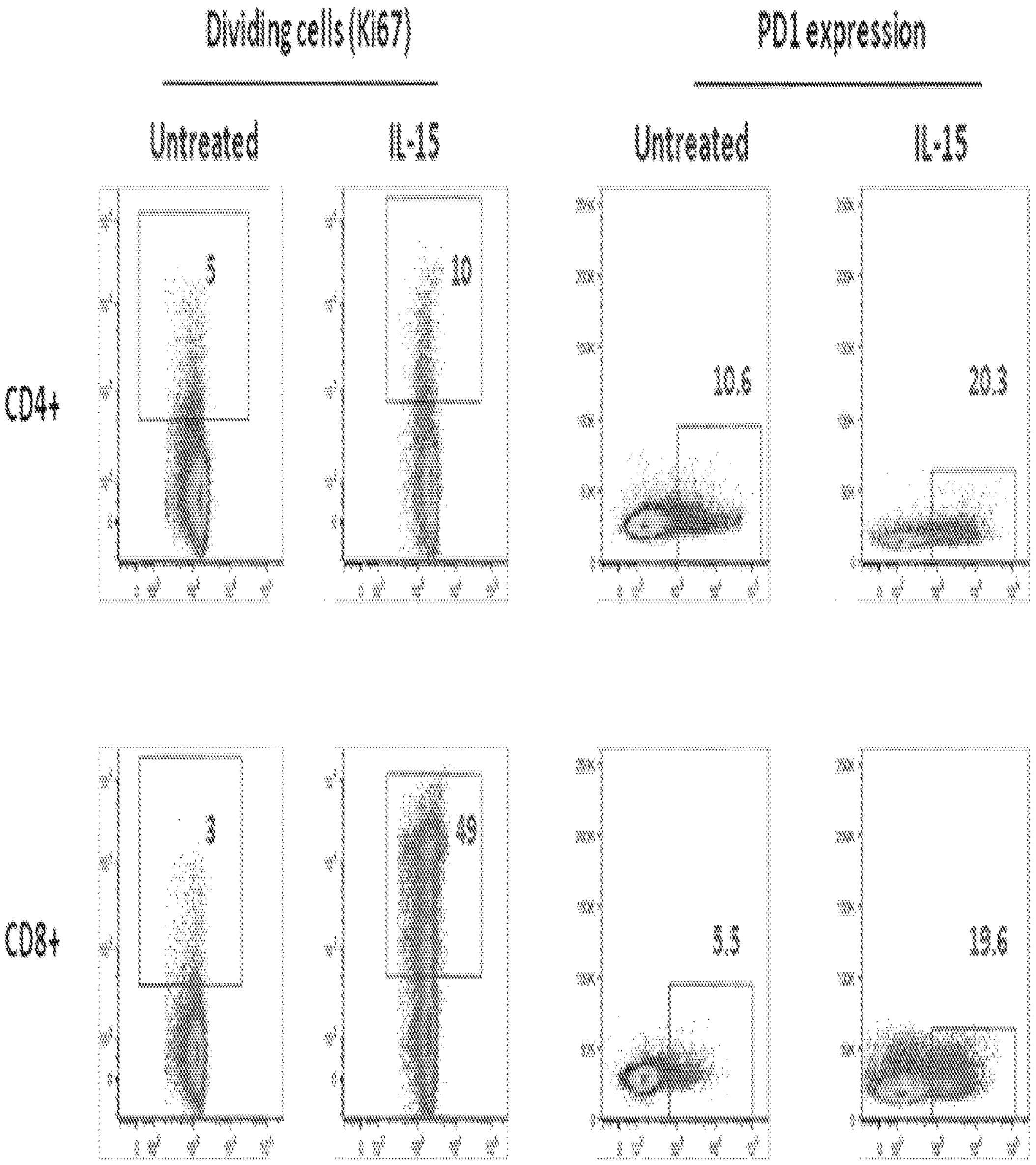

FIG. 8. T lymphocyte proliferation and PD1 expression within the lymph nodes upon IL-15 heterodimer s.c. administration.

Figure 9:
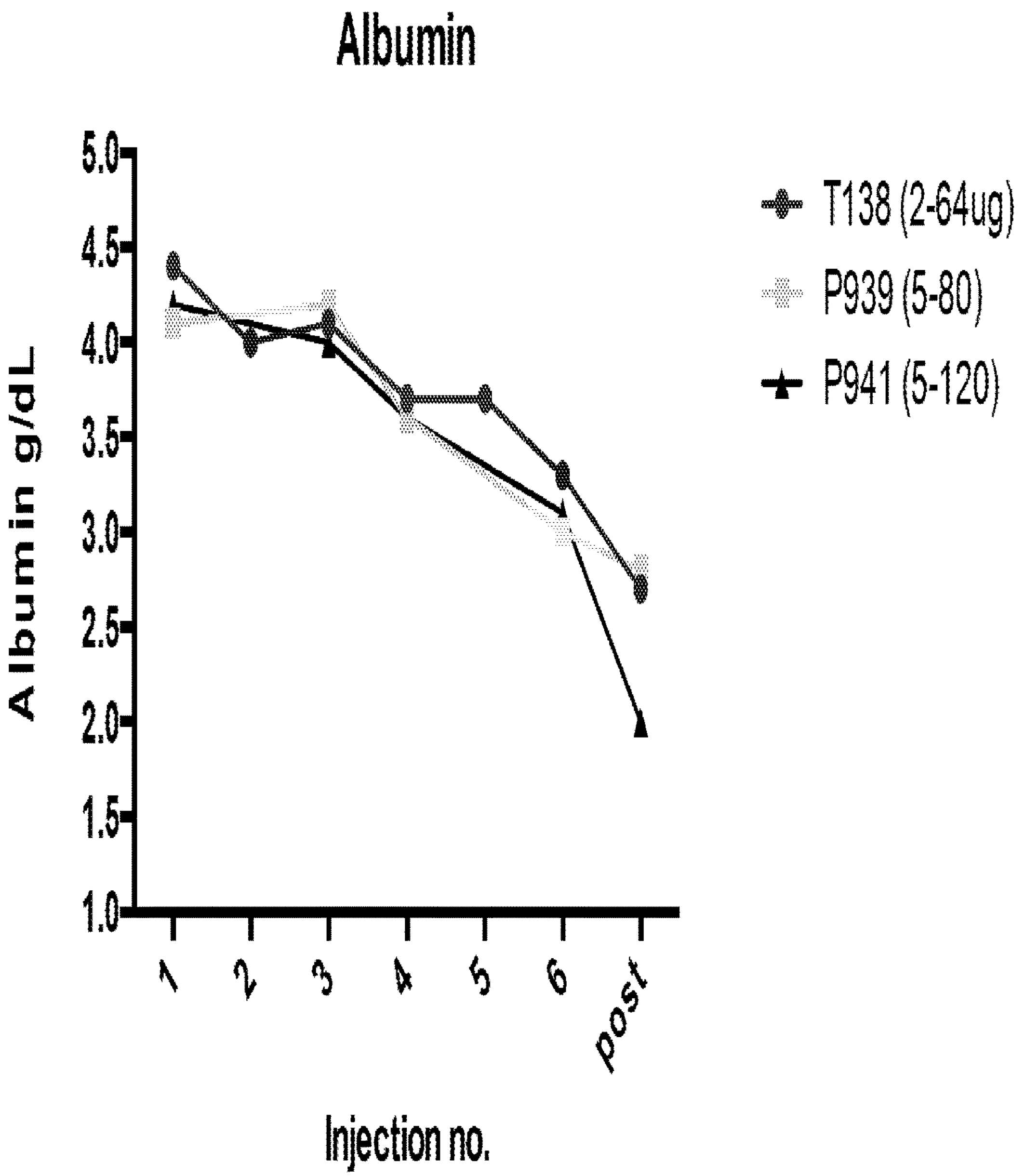

FIG. 9. Serum albumin profile during IL-15 heterodimer s.c. administration. Circles: T138 (2-64 μg/kg); squares: P934 (5-80 μg/kg); triangles: P941 (5-120 μg/kg).

Figure 10:
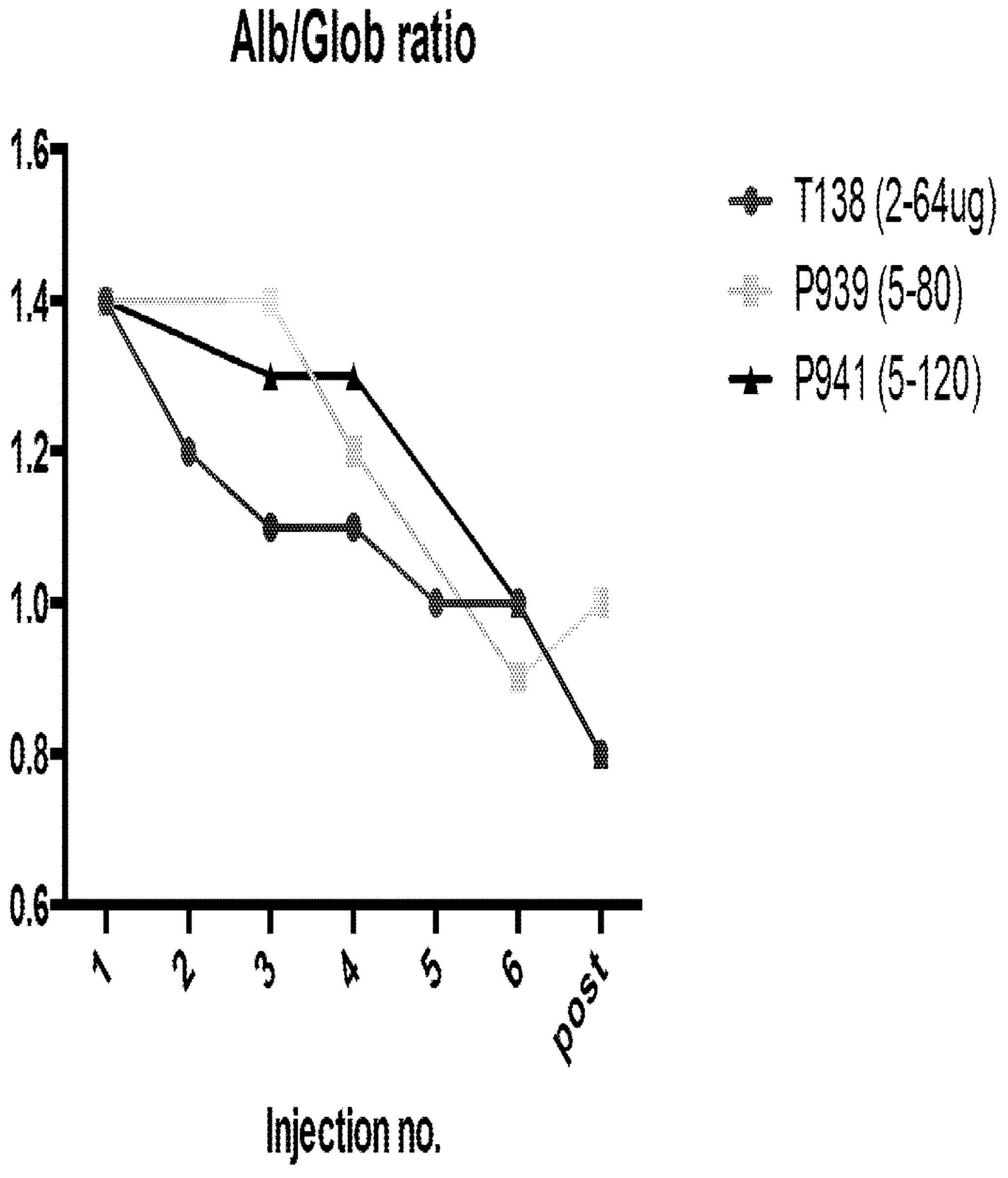

FIG. 10. Serum albumin/globulin (Alb/Glob) Ratio profile during IL-15 heterodimer s.c. administration. Circles: T138 (2-64 μg/kg); squares: P934 (5-80 μg/kg); triangles: P941 (5-120 μg/kg).

Figure 11:
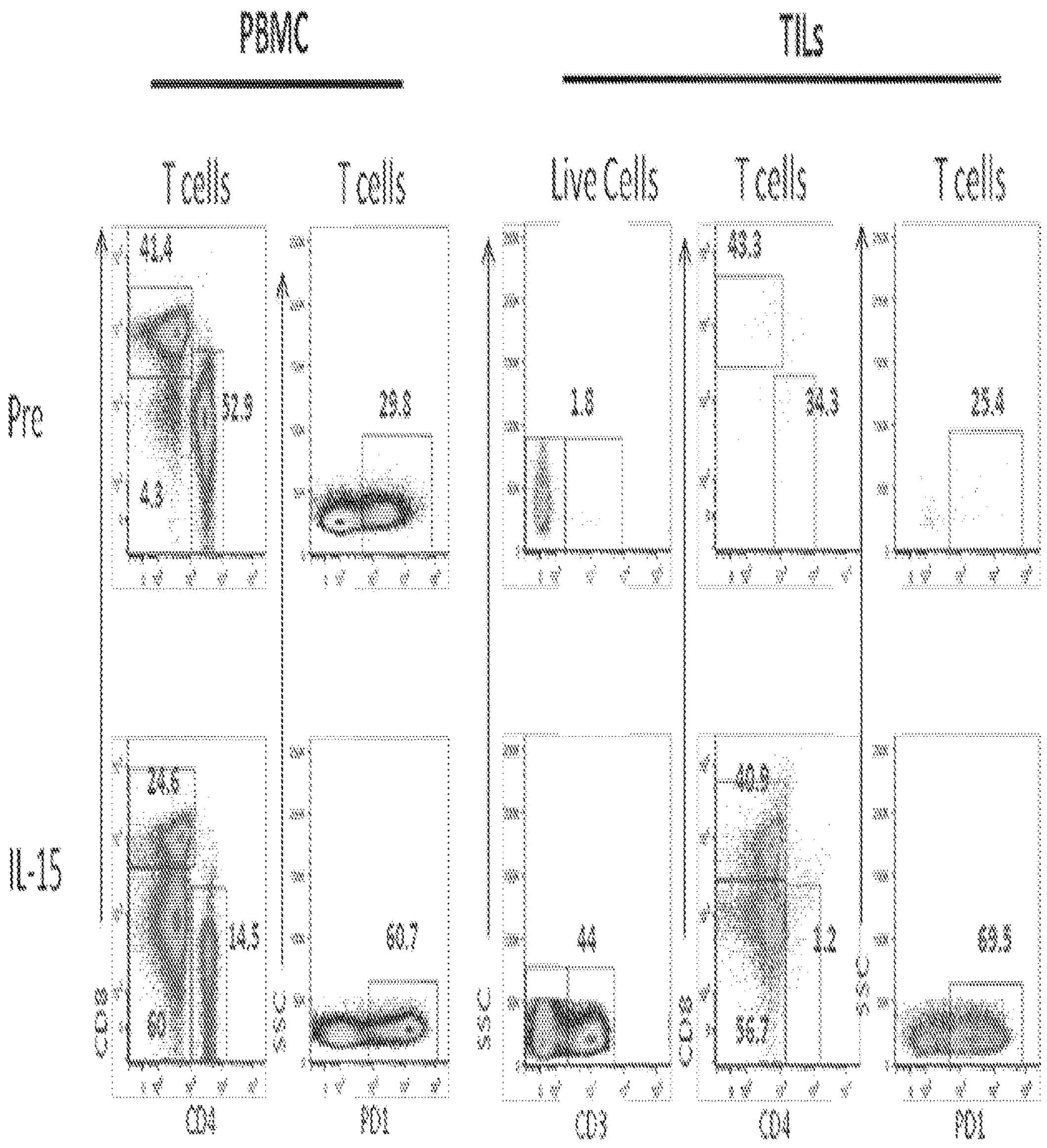

FIG. 11. Lymphocyte infiltration within a macaque tumor and PD1 expression upon IL-15 heterodimer s.c. administration. PBMC (left): Analysis of blood lymphocytes by flow cytometry. TILs (right): Tumor Infiltrating Lymphocytes before (Pre, top) and after (hetIL-15, bottom) heterodimer s.c. administration.

5. DETAILED DESCRIPTION

5.1 Forms of IL-15Rα

Described herein is the naturally occurring soluble form of human IL-15Rα. Also described herein are specific IL-15Rα derivatives that are truncated, soluble forms of human IL-15Rα. These specific IL-15Rα derivatives and the naturally occurring soluble form of human IL-15Rα are based, in part, on the identification of the proteolytic cleavage site of human IL-15Rα. Further described herein are soluble forms of IL-15Rα that are characterized based upon glycosylation of the IL-15Rα.

The proteolytic cleavage of membrane-bound human IL-15Rα takes place between Gly170 and His171 in human IL-15Rα (Chertova et al., 2013, Journal of Biological Chemistry 288(25):18093-103). Thus, the proteolytic cleavage of human IL-15Rα takes place between the residues (i.e., Gly170 and His171) which are shown in bold and underlined in the provided amino acid sequence of the immature form of the native full length human IL-15Rα: MAPRRARGCR TLGLPALLLL LLLRPPATRG ITCPPPMSVE HADIWVKSYS LYSRERYICN SGFKRKAGTS SLTECVLNKA TNVAHWTTPS LKCIRDPALV HQRPAPPSTV TTAGVTPQPE SLSPSGKEPA ASSPSSNNTA ATTAAIVPGS QLMPSKSPST GTTEISSHES SHGTPSQTTA KNWELTASAS HQPPGVYPQ<u>G</u> <u>H</u>SDTTVAIST STVLLCGLSA VSLLACYLKS RQTPPLASVE MEAMEALPVT WGTSSRDEDL ENCSHHL (SEQ ID NO: 3; FIG. 2B).

Accordingly, in one aspect, provided herein is a soluble form of human IL-15Rα (e.g., a purified soluble form of human IL-15Rα), wherein the amino acid sequence of the soluble form of human IL-15Rα terminates at the site of the proteolytic cleavage of the native membrane-bound human IL-15Rα. In particular, provided herein is a soluble form of human IL-15Rα (e.g., a purified soluble form of human IL-15Rα), wherein the amino acid sequence of the soluble form of human IL-15Rα terminates with PQG (SEQ ID NO: 31), wherein G is Gly170. In particular embodiments, provided herein is a soluble form of human IL-15Rα (e.g., a purified soluble form of human IL-15Rα) which has the following amino acid sequence: MAPRRARGCR TLGLPALLLL LLLRPPATRG ITCPPPMSVE HADIWVKSYS LYSRERYICN SGFKRKAGTS SLTECVLNKA TNVAHWTTPS LKCIRDPALV HQRPAPPSTV TTAGVTPQPE SLSPSGKEPA ASSPSSNNTA ATTAAIVPGS QLMPSKSPST GTTEISSHES SHGTPSQTTA KNWELTASAS HQPPGVYPQG (SEQ ID NO: 32). In some embodiments, provided herein is an IL-15Rα derivative (e.g., a purified and/or soluble form of IL-15Rα derivative), which is a polypeptide that: (i) is at least 40%, 45%, 50%, 55%, 60%, 65%, 70%, 75%, 80%, 85%, 90%, 95%, 98% or 99% identical to SEQ ID NO: 32; and (ii) terminates with the amino acid sequence PQG (SEQ ID NO: 31). In other particular embodiments, provided herein is a soluble form of human IL-15Rα (e.g., a purified soluble form of human IL-15Rα) which has the following amino acid sequence: ITCPPPMSVE HADIWVKSYS LYSRERYICN SGFKRKAGTS SLTECVLNKA TNVAHWTTPS LKCIRDPALV HQRPAPPSTV TTAGVTPQPE SLSPSGKEPA ASSPSSNNTA ATTAAIVPGS QLMPSKSPST GTTEISSHES SHGTPSQTTA KNWELTASAS HQPPGVYPQG (SEQ ID NO: 33). In some embodiments, provided herein is an IL-15Rα derivative (e.g., a purified and/or soluble form of an IL-15Rα derivative), which is a polypeptide that is at least 40%, 45%, 50%, 55%, 60%, 65%, 70%, 75%, 80%, 85%, 90%, 95%, 98% or 99% identical to SEQ ID NO: 33, and, optionally, wherein the amino acid sequence of the soluble form of the IL-15Rα derivative terminates with PQG (SEQ ID NO: 31).

In another aspect, provided herein are IL-15Rα derivatives that are truncated, soluble forms of naturally occurring human IL-15Rα. In certain embodiments, provided herein is a soluble form of human IL-15Rα (e.g., a purified soluble form of human IL-15Rα), wherein the amino acid sequence of the soluble form of human IL-15Rα terminates with PQGH (SEQ ID NO: 30), wherein H is His171 of SEQ ID NO:45. In particular embodiments, provided herein is a soluble form of human IL-15Rα (e.g., a purified soluble form of human IL-15Rα) which has the following amino acid sequence: MAPRRARGCR TLGLPALLLL LLLRPPATRG ITCPPPMSVE HADIWVKSYS LYSRERYICN SGFKRKAGTS SLTECVLNKA TNVAHWTTPS LKCIRDPALV HQRPAPPSTV TTAGVTPQPE SLSPSGKEPA ASSPSSNNTA ATTAAIVPGS QLMPSKSPST GTTEISSHES SHGTPSQTTA KNWELTASAS HQPPGVYPQGH (SEQ ID NO: 34). In some embodiments, provided herein is an IL-15Rα derivative (e.g., a purified and/or soluble form of an IL-15Rα derivative), which is a polypeptide that: (i) is at least 40%, 45%, 50%, 55%, 60%, 65%, 70%, 75%, 80%, 85%, 90%, 95%, 98% or 99% identical to SEQ ID NO: 34; and (ii) terminates with the amino acid sequence PQGH (SEQ ID NO: 30). In other particular embodiments, provided herein is a soluble form of human IL-15Rα (e.g., a purified soluble form of human IL-15Rα) which has the following amino acid sequence: ITCPPPMSVE HADIWVKSYS LYSRERYICN SGFKRKAGTS SLTECVLNKA TNVAHWTTPS LKCIRDPALV HQRPAPPSTV TTAGVTPQPE SLSPSGKEPA ASSPSSNNTA ATTAAIVPGS QLMPSKSPST GTTEISSHES SHGTPSQTTA KNWELTASAS HQPPGVYPQGH (SEQ ID NO: 35). In some embodiments, provided herein is an IL-15Rα derivative (e.g., a purified and/or soluble form of an IL-15Rα derivative), which is a polypeptide that: (i) is at least 40%, 45%, 50%, 55%, 60%, 65%, 70%, 75%, 80%, 85%, 90%, 95%, 98% or 99% identical to SEQ ID NO: 35; and (ii) has the amino acid sequence of the soluble form of the IL-15Rα derivative terminates with PQGH (SEQ ID NO: 30).

In certain embodiments, provided herein is a soluble form of human IL-15Rα (e.g., a purified soluble form of human IL-15Rα), wherein the amino acid sequence of the soluble form of human IL-15Rα terminates with PQGHS (SEQ ID NO: 29), wherein S is Ser172 of SEQ ID NO:45. In particular embodiments, provided herein is a soluble form of human IL-15Rα (e.g., a purified soluble form of human IL-15Rα) which has the following amino acid sequence: MAPRRARGCR TLGLPALLLL LLLRPPATRG ITCPPPMSVE HADIWVKSYS LYSRERYICN SGFKRKAGTS SLTECVLNKA TNVAHWTTPS LKCIRDPALV HQRPAPPSTV TTAGVTPQPE SLSPSGKEPA ASSPSSNNTA ATTAAIVPGS QLMPSKSPST GTTEISSHES SHGTPSQTTA KNWELTASAS HQPPGVYPQGHS (SEQ ID NO: 36). In some embodiments, provided herein is an IL-15Rα derivative (e.g., a purified and/or soluble form of an IL-15Rα derivative), which is a polypeptide that: (i) is at least 40%, 45%, 50%, 55%, 60%, 65%, 70%, 75%, 80%, 85%, 90%, 95%, 98% or 99% identical to SEQ ID NO: 36; and (ii) terminates with the amino acid sequence PQGHS (SEQ ID NO: 29). In other particular embodiments, provided herein is a soluble form of human IL-15Rα (e.g., a purified soluble form of human IL-15Rα) which has the following amino acid sequence: ITCPPPMSVE HADIWVKSYS LYSRERYICN SGFKRKAGTS SLTECVLNKA TNVAHWTTPS LKCIRDPALV HQRPAPPSTV TTAGVTPQPE SLSPSGKEPA ASSPSSNNTA ATTAAIVPGS QLMPSKSPST GTTEISSHES SHGTPSQTTA KNWELTASAS HQPPGVYPQGHS (SEQ ID NO: 37). In some embodiments, provided herein is an IL-15Rα derivative (e.g., a purified and/or soluble form of an IL-15Rα derivative), which is a polypeptide that: (i) is at least 40%, 45%, 50%, 55%, 60%, 65%, 70%, 75%, 80%, 85%, 90%, 95%, 98% or 99% identical to SEQ ID NO: 37; and (ii) terminates with the amino acid sequence PQGHS (SEQ ID NO: 29).

In certain embodiments, provided herein is a soluble form of human IL-15Rα (e.g., a purified soluble form of human IL-15Rα), wherein the amino acid sequence of the soluble form of human IL-15Rα terminates with PQGHSD (SEQ ID NO: 28), wherein D is Asp173 of SEQ ID NO:45. In particular embodiments, provided herein is a soluble form of human IL-15Rα (e.g., a purified soluble form of human IL-15Rα) which has the following amino acid sequence: MAPRRARGCR TLGLPALLLL LLLRPPATRG ITCPPPMSVE HADIWVKSYS LYSRERYICN SGFKRKAGTS SLTECVLNKA TNVAHWTTPS LKCIRDPALV HQRPAPPSTV TTAGVTPQPE SLSPSGKEPA ASSPSSNNTA ATTAAIVPGS QLMPSKSPST GTTEISSHES SHGTPSQTTA KNWELTASAS HQPPGVYPQGHSD (SEQ ID NO: 38). In some embodiments, provided herein is an IL-15Rα derivative (e.g., a purified and/or soluble form of an IL-15Rα derivative), which is a polypeptide that: (i) is at least 40%, 45%, 50%, 55%, 60%, 65%, 70%, 75%, 80%, 85%, 90%, 95%, 98% or 99% identical to SEQ ID NO: 38; and (ii) terminates with the amino acid sequence PQGHSD (SEQ ID NO: 28). In other particular embodiments, provided herein is a soluble form of human IL-15Rα (e.g., a purified soluble form of human IL-15Rα) which has the following amino acid sequence: ITCPPPMSVE HADIWVKSYS LYSRERYICN SGFKRKAGTS SLTECVLNKA TNVAHWTTPS LKCIRDPALV HQRPAPPSTV TTAGVTPQPE SLSPSGKEPA ASSPSSNNTA ATTAAIVPGS QLMPSKSPST GTTEISSHES SHGTPSQTTA KNWELTASAS HQPPGVYPQGHSD (SEQ ID NO: 39). In some embodiments, provided herein is an IL-15Rα derivative (e.g., a purified and/or soluble form of an IL-15Rα derivative), which is a polypeptide that: (i) is at least 40%, 45%, 50%, 55%, 60%, 65%, 70%, 75%, 80%, 85%, 90%, 95%, 98% or 99% identical to SEQ ID NO: 39; and (ii) terminates with the amino acid sequence PQGHSD (SEQ ID NO: 28).

In certain embodiments, provided herein is a soluble form of human IL-15Rα (e.g., a purified soluble form of human IL-15Rα), wherein the amino acid sequence of the soluble form of human IL-15Rα terminates with PQGHSDT (SEQ ID NO: 27), wherein T is Thr174 of SEQ ID NO:45. In particular embodiments, provided herein is a soluble form of human IL-15Rα (e.g., a purified soluble form of human IL-15Rα) which has the following amino acid sequence: MAPRRARGCR TLGLPALLLL LLLRPPATRG ITCPPPMSVE HADIWVKSYS LYSRERYICN SGFKRKAGTS SLTECVLNKA TNVAHWTTPS LKCIRDPALV HQRPAPPSTV TTAGVTPQPE SLSPSGKEPA ASSPSSNNTA ATTAAIVPGS QLMPSKSPST GTTEISSHES SHGTPSQTTA KNWELTASAS HQPPGVYPQGHSDT (SEQ ID NO: 40). In some embodiments, provided herein is an IL-15Rα derivative (e.g., a purified and/or soluble form of an IL-15Rα derivative), which is a polypeptide that: (i) is at least 40%, 45%, 50%, 55%, 60%, 65%, 70%, 75%, 80%, 85%, 90%, 95%, 98% or 99% identical to SEQ ID NO: 40; and (ii) terminates with the amino acid sequence PQGHSDT (SEQ ID NO: 27). In other particular embodiments, provided herein is a soluble form of human IL-15Rα (e.g., a purified soluble form of human IL-15Rα) which has the following amino acid sequence: ITCPPPMSVE HADIWVKSYS LYSRERYICN SGFKRKAGTS SLTECVLNKA TNVAHWTTPS LKCIRDPALV HQRPAPPSTV TTAGVTPQPE SLSPSGKEPA ASSPSSNNTA ATTAAIVPGS QLMPSKSPST GTTEISSHES SHGTPSQTTA KNWELTASAS HQPPGVYPQGHSDT (SEQ ID NO: 41). In some embodiments, provided herein is an IL-15Rα derivative (e.g., a purified and/or soluble form of an IL-15Rα derivative), which is a polypeptide that: (i) is at least 40%, 45%, 50%, 55%, 60%, 65%, 70%, 75%, 80%, 85%, 90%, 95%, 98% or 99% identical to SEQ ID NO: 41; and (ii) terminates with the amino acid sequence PQGHSDT (SEQ ID NO: 27).

In certain embodiments, provided herein is a soluble form of human IL-15Rα (e.g., a purified soluble form of human IL-15Rα), wherein the amino acid sequence of the soluble form of human IL-15Rα terminates with PQGHSDTT (SEQ ID NO: 26), wherein T is Thr175 of SEQ ID NO:45. In particular embodiments, provided herein is a soluble form of human IL-15Rα (e.g., a purified soluble form of human IL-15Rα) which has the following amino acid sequence: MAPRRARGCR TLGLPALLLL LLLRPPATRG ITCPPPMSVE HADIWVKSYS LYSRERYICN SGFKRKAGTS SLTECVLNKA TNVAHWTTPS LKCIRDPALV HQRPAPPSTV TTAGVTPQPE SLSPSGKEPA ASSPSSNNTA ATTAAIVPGS QLMPSKSPST GTTEISSHES SHGTPSQTTA KNWELTASAS HQPPGVYPQGHSDTT (SEQ ID NO: 4). In some embodiments, provided herein is an IL-15Rα derivative (e.g., a purified and/or soluble form of an IL-15Rα derivative), which is a polypeptide that: (i) is at least 40%, 45%, 50%, 55%, 60%, 65%, 70%, 75%, 80%, 85%, 90%, 95%, 98% or 99% identical to SEQ ID NO: 4; and (ii) terminates with the amino acid sequence PQGHSDTT (SEQ ID NO: 26). In other particular embodiments, provided herein is a soluble form of human IL-15Rα (e.g., a purified soluble form of human IL-15Rα) which has the following amino acid sequence: ITCPPPMSVE HADIWVKSYS LYSRERYICN SGFKRKAGTS SLTECVLNKA TNVAHWTTPS LKCIRDPALV HQRPAPPSTV TTAGVTPQPE SLSPSGKEPA ASSPSSNNTA ATTAAIVPGS QLMPSKSPST GTTEISSHES SHGTPSQTTA KNWELTASAS HQPPGVYPQGHSDTT (SEQ ID NO: 45). In some embodiments, provided herein is an IL-15Rα derivative (e.g., a purified and/or soluble form of an IL-15Rα derivative), which is a polypeptide that: (i) is at least 40%, 45%, 50%, 55%, 60%, 65%, 70%, 75%, 80%, 85%, 90%, 95%, 98% or 99% identical to SEQ ID NO: 45; and (ii) terminates with the amino acid sequence PQGHSDTT (SEQ ID NO: 26).

In some embodiments, provided herein is an IL-15Rα derivative of naturally occurring human IL-15Rα, wherein the IL-15Rα derivative is soluble and: (a) the last amino acids at the C-terminal end of the IL-15Rα derivative consist of amino acid residues PQGHSDTT (SEQ ID NO: 26), wherein T is at the C-terminal end of the amino acid sequence; (b) the last amino acids at the C-terminal end of the IL-15Rα derivative consist of amino acid residues PQGHSDT (SEQ ID NO: 27), wherein T is at the C-terminal end of the amino acid sequence; (c) the last amino acids at the C-terminal end of the IL-15Rα derivative consist of amino acid residues PQGHSD (SEQ ID NO: 28), wherein D is at the C-terminal end of the amino acid sequence; (d) the last amino acids at the C-terminal end of the IL-15Rα derivative consist of amino acid residues PQGHS (SEQ ID NO: 29), wherein S is at the C-terminal end of the amino acid sequence; or (e) the last amino acids at the C-terminal end of the IL-15Rα derivative consist of amino acid residues PQGH (SEQ ID NO: 30), wherein H is at the C-terminal end of the amino acid sequence. In certain embodiments, the amino acid sequences of these IL-15Rα derivatives are at least 75%, at least 85%, at least 90%, at least 95%, at least 96%, at least 97%, at least 98%, or at least 99% identical to the amino acid sequence of SEQ ID NO: 45. In some embodiments, provided herein is an IL-15Rα derivative of a naturally occurring human IL-15Rα, wherein the IL-15Rα derivative: (i) is soluble; (ii) comprises an amino acid sequence that is at least 75%, at least 80%, at least 90%, at least 95%, at least 96%, at least 97%, or at least 98% identical to the amino acid sequence of SEQ ID NO:45; and (iii) terminates with the amino acid sequence PQG (SEQ ID NO: 31), wherein G is at the C-terminal end of the amino acid sequence of the IL-15Rα derivative. In some embodiments, these IL-15Rα derivatives are purified.

In another aspect, provided herein are IL-15Rα derivatives in which the cleavage site for an endogenous protease that cleaves native IL-15Rα has been mutated. In one embodiment, provided herein are IL-15Rα derivatives comprising one, two, three, four, five, six, seven or eight mutations (e.g., additions, deletions or substitutions; such as deletions or substitutions of one, two, three, four, five, six, seven or eight amino acid residues) in the extracellular domain cleavage site of IL-15Rα such that cleavage of the IL-15Rα by an endogenous protease that cleaves native IL-15Rα is inhibited. As discussed above, the proteolytic cleavage of membrane-bound human IL-15Rα takes place between Gly170 and His171 in human IL-15Rα. In one embodiment, these amino acid residues or surrounding amino acid residues are mutated such that cleavage of IL-15Rα by an endogenous protease that cleaves native IL-15Rα is inhibited. In certain embodiments, the amino acid sequence PQGHSDTT (SEQ ID NO: 26) is mutated such that cleavage by an endogenous protease that cleaves native human IL-15Rα is inhibited. In specific embodiments, one, two, three, four, five, six, seven, or eight amino acid substitutions and/or deletions (such as substitutions and/or deletions of one, two, three, four, five, six, seven or eight amino acid residues) are introduced into the amino acid sequence PQGHSDTT (SEQ ID NO: 26) of human IL-15Rα such that cleavage by an endogenous proteases that cleaves native human IL-15Rα is inhibited. In certain embodiments, the amino acid sequence PQGHSDTT (SEQ ID NO: 26) is replaced with a cleavage site that is recognized and cleaved by a heterologous protease. Non-limiting examples of such heterologous protease cleavage sites include Arg-X-X-Arg (SEQ ID NO: 7), which is recognized and cleaved by furin protease; and A-B-Pro-Arg-X-Y (SEQ ID NO:8) (A and B are hydrophobic amino acids and X and Y are nonacidic amino acids) and Gly-Arg-Gly, which are recognized and cleaved by the thrombin protease.

In another aspect, provided herein are IL-15Rα derivatives, wherein the IL-15Rα derivatives: (i) comprises a mutated extracellular cleavage site that inhibits cleavage by an endogenous protease that cleaves native IL-15Rα, and (ii) lack all or a fragment of the transmembrane domain of native IL-15Rα. In certain embodiments, provided herein are IL-15Rα derivatives, wherein the IL-15Rα derivatives comprise: (i) one, two, three, four, five, six, seven or eight mutations (e.g., substitutions and/or deletions) in the extracellular cleavage site of IL-15Rα such that cleavage of IL-15Rα by an endogenous protease that cleaves native IL-15Rα is inhibited, and (ii) all or a fragment of a transmembrane domain of a heterologous molecule in place of all or a fragment of the transmembrane domain of native IL-15Rα. In some embodiments, provided herein are IL-15Rα derivatives, wherein the IL-15Rα derivatives comprise: (i) one, two, three, four, five, six, seven or eight mutations (e.g., substitutions and/or deletions) in the amino acid sequence PQGHSDTT (SEQ ID NO: 26) such that cleavage of IL-15Rα by an endogenous protease that cleaves native IL-15Rα is inhibited, and (ii) all or a fragment of a transmembrane domain of a heterologous molecule in place of all or a fragment of the transmembrane domain of native IL-15Rα. In accordance with these embodiments, the IL-15Rα derivatives may or may not comprise all or a fragment of the cytoplasmic tail of native IL-15Rα. In certain embodiments, the heterologous molecule is CD4, CD8, or major histocompatibility complex (MHC).

In another aspect, provided herein are glycosylated forms of IL-15Rα (e.g., purified glycosylated forms of IL-15Rα), wherein the glycosylation of the IL-15Rα accounts for at least 20%, at least 25%, at least 30%, at least 35%, at least 40%, at least 45%, at least 50%, or 20% to 25%, 20% to 30%, 25% to 30%, 25% to 35%, 30% to 35%, 30% to 40%, 35% to 40%, 35% to 45%, 40% to 50%, 45% to 50%, 20% to 40%, or 25% to 50% of the mass (molecular weight) of the IL-15Rα as assessed by techniques known to one of skill in the art. The percentage of the mass (molecular weight) of IL-15Rα (e.g., purified IL-15Rα) that glycosylation of IL-15Rα accounts for can be determined using, for example and without limitation, gel electrophoresis and quantitative densitometry of the gels, and comparison of the average mass (molecular weight) of a glycosylated form of IL-15Rα (e.g., a purified glycosylated form of IL-15Rα) to the non-glycosylated form of IL-15Rα (e.g., a purified non-glycosylated form of IL-15Rα). In one embodiment, the average mass (molecular weight) of IL-15Rα (e.g., purified IL-15Rα) can be determined using MALDI-TOF MS spectrum on Voyager De-Pro equipped with CovalX HM-1 high mass detector using sinapic acid as matrix, and the mass of a glycosylated form of IL-15Rα (e.g., purified glycosylated form of IL-15Rα) can be compared to the mass of the non-glycosylated form of IL-15Rα (e.g., purified non-glycosylated form of IL-15Rα) to determine the percentage of the mass that glycosylation accounts for.

In certain embodiments, provided herein is a glycosylated IL-15Rα (e.g., human IL-15Rα), wherein the glycosylation accounts for at least 20%, 25%, 30%, 35%, 40%, 45%, 50%, 55%, 60%, 65%, 70%, 75%, 80%, 85%, 90%, 95% or more of the mass (molecular weight) of the IL-15Rα. In some embodiments, provided herein is a glycosylated IL-15Rα (e.g., human IL-15Rα), wherein the glycosylation accounts for 20% to 25%, 20% to 30%, 25% to 30%, 25% to 35%, 30% to 35%, 30% to 40%, 35% to 40%, 35% to 45%, 40% to 50%, 45% to 50%, 20% to 40%, 25% to 50%, 50% to 75%, 75% to 95%, or 75% to 100% of the mass (molecular weight) of the IL-15Rα. In certain embodiments, provided herein is a glycosylated IL-15Rα (e.g., human IL-15Rα), wherein the glycosylation accounts for about 20%, about 25%, about 30%, about 35%, about 40%, about 45%, about 50%, about 55%, about 60%, about 65%, about 70%, about 75%, about 80%, about 85%, about 90%, or about 95% of the mass (molecular weight) of the IL-15Rα. In specific embodiments, the glycosylated IL-15Rα is a native IL-15Rα (e.g., a native human IL-15Rα). In other specific embodiments, the glycosylated IL-15Rα is an IL-15Rα derivative (e.g., an IL-15Rα derivative of naturally occurring human IL-15Rα). In some embodiments, the glycosylated IL-15Rα is a native soluble human IL-15Rα, such as SEQ ID NO: 32 or 33. In other embodiments, the glycosylated IL-15Rα is an IL-15Rα derivative that is a soluble form of human IL-15Rα. In specific embodiments, the glycosylated IL-15Rα has the amino acid sequence of SEQ ID NO: 4, 34, 35, 36, 37, 38, 39, 40, 41, or 45. In particular embodiments, the glycosylated IL-15Rα has an amino acid sequence that is at least 40%, 45%, 50%, 55%, 60%, 65%, 70%, 75%, 80%, 85%, 90%, 95%, 98% or 99% identical to SEQ ID NO: 3, 4: 32, 33, 34, 35, 36, 37, 38, 39, 40, 41, or 45. In some embodiments, the glycosylated IL-15Rα is glycosylated at one, two, three, four, five, six, seven, or all, of the following glycosylation sites: (i) O-glycosylation on Thr5 of amino acid sequence NWELTASASHQPPGVYPQG (SEQ ID NO: 42) in the IL-15Rα; (ii) O-glycosylation on Ser7 of amino acid sequence NWELTASASHQPPGVYPQG (SEQ ID NO: 42) in the IL-15Rα; (iii) N-glycosylation on Ser 8 of amino acid sequence ITCPPPMSVEHADIWVK (SEQ ID NO: 43) in the IL-15Rα, or Ser 8 of amino acid sequence ITCPPPMSVEHADIWVKSYSLYSRERYICNS (SEQ ID NO: 44) in the IL-15Rα; (iv) N-glycosylation on Ser 18 of amino acid sequence ITCPPPMSVEHADIWVKSYSLYSRERYICNS (SEQ ID NO: 44) in the IL-15Rα; (v) N-glycosylation on Ser 20 of amino acid sequence ITCPPPMSVEHADIWVKSYSLYSRERYICNS (SEQ ID NO: 44) in the IL-15Rα; (vi) N-glycosylation on Ser 23 of amino acid sequence ITCPPPMSVEHADIWVKSYSLYSRERYICNS (SEQ ID NO: 44) in the IL-15Rα; and/or (vii) N-glycosylated on Ser 31 of amino acid sequence ITCPPPMSVEHADIWVKSYSLYSRERYICNS (SEQ ID NO: 44) in the IL-15Rα. In certain embodiments, the glycosylated IL-15Rα is purified or isolated.

In certain embodiments, provided herein is a composition comprising IL-15 and glycosylated IL-15Rα (e.g., human IL-15Rα), wherein the glycosylation of the IL-15Rα accounts for at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% of the mass (molecular weight) of the IL-15Rα as assessed by techniques known to one of skill in the art. In some embodiments, provided herein is provided herein is a composition comprising IL-15 and glycosylated IL-15Rα (e.g., human IL-15Rα), wherein the glycosylation of the IL-15Rα accounts for 20% to 25%, 20% to 30%, 25% to 30%, 25% to 35%, 30% to 35%, 30% to 40%, 35% to 40%, 35% to 45%, 40% to 50%, 45% to 50%, 20% to 40%, 25% to 50%, 50% to 75%, or 75% to 95% of the mass (molecular weight) of the IL-15Rα as assessed by techniques known to one of skill in the art. In other embodiments, provided herein is a composition comprising IL-15 and glycosylated IL-15Rα (e.g., human IL-15Rα), wherein the glycosylation of the IL-15Rα accounts for about 20%, about 25%, about 30%, about 35%, about 40%, about 45%, about 50%, about 55%, about 60%, about 65%, about 70%, about 75%, about 80%, about 85%, about 90%, or about 95% of the mass (molecular weight) of the IL-15Rα as assessed by techniques known to one of skill in the art. In certain embodiments, the IL-15 is glycosylated. In specific embodiments, the glycosylated IL-15Rα is a native IL-15Rα (e.g., a native human IL-15Rα). In other specific embodiments, the glycosylated IL-15Rα is an IL-15Rα derivative (e.g., an IL-15Rα derivative of naturally occurring human IL-15Rα). In some embodiments, the glycosylated IL-15Rα is a native soluble human IL-15Rα, such as SEQ ID NO: 32 or 33. In other embodiments, the glycosylated IL-15Rα is an IL-15Rα derivative that is a soluble form of human IL-15Rα. In specific embodiments, the glycosylated IL-15Rα has the amino acid sequence of SEQ ID NO: 4, 34, 35, 36, 37, 38, 39, 40, 41, or 45. In particular embodiments, the glycosylated IL-15Rα has an amino acid sequence that is at least 40%, 45%, 50%, 55%, 60%, 65%, 70%, 75%, 80%, 85%, 90%, 95%, 98% or 99% identical to SEQ ID NO: 3, 4: 32, 33, 34, 35, 36, 37, 38, 39, 40, 41, or 45. In some embodiments, the glycosylated IL-15Rα is glycosylated at one, two, three, four, five, six, seven, or all, of the following glycosylation sites: (i) O-glycosylation on Thr5 of amino acid sequence NWELTASASHQPPGVYPQG (SEQ ID NO: 42) in the IL-15Rα; (ii) O-glycosylation on Ser7 of amino acid sequence NWELTASASHQPPGVYPQG (SEQ ID NO: 42) in the IL-15Rα; (iii) N-glycosylation on Ser 8 of amino acid sequence ITCPPPMSVEHADIWVK (SEQ ID NO: 43) in the IL-15Rα, or Ser 8 of amino acid sequence ITCPPPMSVEHADIWVKSYSLYSRERYICNS (SEQ ID NO: 44) in the IL-15Rα; (iv) N-glycosylation on Ser 18 of amino acid sequence ITCPPPMSVEHADIWVKSYSLYSRERYICNS (SEQ ID NO: 44) in the IL-15Rα; (v) N-glycosylation on Ser 20 of amino acid sequence ITCPPPMSVEHADIWVKSYSLYSRERYICNS (SEQ ID NO: 44) in the IL-15Rα; (vi) N-glycosylation on Ser 23 of amino acid sequence ITCPPPMSVEHADIWVKSYSLYSRERYICNS (SEQ ID NO: 44) in the IL-15Rα; and/or (vii) N-glycosylated on Ser 31 of amino acid sequence ITCPPPMSVEHADIWVKSYSLYSRERYICNS (SEQ ID NO: 44) in the IL-15Rα.

In certain embodiments, provided herein is an IL-15/IL-15Rα complex comprising glycosylated IL-15Rα (e.g., human IL-15Rα), wherein the glycosylation of the IL-15Rα accounts for at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% of the mass (molecular weight) of the IL-15Rα as assessed by techniques known to one of skill in the art. In some embodiments, provided herein is an IL-15/IL-15Rα complex comprising glycosylated IL-15Rα (e.g., human IL-15Rα), wherein the glycosylation of the IL-15Rα accounts for 20% to 25%, 20% to 30%, 25% to 30%, 25% to 35%, 30% to 35%, 30% to 40%, 35% to 40%, 35% to 45%, 40% to 50%, 45% to 50%, 20% to 40%, 25% to 50%, 50% to 75%, or 75% to 95% of the mass (molecular weight) of the IL-15Rα as assessed by techniques known to one of skill in the art. In other embodiments, provided herein is an IL-15/IL-15Rα complex comprising glycosylated IL-15Rα (e.g., human IL-15Rα), wherein the glycosylation of the IL-15Rα accounts for about 20%, about 25%, about 30%, about 35%, about 40%, about 45%, about 50%, about 55%, about 60%, about 65%, about 70%, about 75%, about 80%, about 85%, about 90%, or about 95% of the mass (molecular weight) of the IL-15Rα as assessed by techniques known to one of skill in the art. In specific embodiments, the glycosylated IL-15Rα is a native IL-15Rα (e.g., a native human IL-15Rα). In other specific embodiments, the glycosylated IL-15Rα is an IL-15Rα derivative (e.g., an IL-15Rα derivative of naturally occurring human IL-15Rα). In some embodiments, the glycosylated IL-15Rα is a native soluble human IL-15Rα, such as SEQ ID NO: 32 or 33. In other embodiments, the glycosylated IL-15Rα is an IL-15Rα derivative that is a soluble form of human IL-15Rα. In specific embodiments, the glycosylated IL-15Rα has the amino acid sequence of SEQ ID NO: 4, 34, 35, 36, 37, 38, 39, 40, 41, or 45. In particular embodiments, the glycosylated IL-15Rα has an amino acid sequence that is at least 40%, 45%, 50%, 55%, 60%, 65%, 70%, 75%, 80%, 85%, 90%, 95%, 98% or 99% identical to SEQ ID NO: 3, 4, 32, 33, 34, 35, 36, 37, 38, 39, 40, 41, or 45. In some embodiments, the glycosylated IL-15Rα is glycosylated at one, two, three, four, five, six, seven, or all, of the following glycosylation sites: (i) 0-glycosylation on Thr5 of amino acid sequence NWELTASASHQPPGVYPQG (SEQ ID NO: 42) in the IL-15Rα; (ii) O-glycosylation on Ser7 of amino acid sequence NWELTASASHQPPGVYPQG (SEQ ID NO: 42) in the IL-15Rα; (iii) N-glycosylation on Ser 8 of amino acid sequence ITCPPPMSVEHADIWVK (SEQ ID NO: 43) in the IL-15Rα, or Ser 8 of amino acid sequence ITCPPPMSVEHADIWVKSYSLYSRERYICNS (SEQ ID NO: 44) in the IL-15Rα; (iv) N-glycosylation on Ser 18 of amino acid sequence ITCPPPMSVEHADIWVKSYSLYSRERYICNS (SEQ ID NO: 44) in the IL-15Rα; (v) N-glycosylation on Ser 20 of amino acid sequence ITCPPPMSVEHADIWVKSYSLYSRERYICNS (SEQ ID NO: 44) in the IL-15Rα; (vi) N-glycosylation on Ser 23 of amino acid sequence ITCPPPMSVEHADIWVKSYSLYSRERYICNS (SEQ ID NO: 44) in the IL-15Rα; and/or (vii) N-glycosylated on Ser 31 of amino acid sequence ITCPPPMSVEHADIWVKSYSLYSRERYICNS (SEQ ID NO: 44) in the IL-15Rα. In certain embodiments, the IL-15/IL-15Rα complex is purified or isolated.

In another aspect, provided herein are glycosylated forms of IL-15Rα, wherein the IL-15Rα is glycosylated (N- or O-glycosylated) at certain amino acid residues. In certain embodiments, provided herein is a human IL-15Rα which is glycosylated at one, two, three, four, five, six, seven, or all, of the following glycosylation sites: (i) O-glycosylation on Thr5 of amino acid sequence NWELTASASHQPPGVYPQG (SEQ ID NO: 42) in the IL-15Rα; (ii) O-glycosylation on Ser7 of amino acid sequence NWELTASASHQPPGVYPQG (SEQ ID NO: 42) in the IL-15Rα; (iii) N-glycosylation on Ser 8 of amino acid sequence ITCPPPMSVEHADIWVK (SEQ ID NO: 43) in the IL-15Rα, or Ser 8 of amino acid sequence ITCPPPMSVEHADIWVKSYSLYSRERYICNS (SEQ ID NO: 44) in the IL-15Rα; (iv) N-glycosylation on Ser 18 of amino acid sequence ITCPPPMSVEHADIWVKSYSLYSRERYICNS (SEQ ID NO: 44) in the IL-15Rα; (v) N-glycosylation on Ser 20 of amino acid sequence ITCPPPMSVEHADIWVK-SYSLYSRERYICNS (SEQ ID NO: 44) in the IL-15Rα; (vi) N-glycosylation on Ser 23 of amino acid sequence ITCP-PPMSVEHADIWVKSYSLYSRERYICNS (SEQ ID NO: 44) in the IL-15Rα; and/or (vii) N-glycosylated on Ser 31 of amino acid sequence ITCPPPMSVEHADIWVKSYSLYSR-ERYICNS (SEQ ID NO: 44) in the IL-15Rα. In specific embodiments, the glycosylated IL-15Rα is a native human IL-15Rα. In other specific embodiments, the glycosylated IL-15Rα is an IL-15Rα derivative of naturally occurring human IL-15Rα. In some embodiments, the glycosylated IL-15Rα is a native soluble human IL-15Rα, such as SEQ ID NO: 32 or 33. In other embodiments, the glycosylated IL-15Rα is an IL-15Rα derivative that is a soluble form of human IL-15Rα. In specific embodiments, the glycosylated IL-15Rα has the amino acid sequence of SEQ ID NO: 4, 34, 35, 36, 37, 38, 39, 40, 41, or 45. In particular embodiments, the glycosylated IL-15Rα has an amino acid sequence that is at least 40%, 45%, 50%, 55%, 60%, 65%, 70%, 75%, 80%, 85%, 90%, 95%, 98% or 99% identical to SEQ ID NO: 3, 4, 32, 33, 34, 35, 36, 37, 38, 39, 40, 41, or 45. In certain embodiments, the glycosylated IL-15Rα is purified or isolated.

In certain embodiments, provided herein is a composition comprising IL-15 and human IL-15Rα, wherein the human IL-15Rα is glycosylated at one, two, three, four, five, six, seven, or all, of the following glycosylation sites: (i) O-glycosylation on Thr5 of amino acid sequence NWEL-TASASHQPPGVYPQG (SEQ ID NO: 42) in the IL-15Rα; (ii) 0-glycosylation on Ser7 of amino acid sequence NWEL-TASASHQPPGVYPQG (SEQ ID NO: 42) in the IL-15Rα; (iii) N-glycosylation on Ser 8 of amino acid sequence ITCPPPMSVEHADIWVK (SEQ ID NO: 43) in the IL-15Rα, or Ser 8 of amino acid sequence ITCPPPMSVE-HADIWVKSYSLYSRERYICNS (SEQ ID NO: 44) in the IL-15Rα; (iv) N-glycosylation on Ser 18 of amino acid sequence ITCPPPMSVEHADIWVKSYSLYSRERYICNS (SEQ ID NO: 44) in the IL-15Rα; (v) N-glycosylation on Ser 20 of amino acid sequence ITCPPPMSVEHADIWVK-SYSLYSRERYICNS (SEQ ID NO: 44) in the IL-15Rα; (vi) N-glycosylation on Ser 23 of amino acid sequence ITCP-PPMSVEHADIWVKSYSLYSRERYICNS (SEQ ID NO: 44) in the IL-15Rα; and/or (vii) N-glycosylated on Ser 31 of amino acid sequence ITCPPPMSVEHADIWVKSYSLYSR-ERYICNS (SEQ ID NO: 44) in the IL-15Rα. In specific embodiments, the glycosylated IL-15Rα is a native human IL-15Rα. In other specific embodiments, the glycosylated IL-15Rα is an IL-15Rα derivative of naturally occurring human IL-15Rα. In some embodiments, the glycosylated IL-15Rα is a native soluble human IL-15Rα, such as SEQ ID NO: 32 or 33. In other embodiments, the glycosylated IL-15Rα is an IL-15Rα derivative that is a soluble form of human IL-15Rα. In specific embodiments, the glycosylated IL-15Rα has the amino acid sequence of SEQ ID NO: 4, 34, 35, 36, 37, 38, 39, 40, 41, or 45. In particular embodiments, the glycosylated IL-15Rα has an amino acid sequence that is at least 40%, 45%, 50%, 55%, 60%, 65%, 70%, 75%, 80%, 85%, 90%, 95%, 98% or 99% identical to SEQ ID NO: 3, 4, 32, 33, 34, 35, 36, 37, 38, 39, 40, 41, or 45. In certain embodiments, the glycosylated IL-15Rα is purified or isolated.

In certain embodiments, provided herein is an IL-15/IL-15Rα complex comprising human IL-15Rα which is glycosylated at one, two, three, four, five, six, seven, or all, of the following glycosylation sites: (i) O-glycosylation on Thr5 of amino acid sequence NWELTASASHQP-PGVYPQG (SEQ ID NO: 42) in the IL-15Rα; (ii) O-glycosylation on Ser7 of amino acid sequence NWEL-TASASHQPPGVYPQG (SEQ ID NO: 42) in the IL-15Rα; (iii) N-glycosylation on Ser 8 of amino acid sequence ITCPPPMSVEHADIWVK (SEQ ID NO: 43) in the IL-15Rα, or Ser 8 of amino acid sequence ITCPPPMSVE-HADIWVKSYSLYSRERYICNS (SEQ ID NO: 44) in the IL-15Rα; (iv) N-glycosylation on Ser 18 of amino acid sequence ITCPPPMSVEHADIWVKSYSLYSRERYICNS (SEQ ID NO: 44) in the IL-15Rα; (v) N-glycosylation on Ser 20 of amino acid sequence ITCPPPMSVEHADIWVK-SYSLYSRERYICNS (SEQ ID NO: 44) in the IL-15Rα; (vi) N-glycosylation on Ser 23 of amino acid sequence ITCP-PPMSVEHADIWVKSYSLYSRERYICNS (SEQ ID NO: 44) in the IL-15Rα; and/or (vii) N-glycosylated on Ser 31 of amino acid sequence ITCPPPMSVEHADIWVKSYSLYSR-ERYICNS (SEQ ID NO: 44) in the IL-15Rα. In specific embodiments, the glycosylated IL-15Rα is a native human IL-15Rα. In other specific embodiments, the glycosylated IL-15Rα is an IL-15Rα derivative of naturally occurring human IL-15Rα. In some embodiments, the glycosylated IL-15Rα is a native soluble human IL-15Rα, such as SEQ ID NO: 32 or 33. In other embodiments, the glycosylated IL-15Rα is an IL-15Rα derivative that is a soluble form of human IL-15Rα. In specific embodiments, the glycosylated IL-15Rα has the amino acid sequence of SEQ ID NO: 4, 34, 35, 36, 37, 38, 39, 40, 41, or 45. In particular embodiments, the glycosylated IL-15Rα has an amino acid sequence that is at least 40%, 45%, 50%, 55%, 60%, 65%, 70%, 75%, 80%, 85%, 90%, 95%, 98% or 99% identical to SEQ ID NO: 3, 4, 32, 33, 34, 35, 36, 37, 38, 39, 40, 41, or 45. In certain embodiments, the IL-15/IL-15Rα complex is purified or isolated.

In certain embodiments, provided herein is a glycosylated form of IL-15Rα (e.g., human IL-15Rα), wherein the glycosylation accounts for at least 20%, at least 25%, at least 30%, at least 35%, at least 40%, at least 45%, at least 50%, or 20% to 25%, 20% to 30%, 25% to 30%, 25% to 35%, 30% to 35%, 30% to 40%, 35% to 40%, 35% to 45%, 40% to 50%, 45% to 50%, 20% to 40%, or 25% to 50% of the mass (molecular weight) of the IL-15Rα, and which is glycosylated on at least one, at least two, at least three, at least four, at least five, at least six, or at least seven of the following sites: (i) Thr5 of amino acid sequence NWEL-TASASHQPPGVYPQG (SEQ ID NO: 42) in the IL-15Rα (e.g., 0-glycosylated); (ii) Ser7 of amino acid sequence NWELTASASHQPPGVYPQG (SEQ ID NO: 42) in the IL-15Rα (e.g., 0-glycosylated); (iii) Ser 8 of amino acid sequence ITCPPPMSVEHADIWVK (SEQ ID NO: 43) or amino acid sequence ITCPPPMSVEHADIWVKSYSLYSR-ERYICNS (SEQ ID NO: 44) in the IL-15Rα (e.g., N-glycosylated); (iv) Ser 18 of amino acid sequence ITCPPPMS-VEHADIWVKSYSLYSRERYICNS (SEQ ID NO: 44) in the IL-15Rα (e.g., N-glycosylated); (v) Ser 20 of amino acid sequence ITCPPPMSVEHADIWVKSYSLYSRERYICNS (SEQ ID NO: 44) in the IL-15Rα (e.g., N-glycosylated); (vi) Ser 23 of amino acid sequence ITCPPPMSVEHADIWVK-SYSLYSRERYICNS (SEQ ID NO: 44) in the IL-15Rα (e.g., N-glycosylated); (vii) Ser 31 of amino acid sequence ITCPPPMSVEHADIWVKSYSLYSRERYICNS (SEQ ID NO: 44) in the IL-15Rα (e.g., N-glycosylated). In a particular embodiment, the glycosylated human IL-15Rα comprises amino acid sequence of SEQ ID NO: 3, 4, 32, 33, 34, 35, 36, 37, 38, 39, 40, 41 or 45. In another embodiment, the glycosylated human IL-15Rα is: (i) soluble; and (ii) (a) the last amino acids at the C-terminal end of the soluble form of human IL-15Rα consist of amino acid residues PQGHSDTT (SEQ ID NO: 26), wherein T is at the C-terminal end of the amino acid sequence; (b) the last amino acids at the C-terminal end of the soluble form of human IL-15Rα consist of amino acid residues PQGHSDT (SEQ ID NO: 27), wherein T is at the C-terminal end of the amino acid sequence; (c) the last amino acids at the C-terminal end of the soluble form of human IL-15Rα consist of amino acid residues PQGHSD (SEQ ID NO: 28), wherein D is at the C-terminal end of the amino acid sequence; (d) the last amino acids at the C-terminal end of the soluble form of IL-15Rα consist of amino acid residues PQGHS (SEQ ID NO: 29), wherein S is at the C-terminal end of the amino acid sequence; (e) the last amino acids at the C-terminal end of the soluble form of human IL-15Rα consist of amino acid residues PQGH (SEQ ID NO: 30), wherein H is at the C-terminal end of the amino acid sequence; or (f) the last amino acids at the C-terminal end of the soluble form of human IL-15Rα consist of amino acid residues PQG (SEQ ID NO: 31), wherein G is at the C-terminal end of the amino acid sequence. In specific embodiments, the glycosylated IL-15Rα is part of a composition comprising IL-15. In certain embodiments, the glycosylated IL-15Rα is part of an IL-15/IL-15Rα complex.

5.2 Therapeutic Agents

Provided herein are complexes that bind to the βγ subunits of the IL-15 receptor, induce IL-15 signal transduction (e.g., Jak/Stat signal transduction) and enhance IL-15-mediated immune function, wherein the complexes comprise IL-15 covalently or noncovalently bound to interleukin-15 receptor alpha ("IL-15Rα") ("IL-15/IL-15Rα complexes" or "Therapeutic Agents"). The IL-15/IL-15Rα complex is able to bind to the βγ receptor complex.

The IL-15/IL-15Rα complexes may be composed of native IL-15 or an IL-15 derivative and native IL-15Rα or an IL-15Rα derivative. In certain embodiments, an IL-15/IL-15Rα complex comprises native IL-15 or an IL-15 derivative and an IL-15Rα described in Section 5.1, supra. In a specific embodiment, an IL-15/IL-15Rα complex comprises native IL-15 or an IL-15 derivative and IL-15Rα with the amino acid sequence of SEQ ID NO: 33, 35, 37, 39, 41 or 45. In another embodiment, an IL-15/IL-15Rα complex comprises native IL-15 or an IL-15 derivative and a glycosylated form of IL-15Rα described in Section 5.1, supra.

In a specific embodiment, an IL-15/IL-15Rα complex comprises native IL-15 or an IL-15Rα derivative and native soluble IL-15Rα (e.g., native soluble human IL-15Rα). In another specific embodiment, an IL-15/IL-15Rα complex comprises native IL-15 and native soluble IL-15Rα. In another specific embodiment, an IL-15/IL-15Rα complex is composed of an IL-15 derivative and an IL-15Rα derivative. In another embodiment, an IL-15/IL-15Rα complex is composed of native IL-15 and an IL-15Rα derivative. In one embodiment, the IL-15Rα derivative is a soluble form of IL-15Rα. Specific examples of soluble forms of IL-15Rα are described in Section 5.1, supra. In a specific embodiment, the soluble form of IL-15Rα lacks the transmembrane domain of native IL-15Rα, and optionally, the intracellular domain of native IL-15Rα. In another embodiment, the IL-15Rα derivative is the extracellular domain of native IL-15Rα or a fragment thereof. In certain embodiments, the IL-15Rα derivative is a fragment of the extracellular domain comprising the sushi domain or exon 2 of native IL-15Rα. In some embodiments, the IL-15Rα derivative comprises a fragment of the extracellular domain comprising the sushi domain or exon 2 of native IL-15Rα and at least one amino acid that is encoded by exon 3. In certain embodiments, the IL-15Rα derivative comprises a fragment of the extracellular domain comprising the sushi domain or exon 2 of native IL-15Rα and an IL-15Rα hinge region or a fragment thereof. In certain embodiments, the IL-15Rα comprises the amino acid sequence of SEQ ID NO:19 or 20. In some embodiments, the IL-15Rα comprises the amino acid sequence of SEQ ID NO: 33, 35, 37, 39, 41 or 45. In certain embodiments, the IL-15Rα is the native soluble human IL-15Rα.

In another embodiment, the IL-15Rα derivative comprises a mutation in the extracellular domain cleavage site that inhibits cleavage by an endogenous protease that cleaves native IL-15Rα. As discussed in Section 5.1, supra, the extracellular cleavage site of native IL-15Rα has been identified. In a specific embodiment, the extracellular domain cleavage site of IL-15Rα is replaced with a cleavage site that is recognized and cleaved by a heterologous known protease. Non-limiting examples of such heterologous protease cleavage sites include Arg-X-X-Arg (SEQ ID NO: 7), which is recognized and cleaved by furin protease; and A-B-Pro-Arg-X-Y (SEQ ID NO: 8) (A and B are hydrophobic amino acids and X and Y are nonacidic amino acids) and Gly-Arg-Gly, which are recognized and cleaved by thrombin protease.

In a specific embodiment, the IL-15Rα is encoded by a nucleic acid sequence optimized to enhance expression of IL-15Rα, e.g., using methods as described in U.S. Provisional Application No. 60/812,566, filed on Jun. 9, 2006; International Patent Application Publication Nos. WO 2007/084342 and WO 2010/020047; and U.S. Pat. Nos. 5,965,726; 6,174,666; 6,291,664; 6,414,132; and 6,794,498, which are incorporated by reference herein in their entireties. In another embodiment, the IL-15 is encoded by a nucleic acid sequence optimized to enhance expression of IL-15, e.g., using methods as described in U.S. Provisional Application No. 60/812,566, filed on Jun. 9, 2006 and 60/758,819, filed on Jan. 13, 2006, and International Patent Application Publication Nos. WO 2007/084342 and WO 2010/020047; and U.S. Pat. Nos. 5,965,726; 6,174,666; 6,291,664; 6,414,132; and 6,794,498, which are incorporated by reference herein in their entireties.

In addition to IL-15 and IL-15Rα, the IL-15/IL-15Rα complexes may comprise a heterologous molecule. In some embodiments, the heterologous molecule is an antigen associated with a disease that one intends to prevent, treat and/or manage (e.g., a viral antigen, bacterial antigen, parasitic antigen, or cancer antigen). Non-limiting examples of such antigens include antigens of the flavivirus, West Nile Virus (WNV) including structural proteins, e.g., C, M, and E, and non-structural proteins, e.g., NS1, NS2A, NS2B, NS3, NS4A, NS4B and NS5; human immunodeficiency virus (HIV) antigens gp41, gp120, gp160, Nef, Gag, and Rev, Tat, Vif, Vpu, Vpr, or vpx; influenza virus hemagglutinin; human respiratory syncytial virus G glycoprotein; core protein, matrix protein or other protein of Dengue virus; measles virus hemagglutinin; herpes simplex virus type 2 glycoprotein gB; poliovirus I VP1 (Emini et al., 1983, Nature 304:699); an envelope glycoprotein of HIV I; hepatitis B surface antigen; diptheria toxin; *streptococcus* 24M epitope; gonococcal pilin; pseudorabies virus g50 (gpD); pseudorabies virus II (gpB); pseudorabies virus gIII (gpC); pseudorabies virus glycoprotein H; pseudorabies virus glycoprotein E; transmissible gastroenteritis glycoprotein 195; transmissible gastroenteritis matrix protein; swine rotavirus glycoprotein 38; swine parvovirus capsid protein; *Serpulina hydodysenteriae* protective antigen; bovine viral diarrhea glycoprotein 55; Newcastle disease virus hemagglutinin-neuraminidase; swine flu hemagglutinin; swine flu neuraminidase; antigens of foot and mouth disease virus; antigens of hog cholera virus; antigens of swine influenza virus; antigens of African swine fever virus; *Mycoplasma hyopneumoniae*; antigens of infectious bovine rhinotracheitis virus (e.g., infectious bovine rhinotracheitis virus glycoprotein E or glycoprotein G); antigens of infectious laryngotracheitis virus (e.g., infectious laryngotracheitis virus glycoprotein G or glycoprotein I); a glycoprotein of La Crosse virus; antigens of neonatal calf diarrhea virus; Venezuelan equine encephalomyelitis virus; punta toro virus; murine leukemia virus; mouse mammary tumor virus; hepatitis B virus core protein and/or hepatitis B virus surface antigen or a fragment or derivative thereof (see, e.g., U.K. Patent Publication No. GB 2034323A published Jun. 4, 1980; Ganem and Varmus, 1987, Ann. Rev. Biochem. 56:651-693; Tiollais et al., 1985, Nature 317:489-495); antigen of equine influenza virus or equine herpesvirus (e.g., equine influenza virus type A/Alaska 91 neuraminidase, equine influenza virus type A/Miami 63 neuraminidase; equine influenza virus type A/Kentucky 81 neuraminidase; equine herpes virus type 1 glycoprotein B; equine herpes virus type 1 glycoprotein D); antigen of bovine respiratory syncytial virus or bovine parainfluenza virus (e.g., bovine respiratory syncytial virus attachment protein (BRSV G); bovine respiratory syncytial virus fusion protein (BRSV F); bovine respiratory syncytial virus nucleocapsid protein (BRSV N); bovine parainfluenza virus type 3 fusion protein; the bovine parainfluenza virus type 3 hemagglutinin neuraminidase); bovine viral diarrhea virus glycoprotein 48 or glycoprotein 53.

Other non-limiting examples of antigens include KS ¼ pan-carcinoma antigen, ovarian carcinoma antigen (CA125), prostatic acid phosphate, prostate specific antigen, melanoma-associated antigen p97, melanoma antigen gp75, high molecular weight melanoma antigen (HMW-MAA), prostate specific membrane antigen, carcinoembryonic antigen (CEA), polymorphic epithelial mucin antigen, human milk fat globule antigen, Colorectal tumor-associated antigens such as: CEA, TAG-72, CO17-1A; GICA 19-9, CTA-1 and LEA, Burkitt's lymphoma antigen-38.13, CD19, human B-lymphoma antigen-CD20, CD33, melanoma specific antigens such as ganglioside GD2, ganglioside GD3, ganglioside GM2, ganglioside GM3, tumor-specific transplantation type of cell-surface antigen (TSTA) such as virally-induced tumor antigens including T-antigen DNA tumor viruses and envelope antigens of RNA tumor viruses, oncofetal antigen-alpha-fetoprotein such as CEA of colon, bladder tumor oncofetal antigen, differentiation antigen such as human lung carcinoma antigen L6, L20, antigens of fibrosarcoma, human leukemia T cell antigen-Gp37, neoglycoprotein, sphingolipids, breast cancer antigen such as EGFR (Epidermal growth factor receptor), HER2 antigen (p185HER2), EphA2 receptor, polymorphic epithelial mucin (PEM), malignant human lymphocyte antigen-APO-1, differentiation antigen such as I antigen found in fetal erthrocytes and primary endoderm, I(Ma) found in gastric adenocarcinomas, M18 and M39 found in breast epithelium, SSEA-1 found in myeloid cells, VEP8, VEP9, My1, VIM-D5, and D156-22 found in colorectal cancer, TRA-1-85 (blood group H), C14 found in colonic adenocarcinoma, F3 found in lung adenocarcinoma, AH6 found in gastric cancer, Y hapten, Ley found in embryonal carcinoma cells, TL5 (blood group A), EGF receptor, E1 series (blood group B) found in pancreatic cancer, FC10.2 found in embryonal carcinoma cells, gastric adenocarcinoma, CO-514 (blood group Lea) found in adenocarcinoma, NS-10 found in adenocarcinomas, CO-43 (blood group Leb), G49, 19.9 found in colon cancer, gastric cancer mucins, T5A7 found in myeloid cells, R24 found in melanoma, 4.2, GD3, D1.1, OFA-1, GM2, OFA-2, GD2, M1:22:25:8 found in embryonal carcinoma cells and SSEA-3, SSEA-4 found in 4-8-cell stage embryos.

In other embodiments, the heterologous molecule is an antibody that specifically binds to an antigen associated with a disease that one intends to prevent, treat and/or manage (e.g., an antibody that specifically binds to a viral antigen, bacterial antigen, parasitic antigen, or cancer antigen). Non-limiting examples of such antibodies include anti-CD34 antibody, anti-CD56 antibody, anti-CD8 antibody, anti-CD22 antibody, anti-CD20 antibody, anti-CD19 antibody, anti-CD3 antibody, anti-EGFR antibody, anti-HER2 antibody, anti-CD34 antibody, anti-ckit antibody, anti-flt3 antibody, anti-hemagglutinin antibody, anti-gp41 antibody, anti-gp120 antibody, and anti-HSV-II glycoprotein gB antibody. In other embodiments, the antibody immunospecifically binds to one of the antigens listed above. In some embodiments, the antibody specifically binds to a cellular antigen (e.g., a receptor or cell surface antigen) expressed by a cell that one desires to target. For example, the IL-15/IL-15Rα complex can be targeted to CD34+ progenitor cells with an anti-CD34 antibody to induce development of such cells into $CD56^+$ NK cells. The IL-15/IL-15Rα complex can be targeted to CD56+NK cells with an anti-CD56 antibody to induce proliferation of such cells.

In some embodiments, the heterologous molecule increases protein stability. Non-limiting examples of such molecules include polyethylene glycol (PEG), Fc domain of an IgG immunoglobulin or a fragment thereof, or albumin that increase the half-life of IL-15 or IL-15Rα in vivo. In certain embodiments, IL-15Rα is conjugated/fused to the Fc domain of an immunoglobulin (e.g., an IgG1) or a fragment thereof. In a specific embodiment, the IL-15RαFc fusion protein comprises the amino acid sequence of SEQ ID NO: 21 or 22. In another embodiment, the IL-15RαFc fusion protein is the IL-15Rα/Fc fusion protein described in Han et al., 20011, Cytokine 56: 804-810, U.S. Pat. No. 8,507,222 or 8,124,084. In certain embodiments, the heterologous molecules is not an Fc domain of an immunoglobulin molecule or a fragment thereof.

In those IL-15/IL-15Rα complexes comprising a heterologous molecule, the heterologous molecule may be conjugated to IL-15 and/or IL-15Rα. In one embodiment, the heterologous molecule is conjugated to IL-15Rα. In another embodiment, the heterologous molecule is conjugated to IL-15.

The components of an IL-15/IL-15Rα complex may be directly fused, using either non-covalent bonds or covalent bonds (e.g., by combining amino acid sequences via peptide bonds), and/or may be combined using one or more linkers. In a specific embodiment, IL-15 and IL-15Rα are directly fused to each other using either non-covalent bonds or covalent bonds (e.g., by combining amino acid sequences via peptide bonds), and/or may be combined using one or more linkers. In specific embodiments, a polypeptide comprising IL-15 and IL-15Rα directly fused to each other using either non-covalent bonds or covalent bonds is functional (e.g., capable of specifically binding to the IL-15R βγ complex and inducing IL-15-mediated signal transduction and/or IL-15-mediated immune function). Linkers suitable for preparing the IL-15/IL-15Rα complexes comprise peptides, alkyl groups, chemically substituted alkyl groups, polymers, or any other covalently-bonded or non-covalently bonded chemical substance capable of binding together two or more components. Polymer linkers comprise any polymers known in the art, including polyethylene glycol ("PEG"). In some embodiments, the linker is a peptide that is 1, 2, 3, 4, 5, 6, 7, 8, 9, 10, 11, 12, 13, 14, 15, 16, 17, 18, 19, 20 or more amino acids long. In a specific embodiment, the linker is long enough to preserve the ability of IL-15 to bind to the IL-15Rα. In other embodiments, the linker is long enough to preserve the ability of the IL-15/IL-15Rα complex to bind to the βγ receptor complex and to act as an agonist to mediate IL-15 signal transduction. In a specific embodiment, the IL-15/IL-15Rα complex is a fusion protein, such as RLI and ILR, disclosed in U.S. Patent Application Publication No. 2009/0238791 and Mortier et al., 2006, J. Biol. Chem. 281(3):1612-9.

In particular embodiments, IL-15/IL-15Rα complexes are pre-coupled prior to use in the methods described herein (e.g., prior to contacting cells with the IL-15/IL-15Rα complexes or prior to administering the IL-15/IL-15Rα complexes to a subject). In other embodiments, the IL-15/IL-15Rα complexes are not pre-coupled prior to use in the methods described herein. In specific embodiments, the IL-15/IL-15Rα complex is administered in combination with a vaccine composition to enhance the immune response elicited by the administration of the vaccine composition to a subject. In a specific embodiment, a Therapeutic Agent comprising IL-15 and IL-15Rα directly fused to each other is administered in combination with a vaccine composition to enhance an immune response elicited by administration of the vaccine composition to a subject.

In a specific embodiment, a Therapeutic Agent enhances or induces immune function in a subject by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to the immune function in a subject not administered the Therapeutic Agent using assays well known in the art, e.g., ELISPOT, ELISA, and cell proliferation assays. In a specific embodiment, the immune function is cytokine release (e.g., interferon-gamma, IL-2, IL-5, IL-10, IL-12, or transforming growth factor (TGF)-beta). In one embodiment, the IL-15 mediated immune function is NK cell proliferation, which can be assayed, e.g., by flow cytometry to detect the number of cells expressing markers of NK cells (e.g., CD56). In another embodiment, the IL-15 mediated immune function is antibody production, which can be assayed, e.g., by ELISA. In some embodiments, the IL-15 mediated immune function is effector function, which can be assayed, e.g., by a cytotoxicity assay or other assays well known in the art.

In specific embodiments, examples of immune function enhanced by the Therapeutic Agent include the proliferation/expansion of lymphocytes (e.g., increase in the number of lymphocytes), inhibition of apoptosis of lymphocytes, activation of dendritic cells (or antigen presenting cells), and antigen presentation. In particular embodiments, an immune function enhanced by the Therapeutic Agent is proliferation/expansion in the number of or activation of $CD4^+$ T cells (e.g., Th1 and Th2 helper T cells), $CD8^+$ T cells (e.g., cytotoxic T lymphocytes, alpha/beta T cells, and gamma/delta T cells), B cells (e.g., plasma cells), memory T cells, memory B cells, dendritic cells (immature or mature), antigen presenting cells, macrophages, mast cells, natural killer T cells (NKT cells), tumor-resident T cells, $CD122^+$ T cells, or natural killer cells (NK cells). In one embodiment, the Therapeutic Agent enhances the proliferation/expansion or number of lymphocyte progenitors. In some embodiments, a Therapeutic Agent increases the number of $CD4^+$ T cells (e.g., Th1 and Th2 helper T cells), $CD8^+$ T cells (e.g., cytotoxic T lymphocytes, alpha/beta T cells, and gamma/delta T cells), B cells (e.g., plasma cells), memory T cells, memory B cells, dendritic cells (immature or mature), antigen presenting cells, macrophages, mast cells, natural killer T cells (NKT cells), tumor-resident T cells, $CD122^+$ T cells, or natural killer cells (NK cells) by approximately 1 fold, 2 fold, 3 fold, 4 fold, 5 fold, 6 fold, 7 fold, 8 fold, 9 fold, 10 fold, 20 fold, or more relative a negative control (e.g., number of the respective cells not treated, cultured, or contacted with a Therapeutic Agent).

5.3 Expression of IL-15 and IL-15Rα

5.3.1 Nucleic Acids

Provided herein are nucleic acids that encode IL-15 and IL-15Rα. The nucleic acids encode IL-15 and IL-15Rα that are capable of covalently or noncovalently binding to each other to form the IL-15/IL-15Rα complexes described in Section 5.2, supra. Such IL-15/IL-15Rα complexes can bind to the βγ receptor complex, and induce IL-15-mediated signal transduction.

Nucleic acid sequences encoding native IL-15 are well known in the art and have been described, for a review, see, Fehniger and Caligiuri, Blood, 2001, 97:14-32, which is incorporated by reference herein in its entirety. For example, the nucleic acid sequences encoding native IL-15 can be readily found in publicly available publications and databases, e.g., National Center for Biotechnology Information website at ncbi.nlm.nih.gov. Nucleic acid sequences encoding native IL-15Rα have been described, e.g., see International Publication No. WO 95/30695, and can also be readily found in publicly available publications and databases, e.g., National Center for Biotechnology Information website at ncbi.nlm.nih.gov. Cloning techniques well known in the art can be used to generate nucleic acids encoding IL-15 and IL-15Rα. See, e.g., Ausubel et al., Current Protocols in Molecular Biology, John Wiley and Sons, Inc. (1995); Sambrook et al., Molecular Cloning, A Laboratory Manual (2d ed.), Cold Spring Harbor Press, Cold Spring Harbor, N.Y. (1989); Birren et al., Genome Analysis: A Laboratory Manual, volumes 1 through 4, Cold Spring Harbor Press, Cold Spring Harbor, N.Y. (1997-1999).

In a specific embodiment, provided herein are nucleic acids that encode the IL-15 and IL-15Rα polypeptides described herein. In a particular embodiment, provided herein are nucleic acids that encode an IL-15Rα polypeptide described in Section 5.1 or 5.2, supra. In another embodiment, provided herein are nucleic acids that encode an IL-15Rα polypeptide comprising the amino acid sequence of SEQ ID NO:3, 4, 32, 33, 34, 35, 36, 37, 38, 39, 40, 41 or 45. In another embodiment, provided herein is a nucleic acid sequence that encodes an IL-15Rα polypeptide, wherein the nucleic acid sequence comprises SEQ ID NO: 5 or 6. In another embodiment, provided herein is a nucleic acid sequence that encodes an IL-15 polypeptide comprising the amino acid sequence of SEQ ID NO: 1 or amino acid residues 49 to 162 of SEQ ID NO: 1. In another embodiment, provided herein is a nucleic acid sequence that encodes an IL-15 polypeptide, wherein the nucleic acid sequence comprises SEQ ID NO:2.

In another specific embodiment, the nucleic acids that encode IL-15 and/or IL-15Rα that are optimized, e.g., by codon/RNA optimization, replacement with heterologous signal sequences, and elimination of mRNA instability elements. Methods to generate optimized nucleic acids encoding IL-15 and IL-15Rα for expression by introducing codon changes and/or eliminating inhibitory regions in the mRNA can be carried out by adapting the optimization methods described in, e.g., U.S. Pat. Nos. 5,965,726; 6,174,666; 6,291,664; 6,414,132; and 6,794,498, for IL-15 and IL-15Rα. The contents of each of these references are incorporated by reference herein in its entirety. See also U.S.

Provisional Application No. 60/812,566, filed on Jun. 9, 2006, and 60/758,819, filed on Jan. 13, 2007, and International Patent Application Publication Nos. WO 2007/084342 and WO 2010/020047, which are also incorporated by reference herein in their entireties. For example, potential splice sites and instability elements (e.g., A/T or A/U rich elements) within the RNA of IL-15 and IL-15Rα can be mutated without altering the amino acids encoded by the nucleic acid sequences to increase stability of the RNA for expression. The alterations utilize the degeneracy of the genetic code, e.g., using an alternative codon for an identical amino acid. In some embodiments, it may be desirable to alter one or more codons to encode a conservative mutation, e.g., a similar amino acid with similar chemical structure and properties and/or function as the original amino acid. Such methods can increase expression of IL-15 and/or IL-15Rα proteins by at least 1 fold, 2 fold, 3 fold, 4 fold, 5 fold, 10 fold, 20 fold, 30 fold, 40 fold, 50 fold, 60 fold, 70 fold, 80 fold, 90 fold, or 100 fold or more relative to the expression of IL-15 and/or IL-15Rα proteins encoded by native nucleic acid sequences.

Further, the native signal peptide sequence of IL-15 and/or IL-15Rα can be replaced with a heterologous signal peptide, e.g., a signal peptide of human GM-CSF, tissue plasminogen activator (tPA), preprolactin, growth hormone or an immunoglobulin protein (e.g., IgE). In a specific embodiment, the signal peptide of IL-15 is replaced with the signal sequence of tPA. In other specific embodiments, the signal peptide of IL-15 is replaced with the signal peptide of human GM-CSF. Such alternations can increase expression of IL-15 and/or IL-15Rα proteins/polypeptides by at least 1 fold, 2 fold, 3 fold, 4 fold, 5 fold, 10 fold, 20 fold, 30 fold, 40 fold, 50 fold, 60 fold, 70 fold, 80 fold, 90 fold, or 100 fold or more relative to the expression of IL-15 and/or IL-15Rα proteins with the respective native signal peptide, as measured/detected by a technique known to one of skill in the art, e.g., ELISA.

In some embodiments, an optimized nucleotide sequence encoding IL-15 or IL-15Rα hybridizes to the nucleotide sequence encoding native IL-15 or IL-15Rα, respectively. In specific embodiments, an optimized nucleotide sequence encoding IL-15 or IL-15Rα hybridizes under high stringency conditions to a nucleotide sequence encoding native IL-15 or IL-15Rα, respectively, or a fragment thereof. In a specific embodiment, an optimized nucleotide sequence encoding IL-15 or IL-15Rα hybridizes under high stringency, intermediate or lower stringency hybridization conditions to a nucleotide sequence encoding native IL-15 or IL-15Rα, respectively, or a fragment thereof. Information regarding hybridization conditions have been described, see, e.g., U.S. Patent Application Publication No. US 2005/0048549 (e.g., paragraphs 72-73).

Also provided herein are nucleic acids encoding IL-15, IL-15Rα, and a heterologous molecule in a form that allows IL-15 to covalently or noncovalently bind to the IL-15Rα to form IL-15/IL-15Rα complexes. In some embodiments, the heterologous molecule is an antigen associated with a disease that one intends to prevent, treat and/or manage. Non-limiting examples of such antigens include those listed above in Section 5.2. In other embodiments, the heterologous molecule is an antibody that specifically binds to an antigen associated with a disease that one intends to prevent, treat and/or manage. Non-limiting examples of such antibodies include those listed above in Section 5.2 and those known in the art. In some embodiments, the antibody specifically binds to a cellular surface antigen (e.g., a receptor) expressed by a cell that one desires to target. In some embodiments, the heterologous molecule increases protein stability. Non-limiting examples of such molecules include polyethylene glycol (PEG), Fc domain of an IgG immunoglobulin or a fragment thereof, or albumin that increase the half-life of IL-15 or IL-15Rα in vivo. In certain embodiments, the heterologous molecules is not an Fc domain of an immunoglobulin molecule or a fragment thereof.

In those IL-15/IL-15Rα complexes comprising a heterologous molecule, the heterologous molecule may be conjugated to IL-15 and/or IL-15Rα. In one embodiment, the heterologous molecule is conjugated to IL-15Rα. In another embodiment, the heterologous molecule is conjugated to IL-15.

In specific embodiments, IL-15 and IL-15Rα are encoded by one nucleic acid construct (e.g., bicistronic construct). In some embodiments, IL-15 and IL-15Rα are encoded by one nucleic acid construct comprising a single open reading frame (ORF) of IL-15 and IL-15Rα. In some embodiments, IL-15 or IL-15Rα encoded by a nucleic acid construct may be conjugated to a nucleic acid encoding a heterologous molecule, such as an antigen or an antibody of interest. In other embodiments, IL-15 and IL-15Rα are encoded by two nucleic acid constructs, wherein a first nucleic acid construct encodes IL-15 and a second nucleic acid construct encodes IL-15Rα. The IL-15 encoded by the first nucleic acid construct may be conjugated to a nucleic acid encoding a heterologous molecule, such as an antigen or an antibody of interest. Alternatively, or in addition, the IL-15Rα encoded by the second nucleic acid construct may be conjugated to a nucleic acid encoding a heterologous molecule, such as an antigen or an antibody of interest.

5.3.2 Constructs & Cells

The nucleic acids encoding IL-15 and/or IL-15Rα can be inserted into nucleic acid constructs for expression in mammalian cells, bacteria, yeast, and viruses. IL-15 and IL-15Rα can be recombinantly expressed from the same nucleic acid construct (e.g., using a bicistronic nucleic acid construct) or from different nucleic acid constructs (e.g., using monocistronic nucleic acid constructs). In one embodiment, IL-15 and IL-15Rα can be recombinantly expressed from a single nucleic acid construct comprising a single open reading frame (ORF) of IL-15 and IL-15Rα. In a particular embodiment, a construct described herein comprises nucleic acid sequences encoding IL-15 and IL-15Rα. In a specific embodiment, a construct described herein comprises nucleic acid sequences encoding IL-15Rα.

The nucleic acid constructs may comprise one or more transcriptional regulatory element(s) operably linked to the coding sequence of IL-15 and/or IL-15Rα. The transcriptional regulatory elements are typically 5' to the coding sequence and direct the transcription of the nucleic acids encoding IL-15 and/or IL-15Rα. In some embodiments, one or more of the transcriptional regulatory elements that are found in nature to regulate the transcription of the native IL-15 and/or native IL-15Rα gene are used to control transcription. In other embodiments, one or more transcriptional regulatory elements that are heterologous to the native IL-15 and/or native IL-15Rα gene are used to control transcription. Any transcriptional regulatory element(s) known to one of skill in the art may be used. Non-limiting examples of the types of transcriptional regulatory element(s) include a constitutive promoter, a tissue-specific promoter, and an inducible promoter. In a specific embodiment, transcription is controlled, at least in part, by a mammalian (in some embodiments, human) transcriptional regulatory element(s). In a specific embodiment, transcription is controlled, at least in part, by a strong promoter, e.g., CMV.

Specific examples of promoters which may be used to control transcription include, but are not limited to, the SV40 early promoter region (Bernoist & Chambon, 1981, Nature 290:304-310), the promoter contained in the 3' long terminal repeat of Rous sarcoma virus (Yamamoto et al., 1980, Cell 22:787-797), the herpes thymidine kinase promoter (Wagner et al., 1981, Proc. Natl. Acad. Sci. U.S.A. 78:1441-1445), the regulatory sequences of the metallothionein gene (Brinster et al., 1982, Nature 296:39-42); adenovirus (ADV), cytomegalovirus (CMV), bovine papilloma virus (BPV), parovirus B19p6 promoter, prokaryotic expression vectors such as the .beta.-lactamase promoter (Villa-Kamaroff et al., 1978, Proc. Natl. Acad. Sci. U.S.A. 75:3727-3731), or the tac promoter (DeBoer et al., 1983, Proc. Natl. Acad. Sci. U.S.A. 80:21-25); see also “Useful proteins from recombinant bacteria” in Scientific American, 1980, 242:74-94; plant expression vectors comprising the nopaline synthetase promoter region (Herrera-Estrella et al., Nature 303:209-213) or the cauliflower mosaic virus 35S RNA promoter (Gardner, et al., 1981, Nucl. Acids Res. 9:2871), and the promoter of the photosynthetic enzyme ribulose biphosphate carboxylase (Herrera-Estrella et al., 1984, Nature 310:115-120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639-646; Ornitz et al., 1986, Cold Spring Harbor Symp. Quant. Biol. 50:399-409; MacDonald, 1987, Hepatology 7:425-515); insulin gene control region which is active in pancreatic beta cells (Hanahan, 1985, Nature 315:115-122), immunoglobulin gene control region which is active in lymphoid cells (Grosschedl et al., 1984, Cell 38:647-658; Adames et al., 1985, Nature 318:533-538; Alexander et al., 1987, Mol. Cell. Biol. 7:1436-1444), mouse mammary tumor virus control region which is active in testicular, breast, lymphoid and mast cells (Leder et al., 1986, Cell 45:485-495), albumin gene control region which is active in liver (Pinkert et al., 1987, Genes and Devel. 1:268-276), alpha-fetoprotein gene control region which is active in liver (Krumlauf et al., 1985, Mol. Cell. Biol. 5:1639-1648; Hammer et al., 1987, Science 235:53-58; alpha 1-antitrypsin gene control region which is active in the liver (Kelsey et al., 1987, Genes and Devel. 1:161-171), beta-globin gene control region which is active in myeloid cells (Mogram et al., 1985, Nature 315:338-340; Kollias et al., 1986, Cell 46:89-94; myelin basic protein gene control region which is active in oligodendrocyte cells in the brain (Readhead et al., 1987, Cell 48:703-712); myosin light chain-2 gene control region which is active in skeletal muscle (Sani, 1985, Nature 314:283-286), and gonadotropic releasing hormone gene control region which is active in the hypothalamus (Mason et al., 1986, Science 234:1372-1378). In other aspects, an inducible promoter can be used.

The nucleic acid constructs also may comprise one or more post-transcriptional regulatory element(s) operably linked to the coding sequence of IL-15 and/or IL-15Rα. The post-transcriptional regulatory elements can be 5' and/or 3' to the coding sequence and direct the post-transcriptional regulation of the translation of RNA transcripts encoding IL-15 and/or IL-15Rα.

In another aspect, the nucleic acid construct can be a gene targeting vector that replaces a gene’s existing regulatory region with a regulatory sequence isolated from a different gene or a novel regulatory sequence as described, e.g., in International Publication Nos. WO 94/12650 and WO 01/68882, which are incorporated by reference herein in their entireties. In certain embodiments, a host cell can be engineered to increase production of endogenous IL-15 and/or IL-15Rα by, e.g., altering the regulatory region of the endogenous IL-15 and/or IL-15Rα genes.

The nucleic acid construct chosen will depend upon a variety of factors, including, without limitation, the strength of the transcriptional regulatory elements and the host cell to be used to express IL-15 and/or IL-15Rα. The nucleic acid constructs can be a plasmid, phagemid, cosmid, viral vector, phage, artificial chromosome, and the like. In one aspect, the vectors can be episomal or non-homologously integrating vectors, which can be introduced into the appropriate host cells by any suitable means (transformation, transfection, conjugation, protoplast fusion, electroporation, calcium phosphate-precipitation, direct microinjection, etc.) to transform them.

The nucleic acid constructs can be a plasmid or a stable integration vector for transient or stable expression of IL-15 and/or IL-15Rα in host cells. For stable expression, the vector can mediate chromosomal integration at a target site or a random chromosomal site. Non-limiting examples of host cell-vector systems that may be used to express IL-15 and/or IL-15Rα include mammalian cell systems infected with virus (e.g., vaccinia virus, adenovirus, retroviruses, lentiviruses, etc.); insect cell systems infected with virus (e.g., baculovirus); microorganisms such as yeast containing yeast vectors, or bacteria transformed with bacteriophage, DNA, plasmid DNA, or cosmid DNA; and stable cell lines generated by transformation using a selectable marker. In some embodiments, the nucleic acid constructs include a selectable marker gene including, but not limited to, neo, gpt, dhfr, ada, pac, hyg, CAD and hisD.

The nucleic acid constructs can be monocistronic or multicistronic. A multicistronic nucleic acid construct may encode 2, 3, 4, 5, 6, 7, 8, 9, 10 or more, or in the range of 2-5, 5-10 or 10-20 genes/nucleotide sequences. For example, a bicistronic nucleic acid construct may comprise in the following order a promoter, a first gene (e.g., IL-15), and a second gene and (e.g., IL-15Rα). In such a nucleic acid construct, the transcription of both genes is driven by the promoter, whereas the translation of the mRNA from the first gene is by a cap-dependent scanning mechanism and the translation of the mRNA from the second gene is by a cap-independent mechanism, e.g., by an IRES.

Techniques for practicing these aspects will employ, unless otherwise indicated, conventional techniques of molecular biology, microbiology, and recombinant DNA manipulation and production, which are routinely practiced by one of skill in the art. See, e.g., Sambrook, 1989, Molecular Cloning, A Laboratory Manual, Second Edition; DNA Cloning, Volumes I and II (Glover, Ed. 1985); Oligonucleotide Synthesis (Gait, Ed. 1984); Nucleic Acid Hybridization (Hames & Higgins, Eds. 1984); Transcription and Translation (Hames & Higgins, Eds. 1984); Animal Cell Culture (Freshney, Ed. 1986); Immobilized Cells and Enzymes (IRL Press, 1986); Perbal, A Practical Guide to Molecular Cloning (1984); Gene Transfer Vectors for Mammalian Cells (Miller & Calos, Eds. 1987, Cold Spring Harbor Laboratory); Methods in Enzymology, Volumes 154 and 155 (Wu & Grossman, and Wu, Eds., respectively), (Mayer & Walker, Eds., 1987); Immunochemical Methods in Cell and Molecular Biology (Academic Press, London, Scopes, 1987), Expression of Proteins in Mammalian Cells Using Vaccinia Viral Vectors in Current Protocols in Molecular Biology, Volume 2 (Ausubel et al., Eds., 1991).

The nucleic acid construct(s) comprising nucleic acids encoding IL-15 and/or IL-15Rα can be administered in vivo to a mammal or transfected into primary or immortalized cells in culture. Such a nucleic acid construct(s) can be used to enhance IL-15-mediated function and/or to prevent, treat and/or manage a disease in which enhancement of IL-15-mediated function is beneficial, such as the diseases described in Sections 5.6 to 5.8, infra. The nucleic acid constructs comprising nucleic acids encoding IL-15 and/or IL-15Rα can be used to generate cells that express IL-15 and/or IL-15Rα. In some embodiments, the cells are primary cells (e.g., tumor cells isolated from a patient). In other embodiments, the cells are mammalian cell lines.

The host cells chosen for expression of nucleic acids will depend upon the intended use of the cells. Factors such as whether a cell glycosylates similar to cells that endogenously express, e.g., IL-15 and/or IL-15Rα, may be considered in selecting the host cells.

Non-limiting examples of hosts cells that can be used to express the protein(s) encoded by the nucleic acid constructs herein include mammalian cells, bacterial cells, yeast cells, primary cells, immortalized cells, plant cells and insect cells. In a specific embodiment, the host cells are a mammalian cell line. Examples of mammalian cell lines include, but are not limited to, COS, CHO, HeLa, NIH3T3, HepG2, MCF7, HEK 293, HEK 293T, RD, PC12, hybridomas, pre-B cells, 293, 293H, K562, SkBr3, BT474, A204, M07Sb, TFβ1, Raji, Jurkat, MOLT-4, CTLL-2, MC-IXC, SK-N-MC, SK-N-MC, SK-N-DZ, SH-SYSY, C127, N0, and BE(2)-C cells. In a specific embodiment, the mammalian cell line used to express the protein(s) encoded by the nucleic acid constructs herein is HEK293 cell line. Other mammalian cell lines available as hosts for expression are known in the art and include many immortalized cell lines available from the American Type Culture Collection (ATCC). In another embodiment, the host cells are immortalized cell lines derived from a subject. In another embodiment, the host cells are primary or secondary cells from a subject. In a particular embodiment, the host cells are cancer cells. In another embodiment, the host cells are irradiated cells. In a particular embodiment, the host cells are irradiated mammalian cell lines or primary cells from a subject. In another embodiment, the host cells are epithelial cells or endothelial cells. In another embodiment, the host cells are fetal/embryonic cells. In some embodiments, the host cells are progenitor cells. In some embodiments, the host cells are lymphocytes (e.g., T cells and B cells). In another embodiment, the host cells are stem cells. In yet another embodiment, the host cells engineered to express the nucleic acid constructs described herein are from an adult.

In some embodiments, isolated cells are utilized herein. In a specific embodiment, the isolated cells are at least 80%, 90%, 95% or 98% free of a different cell type as measured by a technique known to one of skill in the art, such as flow cytometry. In other words, at least 80%, 90%, 95% or 98% of the isolated cells are of the same cell type.

In a specific embodiment, the nucleic acid constructs encoding IL-15 or IL-15Rα can be co-transfected or transfected into the same host cells or different host cells. Optionally, a nucleic acid construct comprising nucleic acids encoding a selectable marker gene can also be transfected into the same cells to select for transfected cells. If the nucleic acid constructs comprising nucleic acids encoding IL-15 and IL-15Rα are transfected into different cells, IL-15 and IL-15Rα expressed by the different cells can be isolated and contacted with each other under conditions suitable to form IL-15/IL-15Rα complexes described in Section 5.2, supra. Any techniques known to one of skill in the art can be used to transfect or transducer host cells with nucleic acids including, e.g., transformation, transfection, conjugation, protoplast fusion, electroporation, calcium phosphate-precipitation, direct microinjection, and infection with viruses, including but not limited to adenoviruses, lentiviruses, and retroviruses.

For long-term, high-yield production of a recombinant of IL-15 and IL-15Rα polypeptides, stable cell lines can be generated. For example, cell lines can be transformed using the nucleic acid constructs described herein which may contain a selectable marker gene on the same or on a separate nucleic acid construct. The selectable marker gene can be introduced into the same cell by co-transfection. Following the introduction of the vector, cells are allowed to grow for 1-2 days in an enriched media before they are switched to selective media to allow growth and recovery of cells that successfully express the introduced nucleic acids. Resistant clones of stably transformed cells may be proliferated using tissue culture techniques well known in the art that are appropriate to the cell type. In a particular embodiment, the cell line has been adapted to grow in serum-free medium. In one embodiment, the cell line has been adapted to grow in serum-free medium in shaker flasks. In one embodiment, the cell line has been adapted to grow in stir or rotating flasks. In certain embodiments, the cell line is cultured in suspension. In particular embodiments, the cell line is not adherent or has been adapted to grow as nonadherent cells. In certain embodiments, the cell line has been adapted to grow in low calcium conditions. In some embodiments, the cell line is cultured or adapted to grow in low serum medium.

In a specific embodiment, a particularly preferred method of high-yield production of a recombinant polypeptide of the present invention is through the use of dihydro folate reductase (DHFR) amplification in DHFR-deficient CHO cells, by the use of successively increasing levels of methotrexate as described in U.S. Pat. No. 4,889,803, which is incorporated by reference herein in its entirety. The polypeptide obtained from such cells may be in a glycosylated form.

In a specific embodiment, a host cell recombinantly expressing IL-15 and IL-15Rα is produced utilizing the techniques described herein. In certain embodiments, a host cell is stably transfected with a first construct encoding IL-15 (e.g., native IL-15) and IL-15Rα (e.g., native IL-15Rα), and a second construct encoding IL-15Rα. In a specific embodiment, the host cell is the HEK293 cell In one embodiment, a host cell recombinantly expresses an IL-15Rα polypeptide that is glycosylated (N- or O-glycosylated) at certain amino acid residues. In some embodiments, a host cell recombinantly expresses an IL-15Rα polypeptide (e.g., a human IL-15Rα polypeptide) that is glycosylated, wherein the glycosylation of the IL-15Rα polypeptide accounts for at least 20%, at least 25%, at least 30%, at least 35%, at least 40%, at least 45%, at least 50%, or 20% to 25%, 20% to 30%, 25% to 30%, 25% to 35%, 30% to 35%, 30% to 40%, 35% to 40%, 35% to 45%, 40% to 50%, 45% to 50%, 20% to 40%, or 25% to 50% of the mass (molecular weight) of the IL-15Rα polypeptide. In certain embodiments, a host cell recombinantly expresses a human IL-15Rα polypeptide which is glycosylated at one, two, three, four, five, six, seven, or all, of the following glycosylation sites: (i) O-glycosylation on Thr5 of amino acid sequence NWELTASASHQPPGVYPQG (SEQ ID NO: 42) in the IL-15Rα; (ii) O-glycosylation on Ser7 of amino acid sequence NWELTASASHQPPGVYPQG (SEQ ID NO: 42) in the IL-15Rα; (iii) N-glycosylation on Ser 8 of amino acid sequence ITCPPPMSVEHADIWVK (SEQ ID NO: 43) in the IL-15Rα, or Ser 8 of amino acid sequence ITCPPPMSVEHADIWVKSYSLYSRERYICNS (SEQ ID NO: 44) in the IL-15Rα; (iv) N-glycosylation on Ser 18 of amino acid sequence ITCPPPMSVEHADIWVKSYSLYSRERYICNS (SEQ ID NO: 44) in the IL-15Rα; (v) N-glycosylation on Ser 20 of amino acid sequence ITCPPPMSVEHADIWVKSYSLYSRERYICNS (SEQ ID NO: 44) in the IL-15Rα; (vi) N-glycosylation on Ser 23 of amino acid sequence ITCPPPMSVEHADIWVKSYSLYSRERYICNS (SEQ ID NO: 44) in the IL-15Rα; and/or (vii) N-glycosylated on Ser 31 of amino acid sequence ITCPPPMSVEHADIWVKSYSLYSRERYICNS (SEQ ID NO: 44) in the IL-15Rα.

In one embodiment, cell lines are engineered to express both IL-15 and soluble IL-15Rα, and the purified stable heterodimer of the IL-15 and soluble IL-15Rα, which can be used in vitro or in vivo, e.g., can be administered to a human. In certain embodiments, cell lines are engineered to express both native human IL-15 and native human IL-15Rα, and the stable heterodimer of native human IL-15 and native soluble human IL-15Rα which is formed can be purified, and this purified heterodimer can be used be administered to a human. In one embodiment, the stability of IL-15 is increased when produced from cell lines recombinantly expressing both IL-15 and IL-15Rα.

In a specific embodiment, the host cell recombinantly expresses IL-15 and the full length IL-15Rα. In another specific embodiment, the host cell recombinantly expresses IL-15 and the soluble form of IL-15Rα. In another specific embodiment, the host cell recombinantly expresses IL-15 and a membrane-bound form of IL-15Rα which is not cleaved from the surface of the cell and remains cell associated. In some embodiments, the host cell recombinantly expressing IL-15 and/or IL-15Rα (full-length or soluble form) also recombinantly expresses another polypeptide (e.g., a cytokine or fragment thereof).

In certain embodiments, a host cell recombinantly expresses an IL-15Rα polypeptide described herein (see, e.g., Section 5.1 and/or Section 5.2, supra). In a specific embodiment, a host cell recombinantly expresses an IL-15Rα polypeptide comprising the amino acid sequence of SEQ ID NO: 3, 4, 32, 33, 34, 35, 36, 37, 38, 39, 40, 41 or 45. In another specific embodiment, a host cell recombinantly expresses a glycosylated IL-15Rα polypeptide described herein (see, e.g., Section 5.1, supra). In certain embodiments, such a host cell recombinantly expresses an IL-15 polypeptide in addition to an IL-15Rα polypeptide.

In some embodiments, a host cell recombinantly expresses an IL-15Rα polypeptide described herein described herein (see, e.g., Section 5.1 and/or Section 5.2, supra), and IL-15 (e.g., the IL-15 described in Section 3.1, supra). In a specific embodiment, a host cell recombinantly expresses an IL-15Rα polypeptide comprising the amino acid sequence of SEQ ID NO: 3, 4, 32, 33, 34, 35, 36, 37, 38, 39, 40, 41 or 45, and IL-15 (e.g., the IL-15 described in Section 3.1, supra). In another specific embodiment, a host cell recombinantly expresses a glycosylated IL-15Rα polypeptide described herein (see, e.g., Section 5.1, supra), and IL-15 (e.g., the IL-15 described in Section 3.1, supra).

In some embodiments, a host cell recombinantly expresses an IL-15Rα polypeptide in which the cleavage site for an endogenous protease that cleaves native IL-15Rα has been mutated. In one embodiment, a host cell recombinantly expresses an IL-15Rα derivative comprising one, two, three, four, five, six, seven or eight mutations in the extracellular domain cleavage site of IL-15Rα such that cleavage of the IL-15Rα by an endogenous protease that cleaves native IL-15Rα is inhibited. In certain embodiments, a host cell recombinantly expresses an IL-15Rα derivative in which the amino acid sequence PQGHSDTT (SEQ ID NO: 26) is mutated such that cleavage by an endogenous protease that cleaves native human IL-15Rα is inhibited. In specific embodiments, one, two, three, four, five, six, seven, or eight amino acid substitutions and/or deletions are introduced into the amino acid sequence PQGHSDTT (SEQ ID NO: 26) of human IL-15Rα such that cleavage by an endogenous proteases that cleaves native human IL-15Rα is inhibited. In certain embodiments, a host cell recombinantly expresses an IL-15Rα derivative in which the amino acid sequence PQGHSDTT (SEQ ID NO: 26) is replaced with a cleavage site that is recognized and cleaved by a heterologous protease. Non-limiting examples of such heterologous protease cleavage sites include Arg-X-X-Arg (SEQ ID NO: 7), which is recognized and cleaved by furin protease; and A-B-Pro-Arg-X-Y (SEQ ID NO:8) (A and B are hydrophobic amino acids and X and Y are nonacidic amino acids) and Gly-Arg-Gly, which are recognized and cleaved by the thrombin protease.

In another embodiment, a host cell recombinantly expresses an IL-15Rα derivative, wherein the IL-15Rα derivative: (i) comprises a mutated extracellular cleavage site that inhibits cleavage by an endogenous protease that cleaves native IL-15Rα, and (ii) lacks all or a fragment of the transmembrane domain of native IL-15Rα. In certain embodiments, a host cell recombinantly expresses an IL-15Rα derivative, wherein the IL-15Rα derivative comprises: (i) one, two, three, four, five, six, seven or eight mutations (e.g., substitutions and/or deletions) in the extracellular cleavage site of IL-15Rα such that cleavage of IL-15Rα by an endogenous protease that cleaves native IL-15Rα is inhibited, and (ii) all or a fragment of a transmembrane domain of a heterologous molecule in place of all or a fragment of the transmembrane domain of native IL-15Rα. In some embodiments, a host cell recombinantly expresses an IL-15Rα derivative, wherein the IL-15Rα derivative comprises: (i) one, two, three, four, five, six, seven or eight mutations (e.g., substitutions and/or deletions) in the amino acid sequence PQGHSDTT (SEQ ID NO: 26) such that cleavage of IL-15Rα by an endogenous protease that cleaves native IL-15Rα is inhibited, and (ii) all or a fragment of a transmembrane domain of a heterologous molecule in place of all or a fragment of the transmembrane domain of native IL-15Rα. In accordance with these embodiments, the IL-15Rα derivatives may or may not comprise all or a fragment of the cytoplasmic tail of native IL-15Rα. In certain embodiments, the heterologous molecule is CD4, CD8, or MHC.

The nucleic acids encoding IL-15 and/or IL-15Rα can be used to generate mammalian cells that recombinantly express IL-15 and IL-15Rα in high amounts for the isolation and purification of IL-15 and IL-15Rα, preferably the IL-15 and the IL-15Rα are associated as complexes. In one embodiment, high amounts of IL-15/IL-15Rα complexes refer to amounts of IL-15/IL-15Rα complexes expressed by cells that are at least 1 fold, 2 fold, 3 fold, 4 fold, 5 fold, 6 fold, 7 fold, 8 fold, 9 fold, 10 fold, 20 fold, or more than 20 fold higher than amounts of IL-15/IL-15Rα complexes expressed endogenously by control cells (e.g., cells that have not been genetically engineered to recombinantly express IL-15, IL-15Rα, or both IL-15 and IL-15Rα, or cells comprising an empty vector). In some embodiments, a host cell described herein expresses approximately 0.1 pg to 25 pg, 0.1 pg to 20 pg, 0.1 pg to 15 pg, 0.1 pg to 10 pg, 0.1 pg to 5 pg, 0.1 pg to 2 pg, 2 pg to 10 pg, or 5 to 20 pg of IL-15 as measured by a technique known to one of skill in the art (e.g., an ELISA). In certain embodiments, a host cell described herein expresses approximately 0.1 to 0.25 pg per day, 0.25 to 0.5 pg per day, 0.5 to 1 pg per day, 1 to 2 pg per day, 2 to 5 pg per day, or 5 to 10 pg per day of IL-15 as measured by a technique known to one of skill in the art (e.g., an ELISA). In certain embodiments, a population of host cells that recombinantly expresses IL-15 and IL-15Rα, expresses between 200 ng/million cells per day to 20,000 ng/million cells per day, 200 ng/million cells per day to 15,000 ng/million cells per day, 200 ng/million cells per day to 10,000 ng/million cells per day, 200 ng/million cells per day to 5,000 ng/million cells per day, 200 ng/million cells per day to 2,000 ng/million cells per day, 200 ng/million cells per day to 1,000 ng/million cells per day, 200 ng/million cells per day to 600 ng/million cells per day, 200 ng/million cells per day to 500 ng/million cells per day, 300 ng/million cells per day to 600 ng/million cells per day of IL-15. In some embodiments, a population of host cells that recombinantly expresses IL-15 and IL-15Rα, expresses about 200 ng/million cells per day, about 300 ng/million cells per day, about 400 ng/million cells per day, about 500 ng/million cells per day, about 600 ng/million cells per day, about 700 ng/million cells per day, about 800 ng/million cells per day, about 900 ng/million cells per day, about 1,000 ng/million cells per day, about 1,500 ng/million cells per day, about 2,000 ng/million cells per day, about 5,000 ng/million cells per day, about 10,000 ng/million cells per day, about 15,000 ng/million cells per day, or about 20,000 ng/million cells per day of IL-15. In a specific embodiment, the IL-15Rα is the soluble form of IL-15Rα. In a specific embodiment, the IL-15Rα is the soluble form of IL-15Rα associated with IL-15 in a stable heterodimer, which increases yields and simplifies production and purification of bioactive heterodimer IL-15/soluble IL-15Rα cytokine.

Recombinant IL-15 and IL-15Rα can be purified using methods of recombinant protein production and purification are well known in the art, e.g., see International Publication No. WO 07/070488, which is incorporated by reference herein in its entirety. Briefly, the polypeptide can be produced intracellularly, in the periplasmic space, or directly secreted into the medium. Cell lysate or supernatant comprising the polypeptide can be purified using, for example, hydroxylapatite chromatography, gel electrophoresis, dialysis, and affinity chromatography. Other techniques for protein purification such as fractionation on an ion-exchange column, ethanol precipitation, Reverse Phase HPLC, chromatography on silica, chromatography on heparin SEPHAROSE™ (gel filtration substance; Pharmacia Inc., Piscataway, N.J.) chromatography on an anion or cation exchange resin (such as a polyaspartic acid column), chromatofocusing, SDS-PAGE, and ammonium sulfate precipitation are also available.

In some embodiments, IL-15 and IL-15Rα are synthesized or recombinantly expressed by different cells and subsequently isolated and combined to form an IL-15/IL-15Rα complex, in vitro, prior to administration to a subject. In other embodiments, IL-15 and IL-15Rα are synthesized or recombinantly expressed by different cells and subsequently isolated and simultaneously administered to a subject an IL-15/IL-15Rα complex in situ or in vivo. In yet other embodiments, IL-15 and IL-15Rα are synthesized or expressed together by the same cell, and the IL-15/IL-15Rα complex formed is isolated.

5.4 Compositions

Provided herein are compositions comprising an IL-15Rα described herein, e.g., a soluble IL-15Rα, such as described in Section 5.1, supra. Also provided herein are compositions comprising the Therapeutic Agents. The compositions include bulk drug compositions useful in the manufacture of pharmaceutical compositions (e.g., impure or non-sterile compositions) and pharmaceutical compositions (i.e., compositions that are suitable for administration to a subject or patient) which can be used in the preparation of unit dosage forms. The compositions (e.g., pharmaceutical compositions) comprise an effective amount of a Therapeutic Agent or a combination of Therapeutic Agents and a pharmaceutically acceptable carrier. In specific embodiments, the compositions (e.g., pharmaceutical compositions) comprise an effective amount of one or more Therapeutic Agents and a pharmaceutically acceptable carrier. In some embodiments, the composition further comprises an additional therapeutic, e.g., anti-cancer agent, anti-viral agent, anti-inflammatory agent, adjuvant. Non-limiting examples of such therapeutics are provided infra.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete) or, more preferably, MF59C.1 adjuvant available from Chiron, Emeryville, Calif.), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. In one embodiment, water is a carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like.

Pharmaceutical compositions may be formulated in any conventional manner using one or more pharmaceutically acceptable carriers or excipients. In a specific embodiment, a Therapeutic Agent administered to a subject in accordance with the methods described herein is administered as a pharmaceutical composition.

Generally, the components of the pharmaceutical compositions comprising Therapeutic Agents are supplied either separately or mixed together in unit dosage form, for example, as a dry lyophilized powder or water free concentrate in a hermetically sealed container such as an ampoule or sachette indicating the quantity of active agent. Where the Therapeutic Agent is to be administered by infusion, it can be dispensed with an infusion bottle containing sterile pharmaceutical grade water or saline (e.g., PBS). Where the Therapeutic Agent is administered by injection, an ampoule of sterile water for injection or saline can be provided so that the ingredients may be mixed prior to administration.

In some embodiments, Therapeutic Agents may be formulated for administration by any method known to one of skill in the art, including but not limited to, parenteral (e.g., subcutaneous, intravenous, or intramuscular) and intratumoral administration. In one embodiment, the Therapeutic Agents are formulated for local or systemic parenteral administration. In a specific embodiment, the Therapeutic Agents are formulated for subcutaneous or intravenous administration. In one embodiment, the Therapeutic Agents are formulated in a pharmaceutically compatible solution.

The Therapeutic Agents can be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient (i.e., Therapeutic Agent) may be in powder form for constitution with a suitable vehicle, e.g., sterile pyrogen-free water, before use.

5.5 Dose Escalation Regimens for Prophylactic and Therapeutic Uses

In one aspect, provided herein are methods for enhancing IL-15-mediated immune function, comprising administering to subjects agents that induce IL-15 signal transduction and enhance IL-15-mediated immune function in a dose escalation regimen. More specifically, provided herein are methods for enhancing IL-15-mediated immune function, comprising administering to subjects in a dose escalation regimen complexes that bind to the βγ subunits of the IL-15 receptor, induce IL-15 signal transduction and enhance IL-15-mediated immune function, wherein the complexes comprise IL-15 covalently or noncovalently bound to interleukin-15 receptor alpha ("IL-15Rα") (referred to herein as "IL-15/IL-15Rα complexes" or "Therapeutic Agents"). Since enhancing IL-15-mediated immune function is beneficial for the prevention, treatment and/or management of certain disorders, such as lymphopenia, cancer, and infectious diseases, provided herein are methods for the prevention, treatment and/or management of such disorders comprising administering to a subject in need thereof IL-15/IL-15Rα complexes in a dose escalation regimen. Further, provided herein are methods for eradicating or reducing HIV in HIV-infected cells in a subject comprising administering to a subject in need thereof IL-15/IL-15Rα complexes in a dose escalation regimen.

In one embodiment, provided herein is a method for preventing, treating and/or managing disorders in a subject, wherein enhancement of IL-15-mediated immune function is beneficial for the prevention, treatment and/or management of such disorders, the method comprising (a) administering at least one initial low dose of an IL-15/IL-15Rα complex to a subject; and (b) administering successively higher doses of the IL-15/IL-15Rα complex to the subject to achieve an effective ratio of IL-15 to lymphocyte cell number. In a specific embodiment, provided herein is a method for preventing, treating and/or managing lymphocytopenia, cancer or an infectious disease in a subject, method comprising (a) administering at least one initial low dose of an IL-15/IL-15Rα complex to the subject; and (b) administering successively higher doses of the IL-15/IL-15Rα complex to the subject to achieve an effective ratio of IL-15 to lymphocyte cell number. In another specific embodiment, provided herein is a method for eradicating or reducing HIV in HIV-infected cells in a subject, the method comprising (a) administering at least one initial low dose of an IL-15/IL-15Rα complex to the subject; and (b) administering successively higher doses of the IL-15/IL-15Rα complex to the subject achieve an effective ratio of IL-15 to lymphocyte cell number. In a particular embodiment, the subject is a human subject. In a specific embodiment, the initial low dose is in the range of 2 μg/kg and 10 μg/kg as determined based on the mass of single chain IL-15. In a specific embodiment, the initial low dose is in the range of 0.5 μg/kg and 10 μg/kg as determined based on the mass of single chain IL-15. In another embodiment, the initial low dose is in the range of 0.5 μg/kg and 5 μg/kg as determined based on the mass of single chain IL-15. In a specific embodiment, the initial low dose is between 0.1 μg/kg and 1 μg/kg as determined based on the mass of single chain IL-15. In another embodiment, the initial low dose is between 0.1 μg/kg and 0.5 μg/kg as determined based on the mass of single chain IL-15. In another embodiment, the initial low dose is about 2 μg/kg as determined based on the mass of single chain IL-15. In another embodiment, the initial low dose is about 5 μg/kg as determined based on the mass of single chain IL-15. In another embodiment, the initial low dose is about 10 μg/kg as determined based on the mass of single chain IL-15. In another embodiment, the initial low dose is 0.1 μg/kg, 0.2 μg/kg, 0.3 μg/kg, 0.4 μg/kg, 0.5 μg/kg, 0.6 μg/kg, 0.7 μg/kg, 0.8 μg/kg, 0.9 μg/kg or 1 μg/kg as determined based on the mass of single chain IL-15. In certain embodiments, the initial low dose is administered 1, 2, 3, 4, 5, 6, 7, 8, 9, 10 or more times, or 1 to 3, 1 to 4, 2 to 4, 2 to 5, 2 to 6, 3 to 6, 4 to 6, 6 to 8, 5 to 8, or 5 to 10 times. In some embodiments, the initial low dose is administered 1, 2, 3, 4, 5, 6, 7, 8, 9, 10 or more times, or 1 to 3, 1 to 4, 2 to 4, 2 to 5, 1 to 5, 2 to 6, 3 to 6, 4 to 6 or 6 to 8 times over a 5 to 7 day, 5 to 10 day, 7 to 12 day, 7 to 14 day, 7 to 21 day or 14 to 21 day period of time. In certain embodiments, each successively higher dose is 1.2, 1.25, 1.3, 1.35, 1.4, 1.45, 1.5, 2, 2.5, 3, 3.5, 4, 4.5, 5, 5.5, or 6 times higher than the previous dose, or 1.2 to 2, 2 to 3, 2 to 4, 1 to 5, 2 to 6, 3 to 4, 3 to 6, or 4 to 6 times higher than the previous dose. In some embodiments, each successively higher dose is 25%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 155%, 160%, 165%, 170%, 175%, 180%, 185%, 190%, 195%, or 200% higher than the previous dose. In specific embodiments, each dose is administered at least 1, 2, 3, 4, 5, 6 or more times over a 5 to 7 day, 5 to 10 day, 7 to 12 day, 7 to 14 day, 7 to 21 day or 14 to 21 day period of time. In another specific embodiment, each dose is administered at least once and the subject is administered a dose three times per 7 day week (e.g., Monday, Wednesday and Friday). In certain embodiments, the subject is monitored for one, two, or more, or all of the following: (i) signs of an enlarged lymph node(s); (ii) signs of an enlarged spleen; (iii) levels of free IL-15 in a sample (e.g., plasma sample) from the subject; (iv) changes (e.g., increases) in body temperature; (v) changes (e.g., decreases) in blood pressure; (vi) changes (e.g., increases) in cytokines, such as pro-inflammatory cytokines (e.g., IL-1 and IL-6) in a sample (e.g., blood sample) from the subject; (vii) elevation of liver enzymes, such as hepatic transaminases (e.g., alanine aminotransferase (ALT) or aspartate aminotransferase (AST)); and/or (viii) adverse events, such as grade 3 or 4 thrombocytopenia, grade 3 or 4 granulocytopenia, grade 3 or 4 leukocytosis (White Blood Cell (WBC) >100,000 $mm^3$), grade 3 or 4 decreases in WBC, absolute lymphocyte count (ALC) and/or absolute neutrophil count (ANC), lymphocytosis and organ dysfunction (e.g., liver or kidney dysfunction). In specific embodiments, the dose is not increased if the trough concentration of free IL-15 in a sample (e.g., plasma sample) from the subject is above 50 pg/ml, 55 pg/ml, 60 pg/ml, 65 pg/ml, 70 pg/ml, 75 pg/ml, 80 pg/ml, 85 pg/ml, 90 pg/ml, 95 pg/ml, or 100 pg/ml. In specific embodiments, the dose is not increased if the trough concentration of free IL-15 in a sample (e.g., plasma sample) from the subject is 50 pg/ml to 75 pg/ml, 60 pg/ml to 75 pg/ml, 75 pg/ml to 85 pg/ml, 75 pg/ml to 100 pg/ml, 85 pg/ml to 100 pg/ml or 50 pg/ml to 100 pg/ml. In certain embodiments, the dose is not increased and the dose may be remain the same, be stopped or reduced if the subject experiences adverse events, such as grade 3 or 4 thrombocytopenia, grade 3 or 4 granulocytopenia, grade 3 or leukocytosis (White Blood Cell >100,000 $mm^3$), grade 3 or 4 decreases in WBC, absolute lymphocyte count (ALC) and/or absolute neutrophil count (ANC), lymphocytosis, and organ dysfunction (e.g., liver or kidney dysfunction). In accordance with these embodiments, the dose of the IL-15/IL-15Rα complex administered to the subject may be reduced or remain the same until the adverse events decrease or disappear. In some embodiments, the method further comprises (c) administering a maintenance dose of the IL-15/IL-15Rα complex to the subject, wherein the maintenance dose reaches trough levels of free IL-15 of approximately 1 pg/ml to approximately 5 pg/ml, approximately 2 pg/ml to approximately 5 pg/ml, approximately 2 pg/ml to approximately 10 pg/ml, approximately 5 pg/ml to approximately 10 pg/ml, approximately 10 pg/ml to approximately 15 pg/ml, approximately 10 pg/ml to approximately 20 pg/ml, approximately 20 pg/ml to approximately 30 pg/ml, approximately 30 pg/ml to approximately 40 pg/ml, or approximately 40 pg/ml to approximately 50 pg/ml, or approximately 5 pg/ml to approximately 50 pg/ml in a sample (e.g., a plasma sample) from the subject. In a specific embodiment, the maintenance dose is equal to or less than the highest dose received by the subject during the dose escalation phase of the therapeutic regimen which does not result in one, two, or more, or all of the following: (i) adverse events, such as grade 3 or 4 thrombocytopenia, grade 3 or 4 granulocytopenia, grade 3 or 4 leukocytosis (White Blood Cell (WBC) >100,000 mm3), grade 3 or 4 decreases in WBC, absolute lymphocyte count (ALC) and/or absolute neutrophil count (ANC), lymphocytosis, and organ dysfunction (e.g., liver or kidney dysfunction); (ii) a significant decrease in blood pressure not easily corrected clinically by, e.g., fluid injection; and/or (iii) an increase in body temperature, e.g., a body temperature of 104° F. or higher. In a specific embodiment, the maintenance dose reaches trough levels of plasma IL-15 that are close to normal levels (approximately 1 pg/ml plasma). In some embodiments, the maintenance dose is 0.1 μg/kg, 0.5 μg/kg, 1 μg/kg, 2 μg/kg, 3 μg/kg, 4 μg/kg, 5 μg/kg, 6 μg/kg, 7 μg/kg, 8 μg/kg, 9 μg/kg, 10 μg/kg, 11 μg/kg, 12 μg/kg, 13 μg/kg, 14 μg/kg, 15 μg/kg, 16 μg/kg, 17 μg/kg, 18 μg/kg, 19 μg/kg, 20 μg/kg, 21 μg/kg, 22 μg/kg, 23 μg/kg, 24 μg/kg, 25 μg/kg, 26 μg/kg, 27 μg/kg, 28 μg/kg, 29 μg/kg, 30 μg/kg, 31 μg/kg, 32 μg/kg, 33 μg/kg, 34 μg/kg, 35 μg/kg or more. In other embodiments, the maintenance dose is between 0.1 μg/kg to 5 μg/kg, 0.1 μg/kg to 10 μg/kg, 2 μg/kg to 5 μg/kg, 2 μg/kg to 10 μg/kg, 5 μg/kg to 10 μg/kg, 5 μg/kg to 15 μg/kg, 10 μg/kg to 15 μg/kg, 0.1 μg/kg to 20 μg/kg, 15 μg/kg to 20 μg/kg, 15 μg/kg to 25 μg/kg, 20 μg/kg to 25 μg/kg, 20 μg/kg to 30 μg/kg, 25 μg/kg to 30 μg/kg, 25 μg/kg to 35 μg/kg, 30 μg/kg to 35 μg/kg, 35 μg/kg to 40 μg/kg, 20 μg/kg to 40 μg/kg, 25 μg/kg to 50 μg/kg, 40 μg/kg to 45 μg/kg or 40 to 50 μg/kg. In certain embodiments, the same dose of IL-15/IL-15Rα complex is administered to the subject continuously for a certain period of time (e.g., days, weeks, months, or years) as the maintenance dose. In other embodiments, the dose of IL-15/IL-15Rα complex administered to the subject as the maintenance dose is slowly decreased so that the elevated lymphocytes (in number and activation) in the subject gradually return to physiological conditions.

In another embodiment, provided herein is method for preventing, treating and/or managing disorders in a subject, wherein enhancement of IL-15-mediated immune function is beneficial for the prevention, treatment and/or management of such disorders, the method comprising (a) administering at least one initial low dose of an IL-15/IL-15Rα complex to the subject; and (b) administering successively higher doses of the IL-15/IL-15Rα complex to the subject, if the concentration of free IL-15 in a sample (e.g., a plasma sample) obtained from the subject a certain period of time after the administration of a dose of the IL-15/IL-15Rα complex and before administration of another dose of the IL-15/IL-15Rα complex (e.g., approximately 24 hours to approximately 48 hours, approximately 24 hours to approximately 36 hours, approximately 24 hours to approximately 72 hours, approximately 48 hours to approximately 72 hours, approximately 36 hours to approximately 48 hours, or approximately 48 hours to 60 hours after the administration of a dose of the IL-15/IL-15Rα complex and before the administration of another dose of the IL-15/IL-15Rα complex) is within normal levels or less than normal levels. In another embodiment, provided herein is a method for preventing, treating and/or managing lymphocytopenia, cancer or an infectious disease in a subject, method comprising (a) administering at least one initial low dose of an IL-15/IL-15Rα complex to the subject; and (b) administering successively higher doses of the IL-15/IL-15Rα complex to the subject, if the concentration of free IL-15 in a sample (e.g., a plasma sample) obtained from the subject a certain period of time after the administration of a dose of the IL-15/IL-15Rα complex and before administration of another dose of the IL-15/IL-15Rα complex (e.g., approximately 24 hours to approximately 48 hours, approximately 24 hours to approximately 36 hours, approximately 24 hours to approximately 72 hours, approximately 48 hours to approximately 72 hours, approximately 36 hours to approximately 48 hours, or approximately 48 hours to 60 hours after the administration of a dose of the IL-15/IL-15Rα complex and before the administration of another dose of the IL-15/IL-15Rα complex) is within normal levels or less than normal levels. In another embodiment, provided herein is a method for eradicating or reducing HIV in HIV-infected cells in a subject, comprising (a) administering at least one initial low dose of an IL-15/IL-15Rα complex to the subject; and (b) administering successively higher doses of the IL-15/IL-15Rα complex to the subject, if the concentration of free IL-15 in a sample (e.g., a plasma sample) obtained from the subject a certain period of time after the administration of a dose of the IL-15/IL-15Rα complex and before administration of another dose of the IL-15/IL-15Rα complex (e.g., approximately 24 hours to approximately 48 hours, approximately 24 hours to approximately 36 hours, approximately 24 hours to approximately 72 hours, approximately 48 hours to approximately 72 hours, approximately 36 hours to approximately 48 hours, or approximately 48 hours to 60 hours after the administration of a dose of the IL-15/IL-15Rα complex and before the administration of another dose of the IL-15/IL-15Rα complex) is within normal levels or less than normal levels. In a particular embodiment, the subject is a human subject. In a specific embodiment, the initial low dose is between 0.1 μg/kg and 1 μg/kg as determined based on the mass of single chain IL-15. In another embodiment, the initial low dose is between 0.1 μg/kg and 0.5 μg/kg as determined based on the mass of single chain IL-15. In another embodiment, the initial low dose is 0.1 μg/kg, 0.2 μg/kg, 0.3 μg/kg, 0.4 μg/kg, 0.5 μg/kg, 0.6 μg/kg, 0.7 μg/kg, 0.8 μg/kg, 0.9 μg/kg or 1 μg/kg as determined based on the mass of single chain IL-15. In certain embodiments, the initial low dose is administered 1, 2, 3, 4, 5, 6, 7, 8, 9, 10 or more times, or 1 to 3, 1 to 4, 1 to 5, 2 to 4, 2 to 5, 1 to 6, 2 to 6, 1 to 6, 3 to 6, 4 to 6, 6 to 8, 5 to 8, or 5 to 10 times. In some embodiments, the initial low dose is administered 1, 2, 3, 4, 5, 6, 7, 8, 9, 10 or more times, or 1 to 3, 1 to 4, 1 to 5, 2 to 4, 2 to 5, 1 to 6, 2 to 6, 3 to 6, 4 to 6 or 6 to 8 times over a 5 to 7 day, 5 to 10 day, 7 to 12 day, 7 to 14 day, 7 to 21 day or 14 to 21 day period of time. In certain embodiments, each successively higher dose is 1.2, 1.25, 1.3, 1.35, 1.4, 1.45, 1.5, 2, 2.5, 3, 3.5, 4, 4.5, 5, 5.5, or 6 times higher than the previous dose, or 1.2 to 2, 2 to 3, 2 to 4, 1 to 5, 2 to 6, 3 to 4, 3 to 6, or 4 to 6 times higher than the previous dose. In some embodiments, each successively higher dose is 25%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 155%, 160%, 165%, 170%, 175%, 180%, 185%, 190%, 195%, or 200% higher than the previous dose. In some embodiments, each dose is administered 1, 2, 3, 4, 5, 6, 7, 8, 9, 10 or more times, or 1 to 3, 1 to 4, 1 to 5, 2 to 4, 2 to 5, 1 to 6, 2 to 6, 1 to 6, 3 to 6, 4 to 6, 6 to 8, 5 to 8, or 5 to 10 times. In specific embodiments, each dose is administered at least 1, 2, 3, 4, 5, 6 or more times, or 1 to 3, 1 to 4, 1 to 5, 2 to 4, 2 to 5, 1 to 6, 2 to 6, 1 to 6, 3 to 6, 4 to 6, 6 to 8, 5 to 8, or 5 to 10 times over a 5 to 7 day, 5 to 10 day, 7 to 12 day, 7 to 14 day, 7 to 21 day or 14 to 21 day period of time. In another specific embodiment, each dose is administered at least once and the subject is administered a dose three times per 7 day week (e.g., Monday, Wednesday and Friday). In certain embodiments, the subject is monitored for one, two, or more, or all of the following: (i) signs of an enlarged lymph node(s); (ii) signs of an enlarged spleen; (iii) levels of free IL-15 in a sample (e.g., plasma sample) from the subject; (iv) changes (e.g., increases) in body temperature; (v) changes (e.g., decreases) in blood pressure; (vi) changes (e.g., increases) in cytokines, such as pro-inflammatory cytokines (e.g., IL-1 and IL-6) in a sample (e.g., blood sample) from the subject; (vii) elevation of liver enzymes, such as hepatic transaminases (e.g., alanine aminotransferase (ALT) or aspartate aminotransferase (AST)); and/or (viii) adverse events, such as grade 3 or 4 thrombocytopenia, grade 3 or 4 granulocytopenia, grade 3 or 4 leukocytosis (White Blood Cell (WBC) >100,000 mm3), grade 3 or 4 decreases in WBC, absolute lymphocyte count (ALC) and/or absolute neutrophil count (ANC), lymphocytosis and organ dysfunction (e.g., liver or kidney dysfunction). In specific embodiments, the dose is not increased if the trough concentration of free IL-15 in a sample (e.g., plasma sample) from the subject is above 50 pg/ml, 55 pg/ml, 60 pg/ml, 65 pg/ml, 70 pg/ml, 75 pg/ml, 80 pg/ml, 85 pg/ml, 90 pg/ml, 95 pg/ml, or 100 pg/ml. In specific embodiments, the dose is not increased if the trough concentration of free IL-15 in a sample (e.g., plasma sample) from the subject is 50 pg/ml to 75 pg/ml, 60 pg/ml to 75 pg/ml, 75 pg/ml to 85 pg/ml, 75 pg/ml to 100 pg/ml, 85 pg/ml to 100 pg/ml or 50 pg/ml to 100 pg/ml. In certain embodiments, the dose is not increased and the dose may be remain the same, be stopped or reduced if the subject experiences adverse events, such as grade 3 or 4 thrombocytopenia, grade 3 or 4 granulocytopenia, grade 3 or leukocytosis (White Blood Cell >100,000 mm3), grade 3 or 4 decreases in WBC, absolute lymphocyte count (ALC) and/or absolute neutrophil count (ANC), lymphocytosis, and organ dysfunction (e.g., liver or kidney dysfunction). In accordance with these embodiments, the dose of the IL-15/IL-15Rα complex administered to the subject may be reduced or remain the same until the adverse events decrease or disappear. In some embodiments, the method further comprises (c) administering a maintenance dose of the IL-15/IL-15Rα complex to the subject, wherein the maintenance dose reaches trough levels of free IL-15 concentration of approximately 1 pg/ml to approximately 5 pg/ml, approximately 2 pg/ml to approximately 5 pg/ml, approximately 2 pg/ml to approximately 10 pg/ml, approximately 5 pg/ml to approximately 10 pg/ml, approximately 10 pg/ml to approximately 15 pg/ml, approximately 10 pg/ml to approximately 20 pg/ml, approximately 20 pg/ml to approximately 30 pg/ml, approximately 30 pg/ml to approximately 40 pg/ml, or approximately 40 pg/ml to approximately 50 pg/ml, approximately 1 pg/ml to 50 pg/ml or approximately 5 pg/ml to approximately 50 pg/ml in a blood sample from the subject. In a specific embodiment, the maintenance dose is equal to or less than the highest dose received by the subject during the dose escalation phase of the therapeutic regimen which does not result in one, two, or more, or all of the following: (i) adverse events, such as grade 3 or 4 thrombocytopenia, grade 3 or 4 granulocytopenia, grade 3 or 4 leukocytosis (White Blood Cell (WBC) >100,000 mm3), grade 3 or 4 decreases in WBC, absolute lymphocyte count (ALC) and/or absolute neutrophil count (ANC), lymphocytosis, and organ dysfunction (e.g., liver or kidney dysfunction); (ii) a significant decrease in blood pressure not easily corrected clinically by, e.g., fluid injection; and/or (iii) an increase in body temperature, e.g., a body temperature of 104° F. or higher. In a specific embodiment, the maintenance dose reaches trough levels of plasma IL-15 that are close to normal levels (approximately 1 pg/ml plasma). In some embodiments, the maintenance dose is 0.1 μg/kg, 0.5 μg/kg, 1 μg/kg, 2 μg/kg, 3 μg/kg, 4 μg/kg, 5 μg/kg, 6 μg/kg, 7 μg/kg, 8 μg/kg, 9 μg/kg, 10 μg/kg, 11 μg/kg, 12 μg/kg, 13 μg/kg, 14 μg/kg, 15 μg/kg, 16 μg/kg, 17 μg/kg, 18 μg/kg, 19 μg/kg, 20 μg/kg, 21 μg/kg, 22 μg/kg, 23 μg/kg, 24 μg/kg, 25 μg/kg, 26 μg/kg, 27 μg/kg, 28 μg/kg, 29 μg/kg, 30 μg/kg, 31 μg/kg, 32 μg/kg, 33 μg/kg, 34 μg/kg, 35 μg/kg or more. In other embodiments, the maintenance dose is between 0.1 μg/kg to 5 μg/kg, 0.1 μg/kg to 10 μg/kg, 2 μg/kg to 5 μg/kg, 2 μg/kg to 10 μg/kg, 5 μg/kg to 10 μg/kg, 5 μg/kg to 15 μg/kg, 10 μg/kg to 15 μg/kg, 0.1 μg/kg to 20 μg/kg, 15 μg/kg to 20 μg/kg, 15 μg/kg to 25 μg/kg, 20 μg/kg to 25 μg/kg, 20 μg/kg to 30 μg/kg, 25 μg/kg to 30 μg/kg, 25 μg/kg to 35 μg/kg, 30 μg/kg to 35 μg/kg, 35 μg/kg to 40 μg/kg, 20 μg/kg to 40 μg/kg, 25 μg/kg to 50 μg/kg, 40 μg/kg to 45 μg/kg or 40 to 50 μg/kg. In certain embodiments, the same dose of IL-15/IL-15Rα complex is administered to the subject continuously for a certain period of time (e.g., days, weeks, months, or years) as the maintenance dose. In other embodiments, the dose of IL-15/IL-15Rα complex administered to the subject as the maintenance dose is slowly decreased so that the elevated lymphocytes (in number and activation) in the subject gradually return to physiological conditions.

In another embodiment, provided herein is a method for preventing, treating and/or managing disorders in a subject, wherein enhancement of IL-15-mediated immune function is beneficial for the prevention, treatment and/or management of such disorders, the method comprising (a) administering at least one initial low dose of an IL-15/IL-15Rα complex to the subject; and (b) administering successively higher doses of the IL-15/IL-15Rα complex to the subject, if the concentration of free IL-15 in a sample (e.g., a plasma sample) obtained from the subject a certain period of time after the administration of a dose of the IL-15/IL-15Rα complex and before administration of another dose of the IL-15/IL-15Rα complex (e.g., approximately 24 hours to approximately 48 hours, approximately 24 hours to approximately 36 hours, approximately 24 hours to approximately 72 hours, approximately 48 hours to approximately 72 hours, approximately 36 hours to approximately 48 hours, or approximately 48 hours to 60 hours after the administration of a dose of the IL-15/IL-15Rα complex and before the administration of another dose of the IL-15/IL-15Rα complex) is approximately 1 pg/ml to 50 pg/ml, or above normal levels but below 10 pg/ml, below 15 pg/ml, below 20 pg/ml, below 25 pg/ml, below 30 pg/ml, below 35 pg/ml, below 40 pg/ml, below 45 pg/ml or below 50 pg/ml. In another embodiment, provided herein is a method for preventing, treating and/or managing lymphocytopenia, cancer or an infectious disease in a subject, method comprising (a) administering at least one initial low dose of an IL-15/IL-15Rα complex to the subject; and (b) administering successively higher doses of the IL-15/IL-15Rα complex to the subject, if the concentration of free IL-15 in a sample (e.g., a plasma sample) obtained from the subject a certain period of time after the administration of a dose of the IL-15/IL-15Rα complex and before administration of another dose of the IL-15/IL-15Rα complex (e.g., approximately 24 hours to approximately 48 hours, approximately 24 hours to approximately 36 hours, approximately 24 hours to approximately 72 hours, approximately 48 hours to approximately 72 hours, approximately 36 hours to approximately 48 hours, or approximately 48 hours to 60 hours after the administration of a dose of the IL-15/IL-15Rα complex and before the administration of another dose of the IL-15/IL-15Rα complex) is approximately 1 pg/ml to 50 pg/ml, or above normal levels but below 10 pg/ml, below 15 pg/ml, below 20 pg/ml, below 25 pg/ml, below 30 pg/ml, below 35 pg/ml, below 40 pg/ml, below 45 pg/ml or below 50 pg/ml. In another embodiment, provided herein is a method for eradicating or reducing HIV in HIV-infected cells in a subject, comprising (a) administering at least one initial low dose of an IL-15/IL-15Rα complex to the subject; and (b) administering successively higher doses of the IL-15/IL-15Rα complex to the subject, if the concentration of free IL-15 in a sample (e.g., a plasma sample) obtained from the subject a certain period of time after the administration of a dose of the IL-15/IL-15Rα complex and before administration of another dose of the IL-15/IL-15Rα complex (e.g., approximately 24 hours to approximately 48 hours, approximately 24 hours to approximately 36 hours, approximately 24 hours to approximately 72 hours, approximately 48 hours to approximately 72 hours, approximately 36 hours to approximately 48 hours, or approximately 48 hours to 60 hours after the administration of a dose of the IL-15/IL-15Rα complex and before the administration of another dose of the IL-15/IL-15Rα complex) is approximately 1 pg/ml to 50 pg/ml, or above normal levels but below 10 pg/ml, below 15 pg/ml, below 20 pg/ml, below 25 pg/ml, below 30 pg/ml, below 35 pg/ml, below 40 pg/ml, below 45 pg/ml or below 50 pg/ml. In a particular embodiment, the subject is a human subject. In a specific embodiment, the initial low dose is between 0.1 μg/kg and 1 μg/kg as determined based on the mass of single chain IL-15. In another embodiment, the initial low dose is between 0.1 μg/kg and 0.5 μg/kg as determined based on the mass of single chain IL-15. In another embodiment, the initial low dose is 0.1 μg/kg, 0.2 μg/kg, 0.3 μg/kg, 0.4 μg/kg, 0.5 μg/kg, 0.6 μg/kg, 0.7 μg/kg, 0.8 μg/kg, 0.9 μg/kg or 1 μg/kg as determined based on the mass of single chain IL-15. In certain embodiments, the initial low dose is administered 1, 2, 3, 4, 5, 6, 7, 8, 9, 10 or more times, or 1 to 3, 1 to 4, 1 to 5, 2 to 4, 2 to 5, 1 to 6, 2 to 6, 1 to 6, 3 to 6, 4 to 6, 6 to 8, 5 to 8, or 5 to 10 times. In some embodiments, the initial low dose is administered 1, 2, 3, 4, 5, 6, 7, 8, 9, 10 or more times, or 1 to 3, 1 to 4, 1 to 5, 2 to 4, 2 to 5, 1 to 6, 2 to 6, 3 to 6, 4 to 6 or 6 to 8 times over a 5 to 7 day, 5 to 10 day, 7 to 12 day, 7 to 14 day, 7 to 21 day or 14 to 21 day period of time. In certain embodiments, each successively higher dose is 1.2, 1.25, 1.3, 1.35, 1.4, 1.45, 1.5, 2, 2.5, 3, 3.5, 4, 4.5, 5, 5.5, or 6 times higher than the previous dose, or 1.2 to 2, 2 to 3, 2 to 4, 1 to 5, 2 to 6, 3 to 4, 3 to 6, or 4 to 6 times higher than the previous dose. In some embodiments, each successively higher dose is 25%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 155%, 160%, 165%, 170%, 175%, 180%, 185%, 190%, 195%, or 200% higher than the previous dose. In some embodiments, each dose is administered 1, 2, 3, 4, 5, 6, 7, 8, 9, 10 or more times, or 1 to 3, 1 to 4, 1 to 5, 2 to 4, 2 to 5, 1 to 6, 2 to 6, 1 to 6, 3 to 6, 4 to 6, 6 to 8, 5 to 8, or 5 to 10 times. In specific embodiments, each dose is administered at least 1, 2, 3, 4, 5, 6 or more times, or 1 to 3, 1 to 4, 1 to 5, 2 to 4, 2 to 5, 1 to 6, 2 to 6, 1 to 6, 3 to 6, 4 to 6, 6 to 8, 5 to 8, or 5 to 10 times over a 5 to 7 day, 5 to 10 day, 7 to 12 day, 7 to 14 day, 7 to 21 day or 14 to 21 day period of time. In another specific embodiment, each dose is administered at least once and the subject is administered a dose three times per 7 day week (e.g., Monday, Wednesday and Friday). In certain embodiments, the subject is monitored for one, two, or more, or all of the following: (i) signs of an enlarged lymph node(s); (ii) signs of an enlarged spleen; (iii) levels of free IL-15 in a sample (e.g., plasma sample) from the subject; (iv) changes (e.g., increases) in body temperature; (v) changes (e.g., decreases) in blood pressure; (vi) changes (e.g., increases) in cytokines, such as pro-inflammatory cytokines (e.g., IL-1 and IL-6) in a sample (e.g., blood sample) from the subject; (vi) elevation of liver enzymes, such as hepatic transaminases (e.g., alanine aminotransferase (ALT) or aspartate aminotransferase (AST)); and/or (vii) adverse events, such as grade 3 or 4 thrombocytopenia, grade 3 or 4 granulocytopenia, grade 3 or 4 leukocytosis (White Blood Cell (WBC) >100,000 mm3), grade 3 or 4 decreases in WBC, absolute lymphocyte count (ALC) and/or absolute neutrophil count (ANC), lymphocytosis, and organ dysfunction (e.g., liver or kidney dysfunction). In specific embodiments, the dose is not increased if the trough concentration of free IL-15 in a sample (e.g., plasma sample) from the subject is above 50 pg/ml, 55 pg/ml, 60 pg/ml, 65 pg/ml, 70 pg/ml, 75 pg/ml, 80 pg/ml, 85 pg/ml, 90 pg/ml, 95 pg/ml, or 100 pg/ml. In specific embodiments, the dose is not increased if the trough concentration of free IL-15 in a sample (e.g., plasma sample) from the subject is 50 pg/ml to 75 pg/ml, 60 pg/ml to 75 pg/ml, 75 pg/ml to 85 pg/ml, 75 pg/ml to 100 pg/ml, 85 pg/ml to 100 pg/ml or 50 pg/ml to 100 pg/ml. In certain embodiments, the dose is not increased and the dose may be remain the same, be stopped or reduced if the subject experiences adverse events, such as grade 3 or 4 thrombocytopenia, grade 3 or 4 granulocytopenia, grade 3 or leukocytosis (White Blood Cell >100,000 mm3), grade 3 or 4 decreases in WBC, absolute lymphocyte count (ALC) and/ or absolute neutrophil count (ANC), lymphocytosis, and organ dysfunction (e.g., liver or kidney dysfunction). In accordance with these embodiments, the dose of the IL-15/IL-15Rα complex administered to the subject may be reduced or remain the same until the adverse events decrease or disappear. In some embodiments, the method further comprises (c) administering a maintenance dose of the IL-15/IL-15Rα complex to the subject, wherein the maintenance dose reaches trough levels of free IL-15 concentration of approximately 1 pg/ml to approximately 5 pg/ml, approximately 2 pg/ml to approximately 5 pg/ml, approximately 2 pg/ml to approximately 10 pg/ml, approximately 5 pg/ml to approximately 10 pg/ml, approximately 10 pg/ml to approximately 15 pg/ml, approximately 10 pg/ml to approximately 20 pg/ml, approximately 20 pg/ml to approximately 30 pg/ml, approximately 30 pg/ml to approximately 40 pg/ml, or approximately 40 pg/ml to approximately 50 pg/ml, approximately 1 pg/ml to 50 pg/ml or approximately 5 pg/ml to approximately 50 pg/ml in a blood sample from the subject. In a specific embodiment, the maintenance dose is equal to or less than the highest dose received by the subject during the dose escalation phase of the therapeutic regimen which does not result in one, two, or more, or all of the following: (i) adverse events, such as grade 3 or 4 thrombocytopenia, grade 3 or 4 granulocytopenia, grade 3 or 4 leukocytosis (White Blood Cell (WBC) >100,000 mm3), grade 3 or 4 decreases in WBC, absolute lymphocyte count (ALC) and/or absolute neutrophil count (ANC), lymphocytosis, and organ dysfunction (e.g., liver or kidney dysfunction); (ii) a significant decrease in blood pressure not easily corrected clinically by, e.g., fluid injection; and/or (iii) an increase in body temperature, e.g., a body temperature of 104° F. or higher. In a specific embodiment, the maintenance dose reaches trough levels of plasma IL-15 that are close to normal levels (approximately 1 pg/ml plasma). In some embodiments, the maintenance dose is 0.1 μg/kg, 0.5 μg/kg, 1 μg/kg, 2 μg/kg, 3 μg/kg, 4 μg/kg, 5 μg/kg, 6 μg/kg, 7 μg/kg, 8 μg/kg, 9 μg/kg, 10 μg/kg, 11 μg/kg, 12 μg/kg, 13 μg/kg, 14 μg/kg, 15 μg/kg, 16 μg/kg, 17 μg/kg, 18 μg/kg, 19 μg/kg, 20 μg/kg, 21 μg/kg, 22 μg/kg, 23 μg/kg, 24 μg/kg, 25 μg/kg, 26 μg/kg, 27 μg/kg, 28 μg/kg, 29 μg/kg, 30 μg/kg, 31 μg/kg, 32 μg/kg, 33 μg/kg, 34 μg/kg, 35 μg/kg or more. In other embodiments, the maintenance dose is between 0.1 μg/kg to 5 μg/kg, 0.1 μg/kg to 10 μg/kg, 2 μg/kg to 5 μg/kg, 2 μg/kg to 10 μg/kg, 5 μg/kg to 10 μg/kg, 5 μg/kg to 15 μg/kg, 10 μg/kg to 15 μg/kg, 0.1 μg/kg to 20 μg/kg, 15 μg/kg to 20 μg/kg, 15 μg/kg to 25 μg/kg, 20 μg/kg to 25 μg/kg, 20 μg/kg to 30 μg/kg, 25 μg/kg to 30 μg/kg, 25 μg/kg to 35 μg/kg, 30 μg/kg to 35 μg/kg, 35 μg/kg to 40 μg/kg, 20 μg/kg to 40 μg/kg, 25 μg/kg to 50 μg/kg, 40 μg/kg to 45 μg/kg or 40 to 50 μg/kg. In certain embodiments, the same dose of IL-15/IL-15Rα complex is administered to the subject continuously for a certain period of time (e.g., days, weeks, months, or years) as the maintenance dose. In other embodiments, the dose of IL-15/IL-15Rα complex administered to the subject as the maintenance dose is slowly decreased so that the elevated lymphocytes (in number and activation) in the subject gradually return to physiological conditions.

In another embodiment, provided herein is a method for preventing, treating and/or managing disorders in a subject, wherein enhancement of IL-15-mediated immune function is beneficial for the prevention, treatment and/or management of such disorders, the method comprising administering an IL-15/IL-15Rα complex to the human subject in an escalating dose regimen beginning with an initial low dose of between 0.1 μg/kg and 1 μg/kg as determined based on the mass of single chain IL-15, and sequentially escalating the dose two to three times over the previous dose, wherein each dose is administered at least once, twice, or thrice before elevating the dose to the next level, and wherein the concentration of free IL-15 in a sample (e.g., a plasma sample) obtained from the subject a certain period of time after the administration of a dose of the IL-15/IL-15Rα complex (e.g., approximately 24 hours to approximately 48 hours, approximately 24 hours to approximately 36 hours, approximately 24 hours to approximately 72 hours, approximately 48 hours to approximately 72 hours, approximately 36 hours to approximately 48 hours, or approximately 48 hours to 60 hours after the administration of a dose of the IL-15/IL-15Rα complex and before the administration of another dose of the IL-15/IL-15Rα complex) is monitored before elevating the dose to the next level. In another embodiment, provided herein is a method for preventing, treating and/or managing lymphocytopenia, cancer or an infectious disease in a subject, method comprising administering an IL-15/IL-15Rα complex to the human subject in an escalating dose regimen beginning with an initial low dose of between 0.1 μg/kg and 1 μg/kg as determined based on the mass of single chain IL-15, and sequentially escalating the dose two to three times over the previous dose, wherein each dose is administered at least once, twice, or thrice before elevating the dose to the next level, and wherein the concentration of free IL-15 in a sample (e.g., a plasma sample) obtained from the subject a certain period of time after the administration of a dose of the IL-15/IL-15Rα complex (e.g., approximately 24 hours to approximately 48 hours, approximately 24 hours to approximately 36 hours, approximately 24 hours to approximately 72 hours, approximately 48 hours to approximately 72 hours, approximately 36 hours to approximately 48 hours, or approximately 48 hours to 60 hours after the administration of a dose of the IL-15/IL-15Rα complex and before the administration of another dose of the IL-15/IL-15Rα complex) is monitored before elevating the dose to the next level. In another embodiment, provided herein is a method for eradicating or reducing HIV in HIV-infected cells in a subject, the method comprising administering an IL-15/IL-15Rα complex to the subject in an escalating dose regimen beginning with an initial low dose of between 0.1 μg/kg and 1 μg/kg as determined based on the mass of single chain IL-15, and sequentially escalating the dose two to three times over the previous dose, wherein each dose is administered at least once, twice, or thrice before elevating the dose to the next level, and wherein the concentration of free IL-15 in a sample (e.g., a plasma sample) obtained from the subject a certain period of time after the administration of a dose of the IL-15/IL-15Rα complex (e.g., approximately 24 hours to approximately 48 hours, approximately 24 hours to approximately 36 hours, approximately 24 hours to approximately 72 hours, approximately 48 hours to approximately 72 hours, approximately 36 hours to approximately 48 hours, or approximately 48 hours to 60 hours after the administration of a dose of the IL-15/IL-15Rα complex and before the administration of another dose of the IL-15/IL-15Rα complex) is monitored before elevating the dose to the next level. In a particular embodiment, the subject is a human subject. In another embodiment, the initial low dose is 0.1 μg/kg, 0.2 μg/kg, 0.3 μg/kg, 0.4 μg/kg, 0.5 μg/kg, 0.6 μg/kg, 0.7 μg/kg, 0.8 μg/kg, 0.9 μg/kg or 1 μg/kg as determined based on the mass of single chain IL-15. In certain embodiments, the initial low dose is administered 1, 2, 3, 4, 5, 6, 7, 8, 9, 10 or more times, or 1 to 3, 1 to 4, 1 to 5, 2 to 4, 2 to 5, 1 to 6, 2 to 6, 1 to 6, 3 to 6, 4 to 6, 6 to 8, 5 to 8, or 5 to 10 times. In some embodiments, the initial low dose is administered 1, 2, 3, 4, 5, 6, 7, 8, 9, 10 or more times, or 1 to 3, 1 to 4, 1 to 5, 2 to 4, 2 to 5, 2 to 6, 1 to 6, 3 to 6, 4 to 6 or 6 to 8 times over a 5 to 7 day, 5 to 10 day, 7 to 12 day, 7 to 14 day, 7 to 21 day or 14 to 21 day period of time. In specific embodiments, each dose is administered at least 1, 2, 3, 4, 5, 6 or more times, or 1 to 3, 1 to 4, 1 to 5, 2 to 4, 2 to 5, 1 to 6, 2 to 6, 1 to 6, 3 to 6, 4 to 6, 6 to 8, 5 to 8, or 5 to 10 times over a 5 to 7 day, 5 to 10 day, 7 to 12 day, 7 to 14 day, 7 to 21 day or 14 to 21 day period of time. In another specific embodiment, each dose is administered at least once and the subject is administered a dose three times per 7 day week (e.g., Monday, Wednesday and Friday). In certain embodiments, the subject is monitored for one, two, or more, or all of the following: (i) signs of an enlarged lymph node(s); (ii) signs of an enlarged spleen; (iii) changes (e.g., increases) in body temperature; (iv) changes (e.g., decreases) in blood pressure; (v) changes (e.g., increases) in cytokines, such as pro-inflammatory cytokines (e.g., IL-1 and IL-6) in a sample (e.g., blood sample) from the subject; (vi) elevation of liver enzymes, such as hepatic transaminases (e.g., alanine aminotransferase (ALT) or aspartate aminotransferase (AST)); and/or (vii) adverse events, such as grade 3 or 4 thrombocytopenia, grade 3 or 4 granulocytopenia, grade 3 or 4 leukocytosis (White Blood Cell (WBC) >100,000 mm3), grade 3 or 4 decreases in WBC, absolute lymphocyte count (ALC) and/or absolute neutrophil count (ANC), lymphocytosis, and organ dysfunction (e.g., liver or kidney dysfunction). In certain embodiments, the dose is not increased and the dose may be remain the same, be stopped or reduced if the subject experiences adverse events, such as grade 3 or 4 thrombocytopenia, grade 3 or 4 granulocytopenia, grade 3 or leukocytosis (White Blood Cell >100,000 mm3), grade 3 or 4 decreases in WBC, absolute lymphocyte count (ALC) and/or absolute neutrophil count (ANC), lymphocytosis, and organ dysfunction (e.g., liver or kidney dysfunction). In accordance with these embodiments, the dose of the IL-15/IL-15Rα complex administered to the subject may be reduced or remain the same until the adverse events decrease or disappear. In some embodiments, the method further comprises administering a maintenance dose of the IL-15/IL-15Rα complex to the subject, wherein the maintenance dose reaches trough levels of a free IL-15 of approximately 1 pg/ml to approximately 5 pg/ml, approximately 2 pg/ml to approximately 5 pg/ml, approximately 2 pg/ml to approximately 10 pg/ml, approximately 5 pg/ml to approximately 10 pg/ml, approximately 10 pg/ml to approximately 15 pg/ml, approximately 10 pg/ml to approximately 20 pg/ml, approximately 20 pg/ml to approximately 30 pg/ml, approximately 30 pg/ml to approximately 40 pg/ml, or approximately 40 pg/ml to approximately 50 pg/ml, or approximately 5 pg/ml to approximately 50 pg/ml in a blood sample from the subject. In a specific embodiment, the maintenance dose is equal to or less than the highest dose received by the subject during the dose escalation phase of the therapeutic regimen which does not result in one, two, or more, or all of the following: (i) adverse events, such as grade 3 or 4 thrombocytopenia, grade 3 or 4 granulocytopenia, grade 3 or 4 leukocytosis (White Blood Cell (WBC) >100,000 mm3), grade 3 or 4 decreases in WBC, absolute lymphocyte count (ALC) and/or absolute neutrophil count (ANC), lymphocytosis, and organ dysfunction (e.g., liver or kidney dysfunction); (ii) a significant decrease in blood pressure not easily corrected clinically by, e.g., fluid injection; and/or (iii) an increase in body temperature, e.g., a body temperature of 104° F. or higher. In a specific embodiment, the maintenance dose reaches trough levels of free IL-15 that are close to normal levels (approximately 1 pg/ml plasma). In some embodiments, the maintenance dose is 0.1 μg/kg, 0.5 μg/kg, 1 μg/kg, 2 μg/kg, 3 μg/kg, 4 μg/kg, 5 μg/kg, 6 μg/kg, 7 μg/kg, 8 μg/kg, 9 μg/kg, 10 μg/kg, 11 μg/kg, 12 μg/kg, 13 μg/kg, 14 μg/kg, 15 μg/kg, 16 μg/kg, 17 μg/kg, 18 μg/kg, 19 μg/kg, 20 μg/kg, 21 μg/kg, 22 μg/kg, 23 μg/kg, 24 μg/kg, 25 μg/kg, 26 μg/kg, 27 μg/kg, 28 μg/kg, 29 μg/kg, 30 μg/kg, 31 μg/kg, 32 μg/kg, 33 μg/kg, 34 μg/kg, 35 μg/kg or more. In other embodiments, the maintenance dose is between 0.1 μg/kg to 5 μg/kg, 0.1 μg/kg to 10 μg/kg, 2 μg/kg to 5 μg/kg, 2 μg/kg to 10 μg/kg, 5 μg/kg to 10 μg/kg, 5 μg/kg to 15 μg/kg, 10 μg/kg to 15 μg/kg, 0.1 μg/kg to 20 μg/kg, 15 μg/kg to 20 μg/kg, 15 μg/kg to 25 μg/kg, 20 μg/kg to 25 μg/kg, 20 μg/kg to 30 μg/kg, 25 μg/kg to 30 μg/kg, 25 μg/kg to 35 μg/kg, 30 μg/kg to 35 μg/kg, 35 μg/kg to 40 μg/kg, 20 μg/kg to 40 μg/kg, 25 μg/kg to 50 μg/kg, 40 μg/kg to 45 μg/kg or 40 to 50 μg/kg. In certain embodiments, the same dose of IL-15/IL-15Rα complex is administered to the subject continuously for a certain period of time (e.g., days, weeks, months, or years) as the maintenance dose. In other embodiments, the dose of IL-15/IL-15Rα complex administered to the subject as the maintenance dose is slowly decreased so that the elevated lymphocytes (in number and activation) in the subject gradually return to physiological conditions.

In another embodiment, provided herein is a method for preventing, treating and/or managing disorders in a subject, wherein enhancement of IL-15-mediated immune function is beneficial for the prevention, treatment and/or management of such disorders, the method comprising administering an IL-15/IL-15Rα complex to the subject in an escalating dose regimen at the following sequential doses: (i) 0.5 μg/kg; (ii) 1 μg/kg; (iv) 2 μg/kg; (v) 4 μg/kg; (v) 8 μg/kg; and (vi) 16 μg/kg, wherein the doses are determined based on the mass of single chain IL-15, wherein each dose is administered at least once, twice or thrice before elevating the dose to the next level, and wherein the concentration of free IL-15 in a sample (e.g., a plasma sample) obtained from the subject a certain period of time after the administration of a dose of the IL-15/IL-15Rα complex (e.g., approximately 24 hours to approximately 48 hours, approximately 24 hours to approximately 36 hours, approximately 24 hours to approximately 72 hours, approximately 48 hours to approximately 72 hours, approximately 36 hours to approximately 48 hours, or approximately 48 hours to 60 hours after the administration of a dose of the IL-15/IL-15Rα complex and before the administration of another dose of the IL-15/IL-15Rα complex) is monitored before elevating the dose to the next level. In another embodiment, provided herein is a method for preventing, treating and/or managing lymphocytopenia, cancer or an infectious disease in a subject, method comprising administering an IL-15/IL-15Rα complex to the subject in an escalating dose regimen at the following sequential doses: (i) 0.5 μg/kg; (ii) 1 μg/kg; (iv) 2 μg/kg; (v) 4 μg/kg; (v) 8 μg/kg; and (vi) 16 μg/kg, wherein the doses are determined based on the mass of single chain IL-15, wherein each dose is administered at least once, twice or thrice before elevating the dose to the next level, and wherein the concentration of free IL-15 in a sample (e.g., a plasma sample) obtained from the subject a certain period of time after the administration of a dose of the IL-15/IL-15Rα complex (e.g., approximately 24 hours to approximately 48 hours, approximately 24 hours to approximately 36 hours, approximately 24 hours to approximately 72 hours, approximately 48 hours to approximately 72 hours, approximately 36 hours to approximately 48 hours, or approximately 48 hours to 60 hours after the administration of a dose of the IL-15/IL-15Rα complex and before the administration of another dose of the IL-15/IL-15Rα complex) is monitored before elevating the dose to the next level. In another embodiment, provided herein is a method for eradicating or reducing HIV in HIV-infected cells in a subject, comprising administering an IL-15/IL-15Rα complex to the subject in an escalating dose regimen at the following sequential doses: (i) 0.5 μg/kg; (ii) 1 μg/kg; (iv) 2 μg/kg; (v) 4 μg/kg; (v) 8 μg/kg; and (vi) 16 μg/kg, wherein the doses are determined based on the mass of single chain IL-15, wherein each dose is administered at least once, twice or thrice before elevating the dose to the next level, and wherein the concentration of free IL-15 in a sample (e.g., a sample sample) obtained from the subject a certain period of time after the administration of a dose of the IL-15/IL-15Rα complex (e.g., approximately 24 hours to approximately 48 hours, approximately 24 hours to approximately 36 hours, approximately 24 hours to approximately 72 hours, approximately 48 hours to approximately 72 hours, approximately 36 hours to approximately 48 hours, or approximately 48 hours to 60 hours after the administration of a dose of the IL-15/IL-15Rα complex and before the administration of another dose of the IL-15/IL-15Rα complex) is monitored before elevating the dose to the next level. In a particular embodiment, the subject is a human subject. In certain embodiments, the initial low dose is administered 1, 2, 3, 4, 5, 6, 7, 8, 9, 10 or more times, or 1 to 3, 1 to 4, 1 to 5, 2 to 4, 2 to 5, 1 to 6, 2 to 6, 1 to 6, 3 to 6, 4 to 6, 6 to 8, 5 to 8, or 5 to 10 times. In some embodiments, the initial low dose is administered 1, 2, 3, 4, 5, 6, 7, 8, 9, 10 or more times, or 1 to 3, 1 to 4, 1 to 5, 2 to 4, 2 to 5, 2 to 6, 1 to 6, 3 to 6, 4 to 6 or 6 to 8 times over a 5 to 7 day, 5 to 10 day, 7 to 12 day, 7 to 14 day, 7 to 21 day or 14 to 21 day period of time. In certain embodiments, each dose is administered 1, 2, 3, 4, 5, 6, 7, 8, 9, 10 or more times, or 1 to 3, 1 to 4, 1 to 5, 2 to 4, 2 to 5, 1 to 6, 2 to 6, 1 to 6, 3 to 6, 4 to 6, 6 to 8, 5 to 8, or 5 to 10 times. In specific embodiments, each dose is administered at least 1, 2, 3, 4, 5, 6 or more times, or 1 to 3, 1 to 4, 1 to 5, 2 to 4, 2 to 5, 1 to 6, 2 to 6, 1 to 6, 3 to 6, 4 to 6, 6 to 8, 5 to 8, or 5 to 10 times over a 5 to 7 day, 5 to 10 day, 7 to 12 day, 7 to 14 day, 7 to 21 day or 14 to 21 day period of time. In another specific embodiment, each dose is administered at least once and the subject is administered a dose three times per 7 day week (e.g., Monday, Wednesday and Friday). In certain embodiments, the subject is monitored for one, two, or more, or all of the following: (i) signs of an enlarged lymph node(s); (ii) signs of an enlarged spleen; (iii) changes (e.g., increases) in body temperature; (iv) changes (e.g., decreases) in blood pressure; (v) changes (e.g., increases) in cytokines, such as pro-inflammatory cytokines (e.g., IL-1 and IL-6) in a sample (e.g., blood sample) from the subject; (vi) elevation of liver enzymes, such as hepatic transaminases (e.g., alanine aminotransferase (ALT) or aspartate aminotransferase (AST)); and/or (vii) adverse events, such as grade 3 or 4 thrombocytopenia, grade 3 or 4 granulocytopenia, grade 3 or 4 leukocytosis (White Blood Cell (WBC) >100,000 mm3), grade 3 or 4 decreases in WBC, absolute lymphocyte count (ALC) and/or absolute neutrophil count (ANC), lymphocytosis, and organ dysfunction (e.g., liver or kidney dysfunction). In certain embodiments, the dose is not increased and the dose may be remain the same, be stopped or reduced if the subject experiences adverse events, such as grade 3 or 4 thrombocytopenia, grade 3 or 4 granulocytopenia, grade 3 or leukocytosis (White Blood Cell >100,000 mm3), grade 3 or 4 decreases in WBC, absolute lymphocyte count (ALC) and/or absolute neutrophil count (ANC), lymphocytosis, and organ dysfunction (e.g., liver or kidney dysfunction). In accordance with these embodiments, the dose of the IL-15/IL-15Rα complex administered to the subject may be reduced or remain the same until the adverse events decrease or disappear. In specific embodiments, the dose is not increased if the trough concentration of free IL-15 in a sample (e.g., plasma sample) from the subject is above 50 pg/ml, 55 pg/ml, 60 pg/ml, 65 pg/ml, 70 pg/ml, 75 pg/ml, 80 pg/ml, 85 pg/ml, 90 pg/ml, 95 pg/ml, or 100 pg/ml. In specific embodiments, the dose is not increased if the trough concentration of free IL-15 in a sample (e.g., plasma sample) from the subject is 50 pg/ml to 75 pg/ml, 60 pg/ml to 75 pg/ml, 75 pg/ml to 85 pg/ml, 75 pg/ml to 100 pg/ml, 85 pg/ml to 100 pg/ml or 50 pg/ml to 100 pg/ml. In some embodiments, the method further comprises administering a maintenance dose of the IL-15/IL-15Rα complex to the subject, wherein the maintenance dose reaches trough levels of free IL-15 concentration of approximately 5 to 50 pg/ml in a sample (e.g., a plasma sample) from the subject. In some embodiments, the maintenance dose reaches trough levels of free IL-15 of approximately 1 pg/ml to approximately 5 pg/ml, approximately 2 pg/ml to approximately 5 pg/ml, approximately 2 pg/ml to approximately 10 pg/ml, approximately 5 pg/ml to approximately 10 pg/ml, approximately 10 pg/ml to approximately 15 pg/ml, approximately 10 pg/ml to approximately 20 pg/ml, approximately 20 pg/ml to approximately 30 pg/ml, approximately 30 pg/ml to approximately 40 pg/ml, or approximately 40 pg/ml to approximately 50 pg/ml, approximately 1 pg/ml to approximately 50 pg/ml, or approximately 5 pg/ml to approximately 50 pg/ml in a sample (e.g., a plasma sample) from the subject. In a specific embodiment, the maintenance dose is equal to or less than the highest dose received by the subject during the dose escalation phase of the therapeutic regimen which does not result in one, two, or more, or all of the following: (i) adverse events, such as grade 3 or 4 thrombocytopenia, grade 3 or 4 granulocytopenia, grade 3 or 4 leukocytosis (White Blood Cell (WBC) >100,000 mm3), grade 3 or 4 decreases in WBC, absolute lymphocyte count (ALC) and/or absolute neutrophil count (ANC), lymphocytosis, and organ dysfunction (e.g., liver or kidney dysfunction); (ii) a significant decrease in blood pressure not easily corrected clinically by, e.g., fluid injection; and/or (iii) an increase in body temperature, e.g., a body temperature of 104° F. or higher. In a specific embodiment, the maintenance dose reaches trough levels of plasma IL-15 that are close to normal levels (approximately 1 pg/ml plasma). In some embodiments, the maintenance dose is 0.1 μg/kg, 0.5 μg/kg, 1 μg/kg, 2 μg/kg, 3 μg/kg, 4 μg/kg, 5 μg/kg, 6 μg/kg, 7 μg/kg, 8 μg/kg, 9 μg/kg, 10 μg/kg, 11 μg/kg, 12 μg/kg, 13 μg/kg, 14 μg/kg, 15 μg/kg, 16 μg/kg, 17 μg/kg, 18 μg/kg, 19 μg/kg, 20 μg/kg, 21 μg/kg, 22 μg/kg, 23 μg/kg, 24 μg/kg, 25 μg/kg, 26 μg/kg, 27 μg/kg, 28 μg/kg, 29 μg/kg, 30 μg/kg, 31 μg/kg, 32 μg/kg, 33 μg/kg, 34 μg/kg, 35 μg/kg or more. In other embodiments, the maintenance dose is between 0.1 μg/kg to 5 μg/kg, 0.1 μg/kg to 10 μg/kg, 2 μg/kg to 5 μg/kg, 2 μg/kg to 10 μg/kg, 5 μg/kg to 10 μg/kg, 5 μg/kg to 15 μg/kg, 10 μg/kg to 15 μg/kg, 0.1 μg/kg to 20 μg/kg, 15 μg/kg to 20 μg/kg, 15 μg/kg to 25 μg/kg, 20 μg/kg to 25 μg/kg, 20 μg/kg to 30 μg/kg, 25 μg/kg to 30 μg/kg, 25 μg/kg to 35 μg/kg, 30 μg/kg to 35 μg/kg, 35 μg/kg to 40 μg/kg, 20 μg/kg to 40 μg/kg, 25 μg/kg to 50 μg/kg, 40 μg/kg to 45 μg/kg or 40 to 50 μg/kg. In certain embodiments, the same dose of IL-15/IL-15Rα complex is administered to the subject continuously for a certain period of time (e.g., days, weeks, months, or years) as the maintenance dose. In other embodiments, the dose of IL-15/IL-15Rα complex administered to the subject as the maintenance dose is slowly decreased so that the elevated lymphocytes (in number and activation) in the subject gradually return to physiological conditions.

In another embodiment, provided herein is a method for preventing, treating and/or managing disorders in a subject, wherein enhancement of IL-15-mediated immune function is beneficial for the prevention, treatment and/or management of such disorders, the method comprising administering an IL-15/IL-15Rα complex to the subject in an escalating dose regimen at the following sequential doses: (i) 0.125 μg/kg; (ii) 0.25 μg/kg; (iv) 0.5 μg/kg; (v) 1 μg/kg; (v) 2 μg/kg; and (vi) 4 μg/kg, wherein the doses are determined based on the mass of single chain IL-15, wherein each dose is administered at least once, twice or thrice before elevating the dose to the next level, and wherein the concentration of free IL-15 in a sample (e.g., a plasma sample) obtained from the subject a certain period of time after the administration of a dose of the IL-15/IL-15Rα complex (e.g., approximately 24 hours to approximately 48 hours, approximately 24 hours to approximately 36 hours, approximately 24 hours to approximately 72 hours, approximately 48 hours to approximately 72 hours, approximately 36 hours to approximately 48 hours, or approximately 48 hours to 60 hours after the administration of a dose of the IL-15/IL-15Rα complex and before the administration of another dose of the IL-15/IL-15Rα complex) is monitored before elevating the dose to the next level. In another embodiment, provided herein is a method for preventing, treating and/or managing lymphocytopenia, cancer or an infectious disease in a subject, method comprising administering an IL-15/IL-15Rα complex to the subject in an escalating dose regimen at the following sequential doses: (i) 0.125 μg/kg; (ii) 0.25 μg/kg; (iv) 0.5 μg/kg; (v) 1 μg/kg; (v) 2 μg/kg; and (vi) 4 μg/kg, wherein the doses are determined based on the mass of single chain IL-15, wherein each dose is administered at least once, twice or thrice before elevating the dose to the next level, and wherein the concentration of free IL-15 in a sample (e.g., a plasma sample) obtained from the subject a certain period of time after the administration of a dose of the IL-15/IL-15Rα complex (e.g., approximately 24 hours to approximately 48 hours, approximately 24 hours to approximately 36 hours, approximately 24 hours to approximately 72 hours, approximately 48 hours to approximately 72 hours, approximately 36 hours to approximately 48 hours, or approximately 48 hours to 60 hours after the administration of a dose of the IL-15/IL-15Rα complex and before the administration of another dose of the IL-15/IL-15Rα complex) is monitored before elevating the dose to the next level. In another embodiment, provided herein is a method for eradicating or reducing HIV in HIV-infected cells in a subject, comprising administering an IL-15/IL-15Rα complex to the subject in an escalating dose regimen at the following sequential doses: (i) 0.125 μg/kg; (ii) 0.25 μg/kg; (iv) 0.5 μg/kg; (v) 1 μg/kg; (v) 2 μg/kg; and (vi) 4 μg/kg, wherein the doses are determined based on the mass of single chain IL-15, wherein each dose is administered at least once, twice or thrice before elevating the dose to the next level, and wherein the concentration of free IL-15 in a sample (e.g., a plasma sample) obtained from the subject a certain period of time after the administration of a dose of the IL-15/IL-15Rα complex (e.g., approximately 24 hours to approximately 48 hours, approximately 24 hours to approximately 36 hours, approximately 24 hours to approximately 72 hours, approximately 48 hours to approximately 72 hours, approximately 36 hours to approximately 48 hours, or approximately 48 hours to 60 hours after the administration of a dose of the IL-15/IL-15Rα complex and before the administration of another dose of the IL-15/IL-15Rα complex) is monitored before elevating the dose to the next level. In a particular embodiment, the subject is a human subject. In certain embodiments, the initial low dose is administered 1, 2, 3, 4, 5, 6, 7, 8, 9, 10 or more times, or 1 to 3, 1 to 4, 1 to 5, 2 to 4, 2 to 5, 1 to 6, 2 to 6, 1 to 6, 3 to 6, 4 to 6, 6 to 8, 5 to 8, or 5 to 10 times. In some embodiments, the initial low dose is administered 1, 2, 3, 4, 5, 6, 7, 8, 9, 10 or more times, or 1 to 3, 1 to 4, 1 to 5, 2 to 4, 2 to 5, 2 to 6, 1 to 6, 3 to 6, 4 to 6 or 6 to 8 times over a 5 to 7 day, 5 to 10 day, 7 to 12 day, 7 to 14 day, 7 to 21 day or 14 to 21 day period of time. In certain embodiments, each dose is administered 1, 2, 3, 4, 5, 6, 7, 8, 9, 10 or more times, or 1 to 3, 1 to 4, 1 to 5, 2 to 4, 2 to 5, 1 to 6, 2 to 6, 1 to 6, 3 to 6, 4 to 6, 6 to 8, 5 to 8, or 5 to 10 times. In specific embodiments, each dose is administered at least 1, 2, 3, 4, 5, 6 or more times, or 1 to 3, 1 to 4, 1 to 5, 2 to 4, 2 to 5, 1 to 6, 2 to 6, 1 to 6, 3 to 6, 4 to 6, 6 to 8, 5 to 8, or 5 to 10 times over a 5 to 7 day, 5 to 10 day, 7 to 12 day, 7 to 14 day, 7 to 21 day or 14 to 21 day period of time. In another specific embodiment, each dose is administered at least once and the subject is administered a dose three times per 7 day week (e.g., Monday, Wednesday and Friday). In certain embodiments, the subject is monitored for one, two, or more, or all of the following: (i) signs of an enlarged lymph node(s); (ii) signs of an enlarged spleen; (iii) changes (e.g., increases) in body temperature; (iv) changes (e.g., decreases) in blood pressure; (v) changes (e.g., increases) in cytokines, such as pro-inflammatory cytokines (e.g., IL-1 and IL-6) in a sample (e.g., blood sample) from the subject; (vi) elevation of liver enzymes, such as hepatic transaminases (e.g., alanine aminotransferase (ALT) or aspartate aminotransferase (AST)); and/or (vii) adverse events, such as grade 3 or 4 thrombocytopenia, grade 3 or 4 granulocytopenia, grade 3 or 4 leukocytosis (White Blood Cell (WBC) >100,000 mm3), grade 3 or 4 decreases in WBC, absolute lymphocyte count (ALC) and/or absolute neutrophil count (ANC), lymphocytosis, and organ dysfunction (e.g., liver or kidney dysfunction). In certain embodiments, the dose is not increased and the dose may be remain the same, be stopped or reduced if the subject experiences adverse events, such as grade 3 or 4 thrombocytopenia, grade 3 or 4 granulocytopenia, grade 3 or leukocytosis (White Blood Cell >100,000 mm3), grade 3 or 4 decreases in WBC, absolute lymphocyte count (ALC) and/or absolute neutrophil count (ANC), lymphocytosis, and organ dysfunction (e.g., liver or kidney dysfunction). In accordance with these embodiments, the dose of the IL-15/IL-15Rα complex administered to the subject may be reduced or remain the same until the adverse events decrease or disappear. In specific embodiments, the dose is not increased if the trough concentration of free IL-15 in a sample (e.g., plasma sample) from the subject is above 50 pg/ml, 55 pg/ml, 60 pg/ml, 65 pg/ml, 70 pg/ml, 75 pg/ml, 80 pg/ml, 85 pg/ml, 90 pg/ml, 95 pg/ml, or 100 pg/ml. In specific embodiments, the dose is not increased if the trough concentration of free IL-15 in a sample (e.g., plasma sample) from the subject is 50 pg/ml to 75 pg/ml, 60 pg/ml to 75 pg/ml, 75 pg/ml to 85 pg/ml, 75 pg/ml to 100 pg/ml, 85 pg/ml to 100 pg/ml or 50 pg/ml to 100 pg/ml. In some embodiments, the method further comprises administering a maintenance dose of the IL-15/IL-15Rα complex to the subject, wherein the maintenance dose reaches trough levels of free IL-15 concentration of approximately 5 to 50 pg/ml in a sample (e.g., a plasma sample) from the subject. In some embodiments, the maintenance dose reaches trough levels of free IL-15 of approximately 1 pg/ml to approximately 5 pg/ml, approximately 2 pg/ml to approximately 5 pg/ml, approximately 2 pg/ml to approximately 10 pg/ml, approximately 5 pg/ml to approximately 10 pg/ml, approximately 10 pg/ml to approximately 15 pg/ml, approximately 10 pg/ml to approximately 20 pg/ml, approximately 20 pg/ml to approximately 30 pg/ml, approximately 30 pg/ml to approximately 40 pg/ml, or approximately 40 pg/ml to approximately 50 pg/ml, approximately 1 pg/ml to approximately 50 pg/ml, or approximately 5 pg/ml to approximately 50 pg/ml in a sample (e.g., a plasma sample) from the subject. In a specific embodiment, the maintenance dose is equal to or less than the highest dose received by the subject during the dose escalation phase of the therapeutic regimen which does not result in one, two, or more, or all of the following: (i) adverse events, such as grade 3 or 4 thrombocytopenia, grade 3 or 4 granulocytopenia, grade 3 or 4 leukocytosis (White Blood Cell (WBC) >100,000 mm3), grade 3 or 4 decreases in WBC, absolute lymphocyte count (ALC) and/or absolute neutrophil count (ANC), lymphocytosis, and organ dysfunction (e.g., liver or kidney dysfunction); (ii) a significant decrease in blood pressure not easily corrected clinically by, e.g., fluid injection; and/or (iii) an increase in body temperature, e.g., a body temperature of 104° F. or higher. In a specific embodiment, the maintenance dose reaches trough levels of plasma IL-15 that are close to normal levels (approximately 1 pg/ml plasma). In some embodiments, the maintenance dose is 0.1 μg/kg, 0.5 μg/kg, 1 μg/kg, 2 μg/kg, 3 μg/kg, 4 μg/kg, 5 μg/kg, 6 μg/kg, 7 μg/kg, 8 μg/kg, 9 μg/kg, 10 μg/kg, 11 μg/kg, 12 μg/kg, 13 μg/kg, 14 μg/kg, 15 μg/kg, 16 μg/kg, 17 μg/kg, 18 μg/kg, 19 μg/kg, 20 μg/kg, 21 μg/kg, 22 μg/kg, 23 μg/kg, 24 μg/kg, 25 μg/kg, 26 μg/kg, 27 μg/kg, 28 μg/kg, 29 μg/kg, 30 μg/kg, 31 μg/kg, 32 μg/kg, 33 μg/kg, 34 μg/kg, 35 μg/kg or more. In other embodiments, the maintenance dose is between 0.1 μg/kg to 5 μg/kg, 0.1 μg/kg to 10 μg/kg, 2 μg/kg to 5 μg/kg, 2 μg/kg to 10 μg/kg, 5 μg/kg to 10 μg/kg, 5 μg/kg to 15 μg/kg, 10 μg/kg to 15 μg/kg, 0.1 μg/kg to 20 μg/kg, 15 μg/kg to 20 μg/kg, 15 μg/kg to 25 μg/kg, 20 μg/kg to 25 μg/kg, 20 μg/kg to 30 μg/kg, 25 μg/kg to 30 μg/kg, 25 μg/kg to 35 μg/kg, 30 μg/kg to 35 μg/kg, 35 μg/kg to 40 μg/kg, 20 μg/kg to 40 μg/kg, 25 μg/kg to 50 μg/kg, 40 μg/kg to 45 μg/kg or 40 to 50 μg/kg. In certain embodiments, the same dose of IL-15/IL-15Rα complex is administered to the subject continuously for a certain period of time (e.g., days, weeks, months, or years) as the maintenance dose. In other embodiments, the dose of IL-15/IL-15Rα complex administered to the subject as the maintenance dose is slowly decreased so that the elevated lymphocytes (in number and activation) in the subject gradually return to physiological conditions.

In another embodiment, provided herein is a method for preventing, treating and/or managing disorders in a subject, wherein enhancement of IL-15-mediated immune function is beneficial for the prevention, treatment and/or management of such disorders, the method comprising administering an IL-15/IL-15Rα complex to the subject in an escalating dose regimen at the following sequential doses: (i) 0.25 μg/kg; (ii) 0.5 μg/kg; (iii) 1 μg/kg; (iv) 2 μg/kg; (v) 4 μg/kg; and (vi) 8 μg/kg, wherein the doses are determined based on the mass of single chain IL-15, wherein each dose is administered at least once, twice or thrice before elevating the dose to the next level, and wherein the concentration of free IL-15 in a sample (e.g., a plasma sample) obtained from the subject a certain period of time after the administration of a dose of the IL-15/IL-15Rα complex (e.g., approximately 24 hours to approximately 48 hours, approximately 24 hours to approximately 36 hours, approximately 24 hours to approximately 72 hours, approximately 48 hours to approximately 72 hours, approximately 36 hours to approximately 48 hours, or approximately 48 hours to 60 hours after the administration of a dose of the IL-15/IL-15Rα complex and before the administration of another dose of the IL-15/IL-15Rα complex) is monitored before elevating the dose to the next level. In another embodiment, provided herein is a method for preventing, treating and/or managing lymphocytopenia, cancer or an infectious disease in a subject, method comprising administering an IL-15/IL-15Rα complex to the subject in an escalating dose regimen at the following sequential doses: (i) 0.25 μg/kg; (ii) 0.5 μg/kg; (iii) 1 μg/kg; (iv) 2 μg/kg; (v) 4 μg/kg; and (vi) 8 μg/kg, wherein the doses are determined based on the mass of single chain IL-15, wherein each dose is administered at least once, twice or thrice before elevating the dose to the next level, and wherein the concentration of free IL-15 in a sample (e.g., a plasma sample) obtained from the subject a certain period of time after the administration of a dose of the IL-15/IL-15Rα complex (e.g., approximately 24 hours to approximately 48 hours, approximately 24 hours to approximately 36 hours, approximately 24 hours to approximately 72 hours, approximately 48 hours to approximately 72 hours, approximately 36 hours to approximately 48 hours, or approximately 48 hours to 60 hours after the administration of a dose of the IL-15/IL-15Rα complex and before the administration of another dose of the IL-15/IL-15Rα complex) is monitored before elevating the dose to the next level. In another embodiment, provided herein is a method for eradicating or reducing HIV in HIV-infected cells in a subject, comprising administering an IL-15/IL-15Rα complex to the subject in an escalating dose regimen at the following sequential doses: (i) 0.25 μg/kg; (ii) 0.5 μg/kg; (iii) 1 μg/kg; (iv) 2 μg/kg; (v) 4 μg/kg; and (vi) 8 μg/kg, wherein the doses are determined based on the mass of single chain IL-15, wherein each dose is administered at least once, twice or thrice before elevating the dose to the next level, and wherein the concentration of free IL-15 in a sample (e.g., a plasma sample) obtained from the subject a certain period of time after the administration of a dose of the IL-15/IL-15Rα complex (e.g., approximately 24 hours to approximately 48 hours, approximately 24 hours to approximately 36 hours, approximately 24 hours to approximately 72 hours, approximately 48 hours to approximately 72 hours, approximately 36 hours to approximately 48 hours, or approximately 48 hours to 60 hours after the administration of a dose of the IL-15/IL-15Rα complex and before the administration of another dose of the IL-15/IL-15Rα complex) is monitored before elevating the dose to the next level. In a particular embodiment, the subject is a human subject. In certain embodiments, the initial low dose is administered 1, 2, 3, 4, 5, 6, 7, 8, 9, 10 or more times, or 1 to 3, 1 to 4, 1 to 5, 2 to 4, 2 to 5, 1 to 6, 2 to 6, 1 to 6, 3 to 6, 4 to 6, 6 to 8, 5 to 8, or 5 to 10 times. In some embodiments, the initial low dose is administered 1, 2, 3, 4, 5, 6, 7, 8, 9, 10 or more times, or 1 to 3, 1 to 4, 1 to 5, 2 to 4, 2 to 5, 2 to 6, 1 to 6, 3 to 6, 4 to 6 or 6 to 8 times over a 5 to 7 day, 5 to 10 day, 7 to 12 day, 7 to 14 day, 7 to 21 day or 14 to 21 day period of time. In certain embodiments, each dose is administered 1, 2, 3, 4, 5, 6, 7, 8, 9, 10 or more times, or 1 to 3, 1 to 4, 1 to 5, 2 to 4, 2 to 5, 1 to 6, 2 to 6, 1 to 6, 3 to 6, 4 to 6, 6 to 8, 5 to 8, or 5 to 10 times. In specific embodiments, each dose is administered at least 1, 2, 3, 4, 5, 6 or more times, or 1 to 3, 1 to 4, 1 to 5, 2 to 4, 2 to 5, 1 to 6, 2 to 6, 1 to 6, 3 to 6, 4 to 6, 6 to 8, 5 to 8, or 5 to 10 times over a 5 to 7 day, 5 to 10 day, 7 to 12 day, 7 to 14 day, 7 to 21 day or 14 to 21 day period of time. In another specific embodiment, each dose is administered at least once and the subject is administered a dose three times per 7 day week (e.g., Monday, Wednesday and Friday). In certain embodiments, the subject is monitored for one, two, or more, or all of the following: (i) signs of an enlarged lymph node(s); (ii) signs of an enlarged spleen; (iii) changes (e.g., increases) in body temperature; (iv) changes (e.g., decreases) in blood pressure; (v) changes (e.g., increases) in cytokines, such as pro-inflammatory cytokines (e.g., IL-1 and IL-6) in a sample (e.g., blood sample) from the subject; (vi) elevation of liver enzymes, such as hepatic transaminases (e.g., alanine aminotransferase (ALT) or aspartate aminotransferase (AST)); and/or (vii) adverse events, such as grade 3 or 4 thrombocytopenia, grade 3 or 4 granulocytopenia, grade 3 or 4 leukocytosis (White Blood Cell (WBC) >100,000 mm3), grade 3 or 4 decreases in WBC, absolute lymphocyte count (ALC) and/or absolute neutrophil count (ANC), lymphocytosis, and organ dysfunction (e.g., liver or kidney dysfunction). In certain embodiments, the dose is not increased and the dose may be remain the same, be stopped or reduced if the subject experiences adverse events, such as grade 3 or 4 thrombocytopenia, grade 3 or 4 granulocytopenia, grade 3 or leukocytosis (White Blood Cell >100,000 mm3), grade 3 or 4 decreases in WBC, absolute lymphocyte count (ALC) and/or absolute neutrophil count (ANC), lymphocytosis, and organ dysfunction (e.g., liver or kidney dysfunction). In accordance with these embodiments, the dose of the IL-15/IL-15Rα complex administered to the subject may be reduced or remain the same until the adverse events decrease or disappear. In specific embodiments, the dose is not increased if the trough concentration of free IL-15 in a sample (e.g., plasma sample) from the subject is above 50 pg/ml, 55 pg/ml, 60 pg/ml, 65 pg/ml, 70 pg/ml, 75 pg/ml, 80 pg/ml, 85 pg/ml, 90 pg/ml, 95 pg/ml, or 100 pg/ml. In specific embodiments, the dose is not increased if the trough concentration of free IL-15 in a sample (e.g., plasma sample) from the subject is 50 pg/ml to 75 pg/ml, 60 pg/ml to 75 pg/ml, 75 pg/ml to 85 pg/ml, 75 pg/ml to 100 pg/ml, 85 pg/ml to 100 pg/ml or 50 pg/ml to 100 pg/ml. In some embodiments, the method further comprises administering a maintenance dose of the IL-15/IL-15Rα complex to the subject, wherein the maintenance dose reaches trough levels of free IL-15 concentration of approximately 5 to 50 pg/ml in a sample (e.g., a plasma sample) from the subject. In some embodiments, the maintenance dose reaches trough levels of free IL-15 of approximately 1 pg/ml to approximately 5 pg/ml, approximately 2 pg/ml to approximately 5 pg/ml, approximately 2 pg/ml to approximately 10 pg/ml, approximately 5 pg/ml to approximately 10 pg/ml, approximately 10 pg/ml to approximately 15 pg/ml, approximately 10 pg/ml to approximately 20 pg/ml, approximately 20 pg/ml to approximately 30 pg/ml, approximately 30 pg/ml to approximately 40 pg/ml, or approximately 40 pg/ml to approximately 50 pg/ml, approximately 1 pg/ml to approximately 50 pg/ml, or approximately 5 pg/ml to approximately 50 pg/ml in a sample (e.g., a plasma sample) from the subject. In a specific embodiment, the maintenance dose is equal to or less than the highest dose received by the subject during the dose escalation phase of the therapeutic regimen which does not result in one, two, or more, or all of the following: (i) adverse events, such as grade 3 or 4 thrombocytopenia, grade 3 or 4 granulocytopenia, grade 3 or 4 leukocytosis (White Blood Cell (WBC) >100,000 mm3), grade 3 or 4 decreases in WBC, absolute lymphocyte count (ALC) and/or absolute neutrophil count (ANC), lymphocytosis, and organ dysfunction (e.g., liver or kidney dysfunction); (ii) a significant decrease in blood pressure not easily corrected clinically by, e.g., fluid injection; and/or (iii) an increase in body temperature, e.g., a body temperature of 104° F. or higher. In a specific embodiment, the maintenance dose reaches trough levels of plasma IL-15 that are close to normal levels (approximately 1 pg/ml plasma). In some embodiments, the maintenance dose is 0.1 μg/kg, 0.5 μg/kg, 1 μg/kg, 2 μg/kg, 3 μg/kg, 4 μg/kg, 5 μg/kg, 6 μg/kg, 7 μg/kg, 8 μg/kg, 9 μg/kg, 10 μg/kg, 11 μg/kg, 12 μg/kg, 13 μg/kg, 14 μg/kg, 15 μg/kg, 16 μg/kg, 17 μg/kg, 18 μg/kg, 19 μg/kg, 20 μg/kg, 21 μg/kg, 22 μg/kg, 23 μg/kg, 24 μg/kg, 25 μg/kg, 26 μg/kg, 27 μg/kg, 28 μg/kg, 29 μg/kg, 30 μg/kg, 31 μg/kg, 32 μg/kg, 33 μg/kg, 34 μg/kg, 35 μg/kg or more. In other embodiments, the maintenance dose is between 0.1 μg/kg to 5 μg/kg, 0.1 μg/kg to 10 μg/kg, 2 μg/kg to 5 μg/kg, 2 μg/kg to 10 μg/kg, 5 μg/kg to 10 μg/kg, 5 μg/kg to 15 μg/kg, 10 μg/kg to 15 μg/kg, 0.1 μg/kg to 20 μg/kg, 15 μg/kg to 20 μg/kg, 15 μg/kg to 25 μg/kg, 20 μg/kg to 25 μg/kg, 20 μg/kg to 30 μg/kg, 25 μg/kg to 30 μg/kg, 25 μg/kg to 35 μg/kg, 30 μg/kg to 35 μg/kg, 35 μg/kg to 40 μg/kg, 20 μg/kg to 40 μg/kg, 25 μg/kg to 50 μg/kg, 40 μg/kg to 45 μg/kg or 40 to 50 μg/kg. In certain embodiments, the same dose of IL-15/IL-15Rα complex is administered to the subject continuously for a certain period of time (e.g., days, weeks, months, or years) as the maintenance dose. In other embodiments, the dose of IL-15/IL-15Rα complex administered to the subject as the maintenance dose is slowly decreased so that the elevated lymphocytes (in number and activation) in the subject gradually return to physiological conditions.

In another embodiment, provided herein is a method for preventing, treating and/or managing disorders in a subject, wherein enhancement of IL-15-mediated immune function is beneficial for the prevention, treatment and/or management of such disorders, the method comprising administering an IL-15/IL-15Rα complex to the subject in an escalating dose regimen at the following sequential doses: (i) 0.1 μg/kg; 0.3 μg/kg; (ii) 1 μg/kg; (iii) 3 μg/kg; and (iv) 9 μg/kg, wherein the doses are determined based on the mass of single chain IL-15, wherein each dose is administered at least once, twice or thrice before elevating the dose to the next level, and wherein the concentration of free IL-15 in a sample (e.g., a plasma sample) obtained from the subject a certain period of time after the administration of a dose of the IL-15/IL-15Rα complex (e.g., approximately 24 hours to approximately 48 hours, approximately 24 hours to approximately 36 hours, approximately 24 hours to approximately 72 hours, approximately 48 hours to approximately 72 hours, approximately 36 hours to approximately 48 hours, or approximately 48 hours to 60 hours after the administration of a dose of the IL-15/IL-15Rα complex and before the administration of another dose of the IL-15/IL-15Rα complex) is monitored before elevating the dose to the next level. In another embodiment, provided herein is a method for preventing, treating and/or managing lymphocytopenia, cancer or an infectious disease in a subject, method comprising administering an IL-15/IL-15Rα complex to the subject in an escalating dose regimen at the following sequential doses: (i) 0.1 μg/kg; 0.3 μg/kg; (ii) 1 μg/kg; (iii) 3 μg/kg; and (iv) 9 μg/kg, wherein the doses are determined based on the mass of single chain IL-15, wherein each dose is administered at least once, twice or thrice before elevating the dose to the next level, and wherein the concentration of free IL-15 in a sample (e.g., a plasma sample) obtained from the subject a certain period of time after the administration of a dose of the IL-15/IL-15Rα complex (e.g., approximately 24 hours to approximately 48 hours, approximately 24 hours to approximately 36 hours, approximately 24 hours to approximately 72 hours, approximately 48 hours to approximately 72 hours, approximately 36 hours to approximately 48 hours, or approximately 48 hours to 60 hours after the administration of a dose of the IL-15/IL-15Rα complex and before the administration of another dose of the IL-15/IL-15Rα complex) is monitored before elevating the dose to the next level. In another embodiment, provided herein is a method for eradicating or reducing HIV in HIV-infected cells in a subject, comprising administering an IL-15/IL-15Rα complex to the subject in an escalating dose regimen at the following sequential doses: (i) 0.1 μg/kg; 0.3 μg/kg; (ii) 1 μg/kg; (iii) 3 μg/kg; and (iv) 9 μg/kg, wherein the doses are determined based on the mass of single chain IL-15, wherein each dose is administered at least once, twice or thrice before elevating the dose to the next level, and wherein the concentration of free IL-15 in a sample (e.g., a plasma sample) obtained from the subject a certain period of time after the administration of a dose of the IL-15/IL-15Rα complex (e.g., approximately 24 hours to approximately 48 hours, approximately 24 hours to approximately 36 hours, approximately 24 hours to approximately 72 hours, approximately 48 hours to approximately 72 hours, approximately 36 hours to approximately 48 hours, or approximately 48 hours to 60 hours after the administration of a dose of the IL-15/IL-15Rα complex and before the administration of another dose of the IL-15/IL-15Rα complex) is monitored before elevating the dose to the next level. In a particular embodiment, the subject is a human subject. In certain embodiments, the initial low dose is administered 1, 2, 3, 4, 5, 6, 7, 8, 9, 10 or more times, or 1 to 3, 1 to 4, 1 to 5, 2 to 4, 2 to 5, 1 to 6, 2 to 6, 1 to 6, 3 to 6, 4 to 6, 6 to 8, 5 to 8, or 5 to 10 times. In some embodiments, the initial low dose is administered 1, 2, 3, 4, 5, 6, 7, 8, 9, 10 or more times, or 1 to 3, 1 to 4, 1 to 5, 2 to 4, 2 to 5, 2 to 6, 1 to 6, 3 to 6, 4 to 6 or 6 to 8 times over a 5 to 7 day, 5 to 10 day, 7 to 12 day, 7 to 14 day, 7 to 21 day or 14 to 21 day period of time. In certain embodiments, each dose is administered 1, 2, 3, 4, 5, 6, 7, 8, 9, 10 or more times, or 1 to 3, 1 to 4, 1 to 5, 2 to 4, 2 to 5, 1 to 6, 2 to 6, 1 to 6, 3 to 6, 4 to 6, 6 to 8, 5 to 8, or 5 to 10 times. In specific embodiments, each dose is administered at least 1, 2, 3, 4, 5, 6 or more times, or 1 to 3, 1 to 4, 1 to 5, 2 to 4, 2 to 5, 1 to 6, 2 to 6, 1 to 6, 3 to 6, 4 to 6, 6 to 8, 5 to 8, or 5 to 10 times over a 5 to 7 day, 5 to 10 day, 7 to 12 day, 7 to 14 day, 7 to 21 day or 14 to 21 day period of time. In another specific embodiment, each dose is administered at least once and the subject is administered a dose three times per 7 day week (e.g., Monday, Wednesday and Friday). In certain embodiments, the subject is monitored for one, two, or more, or all of the following: (i) signs of an enlarged lymph node(s); (ii) signs of an enlarged spleen; (iii) changes (e.g., increases) in body temperature; (iv) changes (e.g., decreases) in blood pressure; (v) changes (e.g., increases) in cytokines, such as pro-inflammatory cytokines (e.g., IL-1 and IL-6) in a sample (e.g., blood sample) from the subject; (vi) elevation of liver enzymes, such as hepatic transaminases (e.g., alanine aminotransferase (ALT) or aspartate aminotransferase (AST)); and/or (vii) adverse events, such as grade 3 or 4 thrombocytopenia, grade 3 or 4 granulocytopenia, grade 3 or 4 leukocytosis (White Blood Cell (WBC) >100,000 mm3), grade 3 or 4 decreases in WBC, absolute lymphocyte count (ALC) and/or absolute neutrophil count (ANC), lymphocytosis, and organ dysfunction (e.g., liver or kidney dysfunction). In certain embodiments, the dose is not increased and the dose may be remain the same, be stopped or reduced if the subject experiences adverse events, such as grade 3 or 4 thrombocytopenia, grade 3 or 4 granulocytopenia, grade 3 or leukocytosis (White Blood Cell >100,000 mm3), grade 3 or 4 decreases in WBC, absolute lymphocyte count (ALC) and/or absolute neutrophil count (ANC), lymphocytosis, and organ dysfunction (e.g., liver or kidney dysfunction). In accordance with these embodiments, the dose of the IL-15/IL-15Rα complex administered to the subject may be reduced or remain the same until the adverse events decrease or disappear. In specific embodiments, the dose is not increased if the trough concentration of free IL-15 in a sample (e.g., plasma sample) from the subject is above 50 pg/ml, 55 pg/ml, 60 pg/ml, 65 pg/ml, 70 pg/ml, 75 pg/ml, 80 pg/ml, 85 pg/ml, 90 pg/ml, 95 pg/ml, or 100 pg/ml. In specific embodiments, the dose is not increased if the trough concentration of free IL-15 in a sample (e.g., plasma sample) from the subject is 50 pg/ml to 75 pg/ml, 60 pg/ml to 75 pg/ml, 75 pg/ml to 85 pg/ml, 75 pg/ml to 100 pg/ml, 85 pg/ml to 100 pg/ml or 50 pg/ml to 100 pg/ml. In some embodiments, the method further comprises administering a maintenance dose of the IL-15/IL-15Rα complex to the subject, wherein the maintenance dose reaches trough levels of free IL-15 concentration of approximately 5 to 50 pg/ml in a sample (e.g., a plasma sample) from the subject. In some embodiments, the maintenance dose reaches trough levels of free IL-15 of approximately 1 pg/ml to approximately 5 pg/ml, approximately 2 pg/ml to approximately 5 pg/ml, approximately 2 pg/ml to approximately 10 pg/ml, approximately 5 pg/ml to approximately 10 pg/ml, approximately 10 pg/ml to approximately 15 pg/ml, approximately 10 pg/ml to approximately 20 pg/ml, approximately 20 pg/ml to approximately 30 pg/ml, approximately 30 pg/ml to approximately 40 pg/ml, or approximately 40 pg/ml to approximately 50 pg/ml, approximately 1 pg/ml to approximately 50 pg/ml, or approximately 5 pg/ml to approximately 50 pg/ml in a sample (e.g., a plasma sample) from the subject. In a specific embodiment, the maintenance dose is equal to or less than the highest dose received by the subject during the dose escalation phase of the therapeutic regimen which does not result in one, two, or more, or all of the following: (i) adverse events, such as grade 3 or 4 thrombocytopenia, grade 3 or 4 granulocytopenia, grade 3 or 4 leukocytosis (White Blood Cell (WBC) >100,000 mm3), grade 3 or 4 decreases in WBC, absolute lymphocyte count (ALC) and/or absolute neutrophil count (ANC), lymphocytosis, and organ dysfunction (e.g., liver or kidney dysfunction); (ii) a significant decrease in blood pressure not easily corrected clinically by, e.g., fluid injection; and/or (iii) an increase in body temperature, e.g., a body temperature of 104° F. or higher. In a specific embodiment, the maintenance dose reaches trough levels of plasma IL-15 that are close to normal levels (approximately 1 pg/ml plasma). In some embodiments, the maintenance dose is 0.1 μg/kg, 0.5 μg/kg, 1 μg/kg, 2 μg/kg, 3 μg/kg, 4 μg/kg, 5 μg/kg, 6 μg/kg, 7 μg/kg, 8 μg/kg, 9 μg/kg, 10 μg/kg, 11 μg/kg, 12 μg/kg, 13 μg/kg, 14 μg/kg, 15 μg/kg, 16 μg/kg, 17 μg/kg, 18 μg/kg, 19 μg/kg, 20 μg/kg, 21 μg/kg, 22 μg/kg, 23 μg/kg, 24 μg/kg, 25 μg/kg, 26 μg/kg, 27 μg/kg, 28 μg/kg, 29 μg/kg, 30 μg/kg, 31 μg/kg, 32 μg/kg, 33 μg/kg, 34 μg/kg, 35 μg/kg or more. In other embodiments, the maintenance dose is between 0.1 μg/kg to 5 μg/kg, 0.1 μg/kg to 10 μg/kg, 2 μg/kg to 5 μg/kg, 2 μg/kg to 10 μg/kg, 5 μg/kg to 10 μg/kg, 5 μg/kg to 15 μg/kg, 10 μg/kg to 15 μg/kg, 0.1 μg/kg to 20 μg/kg, 15 μg/kg to 20 μg/kg, 15 μg/kg to 25 μg/kg, 20 μg/kg to 25 μg/kg, 20 μg/kg to 30 μg/kg, 25 μg/kg to 30 μg/kg, 25 μg/kg to 35 μg/kg, 30 μg/kg to 35 μg/kg, 35 μg/kg to 40 μg/kg, 20 μg/kg to 40 μg/kg, 25 μg/kg to 50 μg/kg, 40 μg/kg to 45 μg/kg or 40 to 50 μg/kg. In certain embodiments, the same dose of IL-15/IL-15Rα complex is administered to the subject continuously for a certain period of time (e.g., days, weeks, months, or years) as the maintenance dose. In other embodiments, the dose of IL-15/IL-15Rα complex administered to the subject as the maintenance dose is slowly decreased so that the elevated lymphocytes (in number and activation) in the subject gradually return to physiological conditions.

In another embodiment, provided herein is a method for preventing, treating and/or managing disorders in a subject, wherein enhancement of IL-15-mediated immune function is beneficial for the prevention, treatment and/or management of such disorders, the method comprising administering an IL-15/IL-15Rα complex to the subject in an escalating dose regimen at the following sequential doses: (i) 0.1 μg/kg; 0.2 μg/kg; (ii) 0.4 μg/kg; (iii) 0.8 μg/kg; (iv) 1.6 μg/kg, and (v) 3.2 μg/kg, wherein the doses are determined based on the mass of single chain IL-15, wherein each dose is administered at least once, twice or thrice before elevating the dose to the next level, and wherein the concentration of free IL-15 in a sample (e.g., a plasma sample) obtained from the subject a certain period of time after the administration of a dose of the IL-15/IL-15Rα complex (e.g., approximately 24 hours to approximately 48 hours, approximately 24 hours to approximately 36 hours, approximately 24 hours to approximately 72 hours, approximately 48 hours to approximately 72 hours, approximately 36 hours to approximately 48 hours, or approximately 48 hours to 60 hours after the administration of a dose of the IL-15/IL-15Rα complex and before the administration of another dose of the IL-15/IL-15Rα complex) is monitored before elevating the dose to the next level. In another embodiment, provided herein is a method for preventing, treating and/or managing lymphocytopenia, cancer or an infectious disease in a subject, method comprising administering an IL-15/IL-15Rα complex to the subject in an escalating dose regimen at the following sequential doses: (i) 0.1 μg/kg; 0.2 μg/kg; (ii) 0.4 μg/kg; (iii) 0.8 μg/kg; (iv) 1.6 μg/kg, and (v) 3.2 μg/kg wherein the doses are determined based on the mass of single chain IL-15, wherein each dose is administered at least once, twice or thrice before elevating the dose to the next level, and wherein the concentration of free IL-15 in a sample (e.g., a plasma sample) obtained from the subject a certain period of time after the administration of a dose of the IL-15/IL-15Rα complex (e.g., approximately 24 hours to approximately 48 hours, approximately 24 hours to approximately 36 hours, approximately 24 hours to approximately 72 hours, approximately 48 hours to approximately 72 hours, approximately 36 hours to approximately 48 hours, or approximately 48 hours to 60 hours after the administration of a dose of the IL-15/IL-15Rα complex and before the administration of another dose of the IL-15/IL-15Rα complex) is monitored before elevating the dose to the next level. In another embodiment, provided herein is a method for eradicating or reducing HIV in HIV-infected cells in a subject, comprising administering an IL-15/IL-15Rα complex to the subject in an escalating dose regimen at the following sequential doses: (i) 0.1 μg/kg; 0.2 μg/kg; (ii) 0.4 μg/kg; (iii) 0.8 μg/kg; (iv) 1.6 μg/kg, and (v) 3.2 μg/kg, wherein the doses are determined based on the mass of single chain IL-15, wherein each dose is administered at least once, twice or thrice before elevating the dose to the next level, and wherein the concentration of free IL-15 in a sample (e.g., a plasma sample) obtained from the subject a certain period of time after the administration of a dose of the IL-15/IL-15Rα complex (e.g., approximately 24 hours to approximately 48 hours, approximately 24 hours to approximately 36 hours, approximately 24 hours to approximately 72 hours, approximately 48 hours to approximately 72 hours, approximately 36 hours to approximately 48 hours, or approximately 48 hours to 60 hours after the administration of a dose of the IL-15/IL-15Rα complex and before the administration of another dose of the IL-15/IL-15Rα complex) is monitored before elevating the dose to the next level. In a particular embodiment, the subject is a human subject. In certain embodiments, the initial low dose is administered 1, 2, 3, 4, 5, 6, 7, 8, 9, 10 or more times, or 1 to 3, 1 to 4, 1 to 5, 2 to 4, 2 to 5, 1 to 6, 2 to 6, 1 to 6, 3 to 6, 4 to 6, 6 to 8, 5 to 8, or 5 to 10 times. In some embodiments, the initial low dose is administered 1, 2, 3, 4, 5, 6, 7, 8, 9, 10 or more times, or 1 to 3, 1 to 4, 1 to 5, 2 to 4, 2 to 5, 2 to 6, 1 to 6, 3 to 6, 4 to 6 or 6 to 8 times over a 5 to 7 day, 5 to 10 day, 7 to 12 day, 7 to 14 day, 7 to 21 day or 14 to 21 day period of time. In certain embodiments, each dose is administered 1, 2, 3, 4, 5, 6, 7, 8, 9, 10 or more times, or 1 to 3, 1 to 4, 1 to 5, 2 to 4, 2 to 5, 1 to 6, 2 to 6, 1 to 6, 3 to 6, 4 to 6, 6 to 8, 5 to 8, or 5 to 10 times. In specific embodiments, each dose is administered at least 1, 2, 3, 4, 5, 6 or more times, or 1 to 3, 1 to 4, 1 to 5, 2 to 4, 2 to 5, 1 to 6, 2 to 6, 1 to 6, 3 to 6, 4 to 6, 6 to 8, 5 to 8, or 5 to 10 times over a 5 to 7 day, 5 to 10 day, 7 to 12 day, 7 to 14 day, 7 to 21 day or 14 to 21 day period of time. In another specific embodiment, each dose is administered at least once and the subject is administered a dose three times per 7 day week (e.g., Monday, Wednesday and Friday). In certain embodiments, the subject is monitored for one, two, or more, or all of the following: (i) signs of an enlarged lymph node(s); (ii) signs of an enlarged spleen; (iii) changes (e.g., increases) in body temperature; (iv) changes (e.g., decreases) in blood pressure; (v) changes (e.g., increases) in cytokines, such as pro-inflammatory cytokines (e.g., IL-1 and IL-6) in a sample (e.g., blood sample) from the subject; (vi) elevation of liver enzymes, such as hepatic transaminases (e.g., alanine aminotransferase (ALT) or aspartate aminotransferase (AST)); and/or (vii) adverse events, such as grade 3 or 4 thrombocytopenia, grade 3 or 4 granulocytopenia, grade 3 or 4 leukocytosis (White Blood Cell (WBC) >100,000 mm3), grade 3 or 4 decreases in WBC, absolute lymphocyte count (ALC) and/or absolute neutrophil count (ANC), lymphocytosis, and organ dysfunction (e.g., liver or kidney dysfunction). In certain embodiments, the dose is not increased and the dose may be remain the same, be stopped or reduced if the subject experiences adverse events, such as grade 3 or 4 thrombocytopenia, grade 3 or 4 granulocytopenia, grade 3 or leukocytosis (White Blood Cell >100,000 mm3), grade 3 or 4 decreases in WBC, absolute lymphocyte count (ALC) and/or absolute neutrophil count (ANC), lymphocytosis, and organ dysfunction (e.g., liver or kidney dysfunction). In accordance with these embodiments, the dose of the IL-15/IL-15Rα complex administered to the subject may be reduced or remain the same until the adverse events decrease or disappear. In specific embodiments, the dose is not increased if the trough concentration of free IL-15 in a sample (e.g., plasma sample) from the subject is above 50 pg/ml, 55 pg/ml, 60 pg/ml, 65 pg/ml, 70 pg/ml, 75 pg/ml, 80 pg/ml, 85 pg/ml, 90 pg/ml, 95 pg/ml, or 100 pg/ml. In specific embodiments, the dose is not increased if the trough concentration of free IL-15 in a sample (e.g., plasma sample) from the subject is 50 pg/ml to 75 pg/ml, 60 pg/ml to 75 pg/ml, 75 pg/ml to 85 pg/ml, 75 pg/ml to 100 pg/ml, 85 pg/ml to 100 pg/ml or 50 pg/ml to 100 pg/ml. In some embodiments, the method further comprises administering a maintenance dose of the IL-15/IL-15Rα complex to the subject, wherein the maintenance dose reaches trough levels of free IL-15 concentration of approximately 5 to 50 pg/ml in a sample (e.g., a plasma sample) from the subject. In some embodiments, the maintenance dose reaches trough levels of free IL-15 of approximately 1 pg/ml to approximately 5 pg/ml, approximately 2 pg/ml to approximately 5 pg/ml, approximately 2 pg/ml to approximately 10 pg/ml, approximately 5 pg/ml to approximately 10 pg/ml, approximately 10 pg/ml to approximately 15 pg/ml, approximately 10 pg/ml to approximately 20 pg/ml, approximately 20 pg/ml to approximately 30 pg/ml, approximately 30 pg/ml to approximately 40 pg/ml, or approximately 40 pg/ml to approximately 50 pg/ml, approximately 1 pg/ml to approximately 50 pg/ml, or approximately 5 pg/ml to approximately 50 pg/ml in a sample (e.g., a plasma sample) from the subject. In a specific embodiment, the maintenance dose is equal to or less than the highest dose received by the subject during the dose escalation phase of the therapeutic regimen which does not result in one, two, or more, or all of the following: (i) adverse events, such as grade 3 or 4 thrombocytopenia, grade 3 or 4 granulocytopenia, grade 3 or 4 leukocytosis (White Blood Cell (WBC) >100,000 mm3), grade 3 or 4 decreases in WBC, absolute lymphocyte count (ALC) and/or absolute neutrophil count (ANC), lymphocytosis, and organ dysfunction (e.g., liver or kidney dysfunction); (ii) a significant decrease in blood pressure not easily corrected clinically by, e.g., fluid injection; and/or (iii) an increase in body temperature, e.g., a body temperature of 104° F. or higher. In a specific embodiment, the maintenance dose reaches trough levels of plasma IL-15 that are close to normal levels (approximately 1 pg/ml plasma). In some embodiments, the maintenance dose is 0.1 µg/kg, 0.5 µg/kg, 1 µg/kg, 2 µg/kg, 3 µg/kg, 4 µg/kg, 5 µg/kg, 6 µg/kg, 7 µg/kg, 8 µg/kg, 9 µg/kg, 10 µg/kg, 11 µg/kg, 12 µg/kg, 13 µg/kg, 14 µg/kg, 15 µg/kg, 16 µg/kg, 17 µg/kg, 18 µg/kg, 19 µg/kg, 20 µg/kg, 21 µg/kg, 22 µg/kg, 23 µg/kg, 24 µg/kg, 25 µg/kg, 26 µg/kg, 27 µg/kg, 28 µg/kg, 29 µg/kg, 30 µg/kg, 31 µg/kg, 32 µg/kg, 33 µg/kg, 34 µg/kg, 35 µg/kg or more. In other embodiments, the maintenance dose is between 0.1 µg/kg to 5 µg/kg, 0.1 µg/kg to 10 µg/kg, 2 µg/kg to 5 µg/kg, 2 µg/kg to 10 µg/kg, 5 µg/kg to 10 µg/kg, 5 µg/kg to 15 µg/kg, 10 µg/kg to 15 µg/kg, 0.1 µg/kg to 20 µg/kg, 15 µg/kg to 20 µg/kg, 15 µg/kg to 25 µg/kg, 20 µg/kg to 25 µg/kg, 20 µg/kg to 30 µg/kg, 25 µg/kg to 30 µg/kg, 25 µg/kg to 35 µg/kg, 30 µg/kg to 35 µg/kg, 35 µg/kg to 40 µg/kg, 20 µg/kg to 40 µg/kg, 25 µg/kg to 50 µg/kg, 40 µg/kg to 45 µg/kg or 40 to 50 µg/kg. In certain embodiments, the same dose of IL-15/IL-15Rα complex is administered to the subject continuously for a certain period of time (e.g., days, weeks, months, or years) as the maintenance dose. In other embodiments, the dose of IL-15/IL-15Rα complex administered to the subject as the maintenance dose is slowly decreased so that the elevated lymphocytes (in number and activation) in the subject gradually return to physiological conditions.

In another embodiment, provided herein is a method for treating lymphocytopenia, cancer or an infectious disease in a human subject, or a method for eradicating or reducing HIV in HIV-infected cells in a human subject, comprising administering an IL-15/IL-15Rα complex to the human subject in an escalating dose regimen beginning with an initial low dose of an IL-15/IL-15Rα complex to the human subject one to five times, and sequentially escalating the dose by at least 25%, 50%, 75%, 100%, 125%, 150%, 175% 200%, 250%, or 300% over the previous dose, wherein each dose is administered at least once, twice, or thrice before elevating the dose to the next level. In a specific embodiment, the concentration of free IL-15 in a sample obtained from the subject a certain period of time after the administration of a dose of the IL-15/IL-15Rα complex is monitored before elevating the dose to the next level.

In another embodiment, provided herein is a method for treating lymphocytopenia, cancer or an infectious disease in a human subject, or a method for eradicating or reducing HIV in HIV-infected cells in a human subject, comprising administering an IL-15/IL-15Rα complex to the human subject in an escalating dose regimen beginning with an initial low dose in the range of 2 µg/kg and 10 µg/kg as determined based on the mass of single chain IL-15, and sequentially escalating the dose by at least 25%, 50%, 75%, 100%, 125%, 150%, 175% 200%, 250%, or 300% over the previous dose, wherein each dose is administered at least once, twice, or thrice before elevating the dose to the next level. In particular embodiments, the concentration of free IL-15 in a sample obtained from the subject a certain period of time after the administration of a dose of the IL-15/IL-15Rα complex is monitored before elevating the dose to the next level.

In another embodiment, provided herein is a method for treating lymphocytopenia, cancer or an infectious disease in a human subject, or a method for eradicating or reducing HIV in HIV-infected cells in a human subject, comprising administering an IL-15/IL-15Rα complex to the human subject in an escalating dose regimen at the following sequential doses: (i) 2 µg/kg; (ii) 4 µg/kg; (iv) 8 µg/kg; (v) 16 µg/kg; (v) 32 µg/kg; and (vi) 64 µg/kg, wherein the doses are determined based on the mass of single chain IL-15, wherein each dose is administered at least once, twice or thrice before elevating the dose to the next level. In a specific embodiment, the concentration of free IL-15 in a sample obtained from the subject a certain period of time after the administration of a dose of the IL-15/IL-15Rα complex is monitored before elevating the dose to the next level.

In another embodiment, provided herein is a method for treating lymphocytopenia, cancer or an infectious disease in a human subject, or a method for eradicating or reducing HIV in HIV-infected cells in a human subject, comprising administering an IL-15/IL-15Rα complex to the human subject in an escalating dose regimen at the following sequential doses: (i) 5 µg/kg; (ii) 10 µg/kg; (iv) 20 µg/kg; (v) 40 µg/kg; (v) 80 µg/kg; and (vi) 120 µg/kg, wherein the doses are determined based on the mass of single chain IL-15, wherein each dose is administered at least once, twice or thrice before elevating the dose to the next level. In a specific embodiment, the concentration of free IL-15 in a sample obtained from the subject a certain period of time after the administration of a dose of the IL-15/IL-15Rα complex is monitored before elevating the dose to the next level.

In another embodiment, provided herein is a method for treating lymphocytopenia, cancer or an infectious disease in a human subject, or a method for eradicating or reducing HIV in HIV-infected cells in a human subject, comprising administering an IL-15/IL-15Rα complex to the human subject in an escalating dose regimen beginning with an initial low dose (in, e.g., the range of 0.1 µg/kg and 1 µg/kg as determined based on the mass of single chain IL-15), and sequentially escalating (e.g., by about 10%, 20%, 30%, 40%, 50%, 60%, 70%, 80%, 90%, 100%, 125%, 150%, 175%, 200%, 225%, 250%, 275% or 300%) the dose over the previous dose every two days initially for a period of time (e.g., 1, 2, 3 or 4 weeks) and then escalating the dose gradually everyday over the previous dose for a period of time (e.g., 1, 2, 3 or 4 weeks). In certain embodiments, the initial low dose is 0.1 µg/kg, 0.2 µg/kg, 0.3 µg/kg, 0.4 µg/kg, 0.5 µg/kg, 0.6 µg/kg, 0.7 µg/kg, 0.8 µg/kg, 0.9 µg/kg, or 1 µg/kg as determined based on the mass of single chain IL-15. In some embodiments, each dose is administered at least once, twice or thrice before the dose is escalated.

In specific embodiments, provided herein is a method for treating lymphocytopenia, cancer or an infectious disease in a human subject, or a method for eradicating or reducing HIV in HIV-infected cells in a human subject, comprising administering an IL-15/IL-15Rα complex to the human subject in an escalating dose regimen beginning with an initial low dose as determined based on the mass of single chain IL-15, and sequentially escalating (e.g., by about 10%, 20%, 30%, 40%, 50%, 60%, 70%, 80%, 90%, 100%, 125%, 150%, 175%, 200%, 250%, or 300%) the dose over the previous dose for a period of time (e.g., 1, 2, 3, 4, 5, 6 or more weeks) and then administering an IL-15/IL-15Rα complex to the human subject in a maintenance dose for a period of time. In certain embodiments, the initial low dose is 0.1 μg/kg, 0.2 μg/kg, 0.3 μg/kg, 0.4 μg/kg, 0.5 μg/kg, 0.6 μg/kg, 0.7 μg/kg, 0.8 μg/kg, 0.9 μg/kg, or 1 μg/kg as determined based on the mass of single chain IL-15. In some embodiments, each dose is administered at least once, twice or thrice before the dose is escalated. In certain embodiments, the dose is escalated every day, every 2 days, or every 3 days. In specific embodiments, in accordance with the methods described herein, the maintenance dose is at least ½ or ¼ lower than the highest escalating dose administered. In specific embodiments, in accordance with the methods described herein, the maintenance dose is at least 1%, 2%, 3%, 4%, 5%, 6%, 7%, 8%, 9%, 10%, 15%, 20%, 25%, 30%, 35%, 40%, 45%, or 50% lower than the highest escalating dose administered.

In specific embodiments, in accordance with the methods described herein, each dose is administered once, three times a week for two weeks. In specific embodiments, in accordance with the methods described herein, each dose is administered once, three times a week for two, three, or four weeks. In specific embodiments, in accordance with the methods described herein, each dose is administered once, six times a week for two, three, or four weeks. In specific embodiments, in accordance with the methods described herein, each dose is administered once, every other day, for two, three, or four weeks. In specific embodiments, in accordance with the methods described herein, each dose is administered once, everyday, for two, three, or four weeks.

In certain embodiments, the IL-15/IL-15Rα complex is administered subcutaneously to a subject in accordance with the methods described herein. In some embodiments, the IL-15/IL-15Rα complex is administered intravenously or intramuscularly to a subject in accordance with the methods described herein. In certain embodiments, the IL-15/IL-15Rα complex is administered intratumorally to a subject in accordance with the methods described herein. In some embodiments, the IL-15/IL-15Rα complex is administered locally to a site (e.g., a site of infection) in a subject in accordance with the methods described herein.

In certain embodiments, a sample obtained from a subject in accordance with the methods described herein is a blood sample. In a specific embodiment, the sample is a plasma sample. Basal plasma levels of IL-15 are approximately 1 pg/ml in humans, approximately 8-10 pg/ml in monkeys (such as macaques), and approximately 12 pg/m in rodents (such as mice). Techniques known to one skilled in the art can be used to obtain a sample from a subject.

In specific embodiments, the methods described herein are not cyclical in nature. In other words, in specific embodiments, the methods described herein do not include a cyclical administration regimen, wherein the cycle comprises administering a dose of the IL-15/IL-15Rα complex for a certain period of time (e.g., 1 to 4 weeks) followed by another period of time when the subject is not administered a dose of the IL-15/IL-15Rα complex (e.g., 1 week to 2 months) and this cycle is repeated any number of times (e.g., the cycle is repeated 2, 3, 4, 5, 6, 7, 8, 9, 10 or more times).

In accordance with the methods described herein, the Therapeutic Agent may be administered to a subject in a pharmaceutical composition. In certain embodiments, the Therapeutic Agent is sole/single agent administered to the subject. In other embodiments, the Therapeutic Agents is administered in combination with one or more other therapies (e.g., an antibody that immunospecifically binds to Her2, PD-1 or a ligand of PD-1 (e.g., PD-L1)). Combination therapy includes concurrent and successive administration of a Therapeutic Agent and another therapy. As used herein, the Therapeutic Agent and another therapy are said to be administered concurrently if they are administered to the patient on the same day, for example, simultaneously, or 1, 2, 3, 4, 5, 6, 7, or 8 hours apart. In contrast, the Therapeutic Agent and the therapy are said to be administered successively if they are administered to the patient on the different days, for example, the Therapeutic Agent and the therapy can be administered at a 1-day, 2-day or 3-day intervals. In the methods described herein, administration of the Therapeutic Agent can precede or follow administration of the second therapy. When administered simultaneously, the Therapeutic Agent and the other therapy can be in the same pharmaceutical composition or in a different pharmaceutical composition.

In specific embodiments, examples of immune function enhanced by the methods described herein include the proliferation/expansion of lymphocytes (e.g., increase in the number of lymphocytes), inhibition of apoptosis of lymphocytes, activation of dendritic cells (or antigen presenting cells), and antigen presentation. In particular embodiments, an immune function enhanced by the methods described herein is proliferation/expansion in the number of or activation of $CD4^+$ T cells (e.g., Th1 and Th2 helper T cells), $CD8^+$ T cells (e.g., cytotoxic T lymphocytes, alpha/beta T cells, and gamma/delta T cells), B cells (e.g., plasma cells), memory T cells, memory B cells, dendritic cells (immature or mature), antigen presenting cells, macrophages, mast cells, natural killer T cells (NKT cells), tumor-resident T cells, $CD122^+$ T cells, or natural killer cells (NK cells). In one embodiment, the methods described herein enhance the proliferation/expansion or number of lymphocyte progenitors. In some embodiments, the methods described herein increases the number of $CD4^+$ T cells (e.g., Th1 and Th2 helper T cells), $CD8^+$ T cells (e.g., cytotoxic T lymphocytes, alpha/beta T cells, and gamma/delta T cells), B cells (e.g., plasma cells), memory T cells, memory B cells, dendritic cells (immature or mature), antigen presenting cells, macrophages, mast cells, natural killer T cells (NKT cells), tumor-resident T cells, $CD122^+$ T cells, or natural killer cells (NK cells) by approximately 1 fold, 2 fold, 3 fold, 4 fold, 5 fold, 6 fold, 7 fold, 8 fold, 9 fold, 10 fold, 20 fold, or more relative a negative control (e.g., number of the respective cells not treated, cultured, or contacted with a Therapeutic Agent).

In a specific embodiment, the methods described herein enhance or induce immune function in a subject by at least 0.2 fold, 0.5 fold, 0.75 fold, 1 fold, 1.5 fold, 2 fold, 2.5 fold, 3 fold, 4 fold, 5 fold, 6 fold, 7 fold, 8 fold 9 fold, or at least 10 fold relative to the immune function in a subject not administered the Therapeutic Agent using assays well known in the art, e.g., ELISPOT, ELISA, and cell proliferation assays. In a specific embodiment, the methods described herein enhance or induce immune function in a subject by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to the immune function in a subject not administered the Therapeutic Agent using assays well known in the art, e.g., ELISPOT, ELISA, and cell proliferation assays. In a specific embodiment, the immune function is cytokine release (e.g., interferon-gamma, IL-2, IL-5, IL-10, IL-12, or transforming growth factor (TGF)-beta). In one embodiment, the IL-15 mediated immune function is NK cell proliferation, which can be assayed, e.g., by flow cytometry to detect the number of cells expressing markers of NK cells (e.g., CD56). In one embodiment, the IL-15 mediated immune function is $CD8^+$ T cell proliferation (see, e.g., FIG. 8 and Example 5), which can be assayed, e.g., by flow cytometry or by a method described in the Examples Section below. In another embodiment, the IL-15 mediated immune function is antibody production, which can be assayed, e.g., by ELISA. In some embodiments, the IL-15 mediated immune function is effector function, which can be assayed, e.g., by a cytotoxicity assay or other assays well known in the art.

The effect of one or more doses of one or more IL-15/IL-15Rα complexes on peripheral blood lymphocyte counts can be monitored/assessed using standard techniques known to one of skill in the art. Peripheral blood lymphocytes counts in a mammal can be determined by, e.g., obtaining a sample of peripheral blood from said mammal, separating the lymphocytes from other components of peripheral blood such as plasma using, e.g., Ficoll-Hypaque (Pharmacia) gradient centrifugation, and counting the lymphocytes using trypan blue. Peripheral blood T-cell counts in mammal can be determined by, e.g., separating the lymphocytes from other components of peripheral blood such as plasma using, e.g., a use of Ficoll-Hypaque (Pharmacia) gradient centrifugation, labeling the T-cells with an antibody directed to a T-cell antigen such as CD3, CD4, and CD8 which is conjugated to FITC or phycoerythrin, and measuring the number of T-cells by FACS. Further, the effect on a particular subset of T cells (e.g., $CD2^+$, $CD4^+$, $CD8^+$, $CD4^+RO^+$, $CD8^+RO^+$, $CD4^+RA^+$, or $CD8^+RA^+$) or NK cells can be determined using standard techniques known to one of skill in the art such as FACS.

The plasma levels of IL-15 can be assessed using standard techniques known to one of skill in the art. For example, a plasma can be obtained from a blood sample obtained from a subject and the levels of IL-15 in the plasma can be measured by ELISA.

5.6 Cancer Treatment

Provided herein are methods for preventing, treating, and/or managing cancer in a dose escalation regimen, comprising administering to a subject an effective amount of a Therapeutic Agent or a composition comprising a Therapeutic Agent to a subject in need thereof. In a specific embodiment, the methods described herein do not involve a cyclical administration regimen of the Therapeutic Agent.

The effect of a Therapeutic Agent on proliferation of cancer cells can be detected by routine assays, such as by assays that measure the uptake of radiolabeled thymidine. Alternatively, cell viability can be measured by assays that measure lactate dehydrogenase (LDH), a stable cytosolic enzyme that is released upon cell lysis, or by the release of [$^{51}Cr$] upon cell lysis. In one embodiment, necrosis measured by the ability or inability of a cell to take up a dye such as neutral red, trypan blue, or ALAMAR™ blue (Page et al., 1993, Intl. J. of Oncology 3:473 476). In such an assay, the cells are incubated in media containing the dye, the cells are washed, and the remaining dye, reflecting cellular uptake of the dye, is measured spectrophotometrically.

In another embodiment, the dye is sulforhodamine B (SRB), whose binding to proteins can be used as a measure of cytotoxicity (Skehan et al., 1990, J. Nat'l Cancer Inst. 82:1107 12). In yet another embodiment, a tetrazolium salt, such as MTT, is used in a quantitative colorimetric assay for mammalian cell survival and proliferation by detecting living, but not dead, cells (see, e.g., Mosmann, 1983, J. Immunol. Methods 65:55 63).

In other embodiments, apoptotic cells are measured in both the attached and "floating" compartments of the cultures. Both compartments are collected by removing the supernatant, trypsinizing the attached cells, and combining both preparations following a centrifugation wash step (10 minutes, 2000 rpm). The protocol for treating tumor cell cultures with sulindac and related compounds to obtain a significant amount of apoptosis has been described in the literature (see, e.g., Piazza et al., 1995, Cancer Research 55:3110 16). Features of this method include collecting both floating and attached cells, identification of the optimal treatment times and dose range for observing apoptosis, and identification of optimal cell culture conditions.

In another embodiment, apoptosis is quantitated by measuring DNA fragmentation. Commercial photometric methods for the quantitative in vitro determination of DNA fragmentation are available. Examples of such assays, including TUNEL (which detects incorporation of labeled nucleotides in fragmented DNA) and ELISA-based assays, are described in Biochemica, 1999, no. 2, pp. 34 37 (Roche Molecular Biochemicals).

In yet another embodiment, apoptosis can be observed morphologically.

Cancer cell lines on which such assays can be performed are well known to those of skill in the art. Apoptosis, necrosis and proliferation assays can also be performed on primary cells, e.g., a tissue explant.

In a specific embodiment, the proliferation or viability of cancer cells contacted with a Therapeutic Agent or a composition comprising a Therapeutic Agent is inhibited or reduced by at least 2 fold, preferably at least 2.5 fold, at least 3 fold, at least 4 fold, at least 5 fold, at least 7 fold, or at least 10 fold relative to the proliferation of the cancer cells when contacted with a negative control as measured using assays well known in the art, e.g., cell proliferation assays using CSFE, BrdU, and $^3H$-Thymidine incorporation. In another embodiment, the proliferation of cancer cells contacted with a Therapeutic Agent or a composition comprising a Therapeutic Agent is inhibited or reduced by at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% relative to cancer cells contacted with a negative control as measured using assays well known in the art, e.g., cell proliferation assays using CSFE, BrdU, and $^3H$-Thymidine incorporation, or those assays described above. In one aspect, the composition comprising a Therapeutic Agent further comprises cells (e.g., NK cells or cytotoxic T cells) that are responsive to IL-15 signaling and that can target and exert cytotoxic effects on the cancer cells.

In specific embodiments, the administration of a Therapeutic Agent to a subject in accordance with the methods described herein achieves one, two, or three or more results: (1) a reduction in the growth of a tumor or neoplasm; (2) a reduction in the formation of a tumor; (3) an eradication, removal, or control of primary, regional and/or metastatic cancer; (4) a reduction in metastatic spread; (5) a reduction in mortality; (6) an increase in survival rate; (7) an increase in length of survival; (8) an increase in the number of patients in remission; (9) a decrease in hospitalization rate; (10) a decrease in hospitalization lengths; and (11) the maintenance in the size of the tumor so that it does not increase by more than 10%, or by more than 8%, or by more than 6%, or by more than 4%; preferably the size of the tumor does not increase by more than 2%.

In a specific embodiment, the administration of a Therapeutic Agent, or a composition comprising a Therapeutic Agent to a subject with cancer (in some embodiments, an animal model for cancer) in accordance with the methods described herein inhibits or reduces the growth of a tumor by at least 2 fold, preferably at least 2.5 fold, at least 3 fold, at least 4 fold, at least 5 fold, at least 7 fold, or at least 10 fold relative to the growth of a tumor in a subject with cancer (in some embodiments, in the same animal model for cancer) administered a negative control as measured using assays well known in the art. In another embodiment, the administration of a Therapeutic Agent or an Engineered Cell(s), or a composition comprising a Therapeutic Agent to a subject with cancer (in some embodiments, an animal model for cancer) in accordance with the methods described herein inhibits or reduces the growth of a tumor by at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% relative to the growth of a tumor in a subject with cancer (in some embodiments, in the same animal model for cancer) administered a negative control as measured using assays well known in the art.

In a specific embodiment, the administration of a Therapeutic Agent, or a composition comprising a Therapeutic Agent to a subject with cancer (in some embodiments, an animal model for cancer) in accordance with the methods described herein reduces the size of a tumor by at least 2 fold, preferably at least 2.5 fold, at least 3 fold, at least 4 fold, at least 5 fold, at least 7 fold, or at least 10 fold relative to the growth of a tumor in a subject with cancer (in some embodiments, the same animal model for cancer) in accordance with the methods described herein administered a negative control as measured using assays well known in the art. In another embodiment, the administration of a Therapeutic Agent, or a composition comprising a Therapeutic Agent to a subject with cancer (in some embodiments, an animal model for cancer) reduces the size of a tumor by at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% relative to the growth of a tumor in a subject with cancer (in some embodiments, the same animal model for cancer) administered a negative control (e.g., saline or PBS) as measured using assays well known in the art. In a specific embodiment, the cancer is melanoma, renal cancer, colon cancer, or prostate cancer. In another embodiment, the cancer is metastatic.

A Therapeutic Agent can be administered in combination with one or more other therapies, e.g., anti-cancer agents, cytokines or anti-hormonal agents, to treat and/or manage cancer. Non-limiting examples anti-cancer agents are described below. See Section 5.9, infra, and in particular, Section 5.9.1, infra. In one embodiment, the combination of Therapeutic Agent and one or more other therapies provides an additive therapeutic effect relative to the therapeutic effects of the Therapeutic Agent alone or the one or more other therapies alone. In one embodiment, the combination of a Therapeutic Agent and one or more other therapies provides more than an additive therapeutic effect relative to the therapeutic effects of the Therapeutic Agent alone or the one or more other therapies alone. In one embodiment, the combination of a Therapeutic Agent and one or more other therapies provides a synergistic therapeutic effect relative to the therapeutic effects of the Therapeutic Agent alone or the one or more other therapies alone.

In one embodiment, the one or more therapies include, but are not limited to cytokines/growth factors, e.g., interleukin (IL) 1, IL-2, IL-3, IL-4, IL-5, IL-6, IL-7, IL-8, IL-10, IL-11, IL-12, Il-15, TNF-α, TNF-β, TGF-β, GM-CSF, and interferon-γ. In one embodiment, the one or more therapies include, but are not limited to receptors, antibodies, or other binding agents that bind to cytokines/growth factors, e.g., interleukin (IL) 1, IL-2, IL-3, IL-4, IL-5, IL-6, IL-7, IL-8, IL-10, IL-11, IL-12, TNF-α, TNF-β, TGF-β, GM-CSF, interferon-α, interferon-β, and interferon-γ. In some embodiments, the one or more therapies include, but are not limited to, cells recombinantly expressing a therapeutic protein (or polypeptides), e.g., a cytokine, a growth factor, a chemokine, or a fragment or derivative thereof. In a particular embodiment, the one or more therapies include, but are not limited to, cells recombinantly expressing IL-12, IL-6, GM-CSF, interferon-α, interferon-β, interferon-γ or TNF-α. In certain embodiments, such therapies are administered prior to, concurrently with, or after administration of a Therapeutic Agent, wherein the Therapeutic Agent is administered in accordance with the methods described herein A Therapeutic Agent can also be administered in combination with radiation therapy comprising, e.g., the use of x-rays, gamma rays and other sources of radiation to destroy the cancer cells. In specific embodiments, the radiation treatment is administered as external beam radiation or teletherapy wherein the radiation is directed from a remote source. In other embodiments, the radiation treatment is administered as internal therapy or brachytherapy wherein a radioactive source is placed inside the body close to cancer cells or a tumor mass. In a specific embodiment, a Therapeutic Agent can be administered in accordance with the methods described herein before, during or after radiation therapy. In one aspect, the Therapeutic Agent can enhance the immune function of cancer patient with a compromised immune system due to anti-cancer therapy. A Therapeutic Agent can also be administered in combination with chemotherapy. In one embodiment, a Therapeutic Agent can be administered in accordance with the methods described herein before, during or after radiation therapy or chemotherapy. In one embodiment, a Therapeutic Agent can be used before, during or after surgery. In one embodiment, methods provided herein include the combination of transplant and a Therapeutic Agent.

Non-limiting examples of anti-hormonal agents are anti-hormonal agents that act to regulate or inhibit hormone action on tumors, such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASIN®V exemestane, formestanie, fadrozole, RIVISOR® vorozole, FEMARA® letrozole, and ARIMIDEX®D anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in aberrant cell proliferation, such as, for example, PKC-alpha, Raf and H-Ras; ribozymes such as a VEGF expression inhibitor (e.g., ANGIOZYME® ribozyme) and a HER2 expression inhibitor; vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELX® rmRH; Vinorelbine and Esperamicins (see U.S. Pat. No. 4,675,187), and pharmaceutically acceptable salts, acids or derivatives of any of the above.

In a specific embodiment, a Therapeutic Agent is administered to a subject in combination with an antibody that immunospecifically binds to programmed cell death (PD-1) or a ligand thereof (e.g., PD-L1). In another specific embodiment, provided herein is a method for preventing, treating and/or managing cancer comprising administering an IL-15/IL-15Rα complex and administering an antibody that immunospecifically binds to PD-1 or a ligand thereof. In certain aspects, administering an IL-15/IL-15Rα complex increases (e.g., approximately 2 fold increase) expression levels of PD-1 (see, e.g., FIG. 8 and Example 5), and an antibody that immunospecifically binds to PD-1 reduces expression levels of PD-1. In certain embodiments, the antibody is administered after the IL-15/IL-15Rα complex is administered. In other embodiments, the antibody is administered before the IL-15/IL-15Rα complex is administered. In specific embodiments, the cancer is melanoma, prostate cancer, or lung cancer.

In another embodiment, a Therapeutic Agent is administered to a subject in combination with an antibody that immunospecifically binds to Her2 (e.g., Herceptin®). In another specific embodiment, provided herein is a method for preventing, treating and/or managing cancer comprising administering an IL-15/IL-15Rα complex and administering an antibody that immunospecifically binds to Her2 (e.g., Herceptin®) In certain embodiments, the antibody is administered after the IL-15/IL-15Rα complex is administered. In other embodiments, the antibody is administered before the IL-15/IL-15Rα complex is administered. In specific embodiments, the cancer is breast cancer.

In a specific embodiment, a Therapeutic Agent is administered to a subject in combination with an antibody that immunospecifically binds to CD20 (e.g., Rituxan/Rituximab). In another specific embodiment, provided herein is a method for preventing, treating and/or managing cancer comprising administering an IL-15/IL-15Rα complex and administering an antibody that immunospecifically binds to CD20. In certain embodiments, the antibody is administered after the IL-15/IL-15Rα complex is administered. In other embodiments, the antibody is administered before the IL-15/IL-15Rα complex is administered. In specific embodiments, the cancer is non-Hodgkin's lymphoma or chronic lymphocytic leukemia.

Cancers and related disorders that can be prevented, treated, or managed in accordance with the methods described herein include, but are not limited to, the following: Leukemias including, but not limited to, acute leukemia, acute lymphocytic leukemia, acute myelocytic leukemias such as myeloblastic, promyelocytic, myelomonocytic, monocytic, erythroleukemia leukemias and myelodysplastic syndrome, chronic leukemias such as but not limited to, chronic myelocytic (granulocytic) leukemia, and chronic lymphocytic leukemia, hairy cell leukemia; polycythemia vera; lymphomas such as but not limited to Hodgkin's disease, and non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenström's macroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, and synovial sarcoma; brain tumors including but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, and primary brain lymphoma; breast cancer including, but not limited to, adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer, including but not limited to, pheochromocytom and adrenocortical carcinoma; thyroid cancer such as but not limited to papillary or follicular thyroid cancer, medullary thyroid cancer and anaplastic thyroid cancer; pancreatic cancer, including but not limited to, insulinoma, gastrinoma, glucagonoma, vipoma, somatostatin-secreting tumor, and carcinoid or islet cell tumor; pituitary cancers including but not limited to, Cushing's disease, prolactin-secreting tumor, acromegaly, and diabetes insipius; eye cancers including but not limited to, ocular melanoma such as iris melanoma, choroidal melanoma, and cilliary body melanoma, and retinoblastoma; vaginal cancers, including but not limited to, squamous cell carcinoma, adenocarcinoma, and melanoma; vulvar cancer, including but not limited to, squamous cell carcinoma, melanoma, adenocarcinoma, basal cell carcinoma, sarcoma, and Paget's disease; cervical cancers including but not limited to, squamous cell carcinoma, and adenocarcinoma; uterine cancers including but not limited to, endometrial carcinoma and uterine sarcoma; ovarian cancers including but not limited to, ovarian epithelial carcinoma, borderline tumor, germ cell tumor, and stromal tumor; esophageal cancers including but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers including but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers including but not limited to hepatocellular carcinoma and hepatoblastoma; gallbladder cancers including but not limited to, adenocarcinoma; cholangiocarcinomas including but not limited to, papillary, nodular, and diffuse; lung cancers including but not limited to, non-small cell lung cancer, squamous cell carcinoma (epidermoid carcinoma), adenocarcinoma, large-cell carcinoma and small-cell lung cancer; testicular cancers including but not limited to, germinal tumor, seminoma, anaplastic, spermatocytic, nonseminoma, embryonal carcinoma, teratoma carcinoma, choriocarcinoma (yolk-sac tumor); prostate cancers including but not limited to, adenocarcinoma, leiomyosarcoma, and rhabdomyosarcoma; penal cancers; oral cancers including but not limited to, squamous cell carcinoma; basal cancers; salivary gland cancers including but not limited to, adenocarcinoma, mucoepidermoid carcinoma, and adenoidcystic carcinoma; pharynx cancers including but not limited to, squamous cell cancer, and verrucous; skin cancers including but not limited to, basal cell carcinoma, squamous cell carcinoma and melanoma, and superficial spreading melanoma, nodular melanoma, lentigo malignant melanoma, acral lentiginous melanoma; kidney cancers including but not limited to, renal cell cancer, renal cancer, adenocarcinoma, hypernephroma, fibrosarcoma, and transitional cell cancer (renal pelvis and/or uterer); Wilms' tumor; bladder cancers including but not limited to, transitional cell carcinoma, squamous cell cancer, adenocarcinoma, and carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, Medicine, 2d Ed., J.B. Lippincott Co., Philadelphia and Murphy et al., 1997, Informed Decisions: The Complete Book of Cancer Diagnosis, Treatment, and Recovery, Viking Penguin, Penguin Books U.S.A., Inc., United States of America).

In one embodiment, the cancer is benign, e.g., polyps and benign lesions. In other embodiments, the cancer is metastatic. The Therapeutic Agents can be used in the treatment of pre-malignant as well as malignant conditions. Premalignant conditions include hyperplasia, metaplasia, and dysplasia. Treatment of malignant conditions includes the treatment of primary as well as metastatic tumors. In a specific embodiment, the cancer is melanoma, prostate cancer, colon cancer, renal cell carcinoma, or lung cancer (e.g., non-small cell lung cancer). In certain embodiments, the cancer is metastatic melanoma, metastaic colon cancer, metastatic renal cell carcinoma, or metastatic lung cancer (e.g., metastatic non-small cell lung cancer).

In some embodiments, a Therapeutic Agent, a composition comprising a Therapeutic Agent, or combination therapies are administered to a subject suffering from or diagnosed with cancer. In other embodiments, a Therapeutic Agent, a composition comprising a Therapeutic Agent, or combination therapies are administered to a subject predisposed or susceptible to developing cancer. In some embodiments, a Therapeutic Agent, a composition comprising a Therapeutic Agent, or combination therapies are administered to a subject that lives in a region where there is a high occurrence rate of cancer. In a specific embodiment, the cancer is characterized by a pre-malignant tumor or a malignant tumor.

In certain embodiments, a Therapeutic Agent, a composition comprising a Therapeutic Agent, or a combination therapy is administered to a mammal which is 0 to 6 months old, 6 to 12 months old, 1 to 5 years old, 5 to 10 years old, 10 to 15 years old, 15 to 20 years old, 20 to 25 years old, 25 to 30 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100 years old. In certain embodiments, a Therapeutic Agent, a composition comprising a Therapeutic Agent, or a combination therapy is administered to a human at risk developing cancer. In certain embodiments, a Therapeutic Agent, a composition comprising a Therapeutic Agent, or a combination therapy is administered to a human with cancer. In certain embodiments, the patient is a human 0 to 6 months old, 6 to 12 months old, 1 to 5 years old, 5 to 10 years old, 5 to 12 years old, 10 to 15 years old, 15 to 20 years old, 13 to 19 years old, 20 to 25 years old, 25 to 30 years old, 20 to 65 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100 years old. In some embodiments, a Therapeutic Agent, a composition comprising a Therapeutic Agent, or a combination therapy is administered to a human infant or a premature human infant. In other embodiments, a Therapeutic Agent, a composition comprising a Therapeutic Agent, or a combination therapy is administered to a human child. In other embodiments, a Therapeutic Agent, a composition comprising a Therapeutic Agent, or a combination therapy is administered to a human adult. In yet other embodiments, a Therapeutic Agent, a composition comprising a Therapeutic Agent, or a combination therapy is administered to an elderly human.

In certain embodiments, a Therapeutic Agent, a composition comprising a Therapeutic Agent, or a combination therapy is administered to a pet, e.g., a dog or cat. In certain embodiments, a Therapeutic Agent, a composition comprising a Therapeutic Agent, or a combination therapy is administered to a farm animal or livestock, e.g., pig, cows, horses, chickens, etc.

In certain embodiments, a Therapeutic Agent, a composition comprising a Therapeutic Agent, or a combination therapy is administered to a primate, preferably a human, or another mammal, such as a pig, cow, horse, sheep, goat, dog, cat and rodent, in an immunocompromised state or immunosuppressed state or at risk for becoming immunocompromised or immunosuppressed. In certain embodiments, a Therapeutic Agent, a composition comprising a Therapeutic Agent, or a combination therapy is administered to a subject receiving or recovering from immunosuppressive therapy. In certain embodiments, a Therapeutic Agent, a composition comprising a Therapeutic Agent, or a combination therapy is administered to a subject that has or is at risk of getting AIDS, a viral infection, or a bacterial infection. In certain embodiments, a subject that is, will or has undergone surgery, chemotherapy and/or radiation therapy. In some embodiments, a Therapeutic Agent, a composition comprising a Therapeutic Agent, or a combination therapy is administered to a subject that lives in a nursing home, a group home (i.e., a home for 10 or more subjects), or a prison.

In some embodiments, a patient is administered a Therapeutic Agent, a composition comprising a Therapeutic Agent, or a combination therapy is before any adverse effects or intolerance to therapies other than Therapeutic Agents develops. In some embodiments, Therapeutic Agents, compositions comprising Therapeutic Agents, or combination therapies are administered to refractory patients. In a certain embodiment, refractory patient is a patient refractory to a standard anti-cancer therapy. In certain embodiments, a patient with cancer, is refractory to a therapy when the cancer has not significantly been eradicated and/or the symptoms have not been significantly alleviated. The determination of whether a patient is refractory can be made either in vivo or in vitro by any method known in the art for assaying the effectiveness of a treatment, using art-accepted meanings of "refractory" in such a context. In various embodiments, a patient with cancer is refractory when a cancerous tumor has not decreased or has increased.

In some embodiments, a Therapeutic Agent, a composition comprising a Therapeutic Agent, or combination therapy(ies) is administered to a patient to prevent the onset or reoccurrence of cancer in a patient at risk of developing such cancer. In some embodiments, a Therapeutic Agent, a composition comprising a Therapeutic Agent, or combination therapy(ies) is administered to a patient who is susceptible to adverse reactions to conventional therapies.

In some embodiments, one or more Therapeutic Agents, compositions comprising Therapeutic Agents, or combination therapies are administered to a patient who has proven refractory to therapies other than Therapeutic Agents, but are no longer on these therapies. In certain embodiments, the patients being managed or treated in accordance with the methods described herein are patients already being treated with antibiotics, anti-cancer agents, or other biological therapy/immunotherapy. Among these patients are refractory patients, patients who are too young for conventional therapies, and patients with reoccurring viral infections despite management or treatment with existing therapies.

In some embodiments, the subject being administered one or more Therapeutic Agents, compositions comprising Therapeutic Agents, or combination therapies has not received a therapy prior to the administration of the Therapeutic Agents, compositions comprising Therapeutic Agents, or combination therapies. In other embodiments, one or more Therapeutic Agents, compositions comprising Therapeutic Agents, or combination therapies are administered to a subject who has received a therapy prior to administration of one or more Therapeutic Agents, compositions comprising Therapeutic Agents, or combination therapies. In some embodiments, the subject administered a Therapeutic Agent or a composition comprising a Therapeutic Agent was refractory to a prior therapy or experienced adverse side effects to the prior therapy or the prior therapy was discontinued due to unacceptable levels of toxicity to the subject.

5.7 Infectious Diseases Treatment

Provided herein are methods for treating, preventing and/or managing an infectious disease in a dose escalation regimen, comprising administering an effective amount of a Therapeutic Agent or a composition comprising a Therapeutic Agent to a subject in need thereof. In a specific embodiment, the methods described herein do not involve a cyclical administration regimen of the Therapeutic Agent.

In a specific embodiment, the induced or enhanced immune response by administration of a Therapeutic Agent to a patient in accordance with the methods described herein is increased production in the patient of antibodies to the infected cells or to the antigens of the pathogen. In a specific embodiment, the induced or enhanced immune response by administration of a Therapeutic Agent to a patient in accordance with the methods described herein is increased production of antibodies to the pathogen. In another embodiment, the induced or enhanced immune response by administration of a Therapeutic Agent to a patient in accordance with the methods described herein is an increase in effector cell function, e.g., antibody-dependent cellular cytotoxicity (ADCC) against the pathogen and/or cells infected with a pathogen in the patient. In some embodiments, the induced or enhanced immune response by administration of a Therapeutic Agent to a patient in accordance with the methods described herein is increase in lymphocyte number, lymphocyte proliferation, and/or lymphocyte activity. In another embodiment, the induced or enhanced immune response by administration of a Therapeutic Agent to a patient in accordance with the methods described herein is an increase in effector cell function, e.g., cytotoxic cells or antibody-dependent cellular cytotoxicity (ADCC) against the infected cells in the patient.

In other embodiments, a Therapeutic Agent can be administered in combination with one or more other therapies. Non-limiting examples of other therapies that can be used in combination with Therapeutic Agents are described herein. See Section 5.9, infra, and in particular, Sections 5.9.2 and 5.9.3, infra. In one embodiment, the combination of a Therapeutic Agent and one or more other therapies provides an additive therapeutic effect relative to the therapeutic effects of the Therapeutic Agent or Engineered Cell(s) alone or the one or more other therapies alone. In one embodiment, the combination of a Therapeutic Agent and one or more other therapies provides more than an additive therapeutic effect relative to the therapeutic effects of the Therapeutic Agent alone or the one or more other therapies alone. In one embodiment, the combination of a Therapeutic Agent and one or more other therapies provides a synergistic therapeutic effect relative to the therapeutic effects of the Therapeutic Agent alone or the one or more other therapies alone. In certain embodiments, the one or more additional therapies are administered prior to, concurrently with, or after administration of a Therapeutic Agent, wherein the Therapeutic Agent is administered in accordance with the methods described herein.

Infectious diseases that can be treated, prevented, and/or managed by Therapeutic Agents are caused by infectious agents including but not limited to bacteria, fungi, protozae, and viruses.

Viral diseases that can be prevented, treated and/or managed in accordance with the methods described herein include, but are not limited to, those caused by hepatitis type A, hepatitis type B, hepatitis type C, influenza, varicella, Epstein-Barr virus, adenovirus, herpes simplex type I (HSV-I), herpes simplex type II (HSV-II), rinderpest, rhinovirus, echovirus, rotavirus, respiratory syncytial virus, papilloma virus, papova virus, cytomegalovirus, echinovirus, arbovirus, huntavirus, coxsackie virus, mumps virus, measles virus, rubella virus, polio virus, small pox virus, Epstein Barr virus, human immunodeficiency virus type I (HIV-I), human immunodeficiency virus type II (HIV-II), and agents of viral diseases such as viral meningitis, encephalitis, pneumonia, infectious mononucleosis, hepatitis, mumps, polio, shingles, dengue or small pox. In a specific embodiment, the viral disease is AIDS, meningitis, hepatitis, or pneumonia.

Bacterial diseases caused by bacteria (e.g., *Escherichia coli, Klebsiella pneumoniae, Staphylococcus aureus, Enterococcus faecials, Candida albicans, S. pneumonia*, Group A *streptococcus* (*Streptococcus pyogenes*), *Clostridium perfringens, Bacteroides fragilis, Aeromonas hydrophil, Borrelia burgdorferi, Bacillus antracis, Proteus vulgaris, Staphylococcus viridans*, mycobacteria *rickettsia, Mycobacterium leprae, Mycobacterium tuberculosis, Clostridium tetani, Neisseria meningitides, Yersinia pestis*, and *Pseudomonas aeruginosa*) that can be prevented, treated and/or managed in accordance with the methods described herein include, but are not limited to, *mycoplasma*, sepsis, and bubonic plague, Lyme disease, anthrax, tetanus, pertissus, cholera, plague, diptheria, *chlamydia*, pneumonia, toxic shock syndrome, scarlet fever, leprosy, meningococcal disease, necrotizing fasciitis, tuberculosis, and *legionella*. In a specific embodiment, the bacterial disease is pneumonia or tuberculosis.

Protozoal diseases caused by protozoa that can be prevented, treated and/or managed in accordance with the methods described herein include, but are not limited to, *leishmania*, kokzidioa, *trypanosoma* or malaria.

Parasitic diseases caused by parasites that can be prevented, treated and/or managed in accordance with the methods described herein include, but are not limited to, *chlamydia* and *rickettsia*.

In certain embodiments, administering a Therapeutic Agent or a composition comprising a Therapeutic Agent to a subject (in some embodiments, an animal model) infected with an infectious agent in accordance with the methods described herein inhibits or reduces replication of the infectious agent by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In some embodiments, administering a Therapeutic Agent or a composition comprising a Therapeutic Agent to a subject (in some embodiments, an animal model) infected with an infectious agent in accordance with the methods described herein inhibits or reduces replication of the infectious agent by at least 1.5 fold, 2 fold, 2.5 fold, 3 fold, 4 fold, 5 fold, 8 fold, 10 fold, 15 fold, 20 fold, or 2 to 5 fold, 2 to 10 fold, 5 to 10 fold, or 5 to 20 fold relative to a negative control as determined using an assay described herein or others known to one of skill in the art. In other embodiments, administering a Therapeutic Agent or a composition comprising a Therapeutic Agent to a subject (in some embodiments, an animal model) infected with an infectious agent in accordance with the methods described herein inhibits or reduces replication of the infectious agent by 1 log, 1.5 logs, 2 logs, 2.5 logs, 3 logs, 3.5 logs, 4 logs, 5 logs or more relative to a negative control as determined using an assay described herein or others known to one of skill in the art.

In certain embodiments, administering a Therapeutic Agent or a composition comprising a Therapeutic Agent to a subject (in some embodiments, an animal model) infected with an infectious agent in accordance with the methods described herein reduces the titer of the infectious agent by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In some embodiments, administering a Therapeutic Agent or a composition comprising a Therapeutic Agent to a subject (in some embodiments, an animal model) infected with an infectious agent in accordance with the methods described herein reduces the titer of the infectious agent by at least 1.5 fold, 2 fold, 2.5 fold, 3 fold, 4 fold, 5 fold, 8 fold, 10 fold, 15 fold, 20 fold, or 2 to 5 fold, 2 to 10 fold, 5 to 10 fold, or 5 to 20 fold relative to a negative control as determined using an assay described herein or others known to one of skill in the art. In other embodiments, administering a Therapeutic Agent or a composition comprising a Therapeutic Agent to a subject (in some embodiments, an animal model) infected with an infectious agent in accordance with the methods described herein reduces the titer of the infectious agent by 1 log, 1.5 logs, 2 logs, 2.5 logs, 3 logs, 3.5 logs, 4 logs, 5 logs or more relative to a negative control as determined using an assay described herein or others known to one of skill in the art.

In some embodiments, a Therapeutic Agent(s), a composition(s) comprising a Therapeutic Agent(s), or a combination therapy(ies) is administered to a subject suffering from an infectious disease caused by infectious agents including, but not limited to bacteria, fungi, protozae, and viruses. In other embodiments, a Therapeutic Agent(s), a composition(s) comprising a Therapeutic Agent(s), or a combination therapy(ies) is administered to a subject predisposed or susceptible to an infectious disease.

In some embodiments, a Therapeutic Agent(s), a composition(s) comprising a Therapeutic Agent(s), or a combination therapy(ies) is administered to a subject that lives in a region where there has been or might be an outbreak with infections by infectious agents. In some embodiments, the infection is a latent infection. In other embodiments, the infection by the infectious agent is an active infection. In yet other embodiments, the infection by the infectious agent is a chronic infection.

In certain embodiments, a Therapeutic Agent(s), a composition(s) comprising a Therapeutic Agent(s), or a combination therapy(ies) is administered to a subject with a chronic infection. In a specific embodiment, a Therapeutic Agent(s), a composition comprising a Therapeutic Agent(s), or a combination therapy(ies) is administered to a subject with an infection that persists for weeks, months, years, decades or a lifetime. In certain embodiments, the infection persists for a period of time (e.g., weeks, months, years or decades) without the subject manifesting symptoms.

Exemplary infectious agents capable of inducing a chronic infection include viruses (e.g., cytomegalovirus, Epstein Barr virus, hepatitis B virus, hepatitis C virus, herpes simplex virus, types I and II, human immunodeficiency virus, types 1 and 2, human papillomavirus, human T lymphotrophic viruses, types 1 and 2, varicella zoster virus and the like), bacteria (e.g., *Mycobacterium tuberculosis, Listeria* spp., *Klebsiella pneumoniae, Streptococcus pneumoniae, Staphylococcus aureus, Borrelia* spp., *Helicobacter pylori*, and the like), protozoan parasites (e.g., *Leishmania* spp., *Plasmodium falciparum, Schistosoma* spp., *Toxoplasma* spp., *Trypanosoma* spp., *Taenia* carssiceps and the like), and fungi (e.g., *Aspergillus* spp., *Candida albicans, Coccidioides immitis, Histoplasma capsulatum, Pneumocystis carinii* and the like). Additional infectious agents include prions or misfolded proteins that affect the brain or neuron structure by further propagating protein misfolding in these tissues, resulting in the formation of amyloid plaques which cause cell death, tissue damage and eventual death. Example of disease resulting from prion infection include: Creutzfeldt-Jakob disease and its varieties, Gerstmann-Straussler-Scheinker syndrome (GSS), fatal familial insomnia (sFI), kuru, scrapie, Bovine spongiform encephalopathy (BSE) in cattle (aka "mad cow" disease), and various other animal forms of encephalopathy (e.g., transmissible mink encephalopathy (TME), chronic wasting disease (CWD) in white-tailed deer, elk and mule deer, feline spongiform encephalopathy, exotic ungulate encephalopathy (EUE) in nyala, oryx and greater kudu, spongiform encephalopathy of the ostrich).

In certain embodiments, a Therapeutic Agent(s), a composition(s) comprising a Therapeutic Agent(s), or a combination therapy(ies) is administered to a subject with a latent infection. In some embodiments, a Therapeutic Agent(s), a composition(s) comprising a Therapeutic Agent(s), or a combination therapy(ies) is administered to a subject with an active infection.

In certain embodiments, a Therapeutic Agent(s), a composition(s) comprising a Therapeutic Agent(s), or a combination therapy(ies) is administered to a subject with a viral infection. In some embodiments, a Therapeutic Agent(s), a composition(s) comprising a Therapeutic Agent(s), or a combination therapy(ies) is administered to a subject with a bacterial infection. In certain embodiments, a Therapeutic Agent(s), a composition(s) comprising a Therapeutic Agent(s), or a combination therapy(ies) with a fungal infection.

In certain embodiments, a Therapeutic Agent(s), a composition(s) comprising a Therapeutic Agent(s), or a combination therapy(ies) is administered to a mammal which is 0 to 6 months old, 6 to 12 months old, 1 to 5 years old, 5 to 10 years old, 10 to 15 years old, 15 to 20 years old, 20 to 25 years old, 25 to 30 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100 years old. In certain embodiments, a Therapeutic Agent(s), a composition(s) comprising a Therapeutic Agent(s) or a combination therapy(ies) is administered to a human at risk for a virus infection. In certain embodiments, a Therapeutic Agent(s), a composition(s) comprising a Therapeutic Agent(s), or a combination therapy(ies) is administered to a human with a virus infection. In certain embodiments, the patient is a human 0 to 6 months old, 6 to 12 months old, 1 to 5 years old, 5 to 10 years old, 5 to 12 years old, 10 to 15 years old, 15 to 20 years old, 13 to 19 years old, 20 to 25 years old, 25 to 30 years old, 20 to 65 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100 years old. In some embodiments, a Therapeutic Agent(s), a composition(s) comprising a Therapeutic Agent(s), or a combination therapy(ies) is administered to a human infant or premature human infant. In other embodiments, a Therapeutic Agent(s), a composition(s) comprising a Therapeutic Agent(s), or a combination therapy(ies) is administered to a human child. In other embodiments, a Therapeutic Agent(s), a composition(s) comprising a Therapeutic Agent(s), or a combination therapy(ies) is administered to a human adult. In yet other embodiments, a Therapeutic Agent(s), a composition(s) comprising a Therapeutic Agent(s), or a combination therapy(ies) is administered to an elderly human.

In certain embodiments, a Therapeutic Agent(s), a composition(s) comprising a Therapeutic Agent(s), or a combination therapy(ies) is administered to a pet, e.g., a dog or cat. In certain embodiments, a Therapeutic Agent(s), a composition(s) comprising a Therapeutic Agent(s), or a combination therapy(ies) is administered to a farm animal or livestock, e.g., pig, cows, horses, chickens, etc. In certain embodiments, a Therapeutic Agent(s), a composition(s) comprising a Therapeutic Agent(s), or a combination therapy(ies) is administered to a bird, e.g., ducks or chicken.

In certain embodiments, a Therapeutic Agent(s), a composition(s) comprising a Therapeutic Agent(s), or a combination therapy(ies) is administered to a primate, preferably a human, or another mammal, such as a pig, cow, horse, sheep, goat, dog, cat and rodent, in an immunocompromised state or immunosuppressed state or at risk for becoming immunocompromised or immunosuppressed. In certain embodiments, a Therapeutic Agent(s), a composition(s) comprising a Therapeutic Agent(s), or a combination therapy(ies) is administered to a subject receiving or recovering from immunosuppressive therapy. In certain embodiments, a Therapeutic Agent(s), a composition(s) comprising a Therapeutic Agent(s), or a combination therapy(ies) is administered to a subject that has or is at risk of getting cancer, AIDS, another infection, or a bacterial infection. In specific embodiments, a Therapeutic Agent(s), a composition(s) comprising a Therapeutic Agent(s), or a combination therapy(ies) is administered to a subject that is HIV positive as assessed by techniques known to one skilled in the art. In certain embodiments, a subject that is, will or has undergone surgery, chemotherapy and/or radiation therapy. In certain embodiments, a Therapeutic Agent(s), a composition(s) comprising a Therapeutic Agent(s), or a combination therapy(ies) is administered to a subject that has cystic fibrosis, pulmonary fibrosis, or another disease which makes the subject susceptible to an infection. In certain embodiments, a Therapeutic Agent(s), a composition(s) comprising a Therapeutic Agent(s), or a combination therapy(ies) is administered to a subject that has, will have or had a tissue transplant. In some embodiments, a Therapeutic Agent(s), a composition(s) comprising a Therapeutic Agent(s), or a combination therapy(ies) is administered to a subject that lives in a nursing home, a group home (i.e., a home for 10 or more subjects), or a prison. In some embodiments, a Therapeutic Agent(s), a composition(s) comprising a Therapeutic Agent(s), or a combination therapy(ies) is administered to a subject that attends school (e.g., elementary school, middle school, junior high school, high school or university) or daycare. In some embodiments, a Therapeutic Agent(s), a composition(s) comprising a Therapeutic Agent(s), or a combination therapy(ies) is administered to a subject that works in the healthcare area, such as a doctor or a nurse, or in a hospital. In certain embodiments, a Therapeutic Agent(s), a composition(s) comprising a Therapeutic Agent(s), or a combination therapy(ies) is administered to a subject that is pregnant or will become pregnant.

In some embodiments, a patient is administered a Therapeutic Agent(s), a composition(s) comprising a Therapeutic Agent(s), or a combination therapy(ies) before any adverse effects or intolerance to therapies other than Therapeutic Agents develops. In some embodiments, a Therapeutic Agent(s), a composition(s) comprising a Therapeutic Agent(s), or a combination therapy(ies) is administered to refractory patients. In a certain embodiment, refractory patient is a patient refractory to a standard therapy. In certain embodiments, a patient with an infection is refractory to a therapy when the infection has not significantly been eradicated and/or the symptoms have not been significantly alleviated. The determination of whether a patient is refractory can be made either in vivo or in vitro by any method known in the art for assaying the effectiveness of a treatment of infections, using art-accepted meanings of "refractory" in such a context. In various embodiments, a patient with an infection is refractory when replication of the infectious agent has not decreased or has increased.

In some embodiments, a Therapeutic Agent(s), a composition(s) comprising a Therapeutic Agent(s), or a combination therapy(ies) is administered to a patient to prevent the onset or reoccurrence of infections (e.g., viral infections) in a patient at risk of developing such infections. In some embodiments, a Therapeutic Agent(s), a composition(s) comprising a Therapeutic Agent(s), or a combination therapy(ies) is administered to a patient who is susceptible to adverse reactions to conventional therapies.

In some embodiments, one or more Therapeutic Agents, compositions comprising Therapeutic Agents, or combination therapies are administered to a patient who has proven refractory to therapies other than Therapeutic Agents, but are no longer on these therapies. In certain embodiments, the patients being managed or treated in accordance with the methods of this invention are patients already being treated with antibiotics, anti-virals, anti-fungals, or other biological therapy/immunotherapy. Among these patients are refractory patients, patients who are too young for conventional therapies, and patients with reoccurring viral infections despite management or treatment with existing therapies.

In some embodiments, the subject being administered one or more Therapeutic Agents, compositions comprising Therapeutic Agents, or combination therapies has not received a therapy prior to the administration of the Therapeutic Agents, compositions comprising Therapeutic Agents, or combination therapies. In other embodiments, one or more Therapeutic Agents, compositions comprising Therapeutic Agents, or combination therapies are administered to a subject who has received a therapy prior to administration of one or more Therapeutic Agents or compositions comprising one or more Therapeutic Agents, or combination therapies. In some embodiments, the subject administered a Therapeutic Agent or a composition comprising a Therapeutic Agent was refractory to a prior therapy or experienced adverse side effects to the prior therapy or the prior therapy was discontinued due to unacceptable levels of toxicity to the subject.

5.8 Immunodeficiencies & Lymhopenia

Provided herein are methods for treating, preventing and/or managing an immunodeficiency or lymphopenia in a dose escalation regimen, comprising administering an effective amount of a Therapeutic Agent or a composition comprising a Therapeutic Agent to a subject in need thereof. In a specific embodiment, the methods described herein do not involve a cyclical administration regimen of the Therapeutic Agent.

In other embodiments, a Therapeutic Agent can be administered in combination with one or more other therapies. Non-limiting examples of other therapies that can be used in combination with Therapeutic Agents are described herein. See Section 5.9, infra. In one embodiment, the combination of a Therapeutic Agent and one or more other therapies provides an additive therapeutic effect relative to the therapeutic effects of the Therapeutic Agent alone or the one or more other therapies alone. In one embodiment, the combination of a Therapeutic Agent and one or more other therapies provides more than an additive therapeutic effect relative to the therapeutic effects of the Therapeutic Agent alone or the one or more other therapies alone. In one embodiment, the combination of a Therapeutic Agent and one or more other therapies provides a synergistic therapeutic effect relative to the therapeutic effects of the Therapeutic Agent alone or the one or more other therapies alone.

In certain embodiments, a Therapeutic Agent, a composition comprising a Therapeutic Agent, or a combination therapy is administered to a mammal which is 0 to 6 months old, 6 to 12 months old, 1 to 5 years old, 5 to 10 years old, 10 to 15 years old, 15 to 20 years old, 20 to 25 years old, 25 to 30 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100 years old. In certain embodiments, the patient is a human 0 to 6 months old, 6 to 12 months old, 1 to 5 years old, 5 to 10 years old, 5 to 12 years old, 10 to 15 years old, 15 to 20 years old, 13 to 19 years old, 20 to 25 years old, 25 to 30 years old, 20 to 65 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100 years old. In some embodiments, a Therapeutic Agent, a composition comprising a Therapeutic Agent, or a combination therapy is administered to a human infant or premature human infant. In other embodiments, a Therapeutic Agent, composition comprising a Therapeutic Agent, or a combination therapy is administered to a human child. In other embodiments, a Therapeutic Agent, composition comprising a Therapeutic Agent, or a combination therapy is administered to a human adult. In yet other embodiments, a Therapeutic Agent, a composition comprising a Therapeutic Agent, or a combination therapy is administered to an elderly human.

In certain embodiments, a Therapeutic Agent, a composition comprising a Therapeutic Agent, or a combination therapy is administered to a pet, e.g., a dog or cat. In certain embodiments, a Therapeutic Agent, a composition comprising a Therapeutic Agent, or a combination therapy is administered to a farm animal or livestock, e.g., pig, cows, horses, chickens, etc. In certain embodiments, a Therapeutic Agent, a composition comprising a Therapeutic Agent, or a combination therapy is administered to a bird, e.g., ducks or chicken.

In certain embodiments, a Therapeutic Agent, a composition comprising a Therapeutic Agent, or a combination therapy is administered to a primate, preferably a human, or another mammal, such as a pig, cow, horse, sheep, goat, dog, cat and rodent, in an immunocompromised state or immunosuppressed state or at risk for becoming immunocompromised or immunosuppressed. In certain embodiments, a Therapeutic Agent, a composition comprising a Therapeutic Agent, or a combination therapy is administered to a primate, preferably a human, or another mammal, such as a pig, cow, horse, sheep, goat, dog, cat and rodent, with an immunodeficiency. In certain embodiments, a Therapeutic Agent, a composition comprising a Therapeutic Agent, or a combination therapy is administered to a subject receiving or recovering from immunosuppressive therapy. In certain embodiments, a Therapeutic Agent, a composition comprising a Therapeutic Agent, or a combination therapy is administered to a subject that has or is at risk of getting cancer, AIDS, another infection, or a bacterial infection. In certain embodiments, a subject that is, will or has undergone surgery, chemotherapy and/or radiation therapy. In certain embodiments, a Therapeutic Agent, a composition comprising a Therapeutic Agent, or a combination therapy is administered to a subject that has, will have or had a tissue transplant. In some embodiments, a Therapeutic Agent, a composition comprising a Therapeutic Agent, or a combination therapy is administered to a subject that lives in a nursing home, a group home (i.e., a home for 10 or more subjects), or a prison. In some embodiments, a Therapeutic Agent, a composition comprising a Therapeutic Agent, or a combination therapy is administered to a subject that attends school (e.g., elementary school, middle school, junior high school, high school or university) or daycare. In some embodiments, a Therapeutic Agent, a composition comprising a Therapeutic Agent, or a combination therapy is administered to a subject that works in the healthcare area, such as a doctor or a nurse, or in a hospital. In certain embodiments, a Therapeutic Agent, a composition comprising a Therapeutic Agent, or a combination therapy is administered to a subject that is pregnant or will become pregnant.

In certain embodiments, a Therapeutic Agent, a composition comprising a Therapeutic Agent, or a combination therapy is administered to a subject that has been diagnosed as lymphopenic. The terms "lymphopenia" or "lymphocytopenia" or "lymphocytic leucopenia" interchangeably refer to an abnormally small number of lymphocytes in the circulating blood or in peripheral circulation. Quantitatively, lymphopenia can be described by various cutoffs. In some embodiments, a patient is suffering from lymphopenia when their circulating blood total lymphocyte count falls below about $600/mm^3$. In some embodiments, a patient suffering from lymphopenia has less than about 2000/μL total circulating lymphocytes at birth, less than about 4500/μL total circulating lymphocytes at about age 9 months, or less than about 1000/μL total circulating lymphocytes patients older than about 9 months.

Lymphocytopenia has a wide range of possible causes, including viral (e.g., HIV or hepatitis infection), bacterial (e.g., active tuberculosis infection), and fungal infections; chronic failure of the right ventricle of the heart, Hodgkin's disease and cancers of the lymphatic system, leukemia, a leak or rupture in the thoracic duct, side effects of prescription medications including anticancer agents, antiviral agents, and glucocorticoids, malnutrition resulting from diets that are low in protein, radiation therapy, uremia, autoimmune disorders, immune deficiency syndromes, high stress levels, and trauma. Lymphopenia may also be of unknown etiology (i.e., idiopathic lymphopenia). Peripheral circulation of all types of lymphocytes or subpopulations of lymphocytes (e.g., $CD4^+$ T cells) may be depleted or abnormally low in a patient suffering from lymphopenia. See, e.g., *Lymphopenia Description*, The Merck Manual ($18^{th}$ Edition, 2006, Merck & Co.).

In some embodiments, a patient is administered a Therapeutic Agent, a composition comprising a Therapeutic Agent, or a combination therapy before any adverse effects or intolerance to therapies other than Therapeutic Agents develops. In some embodiments, Therapeutic Agents, compositions comprising Therapeutic Agents or combination therapies are administered to refractory patients. In a certain embodiment, refractory patient is a patient refractory to a standard therapy.

In some embodiments, Therapeutic Agents, compositions comprising Therapeutic Agents, or combination therapies are administered to a patient to prevent the onset or reoccurrence of an immunodeficiency or lymphopenia in a patient at risk of developing such infections. In some embodiments, Therapeutic Agents, compositions comprising Therapeutic Agents, or combination therapies are administered to a patient who is susceptible to adverse reactions to conventional therapies. In some embodiments, one or more Therapeutic Agents, compositions comprising Therapeutic Agents, or combination therapies are administered to a patient who has proven refractory to therapies other than Therapeutic Agents, but are no longer on these therapies.

In some embodiments, the subject being administered one or more Therapeutic Agents, compositions comprising Therapeutic Agents, or combination therapies has not received a therapy prior to the administration of the Therapeutic Agents, compositions comprising Therapeutic Agents, or combination therapies. In other embodiments, one or more Therapeutic Agents, compositions comprising Therapeutic Agents, or combination therapies are administered to a subject who has received a therapy prior to administration of one or more Therapeutic Agents, compositions comprising Therapeutic Agents, or combination therapies. In some embodiments, the subject administered a Therapeutic Agent or a composition comprising a Therapeutic Agent was refractory to a prior therapy or experienced adverse side effects to the prior therapy or the prior therapy was discontinued due to unacceptable levels of toxicity to the subject.

5.9 Additional/Combination Therapy

Other therapies that can be used in combination with a Therapeutic Agent(s) for the prevention, treatment and/or management of a disease that is affected by IL-15 function/signaling, e.g., cancer, infectious disease, lymphopenia, immunodeficiency and wounds, or the eradication or reduction of HIV in an HIV-infected subject include, but are not limited to, small molecules, synthetic drugs, peptides (including cyclic peptides), polypeptides, proteins, nucleic acids (e.g., DNA and RNA nucleotides including, but not limited to, antisense nucleotide sequences, triple helices, RNAi, and nucleotide sequences encoding biologically active proteins, polypeptides or peptides), antibodies, synthetic or natural inorganic molecules, mimetic agents, and synthetic or natural organic molecules. Specific examples of such therapies include, but are not limited to, immunomodulatory agents (e.g., interferon), anti-inflammatory agents (e.g., adrenocorticoids, corticosteroids (e.g., beclomethasone, budesonide, flunisolide, fluticasone, triamcinolone, methylprednisolone, prednisolone, prednisone, hydrocortisone), glucocorticoids, steriods, and non-steriodal anti-inflammatory drugs (e.g., aspirin, ibuprofen, diclofenac, and COX-2 inhibitors), pain relievers, leukotreine antagonists (e.g., montelukast, methyl xanthines, zafirlukast, and zileuton), beta2-agonists (e.g., albuterol, biterol, fenoterol, isoetharie, metaproterenol, pirbuterol, salbutamol, terbutalin formoterol, salmeterol, and salbutamol terbutaline), anticholinergic agents (e.g., ipratropium bromide and oxitropium bromide), sulphasalazine, penicillamine, dapsone, antihistamines, anti-malarial agents (e.g., hydroxychloroquine), anti-viral agents (e.g., nucleoside analogs (e.g., zidovudine, acyclovir, gangcyclovir, vidarabine, idoxuridine, trifluridine, and ribavirin), foscarnet, amantadine, rimantadine, saquinavir, indinavir, ritonavir, and AZT) and antibiotics (e.g., dactinomycin (formerly actinomycin), bleomycin, erythomycin, penicillin, mithramycin, and anthramycin (AMC)).

Any therapy which is known to be useful, or which has been used or is currently being used for the prevention, management, and/or treatment of a disease that is affected by IL-15 function/signaling can be used in combination with a Therapeutic Agent(s). See, e.g., Gilman et al., Goodman and Gilman's: The Pharmacological Basis of Therapeutics, 10th ed., McGraw-Hill, New York, 2001; The Merck Manual of Diagnosis and Therapy, Berkow, M. D. et al. (eds.), 17th Ed., Merck Sharp & Dohme Research Laboratories, Rahway, N J, 1999; Cecil Textbook of Medicine, 20th Ed., Bennett and Plum (eds.), W.B. Saunders, Philadelphia, 1996, and Physicians' Desk Reference (66th ed. 2012) for information regarding therapies (e.g., prophylactic or therapeutic agents) which have been or are currently being used for preventing, treating and/or managing disease or disorder that is affected by IL-15 function/signaling, e.g., cancer, infectious disease, lymphopenia, immunodeficiency and wounds, or eradicating or reducing HIV in HIV-infected subjects.

5.9.1 Anti-Cancer Agents

Non-limiting examples of one or more other therapies that can be used in combination with a Therapeutic Agent(s) include immunomodulatory agents, such as but not limited to, chemotherapeutic agents and non-chemotherapeutic immunomodulatory agents. Non-limiting examples of chemotherapeutic agents include methotrexate, cyclosporin A, leflunomide, cisplatin, ifosfamide, taxanes such as taxol and paclitaxol, topoisomerase I inhibitors (e.g., CPT-11, topotecan, 9-AC, and GG-211), gemcitabine, vinorelbine, oxaliplatin, 5-fluorouracil (5-FU), leucovorin, vinorelbine, temodal, cytochalasin B, gramicidin D, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin homologs, and cytoxan. Examples of non-chemotherapeutic immunomodulatory agents include, but are not limited to, anti-T cell receptor antibodies (e.g., anti-CD4 antibodies (e.g., cM-T412 (Boeringer), IDEC-CE9.1® (IDEC and SKB), mAB 4162W94, Orthoclone and OKTcdr4a (Janssen-Cilag)), anti-CD3 antibodies (e.g., Nuvion (Product Design Labs) or OKT3 (Johnson & Johnson)), anti-CD20 antibodies (e.g., Rituxan (IDEC)), anti-CD5 antibodies (e.g., an anti-CD5 ricin-linked immunoconjugate), anti-CD7 antibodies (e.g., CHH-380 (Novartis)), anti-CD8 antibodies, anti-CD40 ligand monoclonal antibodies (e.g., IDEC-131 (IDEC)), anti-CD52 antibodies (e.g., CAMPATH 1H (Ilex)), anti-CD2 antibodies (e.g., MEDI-507 (MedImmune, Inc., International Publication Nos. WO 02/098370 and WO 02/069904), anti-CD11a antibodies (e.g., Xanelim (Genentech)), and anti-B7 antibodies (e.g., IDEC-114) (IDEC)); anti-cytokine receptor antibodies (e.g., anti-IFN receptor antibodies, anti-IL-2 receptor antibodies (e.g., Zenapax (Protein Design Labs)), anti-IL-4 receptor antibodies, anti-IL-6 receptor antibodies, anti-IL-10 receptor antibodies, and anti-IL-12 receptor antibodies), anti-cytokine antibodies (e.g., anti-IFN antibodies, anti-TNF-α antibodies, anti-IL-10 antibodies, anti-IL-6 antibodies, anti-IL-8 antibodies (e.g., ABX-IL-8 (Abgenix)), anti-IL-12 antibodies and anti-IL-23 antibodies)); CTLA4-immunoglobulin; LFA-3TIP (Biogen, International Publication No. WO 93/08656 and U.S. Pat. No. 6,162,432); soluble cytokine receptors (e.g., the extracellular domain of a TNF-α receptor or a fragment thereof, the extracellular domain of an IL-1β receptor or a fragment thereof, and the extracellular domain of an IL-6 receptor or a fragment thereof); cytokines or fragments thereof (e.g., interleukin (IL)-2, IL-3, IL-4, IL-5, IL-6, IL-7, IL-8, IL-9, IL-10, IL-11, IL-12, IL-15, IL-23, TNF-α, TNF-β, interferon (IFN)-α, IFN-β, IFN-γ, and GM-CSF); and anti-cytokine antibodies (e.g., anti-IL-2 antibodies, anti-IL-4 antibodies, anti-IL-6 antibodies, anti-IL-10 antibodies, anti-IL-12 antibodies, anti-IL-15 antibodies, anti-TNF-α antibodies, and anti-IFN-γ antibodies), and antibodies that immunospecifically bind to tumor-associated antigens (e.g., Herceptin®). In certain embodiments, an immunomodulatory agent is an immunomodulatory agent other than a chemotherapeutic agent. In other embodiments an immunomodulatory agent is an immunomodulatory agent other than a cytokine or hemapoietic such as IL-1, IL-2, IL-4, IL-12, IL-15, TNF, IFN-α, IFN-β, IFN-γ, M-CSF, G-CSF, IL-3 or erythropoietin. In yet other embodiments, an immunomodulatory agent is an agent other than a chemotherapeutic agent and a cytokine or hemapoietic factor.

Non-limiting examples of anti-cancer agents that can be used as therapies in combination with a Therapeutic Agent(s) include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alpha-2a; interferon alpha-2b; interferon alpha-n1; interferon alpha-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide;

cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; daclix-imab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; HMG-CoA reductase inhibitor (such as but not limited to, Lovastatin, Pravastatin, Fluvastatin, Statin, Simvastatin, and Atorvastatin); loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; Vitaxin®; vorozole; zanoterone; zeniplatin; zilascorb; and zinostatin stimalamer. Additional anti-cancer drugs are 5-fluorouracil and leucovorin. These two agents are particularly useful when used in methods employing thalidomide and a topoisomerase inhibitor. In specific embodiments, a anti-cancer agent is not a chemotherapeutic agent.

5.9.2 Antiviral Agents

Antiviral agents that can be used in combination with a Therapeutic Agent(s) include, but are not limited to, non-nucleoside reverse transcriptase inhibitors, nucleoside reverse transcriptase inhibitors, protease inhibitors, and fusion inhibitors. In one embodiment, the antiviral agent is selected from the group consisting of amantadine, oseltamivir phosphate, rimantadine, and zanamivir. In another embodiment, the antiviral agent is a non-nucleoside reverse transcriptase inhibitor selected from the group consisting of delavirdine, efavirenz, and nevirapine. In another embodiment, the antiviral agent is a nucleoside reverse transcriptase inhibitor selected from the group consisting of abacavir, didanosine, emtricitabine, emtricitabine, lamivudine, stavudine, tenofovir DF, zalcitabine, and zidovudine. In another embodiment, the antiviral agent is a protease inhibitor selected from the group consisting of amprenavir, atazanavir, fosamprenav, indinavir, lopinavir, nelfinavir, ritonavir, and saquinavir. In another embodiment, the antiviral agent is a fusion inhibitor such as enfuvirtide.

Additional, non-limiting examples of antiviral agents for use in combination with a Therapeutic Agent(s) include the following: rifampicin, nucleoside reverse transcriptase inhibitors (e.g., AZT, ddI, ddC, 3TC, d4T), non-nucleoside reverse transcriptase inhibitors (e.g., delavirdine efavirenz, nevirapine), protease inhibitors (e.g., aprenavir, indinavir, ritonavir, and saquinavir), idoxuridine, cidofovir, acyclovir, ganciclovir, zanamivir, amantadine, and palivizumab. Other examples of anti-viral agents include but are not limited to acemannan; acyclovir; acyclovir sodium; adefovir; alovudine; alvircept sudotox; amantadine hydrochloride (SYMMETREL™); aranotin; arildone; atevirdine mesylate; avridine; cidofovir; cipamfylline; cytarabine hydrochloride; delavirdine mesylate; desciclovir; didanosine; disoxaril; edoxudine; enviradene; enviroxime; famciclovir; famotine hydrochloride; fiacitabine; fialuridine; fosarilate; foscamet sodium; fosfonet sodium; ganciclovir; ganciclovir sodium; idoxuridine; kethoxal; lamivudine; lobucavir; memotine hydrochloride; methisazone; nevirapine; oseltamivir phosphate (TAMIFLU™); penciclovir; pirodavir; ribavirin; rimantadine hydrochloride (FLUMADINE™); saquinavir mesylate; somantadine hydrochloride; sorivudine; statolon; stavudine; tilorone hydrochloride; trifluridine; valacyclovir hydrochloride; vidarabine; vidarabine phosphate; vidarabine sodium phosphate; viroxime; zalcitabine; zanamivir (RELENZA™); zidovudine; and zinviroxime.

5.9.3 Antibacterial Agents

Antibacterial agents, including antibiotics, that can be used in combination with a Therapeutic Agent(s) include, but are not limited to, aminoglycoside antibiotics, glycopeptides, amphenicol antibiotics, ansamycin antibiotics, cephalosporins, cephamycins oxazolidinones, penicillins, quinolones, streptogamins, tetracycline, and analogs thereof. In some embodiments, antibiotics are administered in combination with a Therapeutic Agent to prevent, treat and/or manage a bacterial infection.

In a specific embodiment, a Therapeutic Agent(s) are used in combination with other protein synthesis inhibitors, including but not limited to, streptomycin, neomycin, erythromycin, carbomycin, and spiramycin.

In one embodiment, the antibacterial agent is selected from the group consisting of ampicillin, amoxicillin, ciprofloxacin, gentamycin, kanamycin, neomycin, penicillin G, streptomycin, sulfanilamide, and vancomycin. In another embodiment, the antibacterial agent is selected from the group consisting of azithromycin, cefonicid, cefotetan, cephalothin, cephamycin, chlortetracycline, clarithromycin, clindamycin, cycloserine, dalfopristin, doxycycline, erythromycin, linezolid, mupirocin, oxytetracycline, quinupristin, rifampin, spectinomycin, and trimethoprim.

Additional, non-limiting examples of antibacterial agents for use in combination with a Therapeutic Agent(s) include the following: aminoglycoside antibiotics (e.g., apramycin, arbekacin, bambermycins, butirosin, dibekacin, neomycin, neomycin, undecylenate, netilmicin, paromomycin, ribostamycin, sisomicin, and spectinomycin), amphenicol antibiotics (e.g., azidamfenicol, chloramphenicol, florfenicol, and thiamphenicol), ansamycin antibiotics (e.g., rifamide and rifampin), carbacephems (e.g., loracarbef), carbapenems (e.g., biapenem and imipenem), cephalosporins (e.g., cefaclor, cefadroxil, cefamandole, cefatrizine, cefazedone, cefozopran, cefpimizole, cefpiramide, and cefpirome), cephamycins (e.g., cefbuperazone, cefmetazole, and cefminox), folic acid analogs (e.g., trimethoprim), glycopeptides (e.g., vancomycin), lincosamides (e.g., clindamycin, and lincomycin), macrolides (e.g., azithromycin, carbomycin, clarithomycin, dirithromycin, erythromycin, and erythromycin acistrate), monobactams (e.g., aztreonam, carumonam, and tigemonam), nitrofurans (e.g., furaltadone, and furazolium chloride), oxacephems (e.g., flomoxef, and moxalactam), oxazolidinones (e.g., linezolid), penicillins (e.g., amdinocillin, amdinocillin pivoxil, amoxicillin, bacampicillin, benzylpenicillinic acid, benzylpenicillin sodium, epicillin, fenbenicillin, floxacillin, penamccillin, penethamate hydriodide, penicillin o benethamine, penicillin 0, penicillin V, penicillin V benzathine, penicillin V hydrabamine, penimepicycline, and phencihicillin potassium), quinolones and analogs thereof (e.g., cinoxacin, ciprofloxacin, clinafloxacin, flumequine, grepagloxacin, levofloxacin, and moxifloxacin), streptogramins (e.g., quinupristin and dalfopristin), sulfonamides (e.g., acetyl sulfamethoxypyrazine, benzylsulfamide, noprylsulfamide, phthalylsulfacetamide, sulfachrysoidine, and sulfacytine), sulfones (e.g., diathymosulfone, glucosulfone sodium, and solasulfone), and tetracyclines (e.g., apicycline, chlortetracycline, clomocycline, and demeclocycline). Additional examples include cycloserine, mupirocin, tuberin amphomycin, bacitracin, capreomycin, colistin, enduracidin, enviomycin, and 2,4 diaminopyrimidines (e.g., brodimoprim).

5.10 Biological Activity 5.10.1 Assays for Testing the Function of the Therapeutic Agent Provided herein are methods to identify agents that modulate the activity of IL-15/IL-15Rα complexes. The activity of a Therapeutic Agent can be assayed with an IL-15 sensitive cell line, e.g., CTLL-2 cells, a mouse cytotoxic T lymphoma cell line (ATCC Accession No. TIB-214) or TF1-β cells. See, e.g., International Publication No. WO 05/085282. In a specific embodiment, the activity of a Therapeutic Agent can be assessed utilizing the assay described in Example 4, infra.

To assess the activity of Therapeutic Agents, proliferation of CTLL-2 or TF1-β cells cultured in the presence or absence of one or more Therapeutic Agents can be assessed by $^{3}$H-thymidine incorporation assays well known in the art and described in International Publication No. WO 05/085282.

In one aspect, the Therapeutic Agent increases an immune response that can be, e.g., an antibody response (humoral response) or a cellular immune response, e.g., cytokine secretion (e.g., interferon-gamma), helper activity or cellular cytotoxicity. In one embodiment, the increased immune response is increased cytokine secretion, antibody production, effector function, T cell proliferation, and/or NK cell proliferation. Various assays to measure such activities are well known in the art, and exemplary descriptions of such assays are provided below.

For example, enzyme-linked immunosorbent assays (ELISA) are well known in the art and are described, e.g., in Section 2.1 of Current Protocols in Immunology, Coligan et al. (eds.), John Wiley and Sons, Inc. 1997. ELISA can be used, e.g., to assay the amount or concentration of IL-15 or IL-15Rα polypeptide.

In another method, the "tetramer staining" assay (Altman et al., 1996, Science 274: 94-96) may be used to identify antigen-specific T-cells and to assess how Therapeutic Agents modulate (e.g., enhance or suppress) antigen-specific T cell responses. For example, an MHC molecule containing a specific peptide antigen, such as a tumor-specific antigen, is multimerized to make soluble peptide tetramers and labeled, for example, by complexing to streptavidin. The MHC-peptide antigen complex is then mixed with a population of T cells obtained from a subject administered with an immunogenic composition alone or in combination with a Therapeutic Agent. Biotin is then used to stain T cells expressing the tumor-specific antigen of interest.

Furthermore, using the mixed lymphocyte target culture assay, the cytotoxicity of T cells can be tested in a $^{51}Cr$-release assay as described, e.g., in Palladino et al., 1987, Cancer Res. 47:5074-5079. Briefly, the mixed lymphocyte culture is added to a target cell suspension to give different effector:target (E:T) ratios (usually 1:1 to 40:1). The target cells are pre-labeled by incubating $1\times10^6$ target cells in culture medium containing 500 μCi of $^{51}Cr$ per ml for one hour at 37° C. The cells are washed three times following labeling. Each assay point (E:T ratio) is performed in triplicate and the appropriate controls incorporated to measure spontaneous $^{51}Cr$ release (no lymphocytes added to assay) and 100% release (cells lysed with detergent). After incubating the cell mixtures for 4 hours, the cells are pelleted by centrifugation at 200 g for 5 minutes. The amount of $^{51}Cr$ released into the supernatant is measured by a gamma counter. The percent cytotoxicity is measured as cpm in the test sample minus spontaneously released cpm divided by the total detergent released cpm minus spontaneously released cpm.

In another embodiment, an ELISPOT assay can be used to measure cytokine release in vitro by T cells after administration of an effective amount of a Therapeutic Agent to a subject. Cytokine release is detected by antibodies which are specific for a particular cytokine, e.g., interleukin-2, tumor necrosis factor γ or interferon-γ (see, e.g., Scheibenbogen et al., 1997, Int. J. Cancer 71:932-936). The assay is carried out in a microtitre plate which has been pre-coated with an antibody specific for a cytokine of interest which captures the cytokine secreted by T cells. After incubation of T cells for 24-48 hours in the coated wells, the T cells are removed and replaced with a second labeled antibody that recognizes a different epitope on the cytokine. After extensive washing to remove unbound antibody, an enzyme substrate, which produces a colored reaction product is added to the plate. The number of cytokine-producing cells is counted under a microscope. This method has the advantages of short assay time, and sensitivity without the need of a large number of cytotoxic T cells.

In some aspects, the immune response induced or enhanced by a Therapeutic Agent is enhanced or increased by at least 2 fold, 3 fold, 4 fold, 5 fold, 6 fold, 7 fold, 8 fold, 9 fold, 10 fold, 11 fold, or 12 fold relative to an immune response elicited by a negative control as determined by any known assay in the art. In certain embodiments, the immune response induced by the Therapeutic Agent is enhanced by at least 0.5-2 times, at least 2-5 times, at least 5-10 times, at least 10-50 times, at least 50-100 times, at least 100-200 times, at least 200-300 times, at least 300-400 times or at least 400-500 times relative to the immune response induced by a negative control as assayed by any known method in the art. In specific embodiments, the assay used to assess immune response measures the level of antibody production, cytokine production, or cellular cytoxicity, and such assays are well known in the art. In some embodiments, the assay used to measure the immune response is an enzyme-linked immunosorbent assay (ELISA) that determines antibody or cytokine levels, an ELISPOT assay that determines cytokine release, or a $^{51}Cr$ release assay that determines cellular cytotoxicity.

In specific embodiments, the Therapeutic Agent induces or enhances an immune response in a subject that is measured by antibody titer in the serum of the subject, and the antibody titer is at least 0.2 to 5 times, 5 to 20 times, 10 to 30 times, 20 to 50 times, 50 to 200 times, 100 to 500, 200 to 1000 times, or 500 to 2,000 times higher as compared to the antibody titer in the serum of a subject administered a negative control. In specific embodiments, the mean serum antibody titer against an antigen in the subject administered the Therapeutic Agent is increased by at least 0.5-2 times, at least 2-5 times, at least 5-10 times, at least 10-50 times, at least 50-100 times, at least 100-200 times, at least 200-300 times, at least 300-400 times or at least 400-500 times relative to the mean serum antibody titer in the subject administered a negative control as determined by methods well known in the art.

In another specific embodiment, provided herein are methods of administering Therapeutic Agents to induce or enhance the level of cytokine production or secretion, e.g., interferon-γ, (that may be 0.5 to 500 times higher) as compared to the level of cytokine production or secretion in a negative control sample. In specific embodiments, the Therapeutic Agent induces or enhances an immune response that is measured by increased cytokine release, and the cytokine concentration is at least 0.2 to 5 times, 5 to 20 times, 10 to 30 times, 20 to 50 times, 50 to 200 times, 100 to 500, 200 to 1000 times, or 500 to 2,000 times higher as compared to the cytokine concentration of a negative control. In specific embodiments, the mean serum cytokine concentration of samples obtained from a subject administered the Therapeutic Agent is increased by at least 0.5-2 times, at least 2-5 times, at least 5-10 times, at least 10-50 times, at least 50-100 times, at least 100-200 times, at least 200-300 times, at least 300-400 times or at least 400-500 times relative to the mean serum cytokine concentration of samples obtained from a subject administered a negative control as determined by methods well known in the art. In some embodiments, the negative control can be samples from the subject prior to administration of the Therapeutic Agent.

In specific embodiments, the Therapeutic Agent induces or enhances NK cell proliferation in a subject that by at least 0.2 to 5 times, 5 to 20 times, 10 to 30 times, 20 to 50 times, 50 to 200 times, 100 to 500, 200 to 1000 times, or 500 to 2,000 times higher relative to NK cell proliferation in a negative control. In specific embodiments, the Therapeutic Agent induces or enhances T cell proliferation in a subject that by at least 0.2 to 5 times, 5 to 20 times, 10 to 30 times, 20 to 50 times, 50 to 200 times, 100 to 500, 200 to 1000 times, or 500 to 2,000 times higher relative to T cell proliferation in a negative control as determined by methods well known in the art, e.g., flow cytometry, CSFE staining, $^{3}H$-thymidine incorporation.

The increase in antibody (humoral) or cellular immune response induced by an effective amount of the Therapeutic Agent can be assessed using various methods well known in the art.

5.10.2 Animal Models

Therapeutic Agents are preferably assayed in vivo for the desired therapeutic or prophylactic activity prior to use in humans. For example, in one embodiment, a Therapeutic Agent can be administered to the animal at the same time as the onset of a disease or disorder in the animal. In another embodiment, a Therapeutic Agent can be administered to the animal prior to the onset of a disease or disorder in the animal. In another embodiment, a Therapeutic Agent can be administered to the animal subsequent to the onset of a disease or disorder in the animal. In a specific embodiment, the Therapeutic Agent is administered to the animal more than one time. In another specific embodiment, the Therapeutic Agent is administered in combination with another therapy.

Therapeutic Agents can be tested in animal models systems including, but are not limited to, rats, mice, chicken, cows, monkeys, pigs, goats, sheep, dogs, rabbits, guinea pigs, etc. In a specific embodiment, Therapeutic Agents are tested in a mouse model system. Such model systems are widely used and well-known to the skilled artisan.

The anti-cancer activity of a Therapeutic Agent can be determined by using various experimental animal models for the study of cancer well known in the art as described in, e.g., Relevance of Tumor Models for Anticancer Drug Development (1999, eds. Fiebig and Burger); Contributions to Oncology (1999, Karger); The Nude Mouse in Oncology Research (1991, eds. Boven and Winograd); and Anticancer Drug Development Guide (1997 ed. Teicher), incorporated herein by reference in their entireties.

Animal models for cancer can be used to assess the efficacy of a Therapeutic Agent or a composition thereof. Non-limiting examples of animal models for lung cancer include, but are not limited to, lung cancer animal models described by Zhang & Roth (1994, In vivo 8(5):755-69) and a transgenic mouse model with disrupted p53 function (see, e.g., Morris et al., 1998, J La State Med Soc 150(4):179-85). An example of an animal model for breast cancer includes, but is not limited to, a transgenic mouse that overexpresses cyclin D1 (see, e.g., Hosokawa et al., 2001, Transgenic Res 10(5):471-8). An example of an animal model for colon cancer includes, but is not limited to, a TCR-β and p53 double knockout mouse (see, e.g., Kado et al., 2001, Cancer Res 61(6):2395-8). Examples of animal models for pancreatic cancer include, but are not limited to, a metastatic model of Panc02 murine pancreatic adenocarcinoma (see, e.g., Wang et al., 2001, Int J Pancreatol 29(1):37-46) and nu-nu mice generated in subcutaneous pancreatic tumours (see, e.g., Ghaneh et al., 2001, Gene Ther 8(3):199-208). Examples of animal models for non-Hodgkin's lymphoma include, but are not limited to, a severe combined immunodeficiency ("SCID") mouse (see, e.g., Bryant et al., 2000, Lab Invest 80(4):553-73) and an IgHmu-HOX11 transgenic mouse (see, e.g., Hough et al., 1998, Proc Natl Acad Sci USA 95(23):13853-8). An example of an animal model for esophageal cancer includes, but is not limited to, a mouse transgenic for the human papillomavirus type 16 E7 oncogene (see, e.g., Herber et al., 1996, J Virol 70(3):1873-81). Examples of animal models for colorectal carcinomas include, but are not limited to, Apc mouse models (see, e.g., Fodde & Smits, 2001, Trends Mol Med 7(8):369-73 and Kuraguchi et al., 2000, Oncogene 19(50):5755-63).

For animal models of infectious diseases, the effectiveness of a Therapeutic Agent relative to a negative control can be assessed in animals infected with virus. Samples obtained from these animals (e.g., serum, urine, sputum, semen, saliva, plasma, or tissue sample) can be tested for enhancement of immune function, e.g., enhancement in cytokine release, enhancement in antibody production, T cell proliferation, NK cell proliferation, with methods well known in the art and described herein. Samples obtained from these animals (e.g., serum, urine, sputum, semen, saliva, plasma, or tissue sample) can also be tested for reduction in viral replication via well known methods in the art, e.g., those that measure altered viral replication (as determined, e.g., by plaque formation) or the production of viral proteins (as determined, e.g., by Western blot, ELISA, or flow cytometry analysis) or viral nucleic acids (as determined, e.g., by RT-PCR, northern blot analysis or southern blot). For quantitation of virus in tissue samples, tissue samples are homogenized in phosphate-buffered saline (PBS), and dilutions of clarified homogenates are adsorbed for 1 hour at 37° C. onto monolayers of cells (e.g., Vero, CEF or MDCK cells). In other assays, histopathologic evaluations are performed after infection, preferably evaluations of the organ(s) the virus is known to target for infection. Virus immunohistochemistry can be performed using a viral-specific monoclonal antibody. Non-limiting exemplary animal models described below can be adapted for other viral systems.

Various animal models for infectious diseases that are well known in the art can be employed to assess the efficacy of Therapeutic Agents in preventing, treating, and/or managing infectious diseases, e.g.: mouse models of herpes simplex virus (HSV) are described in Crute et al., Nature Medicine, 2002, 8:386-391 and Bolger et al., Antiviral Res., 1997, 35:157-165; guinea pig models of HSV are described in Chen et al., Virol. J, 2004 Nov. 23, 1:11; animal models of mouse cytomegalovirus (MCMV) and human cytomegalovirus (HCMV) are described in Kern et al., Antimicrob. Agents Chemother., 2004, 48:4745-4753; Guinea pig models of CMV is described in Bourne et al., Antiviral Res., 2000, 47:103-109, Bravo et al., Antiviral Res., 2003, 60:41-49 and Bravo et al, J. Infectious Diseases, 2006, 193:591-597; animal models of influenza virus are described in Sidwell et al., Antiviral Res., 2000, 48:1-16; and McCauley et al., Antiviral Res., 1995, 27:179-186; mouse models of hepatitis B virus (HBV) are described in Cavanaugh et al., J. Virol., 1997, 71:3236-3243 and Guidotti et al., J. Virol., 1995, 69:6158-6169; mouse models of hepatitis C virus (HCV) are described in Zhu et al., Antimicrobial Agents and Chemother., 2006, 50:3260-3268, Bright et al., Nature, 2005, 436:973-978, Hsu et al., Nat. Biotechnol., 2003, 21:519-525, Ilan et al., J. Infect. Dis. 2002, 185:153-161, Kneteman et al., Hepatology, 2006, 43:1346-1353, Mercer et al., Nat. Med., 2001, 7:927-933, and Wu et al., Gastroenterology, 2005, 128:1416-1423; animal models of HIV are described in Ayash-Rashkovsky et al., FASEB J., 2005, 19:1149-1151, Mosier et al., Semin. Immunol., 1996, 8:255-262, Mosier et al., Hosp. Pract. (Off Ed)., 1996, 31:41-48, 53-55, 59-60, Bonyhadi et al., Mol. Med. Today, 1997, 3:246-253, Jolicoeur et al., Leukemia, 1999, 13:S78-S80, Browning et al., Proc. Natl. Acad. Sci. USA, 1997, 94:14637-14641, and Sawada et al., J. Exp. Med., 1998, 187:1439-1449, and Schito et al., Curr. HIV Res., 2006, 4:379-386.

Other animal models for viral infections can also be used to assess the efficacy of a Therapeutic Agent or a composition thereof, e.g., animal models for viral infections such as EBV-associated diseases, gammaherpesviruses, infectious mononucleosis, simian immunodeficiency virus ("SIV"), Borna disease virus infection, hepatitis, varicella virus infection, viral pneumonitis, Epstein-Barr virus pathogenesis, feline immunodeficiency virus ("FIV"), HTLV type 1 infection, human rotaviruses, and genital herpes have been developed (see, e.g., Hayashi et al., 2002, Histol Histopathol 17(4):1293-310; Arico et al., 2002, J Interferon Cytokine Res 22(11):1081-8; Flano et al., 2002, Immunol Res 25(3):201-17; Sauermann, 2001, Curr Mol Med 1(4):515-22; Pletnikov et al., 2002, Front Biosci 7:d593-607; Engler et al., 2001, Mol Immunol 38(6):457-65; White et al., 2001, Brain Pathol 11(4):475-9; Davis & Matalon, 2001, News Physiol Sci 16:185-90; Wang, 2001, Curr Top Microbiol Immunol. 258:201-19; Phillips et al., 2000, J Psychopharmacol. 14(3):244-50; Kazanji, 2000, AIDS Res Hum Retroviruses. 16(16):1741-6; Saif et al., 1996, Arch Virol Suppl. 12:153-61; and Hsiung et al., 1984, Rev Infect Dis. 6(1):33-50).

Other animal models for viral respiratory infections include, but not limited to, PIV (see, e.g., Shephard et al., 2003 Res Vet Sci 74(2): 187-190; Ottolini et al., 2002 J Infect Dis 186(12): 1713-1717), and RSV (see, e.g., Culley et al., 2002 J Exp Med 196(10): 1381-1386; and Curtis et al., 2002 Exp Biol Med 227(9): 799-802).

The Therapeutic Agent, composition thereof, or combination therapy comprising the Therapeutic Agent can be tested for their ability to decrease the time course of viral infection.

Animal models for bacterial infections can also be used to assess the efficacy of a Therapeutic Agent or a composition thereo. Animal models for bacterial infections such as *H. pylori*-infection, genital mycoplasmosis, primary sclerosing cholangitis, cholera, chronic lung infection with *Pseudomonas aeruginosa*, Legionnaires' disease, gastroduodenal ulcer disease, bacterial meningitis, gastric *Helicobacter* infection, pneumococcal otitis media, experimental allergic neuritis, leprous neuropathy, mycobacterial infection, endocarditis, *Aeromonas*-associated enteritis, *Bacteroides fragilis* infection, syphilis, streptococcal endocarditis, acute hematogenous osteomyelitis, human scrub typhus, toxic shock syndrome, anaerobic infections, *Escherichia coli* infections, and *Mycoplasma pneumoniae* infections have been developed (see, e.g., Sugiyama et al., 2002, J Gastroenterol. 37 Suppl 13:6-9; Brown et al., 2001, Am J Reprod Immunol. 46(3): 232-41; Vierling, 2001, Best Pract Res Clin Gastroenterol. 15(4):591-610; Klose, 2000, Trends Microbiol. 8(4):189-91; Stotland et al., 2000, Pediatr Pulmonol. 30(5):413-24; Brieland et al., 2000, Immunopharmacology 48(3):249-52; Lee, 2000, Baillieres Best Pract Res Clin Gastroenterol. 14(1): 75-96; Koedel & Pfister, 1999, Infect Dis Clin North Am. 13(3):549-77; Nedrud, 1999, FEMS Immunol Med Microbiol. 24(2):243-50; Prellner et al., 1999, Microb Drug Resist. 5(1):73-82; Vriesendorp, 1997, J Infect Dis. 176 Suppl 2:S164-8; Shetty & Antia, 1996, Indian J Lepr. 68(1):95-104; Balasubramanian et al., 1994, Immunobiology 191(4-5):395-401; Carbon et al., 1994, Int J Biomed Comput. 36(1-2):59-67; Haberberger et al., 1991, Experientia. 47(5):426-9; Onderdonk et al., 1990, Rev Infect Dis. 12 Suppl 2:S169-77; Wicher & Wicher, 1989, Crit Rev Microbiol. 16(3):181-234; Scheld, 1987, J Antimicrob Chemother. 20 Suppl A:71-85; Emslie & Nade, 1986, Rev Infect Dis. 8(6):841-9; Ridgway et al., 1986, Lab Anim Sci. 36(5):481-5; Quimby & Nguyen, 1985, Crit Rev Microbiol. 12(1):1-44; Onderdonk et al., 1979, Rev Infect Dis. 1(2): 291-301; Smith, 1976, Ciba Found Symp. (42):45-72, and Taylor-Robinson, 1976, Infection. 4(1 Suppl):4-8).

The Therapeutic Agent or composition thereof, or combination therapy comprising the Therapeutic Agent can be tested for their ability to decrease the time course of bacterial infection, e.g., a bacterial respiratory infection by at least 25%, at least 50%, at least 60%, at least 75%, at least 85%, at least 95%, or at least 99% relative to a negative control using methods well known in the art.

The efficacy of Therapeutic Agents or compositions thereof for the prevention, treatment and/or management of a fungal infection can be assessed in animal models for such infections. Animal models for fungal infections such as *Candida* infections, zygomycosis, *Candida* mastitis, progressive disseminated trichosporonosis with latent trichosporonemia, disseminated candidiasis, pulmonary paracoccidioidomycosis, pulmonary aspergillosis, *Pneumocystis carinii* pneumonia, cryptococcal meningitis, coccidioidal meningoencephalitis and cerebrospinal vasculitis, *Aspergillus niger* infection, *Fusarium* keratitis, paranasal sinus mycoses, *Aspergillus fumigatus* endocarditis, tibial dyschondroplasia, *Candida glabrata* vaginitis, oropharyngeal candidiasis, X-linked chronic granulomatous disease, tinea pedis, cutaneous candidiasis, mycotic placentitis, disseminated trichosporonosis, allergic bronchopulmonary aspergillosis, mycotic keratitis, *Cryptococcus neoformans* infection, fungal peritonitis, *Curvularia geniculata* infection, staphylococcal endophthalmitis, sporotrichosis, and dermatophytosis have been developed (see, e.g., Arendrup et al., 2002, Infection 30(5):286-91; Kamei, 2001, Mycopathologia 152 (1):5-13; Guhad et al., 2000, FEMS Microbiol Lett.192(1): 27-31; Yamagata et al., 2000, J Clin Microbiol. 38(9):32606; Andrutis et al., 2000, J Clin Microbiol. 38(6):2317-23; Cock et al., 2000, Rev Inst Med Trop Sao Paulo 42(2):59-66; Shibuya et al., 1999, Microb Pathog. 27(3):123-31; Beers et al., 1999, J Lab Clin Med. 133(5):423-33; Najvar et al., 1999, Antimicrob Agents Chemother.43(2):413-4; Williams et al., 1988, J Infect Dis. 178(4):1217-21; Yoshida, 1988, Kansenshogaku Zasshi. 1998 June; 72(6):621-30; Alexandrakis et al., 1998, Br J Ophthalmol. 82(3):306-11; Chakrabarti et al., 1997, J Med Vet Mycol. 35(4):295-7; Martin et al., 1997, Antimicrob Agents Chemother. 41(1): 13-6; Chu et al., 1996, Avian Dis. 40(3):715-9; Fidel et al., 1996, J Infect Dis. 173(2):425-31; Cole et al., 1995, FEMS Microbiol Lett. 15; 126(2):177-80; Pollock et al., 1995, Nat Genet. 9(2):202-9; Uchida et al., 1994, Jpn J Antibiot. 47(10):1407-12: Maebashi et al., 1994, J Med Vet Mycol. 32(5):349-59; Jensen & Schonheyder, 1993, J Exp Anim Sci. 35(4):155-60; Gokaslan & Anaissie, 1992, Infect Immun. 60(8):3339-44; Kurup et al., 1992, J Immunol. 148(12):3783-8; Singh et al., 1990, Mycopathologia. 112 (3):127-37; Salkowski & Balish, 1990, Infect Immun. 58(10):3300-6; Ahmad et al., 1986, Am J Kidney Dis. 7(2):153-6; Alture-Werber E, Edberg S C, 1985, Mycopathologia. 89(2):69-73; Kane et al., 1981, Antimicrob Agents Chemother. 20(5):595-9; Barbee et al., 1977, Am J Pathol. 86(1):281-4; and Maestrone et al., 1973, Am J Vet Res. 34(6):833-6). Animal models for fungal respiratory infections such as *Candida albicans, Aspergillus fumigatus*, invasive pulmonary aspergillosis, *Pneumocystis carinii*, pulmonary cryptococcosis, *Pseudomonas aeruginosa, Cunninghamella bertholletia* (see, e.g., Aratani et al., 2002 Med Mycol 40(6):557-563; Bozza et al., 2002 Microbes Infect 4(13): 1281-1290; Kurup et al., 2002 Int Arch Allergy Immunol 129(2):129-137; Hori et al., 2002 Eur J Immuno 32(5): 1282-1291; Rivera et al., 2002 J Immuno 168(7): 3419-3427; Vassallo et al., 2001, Am J Respir Cell Mol Biol 25(2): 203-211; Wilder et al., 2002 Am J Respir Cell Mol Biol 26(3): 304-314; Yonezawa et al., 2000 J Infect Chemother 6(3): 155-161; Cacciapuoti et al., 2000 Antimicrob Agents Chemother 44(8): 2017-2022; and Honda et al., 1998 Mycopathologia 144(3):141-146).

The Therapeutic Agents or compositions thereof can be tested for their ability to decrease the time course of fungal respiratory infection by at least 25%, at least 50%, at least 60%, at least 75%, at least 85%, at least 95%, or at least 99%. Techniques known to those of skill in the art can be used to analyze the function of the Therapeutic Agents or compositions thereof in vivo.

6. EXAMPLES

6.1 Example 1. Study Evaluating Toxicity, Plasma Levels of IL-15 and Immunological Parameters after Subcutaneous Injections of Rhesus Macaques with IL-15/sIL-15Rα at Different Doses This example describes a dose escalation study performed in order to evaluate toxicity, immunogenicity and effects on immune system homeostasis of human IL-15/soluble IL-15Rα after subcutaneous injections. IL-15/soluble IL-15Rα, a non-covalently linked but stable heterodimer of IL-15 and soluble form of IL-15Rα, was made as follows. Human HEK 293T cells were transfected with nucleic acid expression construct for IL-15 (e.g., SEQ ID NO: 23) in combination with a nucleic acid expression construct for IL-15Rα (e.g., SEQ ID NO: 25). IL-15/soluble IL-15Rα complex composed of IL-15 (e.g., SEQ ID NO: 24 or SEQ ID NO: 1 without the signal peptide) and IL-15Rα (e.g., SEQ ID NO:33) were purified. In this example, the IL-15/soluble IL-15Rα complex (otherwise referred to as heterodimeric IL-15 or IL-15 heterodimer) was composed of IL-15 (SEQ ID NO:1 without the signal peptide) and soluble IL-15Rα (SEQ ID NO: 33). As outlined in Table 1, Group 1 included 2 rhesus macaques that received 6 s.c. injections of IL-15/soluble IL-15Rα at the dose of 1 μg/kg on day 0, 2, 4, 7, 9 and 11. Group 2 included 2 rhesus macaques that received 6 s.c. injections of IL-15/sIL-15Rα at the dose of 20 μg/kg on day 0, 2, 4, 7, 9 and 11. Group 3 included 2 rhesus macaques that received 6 s.c. injections of IL-15/soluble IL-15Rα at the dose of 50 μg/Kg on day 0, 2, 4, 7, 9 and 11.

TABLE 1

Study design to evaluate toxicity, immunogenicity and immunological effects of IL-15/IL-15Rα heterodimer after repeated s.c. injections.

| Group | Treatment | Dose (μg/Kg/ injection) | Route of Administration | Duration of Treatment | Total Doses/ Cycle | # Cycles | # Rhesus Macaques |
|---|---|---|---|---|---|---|---|
| 1 | IL-15/ IL-15Rα | 1 | s.c. | 12 days (s.c. at 0, 2, 4, 7, 9 and 11) | 6 | 1 | 2 |
| 2 | IL-15/ IL-15Rα | 20 | s.c. | 12 days (s.c. at 0, 2, 4, 7, 9 and 11) | 6 | 1 | 2 |
| 3 | IL-15/ IL-15Rα | 50 | s.c. | 12 days (s.c. at 0, 2, 4, 7, 9 and 11) | 6 | 1 | 2 |

Six macaques were sedated and received IL-15/sIL-15Rα (2 animals/dose) in 0.5 ml saline solution (PBS) s.c. Blood pressure and temperature were followed over time. No changes in blood pressure and animal temperature were observed, with the following exception: one animal (P995) receiving 50 μg/kg had elevated temperature after the third injection, which reached 105° F. at 6 hours post-treatment and was still elevated at 104° F. after 24 hours. All animals were off anesthesia at 1 hour after injections and had normal recoveries.

Blood was drawn at 0, 6, 8, 12 and 24 hours after the first and the last s.c. injection and at 0 and 6 hours after the second, third and fourth s.c. injections. The concentration of human IL-15 in macaque plasma was evaluated using a colorimetric immunoassay (Quantikine human IL-15, R&D Systems), according to the manufacturer's recommendations. The results are presented in Table 2 and FIG. 4. FIG. 4 shows plasma IL-15 levels in 6 macaques injected with IL-15 heterodimer at escalated doses.

TABLE 2

Levels of plasma IL-15 in 6 macaques injected with IL-15 heterodimer at escalated doses of 1 μg/kg, 20 μg/kg, and 50 μg/kg. Plasma IL-15 (pg/ml)

| | Animal: | | | | | |
|---|---|---|---|---|---|---|
| | P942 50 μg | P995 50 μg | P990 20 μg | P999 20 μg | P950 1 μg | P994 1 μg |
| Hours | | | | | | |
| 0 | 9.1 | 8.6 | 8 | 9.8 | 8.2 | 8.2 |
| 6 | 6978 | 15320.6 | 3180.3 | 7427 | 53.2 | 58.2 |
| 8 | 8520.5 | 18173.6 | 2122.9 | 4742.5 | 39.1 | 40.1 |
| 12 | 7320.1 | 10657.4 | 1872.4 | 4395.8 | 25.4 | 36.7 |
| 24 | 4350 | 10828.5 | 1947.5 | 2266.5 | 27.1 | 44.3 |
| 48 | 1114.5 | 887.8 | 370.9 | 283.4 | 9.9 | 13.8 |
| 54 | 4530.4 | 14741.8 | 2872.1 | 12031.1 | 82.3 | 114.6 |
| 96 | 39 | 105.9 | 30.4 | 13.6 | 6.9 | 11.8 |
| 120 | 18.9 | 14.1 | 7.5 | 309.1 | 7.6 | 9.8 |
| 126 | 630 | 2285 | 619.6 | 4715.7 | 71.4 | 164 |
| 168 | 49.8 | 97.9 | 5.9 | 11.5 | 6.3 | 7.4 |
| 174 | 895.5 | 1597.5 | 376.9 | 1099.7 | 49.6 | 65.1 |

TABLE 2-continued

Levels of plasma IL-15 in 6 macaques injected with IL-15 heterodimer at escalated doses of 1 μg/kg, 20 μg/kg, and 50 μg/kg. Plasma IL-15 (pg/ml)

| | Animal: | | | | | |
|---|---|---|---|---|---|---|
| | P942 50 μg | P995 50 μg | P990 20 μg | P999 20 μg | P950 1 μg | P994 1 μg |
| 216 | 57.3 | 293.7 | 8.5 | 6.9 | 6.5 | 9.9 |
| 222 | 1746.2 | 2303 | 624.7 | 384.6 | 37.6 | 93.4 |
| 264 | 24.5 | 8.5 | 4.3 | 7.6 | 5 | 20.5 |
| 270 | 86.6 | 1400.6 | 1444.6 | 607.6 | 39.2 | 233 |
| 272 | 39.9 | 867.8 | 540.6 | 612.7 | 31.6 | 191 |
| 276 | 45.9 | 833.6 | 560.2 | 855.1 | 15.3 | 111.3 |
| 288 | 34.3 | 381.7 | 202.6 | 594.6 | 7.4 | 26.1 |
| 312 | 17.1 | 9.5 | | | 5.7 | |
| 336 | | | 3.7 | 6.2 | | 7.6 |

The blood counts and lymphocytes subsets of all the animals were monitored and evaluated before, during and after IL-15 heterodimer administration. Samples of PBMC were taken from the macaques prior, during and after IL-15 heterodimer administration and were stained with antibodies binding to CD3, CD4, CD8 and CD16, and examined by flow cytometry. The results are presented in FIG. 5. All doses of IL-15 heterodimer resulted in a 4 to 8-fold increase in the absolute count of NK cells that peaked between day 7 and 14 after start of the treatment. These results suggest that NK cells respond to lower level of IL-15, and even a dose of 1 μg/kg is sufficient to induce a marked expansion. The absolute count of CD8+ T cell in peripheral blood also increased, but in a dose-dependent manner. The highest dose of IL-15 that resulted at peak plasma levels of more than 10 ng/ml showed a 10 fold increase in the absolute counts of CD8 T cells. FIG. 5 shows the fold over baseline increase of NK cells and CD8 T cells in peripheral blood in 6 macaques injected with IL-15 heterodimer at escalated doses of 1 μg/kg, 20 μg/kg, and 50 μg/kg.

Animals were sacrificed at day 14 after the first injection (3 days after the last injection) and immunophenotypical analysis was performed in different tissues. The results are presented in FIG. 6. FIG. 6 shows dose-dependent proliferation of lymphocytes in different tissues upon IL-15 heterodimer s.c. administration. IL-15 heterodimer treatment resulted in great expansion of CD8, NK and gammadelta TCR T cells in lymph nodes, peripheral blood, liver and spleen. In all the tissue analyzed, all the lymphocyte subsets responded to IL-15 in a dose-dependent manner (FIG. 6).

Administration of doses of 1, 5, 20 and 50 μg/kg s.c. of heterodimeric IL-15 to macques showed that heterodimeric IL-15 is well tolerated in macaques and that no major side effects were observed. One of the two macaques that received the dose of 50 μg/kg of IL-15 heterodimer showed enlarged lymph nodes (axillary and mesenteric) at necropsy.

6.2 Example 2. Dose Escalation Study

This example describes a dose escalation study to evaluate the effects of escalation of doses of a human IL-15/soluble IL-15Rα complex within individual macques. The IL-15/soluble IL-15Rα complex used in this study is composed of IL-15 (SEQ ID NO:1 without the signal peptide) and soluble IL-15Rα (SEQ ID NO: 33). The complex is produced as described in Example 1, supra. Rhesus macaques are each administered subcutaneous injections of IL-15/soluble IL-15Rα complex at the following doses of 2 μg/kg, 4 μg/kg, 8 μg/kg, 16 μg/kg, 32 μg/kg, 64 μg/kg of IL-15 determined based on the mass of single chain IL-15, wherein each dose is administered once three times per week for two weeks (e.g., Monday, Wednesday, Friday, Monday, Wednesday and Friday).

Blood pressure and temperature of the macques are monitored over time. Blood is drawn at before and after the first and the last subcutaneous injections (e.g., 0, 6, 8, 12 and 24 hours after the last injections) and before and after the other injections (e.g., 0 and 6 hours after the injections). The concentration of human IL-15 in macaque plasma is evaluated using a colorimetric immunoassay (Quantikine human IL-15, R&D Systems), according to the manufacturer's recommendations.

6.3 Example 3. SHIV Plasma Viral Load

Administration of two cycles of 6 SC injections each of hetIL-15 (IL-15/IL-15Rα) (5 μg/kg per dose, 3× per week, MWF MWF, calculated as single-chain IL-15 equivalent) was performed in 8 macaques. The hetIL-15 used in this study is composed of IL-15 (SEQ ID NO:1 without the signal peptide) and soluble IL-15Rα (SEQ ID NO: 33). The hetIL-15 was produced as described in Example 1, supra. There were no changes in blood pressure or temperature after treatment, whereas T lymphocytes and NK cells showed enhanced proliferation and an increase in numbers. The use of SHIV-infected animals allowed for the evaluation of the effect of hetIL-15 treatment on viral load. No changes in viral load were detected, suggesting that IL-15 treatment is safe in the context of HIV infection.

The animals were previously vaccinated against SHIV and subsequently challenged with SHIV and became infected. At the time of hetIL-15 injection the animals were healthy, their immune system was normal and the viral load in the plasma was not detectable, for the majority of the animals. No changes in viral load were observed as consequence of hetIL-15 treatment. Viral load levels pre and during treatment are reported in Table 3.

TABLE 3

Viral Load (viral RNA copies/ml plasma)

| | DAY-31 | DAY 14 | DAY 28 |
|---|---|---|---|
| | | Date: | |
| | Jun. 12, 2012 | Jul. 27, 2012 | Aug. 10, 2012 |
| P949 | <50 | <50 | <50 |
| P966 | <50 | <50 | <50 |
| P981 | 2742 | 1865 | <50 |
| P968 | <50 | <50 | 2996 |
| P976 | <50 | <50 | <50 |
| P952 | <50 | <50 | <50 |
| P971 | <50 | <50 | <50 |
| P983 | 828 | <50 | <50 |

6.4 Example 4. Measurement of IL-15 Activity Using NK92 Cells in a Bioassay

This example describes a study to test IL-15 bioactivity in a cell proliferation assay using the NK92 cell line. NK92 cells are human lymphoblasts from a malignant non-Hodgkin's lymphoma, which requires cytokine signals for growth and can be maintained in media that is supplemented with IL-2 or IL-15.

The NK92 cell line was cultured in media supplemented with Hoffmann-La Roche IL-2 plus IL-15 at 37° C. and 5% $CO_2$. The day before assay, the cells were harvested, washed, counted and returned to culture in media without IL-2 or IL-15. The concentrations for the IL-15/IL-15Rα Reference Standard Clone 19.7 and IL-15/IL-15Rα test sample EN627-01-13-001 were at 1000 μg/ml and 576 μg/ml, respectively. Both the IL-15/IL-15Rα Reference Standard Clone 19.7 and IL-15/IL-15Rα test sample EN627-01-13-001 were serially diluted to produce 9 different concentrations: 25 ng/ml, 10 ng/ml, 4 ng/ml, 2 ng/ml, 1 ng/ml, 0.5 ng/ml, 0.25 ng/ml, 0.05 ng/ml, 0.01 ng/ml. Testing was performed to compare the bioactivity of IL-15/IL-15Rα Reference Standard Clone 19.7 to the IL-15/IL-15Rα test sample EN627-01-13-001 by culturing NK-92 cells with IL-15/IL-15Rα at the 9 concentrations. The assay was set up with triplicate wells for each test dilution. Each plate was set up according to the plate map in Table 4.

TABLE 4

Table Map for the NK92 Bioassay.

| | 1 | 2 | 3 | 4 | 5 | 6 | 7 | 8 | 9 | 10 | 11 | 12 |
|---|---|---|---|---|---|---|---|---|---|---|---|---|
| A | | | | | | Media | | | | | | |
| B | | Std | | | | | | | | | | |
| C | | 25 | 10 | 4 | 2 | 1 | 0.5 | 0.25 | 0.05 | 0.01 | 0 | |

TABLE 4-continued

| Table Map for the NK92 Bioassay. | | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| D | | | | | | | | | | | | |
| E | | Test | Samp | | | | | | | | | |
| F | | 25 | 10 | 4 | 2 | 1 | 0.5 | 0.25 | 0.05 | 0.01 | 0 | |
| G | | | | | | | | | | | | |
| H | | | | | | Media | | | | | | |

Two assays were run on different dates. Assay ID 11362 was set up on a total of 4 plates, and Assay ID 11436 was set up on a total of 2 plates. After culture for 72 hours at 37° C., MTT was added to each well of the culture, and the plates were returned to the incubator for an additional 5 hours. Sodium dodecyl sulfate was then added to each well to stop the reaction and solubilize the formazan generated by metabolic activity of the cells. The plates were incubated for an additional 20-26 hours at which point the plates were read on a spectrophotometer using a detection wavelength of 570 nm with a reference wavelength of 690 nm. Results of the assay were collected using SoftMax Pro software and a 4-parameter standard curve was generated. The calculated concentration of IL-15/IL-15Rα test sample EN627-01-13-001 was evaluated against the standard curve and the mean dilution-corrected concentration of wells on the transitional portion of the standard curve (dilutions 5-7) were averaged. The test sample was determined to have potency equivalent to the IL-15/IL-15Rα Reference Standard Clone 19.7 if mean calculated activity was in the range of 50% to 200% of the expected 25 ng/ml starting dilution.

The results of the NK92 bioassays were summarized in Table 5.

TABLE 5

Test results for the NK92 Bioassays.

| Assay No. | Plate No. | Calculated Activity (ng/ml) | Calculated Activity (compared with 25 ng/ml) | Conclusion |
|---|---|---|---|---|
| 11362 | 1 | 32.298 | 129.2% | PASS |
| | 2 | 29.747 | 119.0% | PASS |
| | 3 | 33.559 | 134.2% | PASS |
| | 4 | 33.888 | 135.5% | PASS |
| 11436 | 1 | 32.828 | 131.3% | PASS |
| | 2 | 36.344 | 145.4% | PASS |

Table 5 shows that the IL-15/IL-15Rα test sample EN627-01-13-001 had bioactivity in the bioassay that fell within the specified range of 50% to 200% of the IL-15/IL-15Rα Reference Standard Clone 19.7 of the expected value of 25 ng/ml. Under both Assay ID 11362 and Assay ID 11436, the IL-15/IL-15Rα test sample EN627-01-13-001 passed the bioactivity test.

6.5 Example 5. Dose Escalation Study

This example describes a dose escalation study to evaluate the effects of escalation of doses of a human IL-15/soluble IL-15Rα complex ("hetIL-15") within individual macques. The IL-15/soluble IL-15Rα complex used in this study was composed of IL-15 (SEQ ID NO:1 without the signal peptide) and soluble IL-15Rα (SEQ ID NO: 33). The complex was produced as described in Example 1, supra. Rhesus macaque T138 was administered subcutaneous injections of IL-15/soluble IL-15Rα complex at the following doses of 2 μg/kg, 4 μg/kg, 8 μg/kg, 16 μg/kg, 32 μg/kg, and 64 μg/kg of IL-15 determined based on the mass of single chain IL-15, wherein each dose was administered once. The macaque was treated three times per week for two weeks (e.g., Monday, Wednesday, Friday, Monday, Wednesday and Friday).

Blood and lymph node samples were analyzed before, during and after the two week hetIL-15 treatment. The results are presented in FIG. 7, which shows that, in addition to blood increase, lymphocytes also increased in the lymph nodes. The effect on the increase of effector CD8 was strong, that is, hetIL-15 preferentially increased the presence of the effector CD8 population ($CD28^{-}CD95^{+}$), which is normally very low in the lymph nodes. FIG. 8 shows T lymphocyte proliferation and PD1 expression within the lymph nodes with hetIL-15 treatment. The results indicate that both the proliferation and the PD1 marker expression increased in the lymph node lymphocytes after hetIL-15 treatment.

Table 6 compares the dose design in this example (Treatment No. 3) with other hetIL-15 treatment regimens. Table 7 shows the symptoms and therapy for the animals under different hetIL-15 treatment regimens. Table 8 shows the effects of different hetIL-15 treatments. Necropsy indicates the period after hetIL-15 administration, when the animals were sacrificed and their tissues studied extensively. Animal T138 was not sacrificed, but was biopsied at the same time after hetIL-15 administration.

TABLE 6

Dose Design Under Different hetIL-15 Treatment Regimens.

| Treatment No. | Treatment Name | Total Dose (μg/kg) | Injection No. 1 | 2 | 3 | 4 | 5 | 6 |
|---|---|---|---|---|---|---|---|---|
| 1 | 6 × 50[1] | 300 | 50 | 50 | 50 | 50 | 50 | 50 |
| 2 | 6 × 20[2] | 120 | 20 | 20 | 20 | 20 | 20 | 20 |
| 3 | lowDoseEsc 1[3] | 126 | 2 | 4 | 8 | 16 | 32 | 64 |
| 4 | highDoseEsc 1[4] | 275 | 5 | 10 | 20 | 40 | 80 | 120 |
| 5 | highDoseEsc 1[4] | 155 | 5 | 10 | 20 | 40 | 80 | N/A |

[1]Animals identified in Table 8 as P942 and P995 received this dosing protocol.
[2]Animals identified in Table 8 as P990 and P999 received this dosing protocol.
[3]The animal identified as T138 received this dosing protocol
[4]The animals identified as P941 and P934 received this dosing protocol. See Example 6 below for additional information regarding these animals and the dosing regimen.

TABLE 7

Symptoms and Therapy for the Animals Under Different hetIL-15 Treatment Regimens.

| Treatment No. | Animal No. | Fever @Dose | Diarhea @Dose | systBP nadir | diastBP nadir | edema @Dose | Therapy |
|---|---|---|---|---|---|---|---|
| 3 | T138 | 8 (3rd inj) | none | 95 | 60 | 64 (6th inj) | antipyretic, NSAID, and antihistamine |

TABLE 7-continued

| Symptoms and Therapy for the Animals Under Different hetIL-15 Treatment Regimens. | | | | | | | |
|---|---|---|---|---|---|---|---|
| Treatment No. | Animal No. | Fever @Dose | Diarhea @Dose | systBP nadir | diastBP nadir | edema @Dose | Therapy |
| 4 | P941 | 80 (5th inj) | post 120 µg. | 85 | 48 | post-120 ug | Fluid resuscitation, antidiarrheal, NSAID, analgesic |
| 5 | P934 | 80 (5th inj) | 20 µg. Severe after 80 µg | 91 | 60 | post-80 ug | ICU, fluid resusciation, NSAID, antidiarrheal |

TABLE 8

| Effects of Different hetIL-15 Treatment Regimens. | | | | | | | | | | | |
|---|---|---|---|---|---|---|---|---|---|---|---|
| Treatment | Animal | LN CD8 effectors % | | Blood CD8 effectors % | | LN CD8 Ki67 (dividing) % | | Blood CD8 Ki67 (dividing) % | | Albumin | |
| No. | No. | before | necropsy | before | necropsy | Before | necropsy | before | necropsy | before | necropsy |
| 1 | P942 | 8.6 | 22.6 | 26.4 | 62 | 4.8 | 36.5 | 6.9 | 44.1 | | |
| 1 | P995 | 6.9 | 29.3 | 50.3 | 62 | 2.5 | 56.7 | 11.1 | 57.6 | | |
| 2 | P990 | 7 | 8.8 | 61.4 | 54 | 3.4 | 31.6 | 10.2 | 65.9 | | |
| 2 | P999 | 6.6 | 9.4 | 44.5 | 44 | 2.9 | 25.5 | 12.3 | 50.1 | | |
| 3 | T138 | 5 | 13 | 23.2 | 21.3 | 3 | 49 | 9.6 | 60 | 4.4 | 2.7 |
| 4 | P941 | 20 | 47 | 38 | 82 | 34.3 | 60.7 | 46.4 | 79 | 4.2 | 2 |
| 5 | P934 | 13 | 36.7 | 31 | 66.3 | 4.4 | 70 | 20.4 | 81.3 | 4.1 | 2.8 |

The dose escalation treatment in this example (Treatment No. 3) was well tolerated in macaque T138. Tables 6 and 7 show comparison of this regimen with others, and indicates that the symptoms developed in Treatment No. 3 were mild and reversible. High fever was present only after the highest dose administered, and the decrease in blood pressure was minimal. In the low dose escalation treatment (treatment #3), low fever was seen at after the third dose (8 µg/kg), and in the high dose escalation treatment (Treatment No. 4), low fever was seen after the fifth injection (80 µg/kg). Generally, the symptoms in the low dose escalation animal were much milder and transient compared to those of the high dose escalation animal. For example, diarrhea, a more severe side effect, was seen only in the animal in the high dose escalation treatment, see below. In addition, animals (e.g., T138) receiving the IL-15 heterodimer in a dose escalation regimen achieved high levels of proliferating lymphocytes with a lower level of exposure to the heterodimer than other animals.

6.6 Example 6. Dose Escalation Study

This example describes a dose escalation study to evaluate the effects of escalation of doses of a human IL-15/soluble IL-15Rα complex (hetIL-15) within individual macques. The IL-15/soluble IL-15Rα complex used in this study was composed of IL-15 (SEQ ID NO:1 without the signal peptide) and soluble IL-15Rα (SEQ ID NO: 33). The complex was produced as described in Example 1, supra. Rhesus macaque were each administered subcutaneous injections of IL-15/soluble IL-15Rα complex (hetIL-15) at the following doses of 5 µg/kg, 10 µg/kg, 20 µg/kg, 40 µg/kg, 80 µg/kg, and 120 µg/kg of IL-15 determined based on the mass of single chain IL-15, wherein each dose was administered once. Animals were treated three times per week for two weeks (e.g., Monday, Wednesday, Friday, Monday, Wednesday and Friday).

Two female rhesus macaques (P934 and P941) received a dose escalation regimen of subcutaneous hetIL-15 (six doses over the course of two weeks). Subjects were monitored with clinical assessment and lab tests throughout the study. While P941 completed the dose escalation regimen, P934 did not receive the final 120 ug/kg dose due to hetIL-15 associated toxicity, consisting of fever, significant diarrhea, and grossly enlarged lymph nodes. This resulted in subject P934 being treated with fluid resuscitation and supportive care following the 80 µg/kg hetIL15 administration.

Besides the toxicity experienced by P934, both macaques developed a broad spectrum of IL-15 on- and off-target effects that reflected the pharmacological activity of the cytokine. Moreover, the study in this example provided information about the pattern of hetIL-15 adverse effects that may help with recognizing individuals prone to toxicity early on during administration.

(1) Body Temperature—a Sensitive Clinical Indicator of hetIL-15 Activity

While baseline body temperature may vary from individual to individual, any difference between pre-administration and 4 h post-temperature was attributed to drug effect. For subject P941, the first time that rectal temperature increased 4 h post injection was at administration #5 (80 µg/kg), from 100.6 to 102.4° F. Contrarily, by injection #4, P934 had baseline fever (102.6° F.), increasing to 103.5° F. before the next injection. Of note, the final injection in P934 (80 µg/kg) further increased body temperature to 105° F., and triggered severe diarrhea lasting to necropsy. Just as with the temperature spike 4 h post-administration, the acute onset diarrhea is likely linked to hetIL15-associated immune activation, similar to what can occur from systemic, non-gastrointestinal infection as part of systemic inflammatory response syndrome.

Taken together with the above (40 μg/kg vs. 120 μg/kg), and in view of the more grossly enlarged lymph nodes present in P934, it appears that this macaque was more susceptible to the on-target effects of hetIL-15 treatment (immunological stimulation).

(2) Vascular Leak Syndrome

Under normal circumstances, the vascular endothelium comprises a significant barrier for large molecules and cells. Specifically, passive transport is possible only for small molecular weight blood components, while larger proteins and cells can enter the interstitial space through transport mechanisms and diapedesis. However, during systemic immunological activation, the endothelial barrier becomes more permissive, allowing for the "leakage" of large molecular weight components, such as albumin through the capillary vasculature. This results in a loss of osmotic pressure in the circulating blood, and thus a loss of water to the interstitial space. Clinically, this manifests in bilateral interstitial edema (including lungs) and hypotension. Hypotension may be enhanced by vasodilatory effects of immune mediators.

In the case of hetIL-15 administration, it is unclear whether any of these effects was a direct result of the administered cytokine's signaling on endothelial cells or whether it was a sequela of the entire immune activation, which occurred. In any case, as with the monkeys receiving the highest (50 μg/kg) dose in the toxicology study, subjects P941 and P934 both displayed a clinical picture and lab findings consistent with vascular leak syndrome.

In both macaques P934 and P941, a modest decline in serum albumin was present from injection #4, with more dramatic decline ensuing thereafter. Although blood pressure measurements were to some extent not as reliable in this setting since the monkeys were sedated, there was evidence of a narrowing of the pulse pressure (systolic diastolic blood pressure). By injection #6, P941 experienced frank hypotension and clinically evident edema. Interestingly, frank hypotension in P934 developed after hetIL-15 was withdrawn. As indicators of vascular leakage, comparison of albumin profile is presented in FIG. 9 and albumin/globulin (Alb/Glob) Ratio is presented in FIG. 10.

6.7 Example 7. Tumor Infiltration by Lymphocytes Upon hetIL-15 Treatment with a Dose Escalation Procedure This example describes a dose escalation study to evaluate the effects of escalation of doses of a human IL-15/soluble IL-15Rα complex in a macaque tumor. Animal T138 developed a malignant hemangiosarcoma tumor, which was biopsied and studied before and after a 2 week dose escalation regimen with hetIL-15. The animal remained free from tumor regrowth for at least three months. The IL-15/soluble IL-15Rα complex used in this study was composed of IL-15 (SEQ ID NO:1 without the signal peptide) and soluble IL-15Rα (SEQ ID NO: 33). The complex was produced as described in Example 1, supra. Rhesus macaque T138 was administered subcutaneous injections of IL-15/soluble IL-15Rα complex at the following doses of 2 μg/kg, 4 μg/kg, 8 μg/kg, 16 μg/kg, 32 μg/kg, and 64 μg/kg of IL-15 determined based on the mass of single chain IL-15, wherein each dose is administered once. The animal was injected three times per week for two weeks (e.g., Monday, Wednesday, Friday, Monday, Wednesday and Friday).

Macaque T138 developed a malignant tumor classified as malignant hemangiosarcoma. The tumor was biopsied, and isolated cells were evaluated by flow cytometry analysis both before and also after a 2 week dose escalation regimen of hetIL-15. The results suggest that hetIL-15 treatment promoted lymphocyte infiltration within the tumor and increased the expression of PD1, as shown in FIG. 11.

In addition, the malignant tumor was removed and no tumor regrowth has been detected for over 3 months.

6.8 Example 8. hetIL-15 and Therapeutic Vaccination

This example describes a study to induce potent de novo and recall CTL responses in infected macaques, treated with antiretroviral therapy ("ART") by combining Conserved Element DNA vaccine and hetIL-15 recombinant cytokine, in order to compare the size of the virus reservoir upon ART treatment, in the presence or absence of therapeutic vaccination and hetIL-15 treatment.

The combination of optimized therapeutic vaccination of SIV infected macaques and hetIL-15 to reduce virus reservoirs is used. Therapeutic vaccination increases both de novo and recall immune responses. hetIL-15 is used to enhance the effects of therapeutic vaccination.

The DNA vaccine contains vectors expressing seven conserved epitopes ("CE") from SIV p27gag (Mothe et al., 2015, A Human Immune Data-Informed Vaccine Concept Elicits Strong and Broad T-cell Specificities Associated with HIV-1 Control in Mice and Macaques. J Transl Med in press; Kulkarni et al., HIV-1 Conserved Elements p24CE DNA Vaccine Induces Humoral Immune Responses with Broad Epitope Recognition in Macaques. PLoS One 9 e111085; Kulkarni et al., 2014, Altered Response Hierarchy and Increased T-cell Breadth upon HIV-1 Conserved Element DNA Vaccination in Macaques. PLoS One 9: e86254.). CE DNA vaccination induces potent CTL responses to subdominant epitopes that is not achieved by gag DNA vaccine. Therefore, the CE DNA vaccine is able to induce responses not previously detectable in the infected animals, and that these responses have cytotoxic potential.

The combination of CE DNA vaccine and hetIL-15 treatment is evaluated as an immunotherapeutic approach using SIV-infected, ART-treated macaques. After a certain number of vaccinations, for example after 3 vaccinations, the animals receive treatment with hetIL-15 to enhance cytotoxicity of the SIV-specific CTL. Toxicity as well as other factors, such as antigen-specific T cell responses and viremia, are determined throughout the course of treatment. The animals are subsequently released from ART, in order to determine the therapeutic benefit of the treatment, measured as lower viremia or no virus rebound. In addition, infectious virus units assays and other specific assays are employed to measure the virus reservoir.

6.9 Example 9. hetIL-15 Combination Therapy

This example describes a study to induce potent de novo and recall CTL responses able to reduce virus reservoir using infected ART-treated macaques by combining hetIL-15 with other therapies.

hetIL-15 can be combined with other factors reported to induce virus activation or replication, or to induce infected cells to cycle and thus become more vulnerable to immune-mediated killing due to enhanced recognition or to movement into different compartments. For example, hetIL-15 can be combined with: (1) HDAC (histone deacetylase)

inhibitors, such as Panobinostat or Vorinostat, for latent-virus reactivation in HIV-infected patients on suppressive antiretroviral therapy; (2) TLR7 agonists; (3) Cytokines such as IL-7. See, e.g., Wang et al., J. Clin. Invest., 115: 128-137, 2005; Levy et al., J. Clin. Invest., 119:997-1007, 2009; and Rasmussen et al., Lancet HIV, 1:e13-e21, 2014; or (4) Therapeutic antibodies (e.g., monoclonal antibodies), such as ENV binding monoclonal antibodies.

The study is carried out as follows. Macaques are infected by SIV and put in ART. When the plasma Virus Load ("VL") becomes undetected or low, macaques are treated with therapeutic vaccination and/or hetIL-15. hetIL-15 treatment is provided in cycles of low or high dose. A specific high dose safe administration protocol is a 2 week every other day (e.g., Monday, Wednesday, Friday, Monday, Wednesday and Friday) SC administration as described in the previous examples. hetIL-15 treatment can be combined with a HDAC inhibitor such as Panobinostat, which induces virus activation or with TLR7 agonists, or with IL-7. An exemplary treatment sequence is treatment with hetIL-15 first and then with Panobinostat, TLR7 agonist, or IL-7. Another exemplary sequence of treatment is therapeutic vaccination, hetIL-15, and then Panobinostat, TLR7 agonist, or IL-7. Another exemplary sequence of treatment is therapeutic vaccination and simultaneous hetIL-15 and Panobinostat or TLR7 agonist.

7. SPECIFIC EMBODIMENTS, CITATION AND REFERENCES

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various references, including patent applications, patents, and scientific publications, are cited herein; the disclosure of each such reference is hereby incorporated herein by reference in its entirety.

What is claimed is:

1. A method for treating lymphocytopenia, cancer or an infectious disease in a human subject, comprising:
(a) administering an initial low dose of a human IL-15/IL-15Rα complex to the human subject, wherein the initial low dose is between 0.1 μg/kg and 1 μg/kg as determined based on the mass of single chain IL-15;
(b) obtaining a plasma sample taken from a human subject; and
(c) detecting a concentration of free IL-15 of 1 pg/ml to 50 pg/ml in the sample obtained from the subject after the administration of the initial low dose of the human IL-15/IL-15Rα complex and administration of successively higher doses of the human IL-15/IL-15Rα complex, wherein each successively higher dose is from two to three times higher than the previous dose.

2. The method of claim 1, wherein the initial low dose is administered one to six times over a 7 to 14 day period.

3. The method of claim 1 or 2, wherein each dose is administered at least once, twice or thrice over a 7 to 14 day period.

4. The method of claim 1, wherein the detecting is done 24 hours, to 48 hours, or 72 hours after the administration of a dose of the IL-15/IL-15Rα complex and before the administration of another dose of the IL-15/IL-15Rα complex.

5. The method of claim 1, wherein the dose is not increased if the levels of free IL-15 is above 50 pg/ml in a sample from the subject.

6. The method of claim 1 further comprising (d) administering a maintenance dose of the IL-15/IL-15Rα complex to the subject, wherein the maintenance dose reaches levels of free IL-15 of approximately 1 pg/ml to 50 pg/ml in the sample from the subject.

7. The method of claim 1, wherein the cancer is melanoma, colon cancer, lung cancer, prostate cancer or renal cell carcinoma.

8. The method of claim 7, wherein the cancer has metastasized.

9. The method of claim 1, wherein the infectious disease is HIV.

10. The method of claim 1, wherein the infectious disease is pneumonia or tuberculosis.

11. The method of claim 1, wherein the lymphocytopenia is due to the administration of an anti-cancer agent.

12. The method of claim 1, wherein the IL-15/IL-15Rα complex is administered subcutaneously, intravenously, intramuscularly, or intratumorally to the subject.

13. The method of claim 1, wherein: (a) the human IL-15 comprises amino acid residues 49 to 162 of the amino acid sequence of SEQ ID NO: 1; and (b) the human IL-15Rα comprises the amino acid sequence of SEQ ID NO: 33.

14. The method of claim 1, further comprising administering to the human subject one or more other therapies.

15. The method of claim 14, wherein the one or more other therapies is an antibody.

16. The method of claim 15, wherein the antibody immunospecifically binds to Her2, PD-1, a ligand of PD-1 or CD19.

17. The method of claim 15, wherein the antibody is administered after the IL-15/IL-15Rα complex is administered or is administered before the IL-15/IL-15Ra complex is administered.

18. The method of claim 14, wherein the one or more other therapies is a histone deacetylase (HDAC) inhibitor, TLR7 agonist, or a cytokine.

19. The method of claim 18, wherein the cytokine is IL-7.

* * * * *